US012563965B2

(12) United States Patent
Montenegro et al.

(10) Patent No.: US 12,563,965 B2
(45) Date of Patent: Feb. 24, 2026

(54) MATERIALS FOR ELECTRONIC DEVICES

(71) Applicant: Merck Patent GmbH, Darmstadt (DE)

(72) Inventors: Elvira Montenegro, Weinheim (DE); Teresa Mujica-Fernaud, Darmstadt (DE); Florian Maier-Flaig, Weinheim (DE); Frank Voges, Bad Duerkheim (DE)

(73) Assignee: Merck Patent GmbH, Darmstadt (DE)

( * ) Notice: Subject to any disclaimer, the term of this patent is extended or adjusted under 35 U.S.C. 154(b) by 1095 days.

(21) Appl. No.: 16/645,159

(22) PCT Filed: Sep. 5, 2018

(86) PCT No.: PCT/EP2018/073827

§ 371 (c)(1),
(2) Date: Aug. 1, 2021

(87) PCT Pub. No.: WO2019/048458

PCT Pub. Date: Mar. 14, 2019

(65) Prior Publication Data

US 2023/0329092 A1 Oct. 12, 2023

(30) Foreign Application Priority Data

Sep. 8, 2017 (EP) .................................... 17190206
May 22, 2018 (EP) .................................... 18173679

(51) Int. Cl.

| | |
|---|---|
| ***C07C 211/54*** | (2006.01) |
| ***C07C 211/61*** | (2006.01) |
| ***C07D 209/86*** | (2006.01) |
| ***C07D 307/91*** | (2006.01) |
| ***C07D 333/76*** | (2006.01) |
| ***H10K 50/11*** | (2023.01) |
| ***H10K 50/15*** | (2023.01) |
| ***H10K 50/17*** | (2023.01) |
| ***H10K 50/18*** | (2023.01) |
| ***H10K 85/60*** | (2023.01) |
| *H10K 101/10* | (2023.01) |

(52) U.S. Cl.

CPC .......... *H10K 85/636* (2023.02); *C07C 211/54* (2013.01); *C07C 211/61* (2013.01); *C07D 209/86* (2013.01); *C07D 307/91* (2013.01); *C07D 333/76* (2013.01); *H10K 50/11* (2023.02); *H10K 50/15* (2023.02); *H10K 50/17* (2023.02); *H10K 50/181* (2023.02); *H10K 85/633* (2023.02); *H10K 85/623* (2023.02); *H10K 85/626* (2023.02); *H10K 85/6572* (2023.02); *H10K 85/6574* (2023.02); *H10K 85/6576* (2023.02); *H10K 2101/10* (2023.02)

(58) Field of Classification Search

CPC ... C07C 211/54; C07C 211/61; H10K 85/624; H10K 85/633; H10K 85/654

USPC .................................... 428/690, 917; 257/40

See application file for complete search history.

(56) References Cited

U.S. PATENT DOCUMENTS

| | | | | |
|---|---|---|---|---|
| 8,241,763 | B2 | 8/2012 | Buesing et al. | |
| 8,334,058 | B2 | 12/2012 | Heil et al. | |
| 8,766,001 | B2 | 7/2014 | Pflumm et al. | |
| 8,852,756 | B2 | 10/2014 | Vestweber et al. | |
| 9,475,792 | B2 | 10/2016 | Parham et al. | |
| 9,748,494 | B2 | 8/2017 | Ito et al. | |
| 10,312,452 | B2 | 6/2019 | Kimura et al. | |
| 2008/0220285 | A1* | 9/2008 | Vestweber | C07C 13/72 564/426 |
| 2011/0092701 | A1 | 4/2011 | Pflumm et al. | |
| 2011/0266531 | A1 | 11/2011 | Kim et al. | |
| 2012/0305852 | A1 | 12/2012 | Anemian et al. | |
| 2014/0332793 | A1 | 11/2014 | Park et al. | |
| 2015/0155498 | A1 | 6/2015 | Ahn et al. | |
| 2015/0255720 | A1 | 9/2015 | Heil et al. | |
| 2016/0190472 | A1 | 6/2016 | Yen et al. | |
| 2017/0047526 | A1* | 2/2017 | Chung | C07D 495/04 |
| 2018/0269400 | A1 | 9/2018 | Jatsch et al. | |
| 2018/0327339 | A1 | 11/2018 | Rodriguez et al. | |
| 2019/0346517 | A1 | 11/2019 | Duensing et al. | |
| 2019/0372010 | A1* | 12/2019 | Lin | H10K 50/11 |
| 2020/0144517 | A1 | 5/2020 | Chung et al. | |

FOREIGN PATENT DOCUMENTS

| | | | |
|---|---|---|---|
| CN | 102060748 | A | 5/2011 |
| CN | 103524399 | A | 1/2014 |
| CN | 107235997 | A | 10/2017 |
| CN | 107663169 | A | 2/2018 |
| EP | 3130591 | A1 | 2/2017 |
| JP | 2008-545630 | A | 12/2008 |
| JP | 2011-523943 | A | 8/2011 |
| JP | 2012-028548 | A | 2/2012 |
| JP | 2013-519740 | A | 5/2013 |
| JP | 2015-520772 | A | 7/2015 |
| JP | 2015177137 | A | 10/2015 |

(Continued)

OTHER PUBLICATIONS

International Search Report for PCT/EP2018/073794 mailed Nov. 19, 2018.

International Search Report for PCT/EP2018/073827 mailed Nov. 19, 2018.

Shirota, Y., et al., "Charge Carrier Transporting Molecular Materials and Their Applicaitons in Devices", Chemical Reviews, vol. 107, No. 4, (2007), pp. 953-1010.

Written Opinion of the International Searching Authority for PCT/EP2018/073794 mailed Nov. 19, 2018.

(Continued)

*Primary Examiner* — Ruiyun Zhang

(74) *Attorney, Agent, or Firm* — Faegre Drinker Biddle & Reath LLP

(57) ABSTRACT

The present application relates to compounds of formula (I) and (II), to processes for preparation thereof, and to the use thereof in electronic devices.

18 Claims, No Drawings

(56) References Cited

FOREIGN PATENT DOCUMENTS

| | | | |
|---|---|---|---|
| JP | 2015177138 | A | 10/2015 |
| JP | 2015-534543 | A | 12/2015 |
| JP | 2016-155797 | A | 9/2016 |
| JP | 2017-039693 | A | 2/2017 |
| JP | 2020-513924 | A | 5/2020 |
| KR | 10-2012-0117692 | A | 10/2012 |
| KR | 10-2014-0009838 | A | 1/2014 |
| KR | 10-2015-0111271 | A | 10/2015 |
| KR | 10-2017-0030145 | A | 3/2017 |
| TW | 201726589 | A | 8/2017 |
| WO | WO-2006100896 | A1 | 9/2006 |
| WO | WO-2006108497 | A1 | 10/2006 |
| WO | WO-2006122630 | A1 | 11/2006 |
| WO | WO-2008006449 | A1 | 1/2008 |
| WO | 2009/038156 | A1 | 3/2009 |
| WO | WO-2009099060 | A1 | 8/2009 |
| WO | WO-2009141026 | A1 | 11/2009 |
| WO | 2009/148062 | A1 | 12/2009 |
| WO | WO-2010008371 | A1 | 1/2010 |
| WO | WO-2010008373 | A1 | 1/2010 |
| WO | WO-20100083872 | A2 | 7/2010 |
| WO | 2014/010910 | A1 | 1/2014 |
| WO | WO-2015002208 | A1 | 1/2015 |
| WO | 2017/043835 | A1 | 3/2017 |
| WO | WO-2017036573 | A1 | 3/2017 |
| WO | WO-2017041874 | A1 | 3/2017 |

OTHER PUBLICATIONS

Written Opinion of the International Searching Authority for PCT/EP2018/073827 mailed Nov. 19, 2018.

Lai et al., "Synthesis and Characterization of 2,3,7,8,12,13-Hexabromotruxene and Its Hexaaryl Derivatives," Chemistry Letters, vol. 38, No. 3, Feb. 21, 2009, pp. 286-287.

* cited by examiner

MATERIALS FOR ELECTRONIC DEVICES

CROSS-REFERENCE TO RELATED APPLICATIONS

This application is a national stage application (under 35 U.S.C. § 371) of PCT/EP2018/073827, filed Sep. 5, 2018, which claims benefit of European Application Nos. 17190206.7, filed Sep. 8, 2017 and 18173679.4, filed May 22, 2018, all of which are incorporated herein by reference in their entirety.

The present application relates to aromatic compounds containing a group selected from amino groups, bridged amino groups and carbazole groups, according to the formulae (I) and (II) defined below. These compounds are suitable for use in electronic devices.

Electronic devices in the context of this application are understood to mean what are called organic electronic devices, which contain organic semiconductor materials as functional materials. More particularly, these are understood to mean OLEDs (organic electroluminescent devices). The term OLEDs is understood to mean electronic devices which have one or more layers comprising organic compounds and emit light on application of electrical voltage. The construction and general principle of function of OLEDs are known to those skilled in the art.

In electronic devices, especially OLEDs, there is great interest in an improvement in the performance data, especially lifetime, efficiency and operating voltage. In these aspects, it has not yet been possible to find any entirely satisfactory solution.

There is additionally a search for materials having a high glass transition temperature, a low tendency to crystallization and a high refractive index, especially for use in hole-transporting layers of OLEDs.

A great influence on the performance data of electronic devices is possessed by emission layers and layers having a hole-transporting function. Novel compounds are also being sought for use in these layers, especially hole-transporting compounds and compounds that can serve as matrix material, especially for phosphorescent emitters, in an emitting layer.

A variety of aromatic compounds containing a group selected from amino groups, bridged amino groups and carbazole groups is known in the prior art as hole transport materials and/or matrix materials in electronic devices.

However, there is still a need for alternative compounds suitable for use in electronic devices. There is also a need for improvement with regard to the performance data in use in electronic devices, especially with regard to lifetime, operating voltage and efficiency.

It has now been found that particular compounds from the abovementioned structure class are of excellent suitability for use in electronic devices, especially for use in OLEDs, even more especially for use therein as hole transport materials and for use as matrix materials for phosphorescent emitters. The compounds preferably lead to high lifetime, high efficiency and low operating voltage of the devices. Further preferably, the compounds have a low tendency to crystallization, a high glass transition temperature and a high refractive index.

The present application provides a compound of the following formula (I) or (II):

Formula (I)

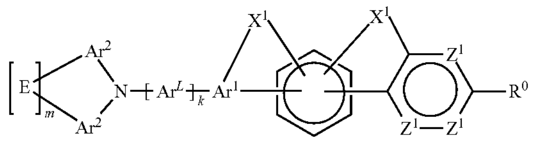

Formula (II)

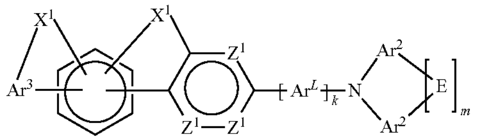

where the variables that occur are as follows:

$Z^1$ is the same or different at each instance and is selected from $CR^1$ and $CR^3$;

$Ar^1$ is an aryl group which has 6 to 20 aromatic ring atoms and may be substituted by one or more $R^3$ radicals, or a heteroaryl group which has 5 to 20 aromatic ring atoms and may be substituted by one or more $R^3$ radicals;

$Ar^2$ is the same or different at each instance and is selected from aromatic ring systems which have 6 to 40 aromatic ring atoms and may be substituted by one or more $R^5$ radicals, and heteroaromatic ring systems which have 5 to 40 aromatic ring atoms and may be substituted by one or more $R^5$ radicals;

$Ar^3$ is an aryl group which has 6 to 20 aromatic ring atoms and may be substituted by one or more $R^2$ radicals, or a heteroaryl group which has 5 to 20 aromatic ring atoms and may be substituted by one or more $R^2$ radicals;

$X^1$ is the same or different at each instance and is a divalent group selected from $—C(R^4)_2—$, $—C(R^4)_2—C(R^4)_2—$, $—CR^4═CR^4—$, $—Si(R^4)_2—$, $NR^4$, O and S;

$Ar^L$ is selected from aromatic ring systems which have 6 to 40 aromatic ring atoms and may be substituted by one or more $R^5$ radicals, and heteroaromatic ring systems which have 5 to 40 aromatic ring atoms and may be substituted by one or more $R^5$ radicals;

E is a single bond or a divalent group selected from $C(R^5)_2$, $Si(R^5)_2$, $N(R^5)$, O, and S;

$R^0$ is selected from H, D, aromatic ring systems which have 6 to 40 aromatic ring atoms and may be substituted by one or more $R^6$ radicals, and heteroaromatic ring systems which have 5 to 40 aromatic ring atoms and may be substituted by one or more $R^6$ radicals;

$R^1$ is the same or different at each instance and is selected from aromatic ring systems which have 6 to 40 aromatic ring atoms and may be substituted by one or more $R^6$ radicals, and heteroaromatic ring systems which have 5 to 40 aromatic ring atoms and may be substituted by one or more $R^6$ radicals;

$R^2$ is the same or different at each instance and is selected from H, D, F, CN, $Si(R^6)_3$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^0$ radicals may be joined to one another and may form a ring; where the alkyl, alkoxy, alkenyl and alkynyl groups mentioned and the aromatic ring systems and heteroaromatic ring systems mentioned may each be substituted by one or more $R^6$ radicals; and where one or more $CH_2$ groups in the alkyl, alkoxy, alkenyl and alkynyl groups mentioned may be replaced by $—R^6C{=}CR^6—$, $—C{\equiv}C—$, $Si(R^6)_2$, $C{=}O$, $C{=}NR^6$, $—C({=}O)O—$, $—C({=}O)NR^6—$, $NR^6$, $P({=}O)(R^6)$, —O—, —S—, SO or $SO_2$;

$R^3$, $R^4$, $R^5$ are the same or different at each instance and are selected from H, D, F, $C({=}O)R^6$, CN, $Si(R^6)_3$, $N(R^6)_2$, $P({=}O)(R^6)_2$, $OR^6$, $S({=}O)R^6$, $S({=}O)_2R^6$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^3$ or $R^4$ or $R^5$ radicals may be joined to one another and may form a ring; where the alkyl, alkoxy, alkenyl and alkynyl groups mentioned and the aromatic ring systems and heteroaromatic ring systems mentioned may each be substituted by one or more $R^6$ radicals; and where one or more $CH_2$ groups in the alkyl, alkoxy, alkenyl and alkynyl groups mentioned may be replaced by $—R^6C{=}CR^6—$, $—C{\equiv}C—$, $Si(R^6)_2$, $C{=}O$, $C{=}NR^6$, $—C({=}O)O—$, $—C({=}O)NR^6—$, $NR^6$, $P({=}O)(R^6)$, —O—, —S—, SO or $SO_2$;

$R^6$ is the same or different at each instance and is selected from H, D, F, $C({=}O)R^7$, CN, $Si(R^7)_3$, $N(R^7)_2$, $P({=}O)(R^7)_2$, $OR^7$, $S({=}O)R^7$, $S({=}O)_2R^7$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^6$ radicals may be joined to one another and may form a ring; where the alkyl, alkoxy, alkenyl and alkynyl groups mentioned and the aromatic ring systems and heteroaromatic ring systems mentioned may each be substituted by one or more $R^7$ radicals; and where one or more $CH_2$ groups in the alkyl, alkoxy, alkenyl and alkynyl groups mentioned may be replaced by $—R^7C{=}CR^7—$, $—C{\equiv}C—$, $Si(R^7)_2$, $C{=}O$, $C{=}NR^7$, $—C({=}O)O—$, $—C({=}O)NR^7—$, $NR^7$, $P({=}O)(R^7)$, —O—, —S—, SO or $SO_2$;

$R^7$ is the same or different at each instance and is selected from H, D, F, CN, alkyl or alkoxy groups having 1 to 20 carbon atoms, alkenyl or alkynyl groups having 2 to 20 carbon atoms, aromatic ring systems having 6 to 40 aromatic ring atoms and heteroaromatic ring systems having 5 to 40 aromatic ring atoms; where two or more $R^7$ radicals may be joined to one another and may form a ring; and where the alkyl, alkoxy, alkenyl and alkynyl groups, aromatic ring systems and heteroaromatic ring systems mentioned may be substituted by F or CN;

k is 0, 1, 2 or 3, where, in the case that k=0, the $Ar^L$ group is absent and the nitrogen atom of the group of the formula (N) constitutes the attachment position;

m is 0 or 1, where, in the case that m=0, the E group is absent and the $Ar^2$ groups are not bonded to one another;

where, in formula (I) and (II), all positions shown as unsubstituted may each be substituted by an $R^3$ radical; and where, in formula (I) and in formula (II), there is in each case at least one $Z^1$ group which is $CR^1$.

The circles drawn into the six-membered rings of the formula (I) and (II) mean that the six-membered rings in question have aromaticity.

The definitions which follow are applicable to the chemical groups that are used in the present applications. They are applicable unless any more specific definitions are given.

An aryl group in the context of this invention is understood to mean either a single aromatic cycle, i.e. benzene, or a fused aromatic polycycle, for example naphthalene, phenanthrene or anthracene. A fused aromatic polycycle in the context of the present application consists of two or more single aromatic cycles fused to one another. Fusion between cycles is understood here to mean that the cycles share at least one edge with one another. An aryl group in the context of this invention contains 6 to 40 aromatic ring atoms of which none is a heteroatom.

A heteroaryl group in the context of this invention is understood to mean either a single heteroaromatic cycle, for example pyridine, pyrimidine or thiophene, or a fused heteroaromatic polycycle, for example quinoline or carbazole. A fused heteroaromatic polycycle in the context of the present application consists of two or more single aromatic or heteroaromatic cycles that are fused to one another, where at least one of the aromatic and heteroaromatic cycles is a heteroaromatic cycle. Fusion between cycles is understood here to mean that the cycles share at least one edge with one another. A heteroaryl group in the context of this invention contains 5 to 40 aromatic ring atoms of which at least one is a heteroatom. The heteroatoms of the heteroaryl group are preferably selected from N, O and S.

An aryl or heteroaryl group, each of which may be substituted by the abovementioned radicals, is especially understood to mean groups derived from benzene, naphthalene, anthracene, phenanthrene, pyrene, dihydropyrene, chrysene, perylene, triphenylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aromatic ring system in the context of this invention is a system which does not necessarily contain solely aryl groups, but which may additionally contain one or more non-aromatic rings fused to at least one aryl group. These non-aromatic rings contain exclusively carbon atoms as ring atoms. Examples of groups covered by this definition are tetrahydronaphthalene, fluorene and spirobifluorene. In addition, the term "aromatic ring system" includes systems that consist of two or more aromatic ring systems joined to one another via single bonds, for example biphenyl, terphenyl, 7-phenyl-2-fluorenyl, quaterphenyl and 3,5-diphenyl-1-phenyl. An aromatic ring system in the context of this invention contains 6 to 40 carbon atoms and no heteroatoms in the ring system. The definition of "aromatic ring system" does not include heteroaryl groups.

A heteroaromatic ring system conforms to the abovementioned definition of an aromatic ring system, except that it must contain at least one heteroatom as ring atom. As is the case for the aromatic ring system, the heteroaromatic ring system need not contain exclusively aryl groups and heteroaryl groups, but may additionally contain one or more non-aromatic rings fused to at least one aryl or heteroaryl group. The non-aromatic rings may contain exclusively carbon atoms as ring atoms, or they may additionally contain one or more heteroatoms, where the heteroatoms are preferably selected from N, O and S. One example of such a heteroaromatic ring system is benzopyranyl. In addition, the term "heteroaromatic ring system" is understood to mean systems that consist of two or more aromatic or heteroaromatic ring systems that are bonded to one another via single bonds, for example 4,6-diphenyl-2-triazinyl. A heteroaromatic ring system in the context of this invention contains 5 to 40 ring atoms selected from carbon and heteroatoms, where at least one of the ring atoms is a heteroatom. The heteroatoms of the heteroaromatic ring system are preferably selected from N, O and S.

The terms "heteroaromatic ring system" and "aromatic ring system" as defined in the present application thus differ from one another in that an aromatic ring system cannot have a heteroatom as ring atom, whereas a heteroaromatic ring system must have at least one heteroatom as ring atom. This heteroatom may be present as a ring atom of a non-aromatic heterocyclic ring or as a ring atom of an aromatic heterocyclic ring.

In accordance with the above definitions, any aryl group is covered by the term "aromatic ring system", and any heteroaryl group is covered by the term "heteroaromatic ring system".

An aromatic ring system having 6 to 40 aromatic ring atoms or a heteroaromatic ring system having 5 to 40 aromatic ring atoms is especially understood to mean groups derived from the groups mentioned above under aryl groups and heteroaryl groups, and from biphenyl, terphenyl, quaterphenyl, fluorene, spirobifluorene, dihydrophenanthrene, dihydropyrene, tetrahydropyrene, indenofluorene, truxene, isotruxene, spirotruxene, spiroisotruxene, indenocarbazole, or from combinations of these groups.

In the context of the present invention, a straight-chain alkyl group having 1 to 20 carbon atoms and a branched or cyclic alkyl group having 3 to 20 carbon atoms and an alkenyl or alkynyl group having 2 to 40 carbon atoms in which individual hydrogen atoms or $CH_2$ groups may also be substituted by the groups mentioned above in the definition of the radicals are preferably understood to mean the methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl radicals.

An alkoxy or thioalkyl group having 1 to 20 carbon atoms in which individual hydrogen atoms or $CH_2$ groups may also be replaced by the groups mentioned above in the definition of the radicals is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The wording that two or more radicals together may form a ring, in the context of the present application, shall be understood to mean, inter alia, that the two radicals are joined to one another by a chemical bond. In addition, however, the abovementioned wording shall also be understood to mean that, if one of the two radicals is hydrogen, the second radical binds to the position to which the hydrogen atom was bonded, forming a ring.

The compounds of the formula (I) and (II) preferably contain only one triarylamino group. They more preferably contain only one amino group. A triarylamino group is understood to mean an amino group to which three groups selected from aromatic ring systems and heteroaromatic ring systems are bonded.

Preferably, one or two $Z^1$ groups are $CR^1$, and the other $Z^1$ groups are $CR^3$. More preferably, one $Z^1$ group is $CR^1$, and the other two $Z^1$ groups are $CR^3$.

Preferably, $Ar^1$ is an aryl group which has 6 to 14 aromatic ring atoms and may be substituted by one or more $R^3$ radicals; more preferably, $Ar^1$ is a benzene group which may be substituted by one or more $R^3$ radicals.

Preferably, $Ar^3$ is an aryl group which has 6 to 14 aromatic ring atoms and may be substituted by one or more $R^2$ radicals; more preferably, $Ar^3$ is a benzene group which may be substituted by one or more $R^2$ radicals.

Preferably, $X^1$ is the same at each instance. Preferably, $X^1$ at each instance is $C(R^4)_2$ or $Si(R^4)_2$; more preferably $C(R^4)_2$.

$Ar^L$ groups are preferably selected from aromatic ring systems which have 6 to 20 aromatic ring atoms and may be substituted by one or more $R^5$ radicals, and heteroaromatic ring systems which have 5 to 20 aromatic ring atoms and may be substituted by one or more $R^5$ radicals. Particularly preferred $Ar^L$ groups are selected from divalent groups derived from benzene, biphenyl, terphenyl, naphthalene, fluorene, indenofluorene, indenocarbazole, spirobifluorene, dibenzofuran, dibenzothiophene, and carbazole, each of which may be substituted by one or more $R^5$ radicals. Most preferably, $Ar^L$ is a divalent group derived from benzene that may be substituted in each case by one or more $R^5$ radicals. $Ar^L$ groups may be selected identically or differently at each instance.

Preferably, k is selected from 0 or 1; more preferably, k is 0.

Preferred $—(Ar^L)_k—$ groups conform to the following formulae:

Ar$^L$-1
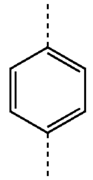
Ar$^L$-2
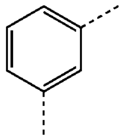
Ar$^L$-3
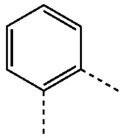
Ar$^L$-4
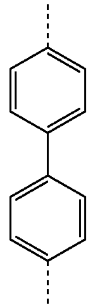
Ar$^L$-5
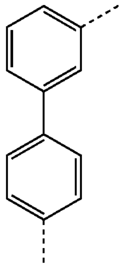
Ar$^L$-6
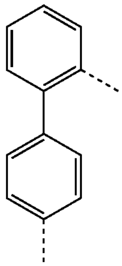
Ar$^L$-7
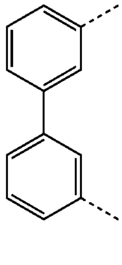
-continued
Ar$^L$-8
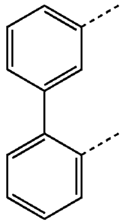
Ar$^L$-9
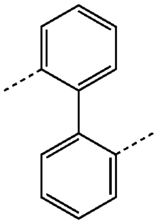
Ar$^L$-10
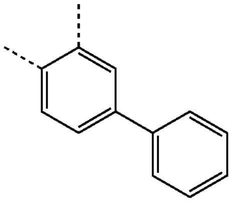
Ar$^L$-11
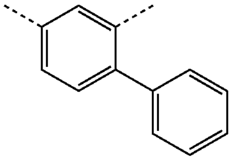
Ar$^L$-12
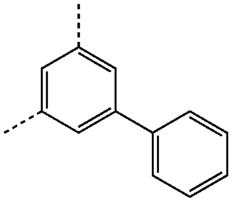
Ar$^L$-13
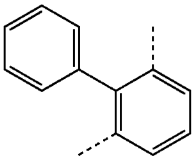
Ar$^L$-14
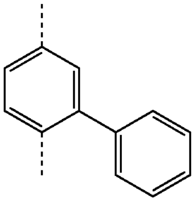

-continued
Ar$^L$-15
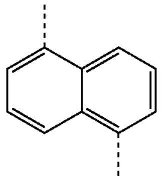
Ar$^L$-16
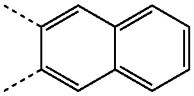
Ar$^L$-17
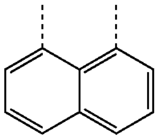
Ar$^L$-18
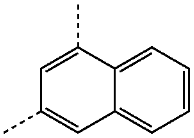
Ar$^L$-19
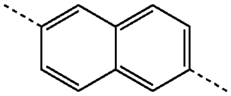
Ar$^L$-20
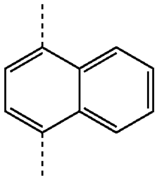
Ar$^L$-21
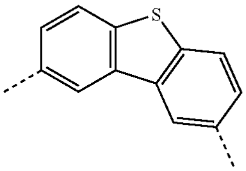
Ar$^L$-22
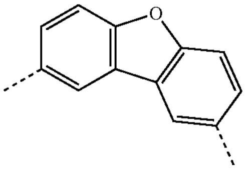
Ar$^L$-23
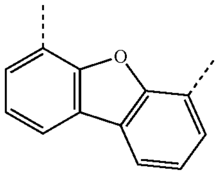
-continued
Ar$^L$-24
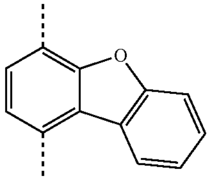
Ar$^L$-25
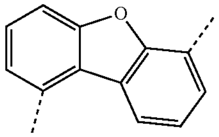
Ar$^L$-26
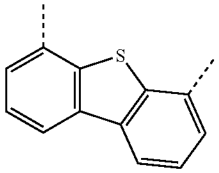
Ar$^L$-27
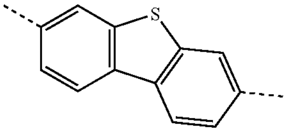
Ar$^L$-28
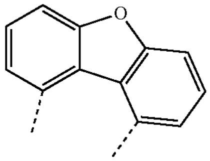
Ar$^L$-29
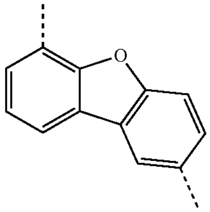
Ar$^L$-30
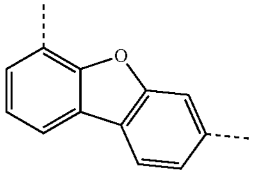
Ar$^L$-31
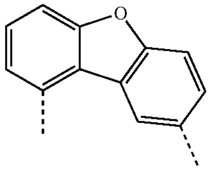
Ar$^L$-32
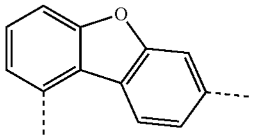

-continued
Ar$^L$-33
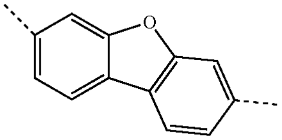
Ar$^L$-34
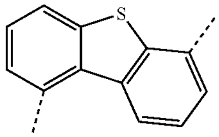
Ar$^L$-35
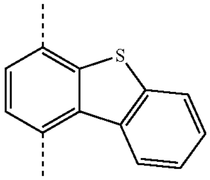
Ar$^L$-36
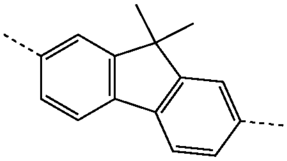
Ar$^L$-37
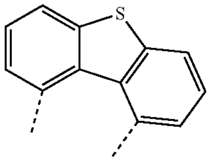
Ar$^L$-38
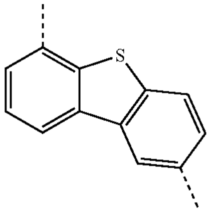
Ar$^L$-39
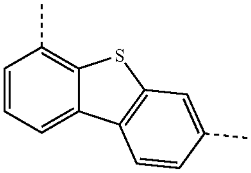
Ar$^L$-40
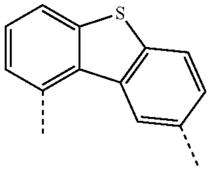
Ar$^L$-41
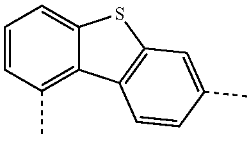
-continued
Ar$^L$-42
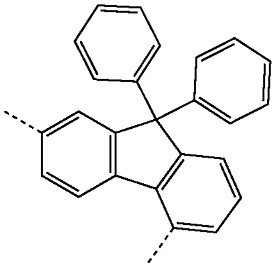
Ar$^L$-43
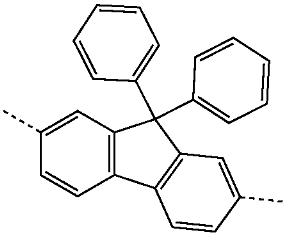
Ar$^L$-44
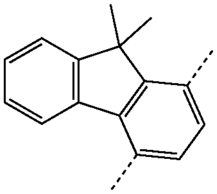
Ar$^L$-45
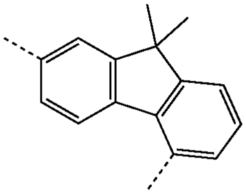
Ar$^L$-46
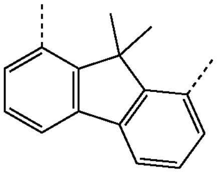
Ar$^L$-47
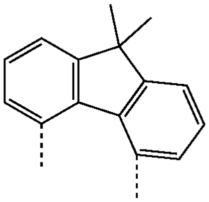
Ar$^L$-48
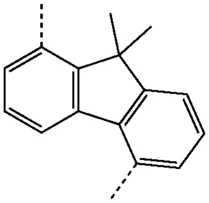

-continued
Ar$^L$-49
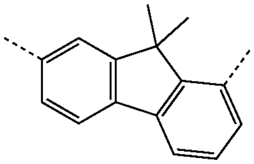
Ar$^L$-50
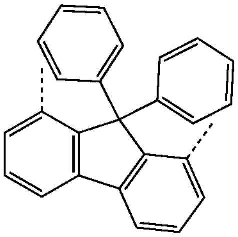
Ar$^L$-51
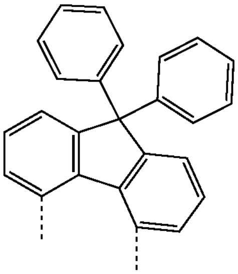
Ar$^L$-52
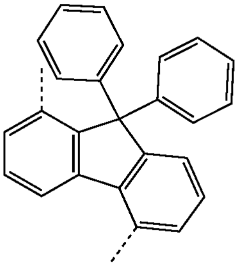
Ar$^L$-53
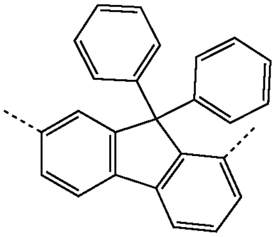
Ar$^L$-54
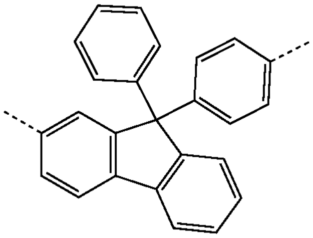
-continued
Ar$^L$-55
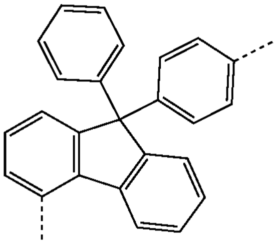
Ar$^L$-56
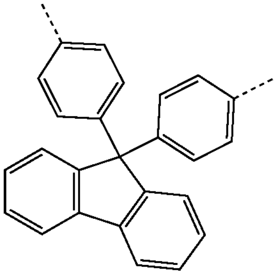
Ar$^L$-57
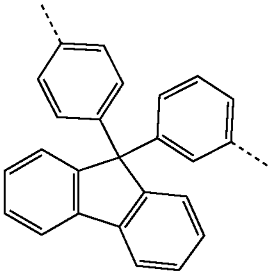
Ar$^L$-58
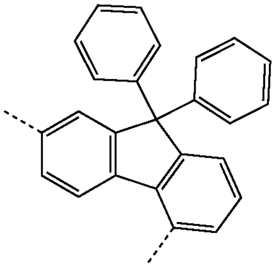
Ar$^L$-59
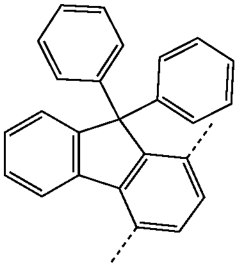

-continued
Ar$^{L}$-60
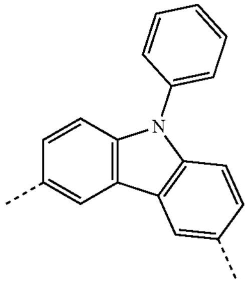
Ar$^{L}$-61
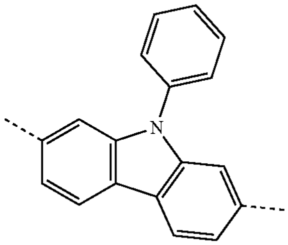
Ar$^{L}$-62
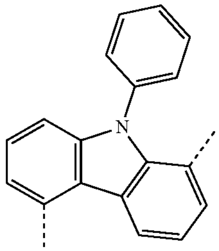
Ar$^{L}$-63
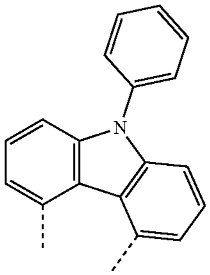
Ar$^{L}$-64
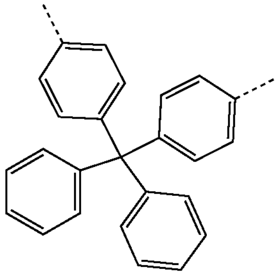
Ar$^{L}$-65
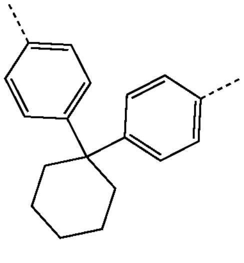
-continued
Ar$^{L}$-66
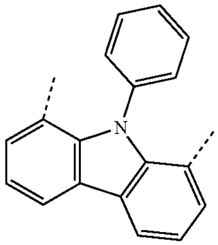
Ar$^{L}$-67
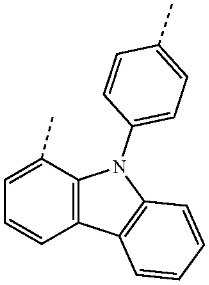
Ar$^{L}$-68
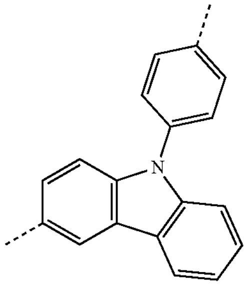
Ar$^{L}$-69
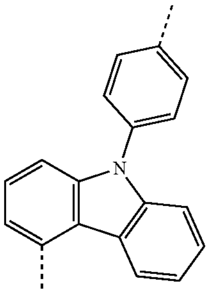
Ar$^{L}$-70
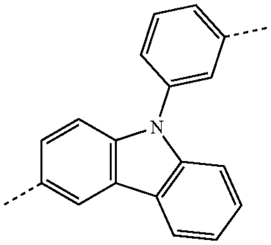

-continued

Ar$^{L}$-71

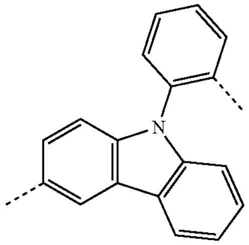

Ar$^{L}$-72

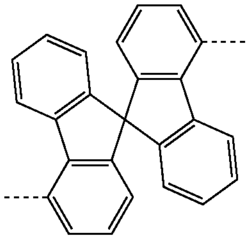

Ar$^{L}$-73

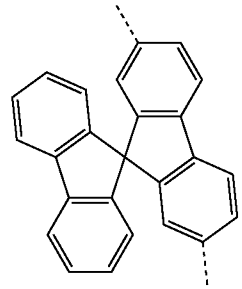

Ar$^{L}$-74

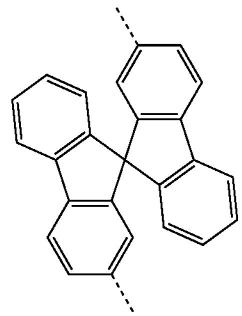

Ar$^{L}$-75

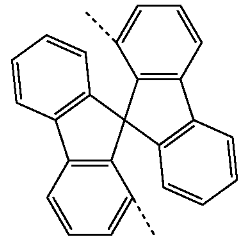

where the dotted lines represent the bonds to the rest of the formula (I) or (II).

It is preferable that the group of $Ar^2$ that binds directly to the nitrogen atom is an aromatic ring system.

Preferably, $Ar^2$ groups are the same or different at each instance and are selected from monovalent groups derived from benzene, biphenyl, terphenyl, quaterphenyl, naphthalene, fluorene, especially 9,9'-dimethylfluorene and 9,9'-diphenylfluorene, benzofluorene, spirobifluorene, indenofluorene, indenocarbazole, dibenzofuran, dibenzothiophene, benzocarbazole, carbazole, benzofuran, benzothiophene, indole, quinoline, pyridine, pyrimidine, pyrazine, pyridazine and triazine, where the monovalent groups may each be substituted by one or more $R^5$ radicals. Alternatively, $Ar^2$ groups may preferably be the same or different at each instance and be selected from combinations of groups derived from benzene, biphenyl, terphenyl, quaterphenyl, naphthalene, fluorene, especially 9,9'-dimethylfluorene and 9,9'-diphenylfluorene, benzofluorene, spirobifluorene, indenofluorene, indenocarbazole, dibenzofuran, dibenzothiophene, carbazole, benzofuran, benzothiophene, indole, quinoline, pyridine, pyrimidine, pyrazine, pyridazine and triazine, where the groups may each be substituted by one or more $R^5$ radicals.

Particularly preferred $Ar^2$ groups are the same or different at each instance and are selected from phenyl, biphenyl, terphenyl, quaterphenyl, naphthyl, fluorenyl, especially 9,9'-dimethylfluorenyl and 9,9'-diphenylfluorenyl, benzofluorenyl, spirobifluorenyl, indenofluorenyl, indenocarbazolyl, dibenzofuranyl, dibenzothiophenyl, carbazolyl, benzofuranyl, benzothiophenyl, benzofused dibenzofuranyl, benzofused dibenzothiophenyl, naphthyl-substituted phenyl, fluorenyl-substituted phenyl, spirobifluorenyl-substituted phenyl, dibenzofuranyl-substituted phenyl, dibenzothiophenyl-substituted phenyl, carbazolyl-substituted phenyl, pyridyl-substituted phenyl, pyrimidyl-substituted phenyl, and triazinyl-substituted phenyl, where the groups mentioned may each be substituted by one or more $R^5$ radicals.

Particularly preferred $Ar^2$ groups are selected from the following formulae:

Ar-1

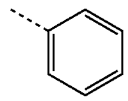

Ar-2

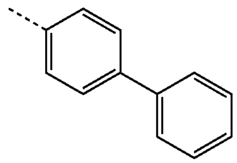

Ar-3

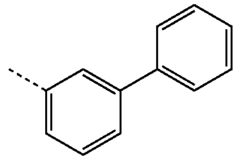

Ar-4

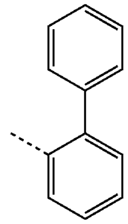

-continued
Ar-5
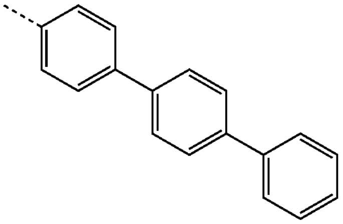
Ar-6
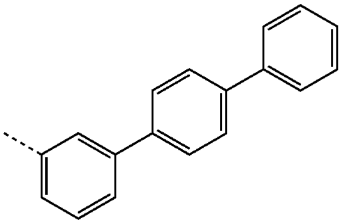
Ar-7
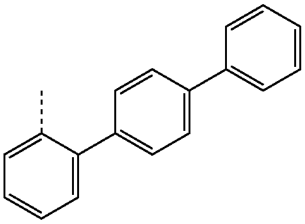
Ar-8
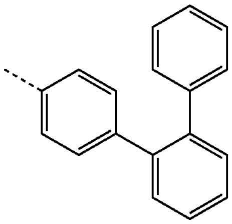
Ar-9
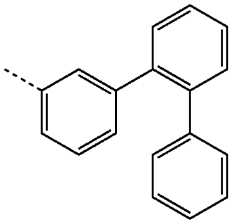
Ar-10
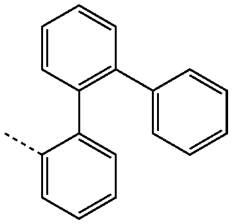
Ar-11
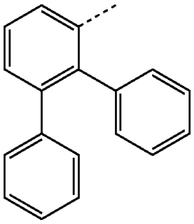
-continued
Ar-12
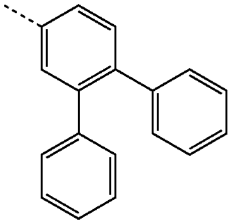
Ar-13
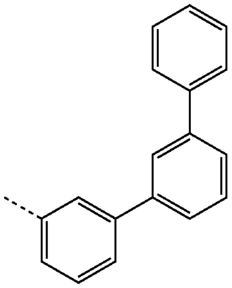
Ar-14
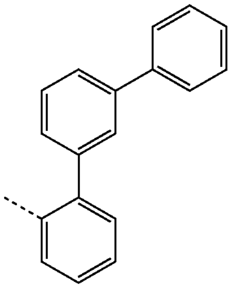
Ar-15
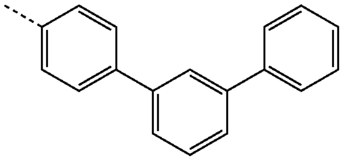
Ar-16
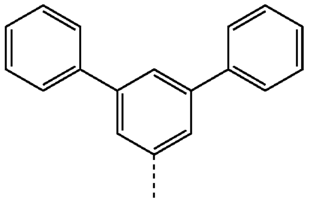
Ar-17
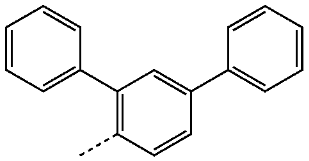
Ar-18
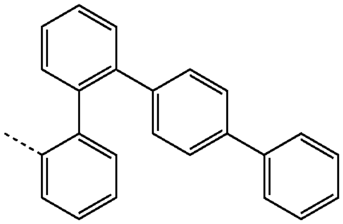

-continued
Ar-19
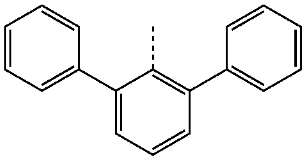
Ar-20
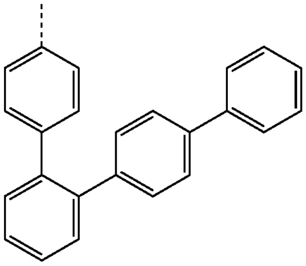
Ar-21
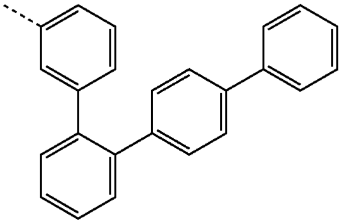
Ar-22
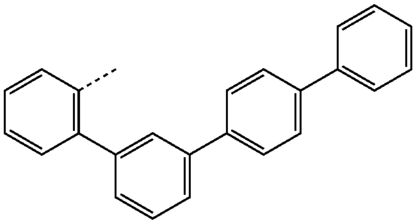
Ar-23
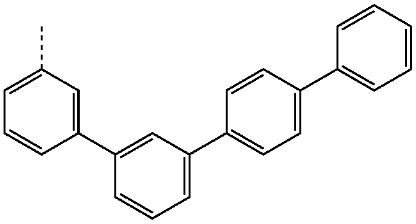
Ar-24
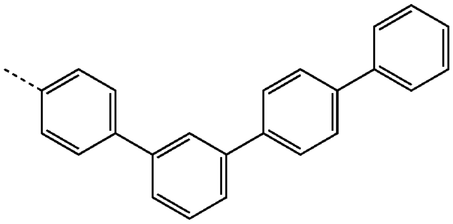
Ar-25
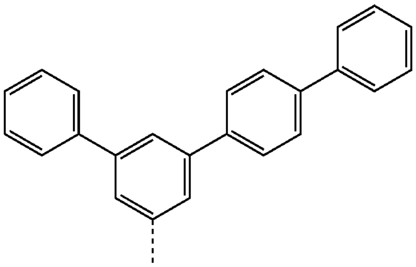
-continued
Ar-26
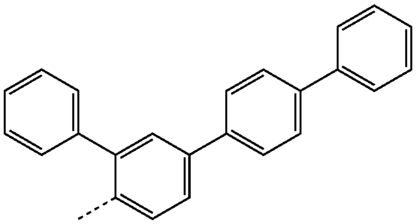
Ar-27
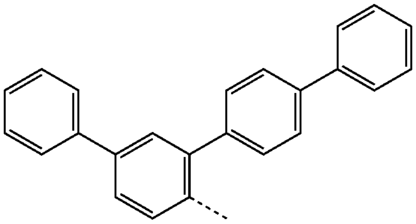
Ar-28
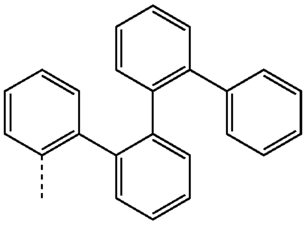
Ar-29
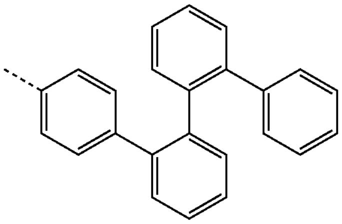
Ar-30
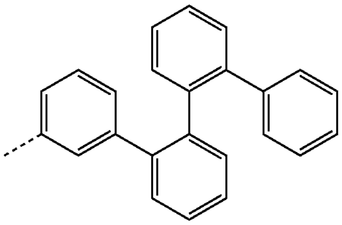
Ar-31
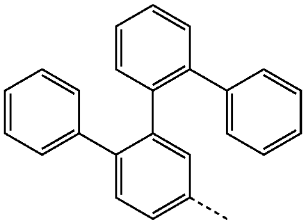
Ar-32
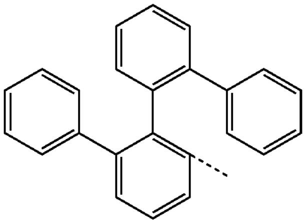

-continued
Ar-33
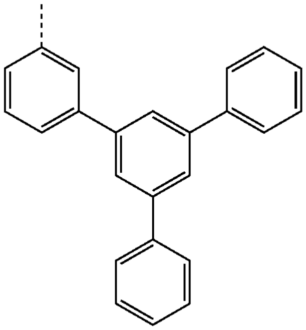
Ar-34
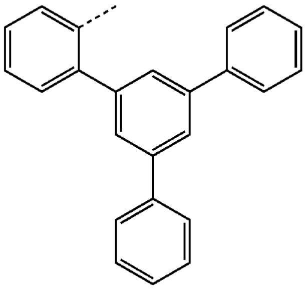
Ar-35
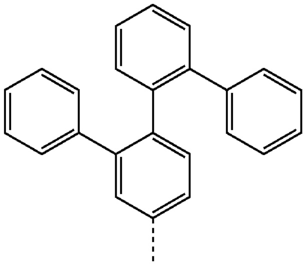
Ar-36
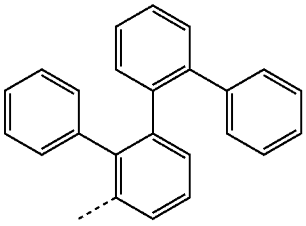
Ar-37
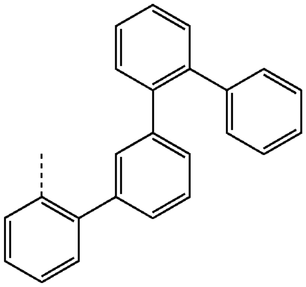
-continued
Ar-38
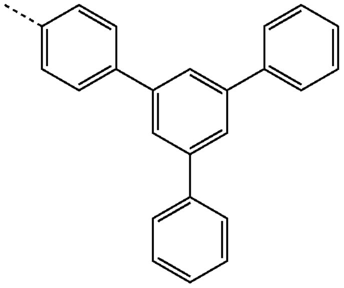
Ar-39
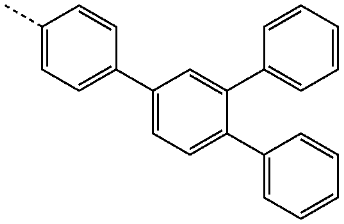
Ar-40
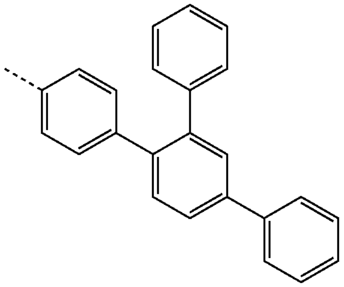
Ar-41
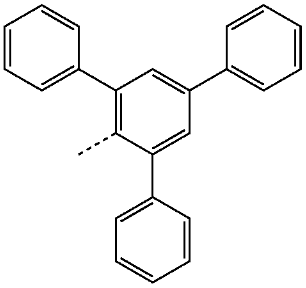
Ar-42
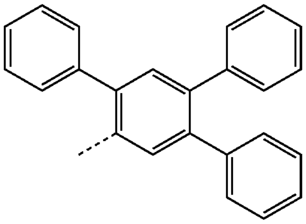
Ar-43
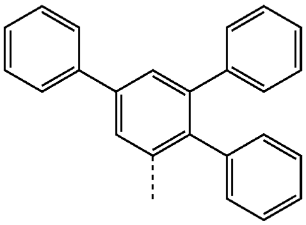

-continued
Ar-44
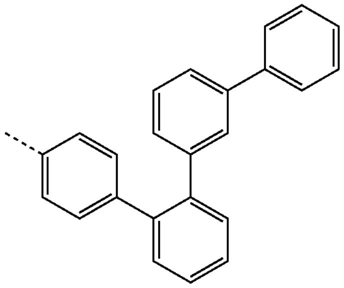
Ar-45
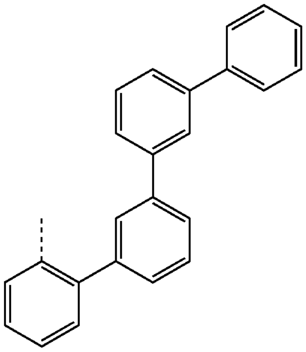
Ar-46
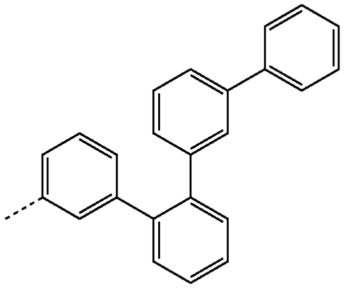
Ar-47
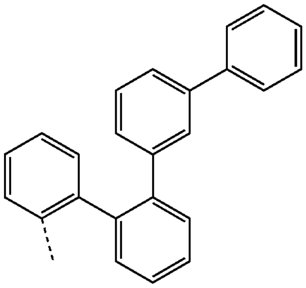
Ar-48
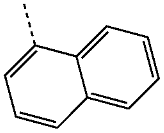
Ar-49
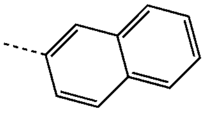
-continued
Ar-50
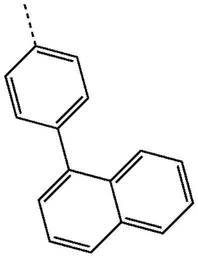
Ar-51
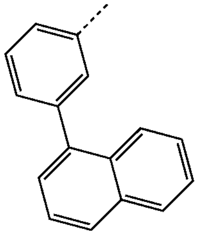
Ar-52
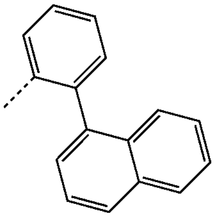
Ar-53
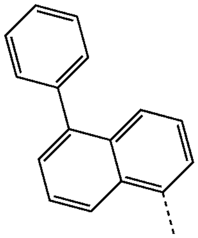
Ar-54
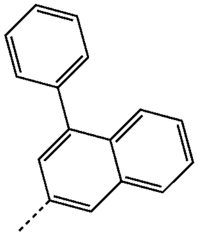
Ar-55
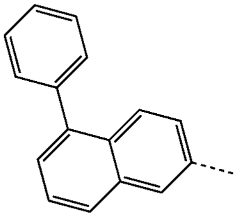

-continued
Ar-56
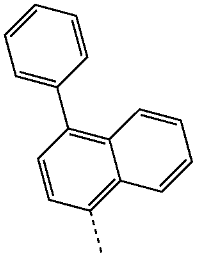
Ar-57
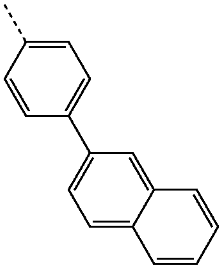
Ar-58
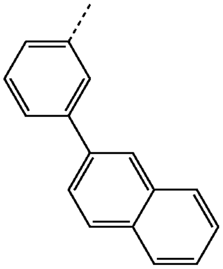
Ar-59
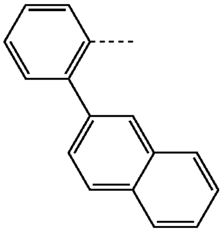
Ar-60
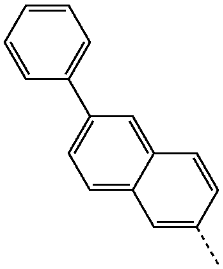
Ar-61
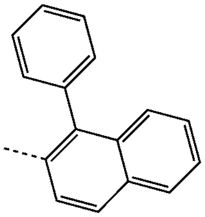
-continued
Ar-62
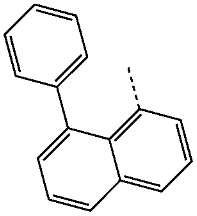
Ar-63
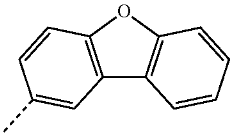
Ar-64
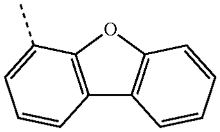
Ar-65
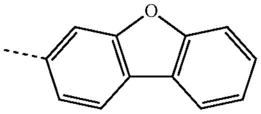
Ar-66
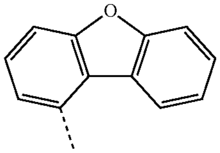
Ar-67
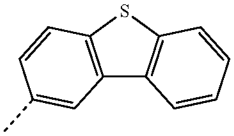
Ar-68
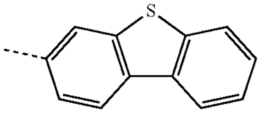
Ar-69
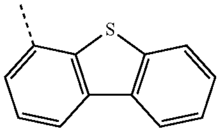
Ar-70
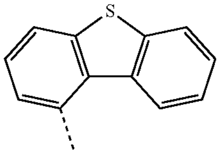
Ar-71
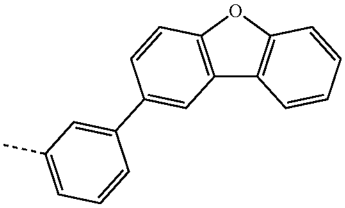

-continued
Ar-72
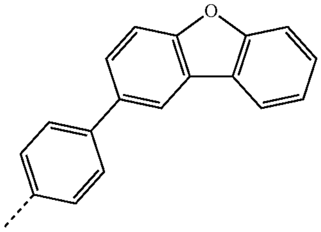
Ar-73
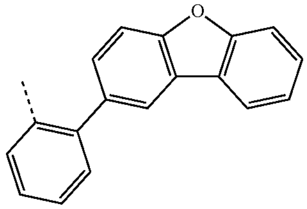
Ar-74
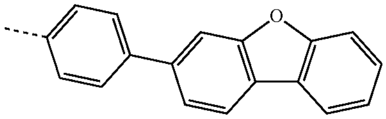
Ar-75
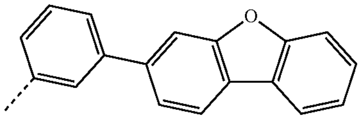
Ar-76
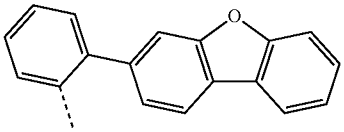
Ar-77
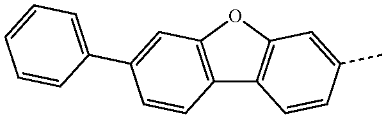
Ar-78
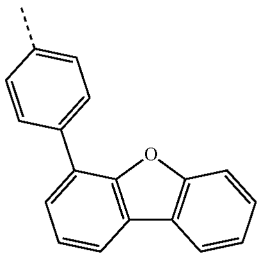
Ar-79
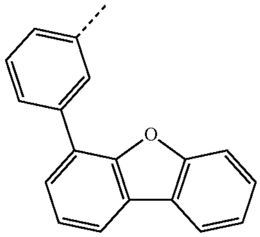
-continued
Ar-80
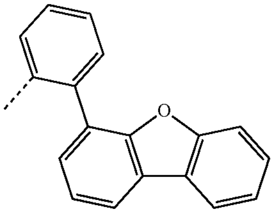
Ar-81
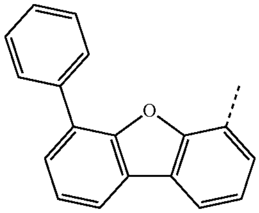
Ar-82
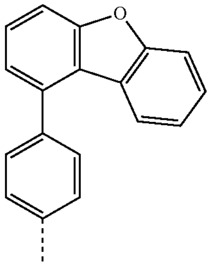
Ar-83
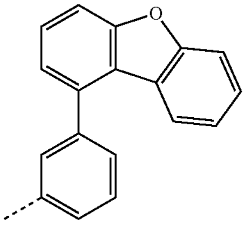
Ar-84
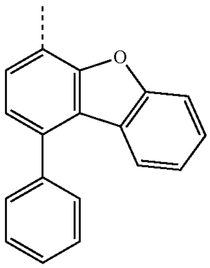
Ar-85
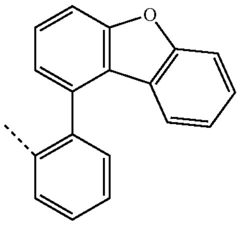

-continued
Ar-86
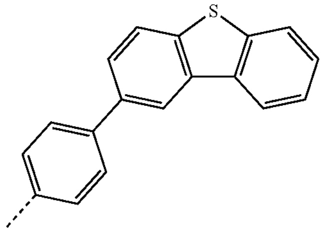
Ar-87
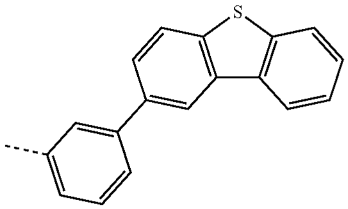
Ar-88
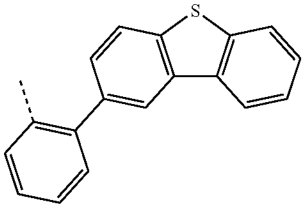
Ar-89
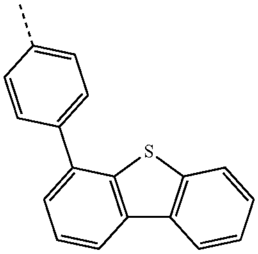
Ar-90
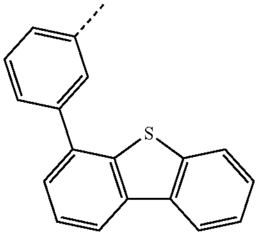
Ar-91
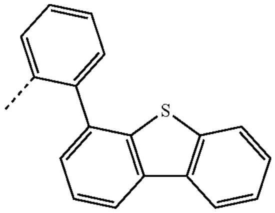
Ar-92
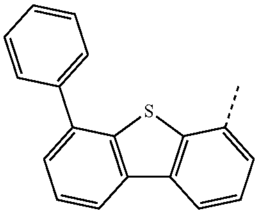
-continued
Ar-93
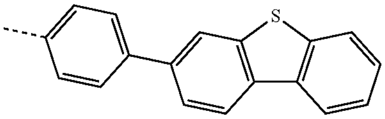
Ar-94
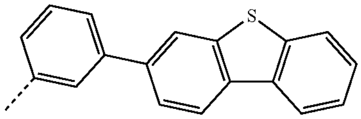
Ar-95
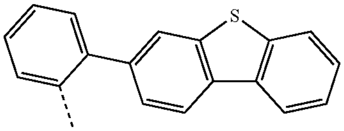
Ar-96
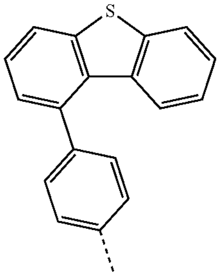
Ar-97
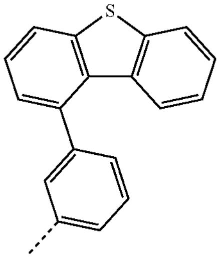
Ar-98
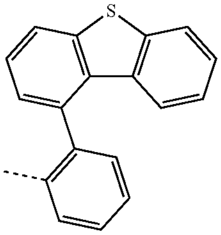
Ar-99
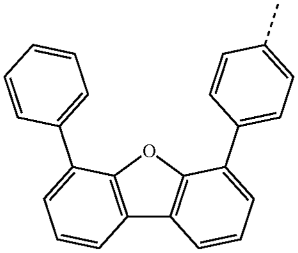

-continued
Ar-100
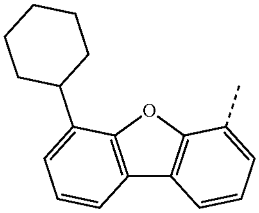
Ar-101
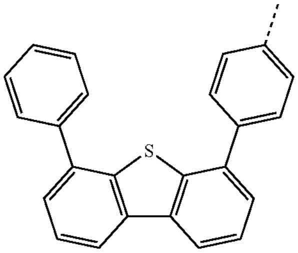
Ar-102
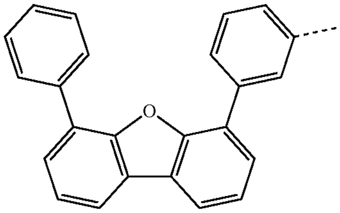
Ar-103
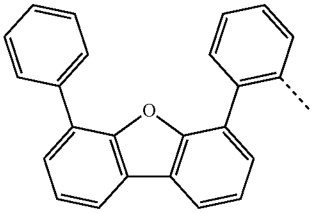
Ar-104
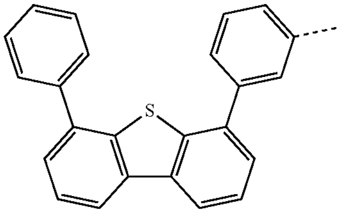
Ar-105
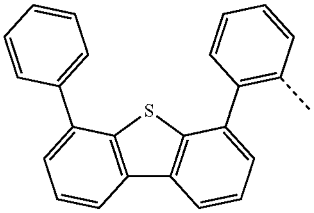
Ar-106
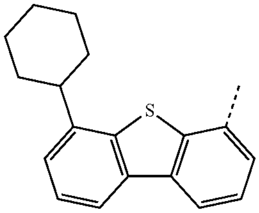
Ar-107
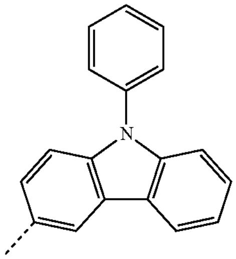
Ar-108
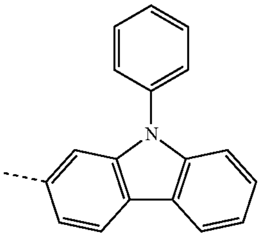
Ar-109
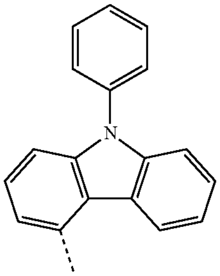
Ar-110
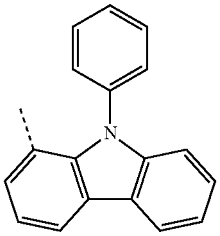
Ar-111
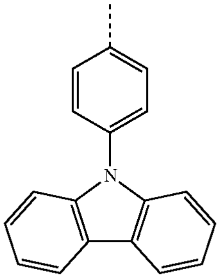

-continued
Ar-112
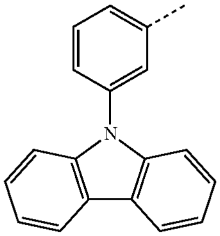
Ar-113
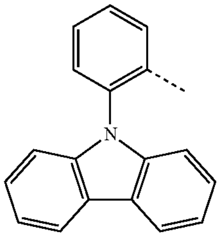
Ar-114
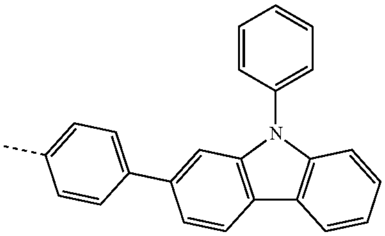
Ar-115
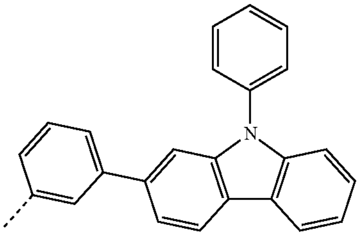
Ar-116
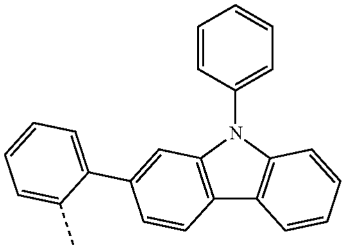
Ar-117
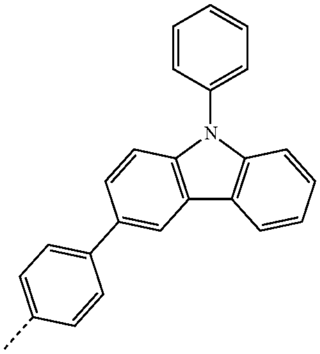
-continued
Ar-118
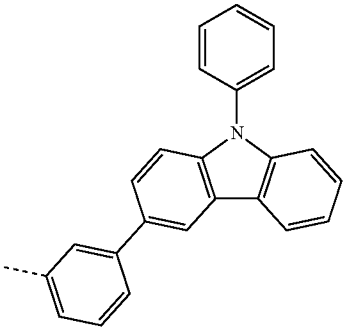
Ar-119
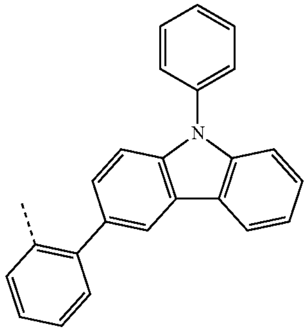
Ar-120
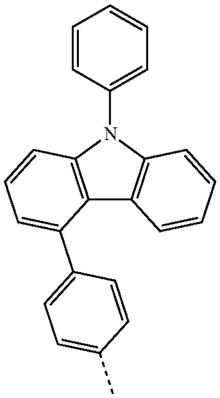
Ar-121
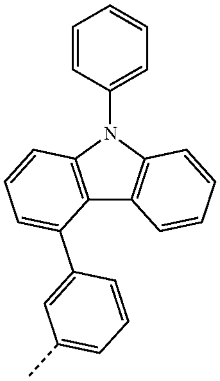

-continued
Ar-122
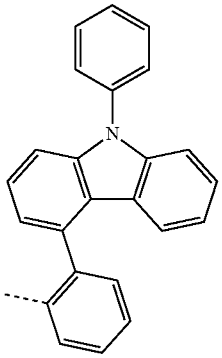
Ar-123
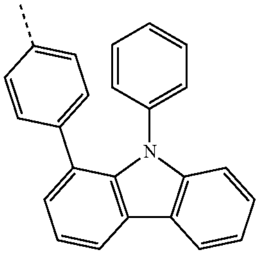
Ar-124
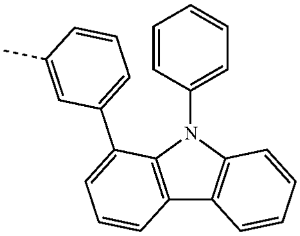
Ar-125
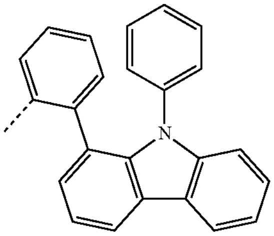
Ar-126
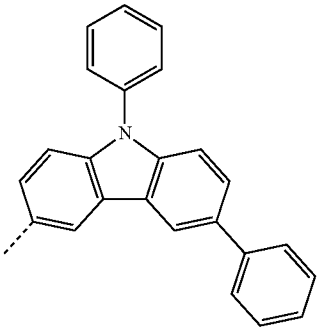
-continued
Ar-127
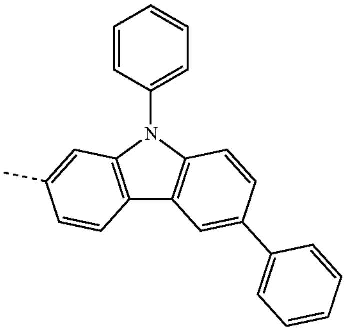
Ar-128
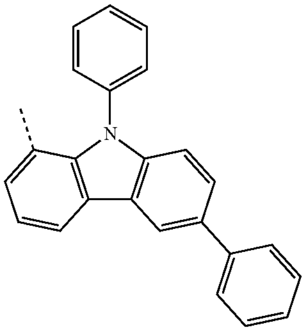
Ar-129
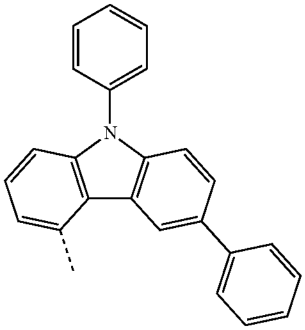
Ar-130
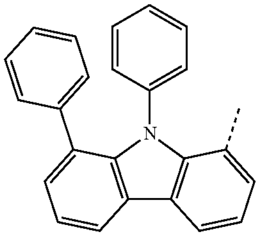
Ar-131
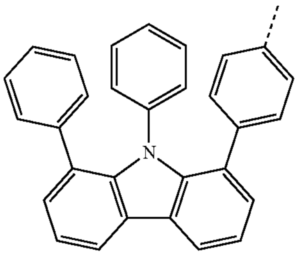

-continued
Ar-132
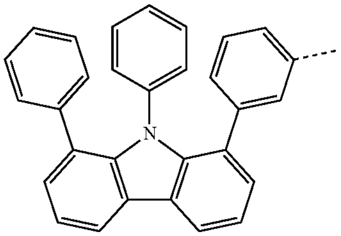
Ar-133
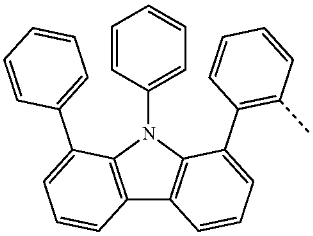
Ar-134
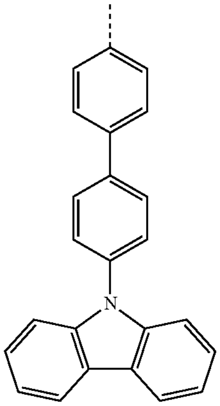
Ar-135
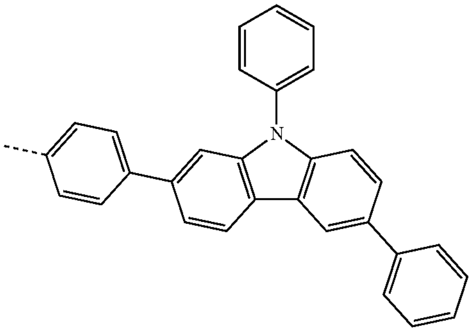
Ar-136
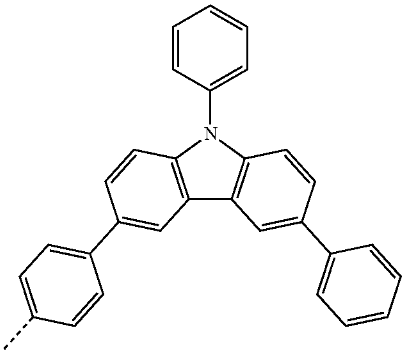
-continued
Ar-137
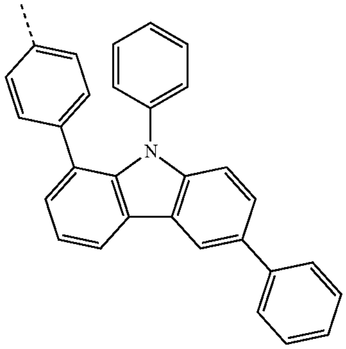
Ar-138
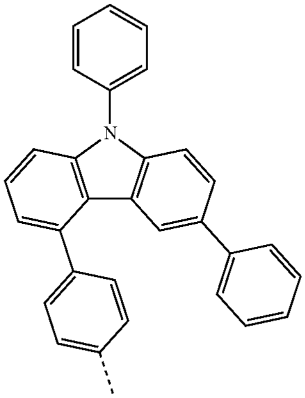
Ar-139
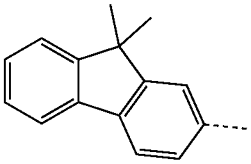
Ar-140
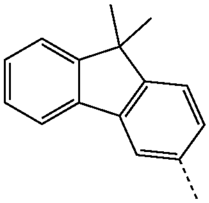
Ar-141
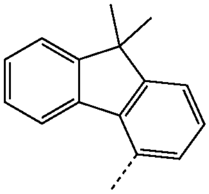
Ar-142
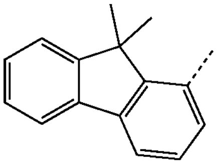

-continued
Ar-143
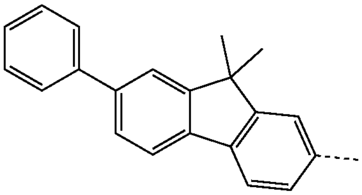
Ar-144
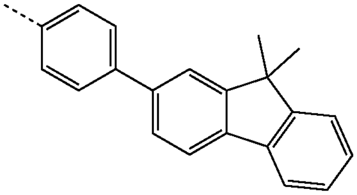
Ar-145
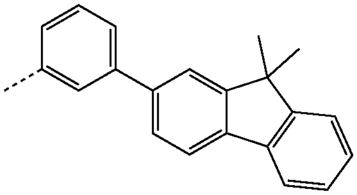
Ar-146
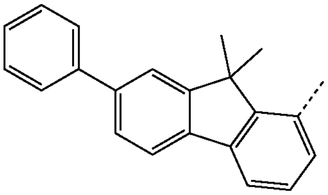
Ar-147
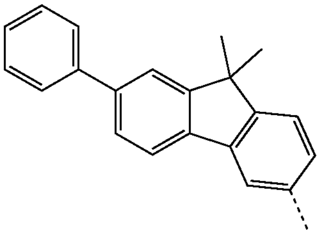
Ar-148
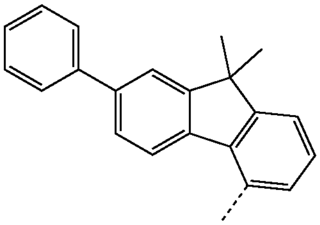
Ar-149
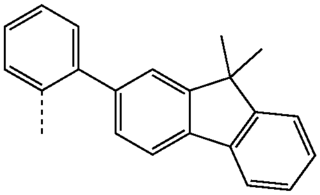
-continued
Ar-150
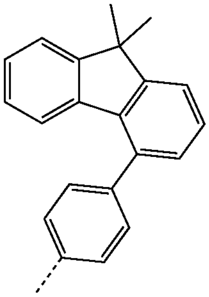
Ar-151
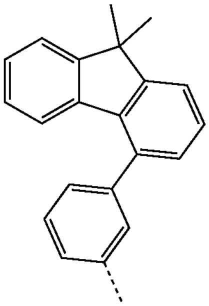
Ar-152
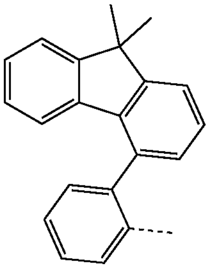
Ar-153
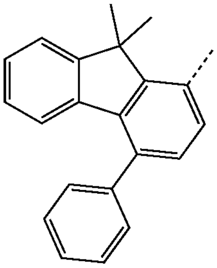
Ar-154
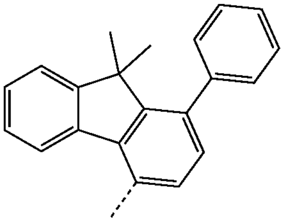
Ar-155
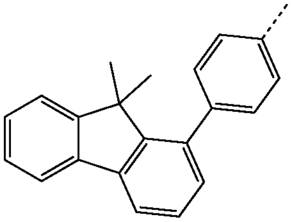

-continued
Ar-156
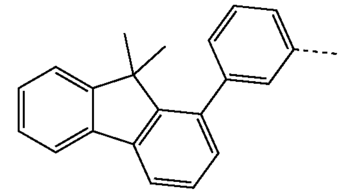
Ar-157
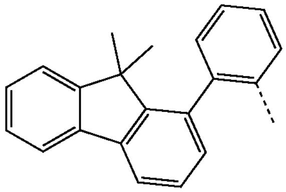
Ar-158
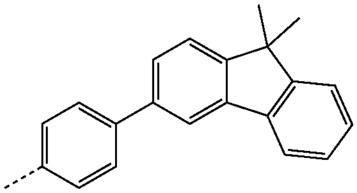
Ar-159
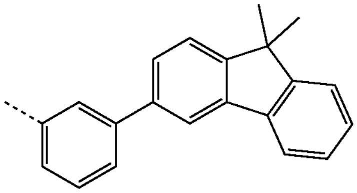
Ar-160
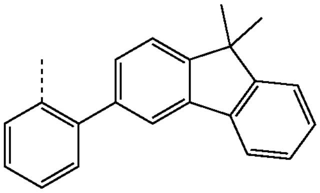
Ar-161
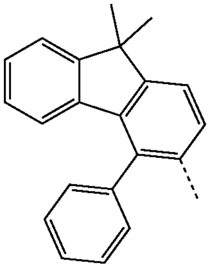
Ar-162
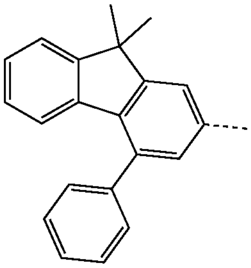
-continued
Ar-163
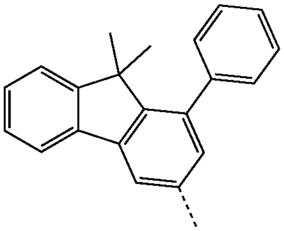
Ar-16
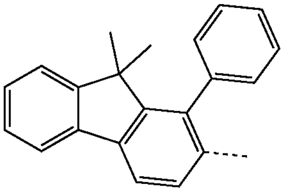
Ar-165
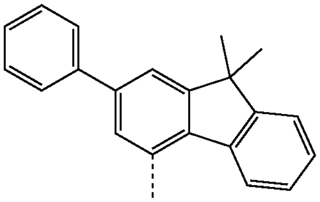
Ar-166
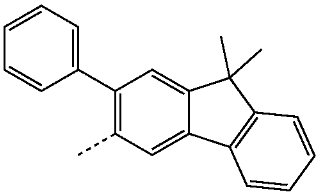
Ar-167
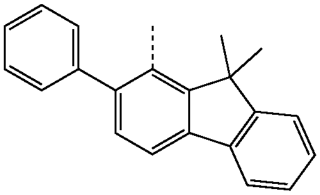
Ar-168
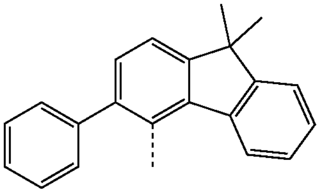
Ar-169
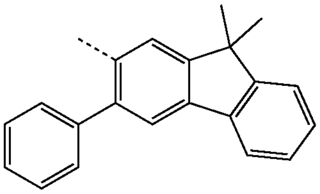

-continued
Ar-170
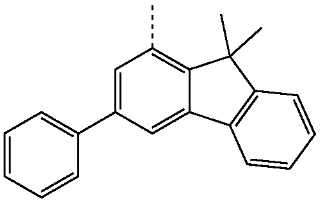
Ar-171
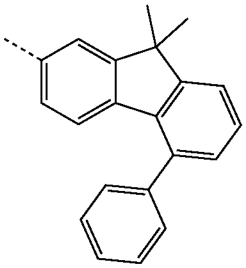
Ar-172
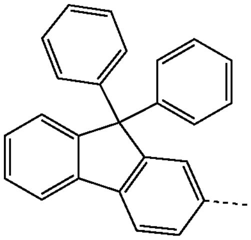
Ar-173
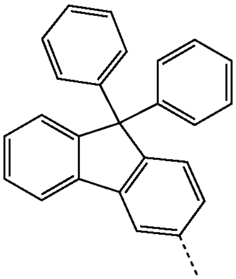
Ar-174
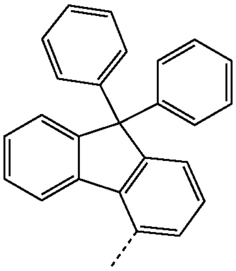
Ar-175
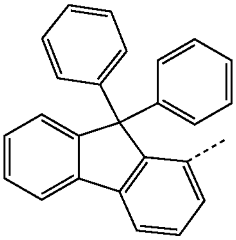
-continued
Ar-176
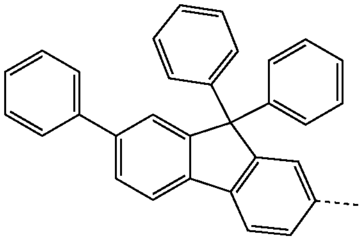
Ar-177
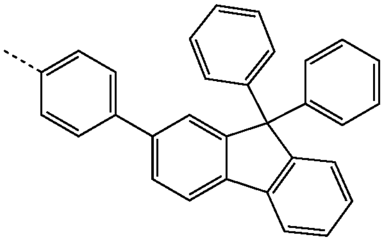
Ar-178
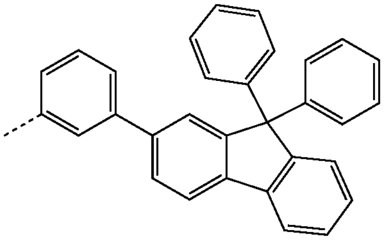
Ar-179
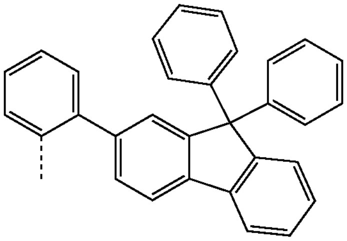
Ar-180
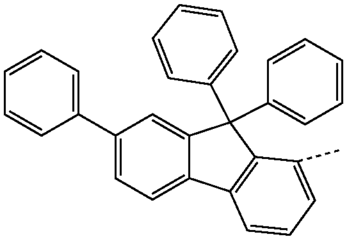
Ar-181
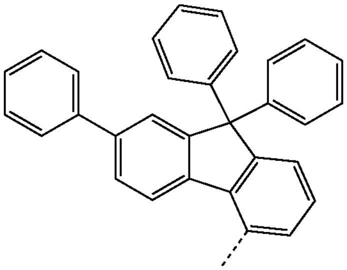

-continued
Ar-182
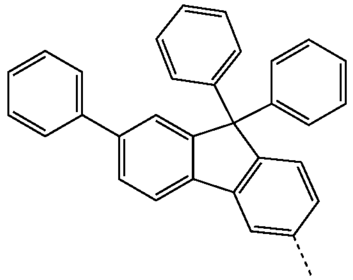
Ar-183
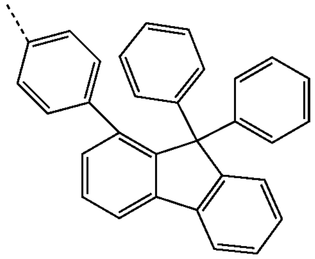
Ar-184
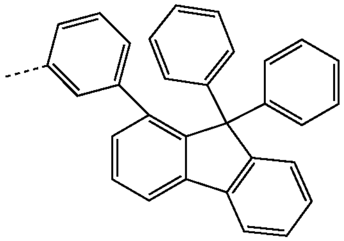
Ar-185
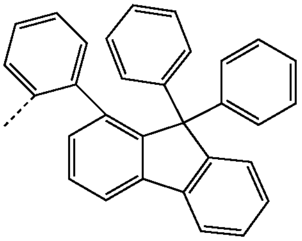
Ar-186
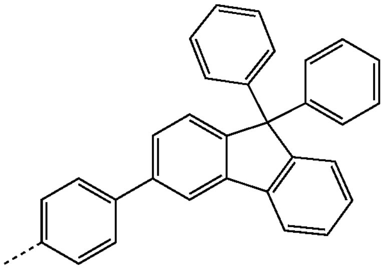
Ar-187
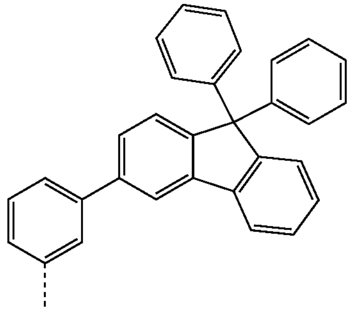
-continued
Ar-188
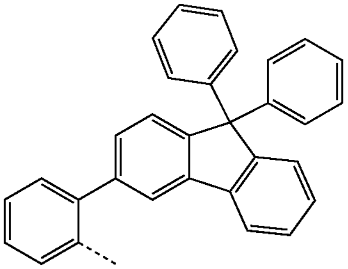
Ar-189
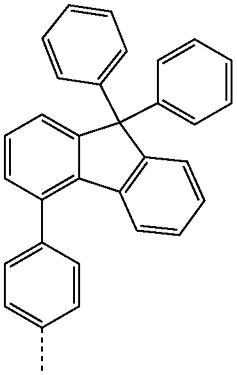
Ar-190
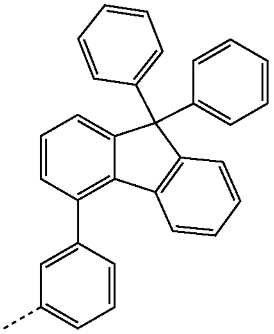
Ar-191
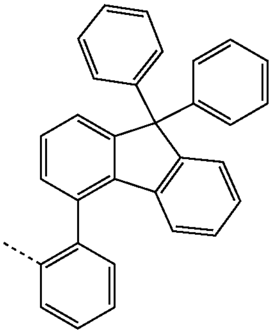
Ar-192
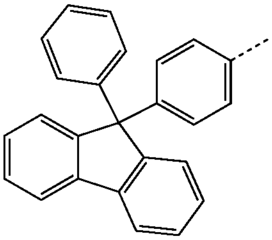

-continued
Ar-193
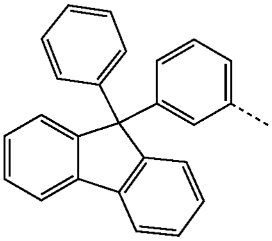
Ar-194
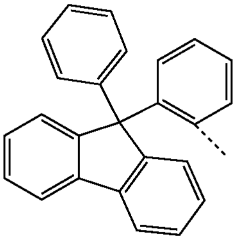
Ar-195
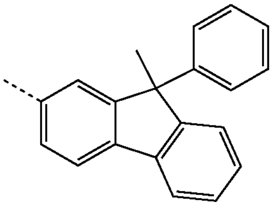
Ar-196
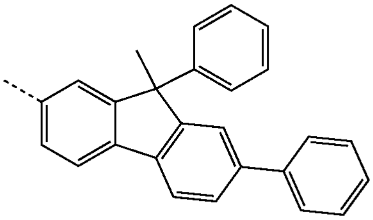
Ar-197
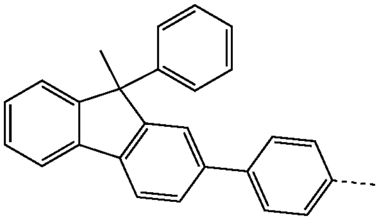
Ar-198
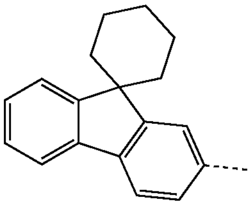
Ar-199
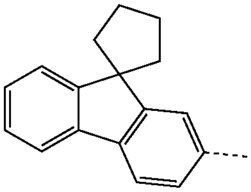
-continued
Ar-200
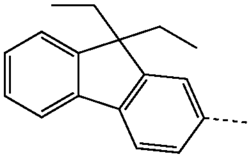
Ar-201
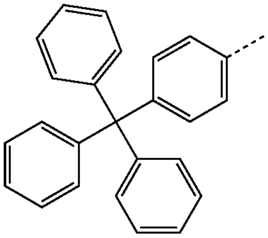
Ar-202
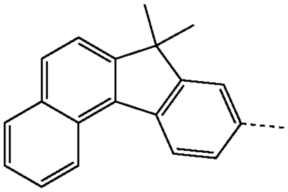
Ar-203
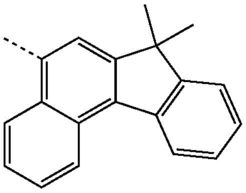
Ar-204
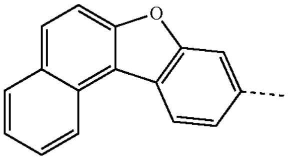
Ar-205
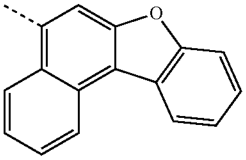
Ar-206
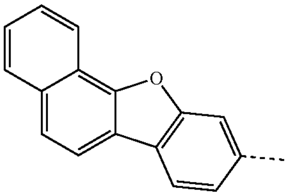

-continued
Ar-207
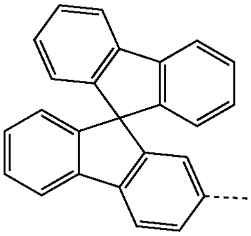
Ar-208
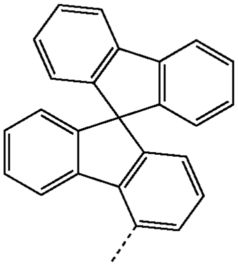
Ar-209
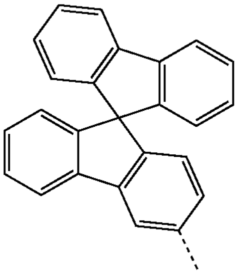
Ar-210
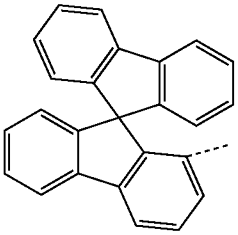
Ar-211
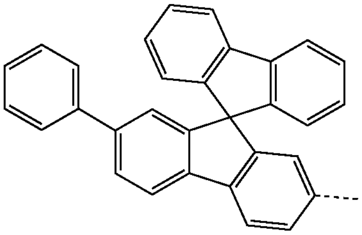
Ar-212
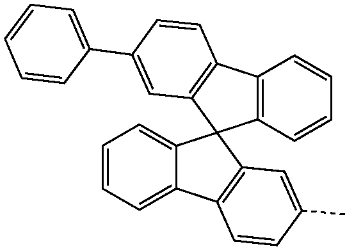
-continued
Ar-213
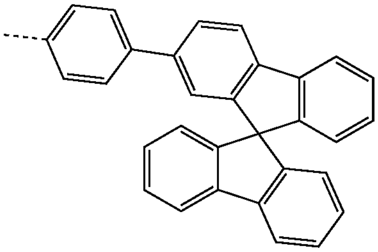
Ar-214
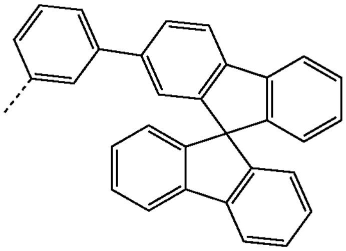
Ar-215
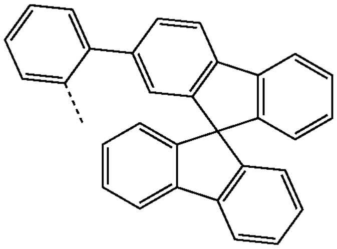
Ar-216
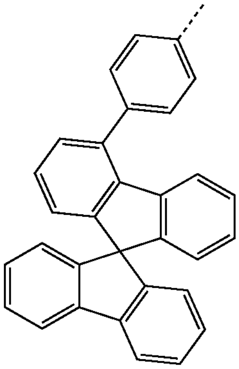
Ar-217
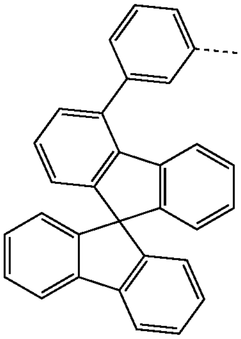

-continued
Ar-218
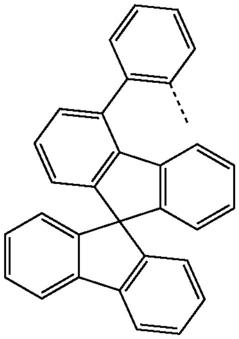
Ar-219
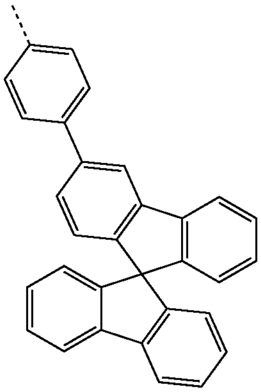
Ar-220
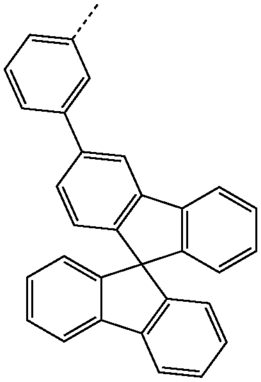
Ar-221
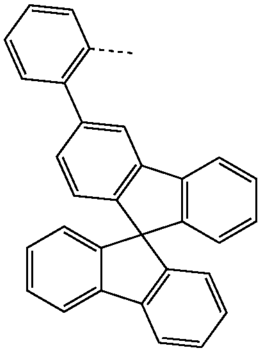
-continued
Ar-222
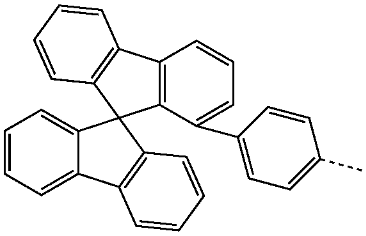
Ar-223
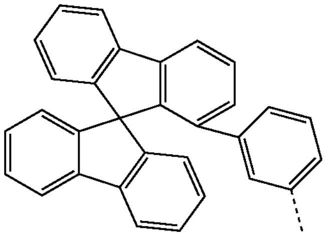
Ar-224
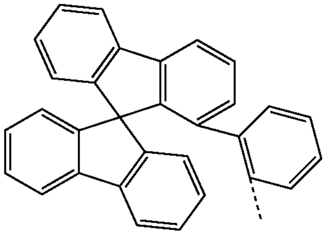
Ar-225
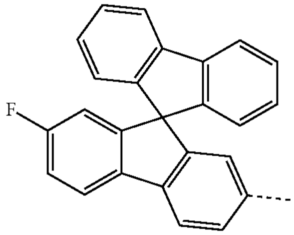
Ar-226
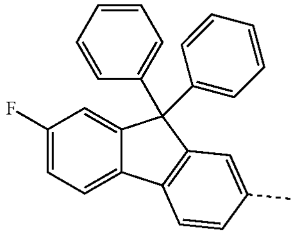
Ar-227
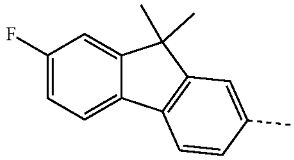
Ar-228
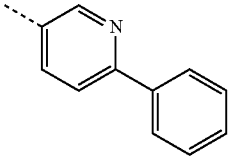

-continued
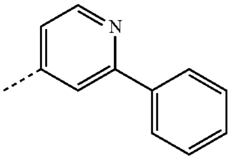
Ar-229
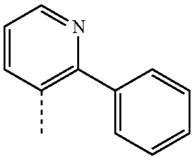
Ar-230
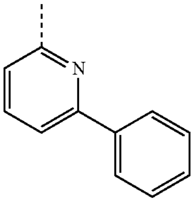
Ar-231
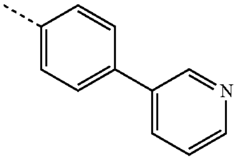
Ar-232
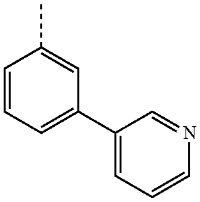
Ar-233
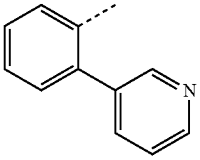
Ar-234
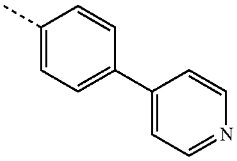
Ar-235
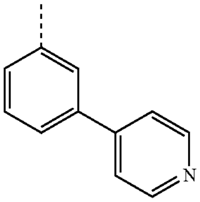
Ar-236
-continued
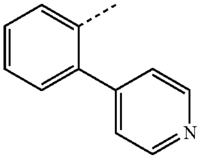
Ar-237
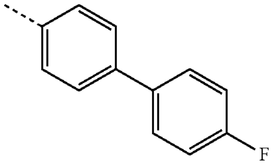
Ar-238
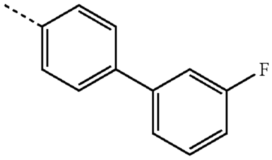
Ar-239
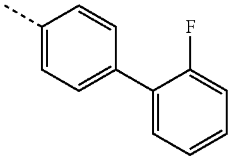
Ar-240
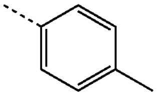
Ar-241
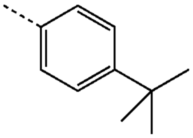
Ar-242
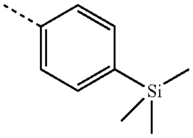
Ar-243
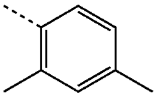
Ar-244
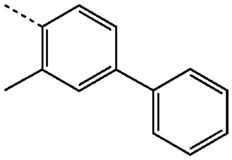
Ar-245
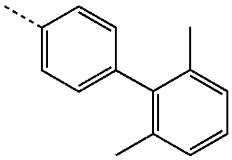
Ar-246

-continued

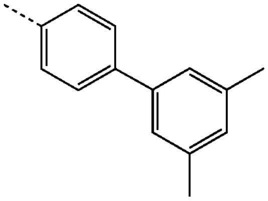

Ar-247

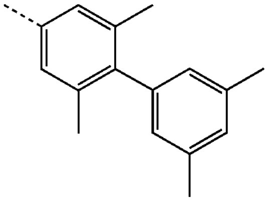

Ar-248

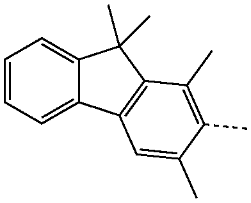

Ar-250

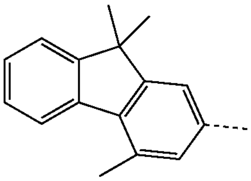

Ar-251

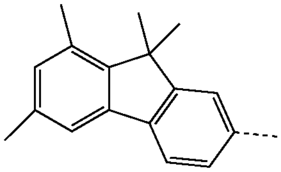

Ar-252

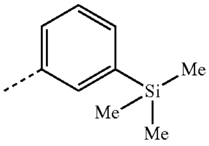

Ar-253

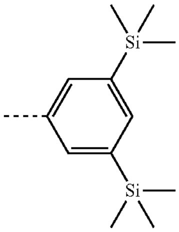

Ar-254

-continued

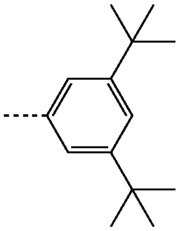

Ar-255

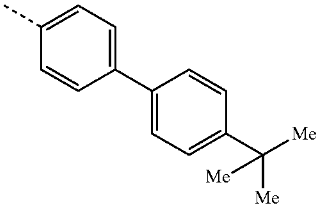

Ar-256

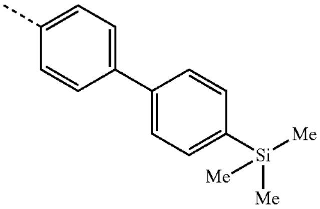

Ar-257

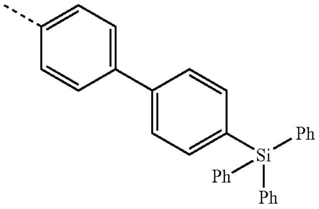

Ar-258

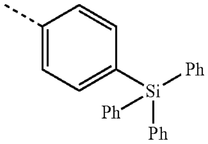

Ar-259

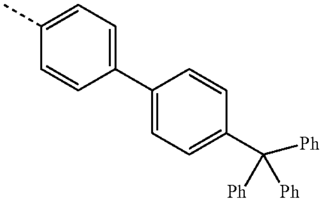

Ar-260 where the groups may each be substituted by an $R^5$ radical at all unoccupied positions and where the dashed bond represents the bond to the amine nitrogen atom.

It is preferable that two different $Ar^2$ groups in each case are bonded to an amine nitrogen atom.

The E group is preferably a single bond or a $C(R^4)_2$ group, more preferably a single bond.

Preferably, m=0, such that no E group is present.

In an alternative embodiment, which is likewise preferred, m=1, such that the $Ar^2$ groups are bonded to one another via an E group. In this case, it is preferable that the $Ar^2$ groups are selected from phenyl and fluorenyl, each of which may be substituted by one or more $R^5$ radicals. In addition, it is preferable in this case that the E group that joins the two $Ar^2$ groups to one another is bonded to the $Ar^2$ groups in question in the ortho position to the bond of the $Ar^2$ group to the amine nitrogen. In addition, it is preferable that the E group forms a six-membered ring together with the $Ar^2$ groups if E is selected from $C(R^5)_2$, $Si(R^5)_2$, $NR^5$, O and S; and a five-membered ring if E is a single bond.

Preferred embodiments of the unit

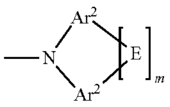

when m=1 are the groups depicted below:

N-1

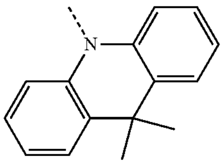

N-2

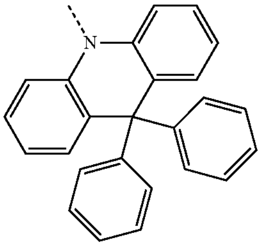

N-3

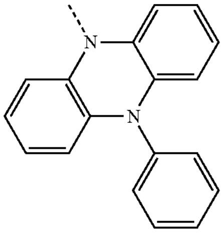

N-4

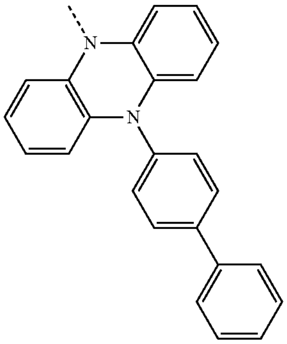

N-5

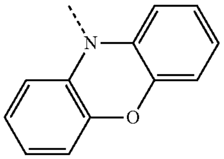

-continued

N-6

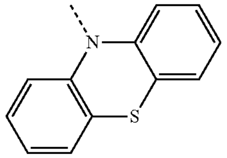

N-7

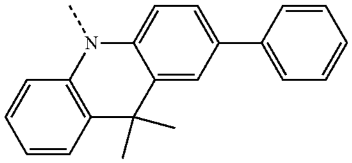

N-8

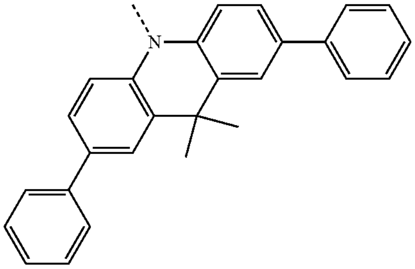

N-9

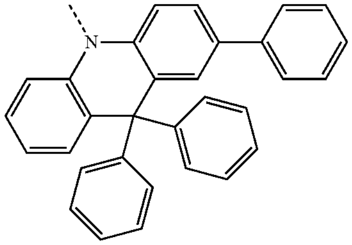

N-10

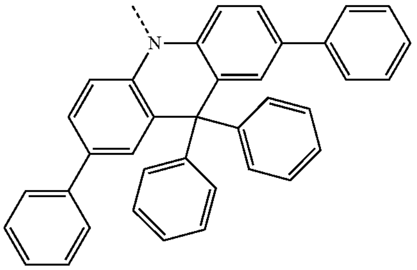

N-11

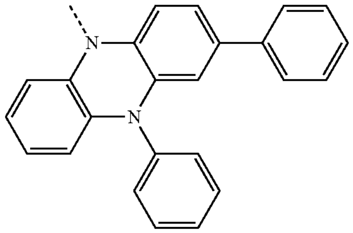

-continued
N-12
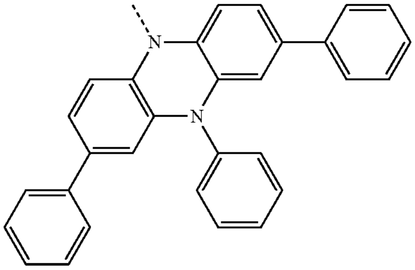
N-13
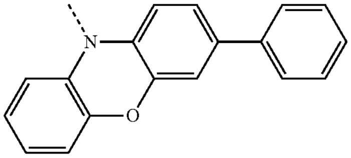
N-14
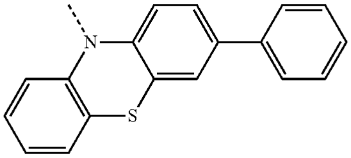
N-15
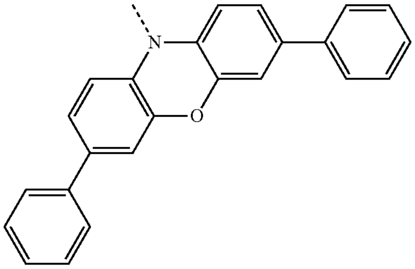
N-16
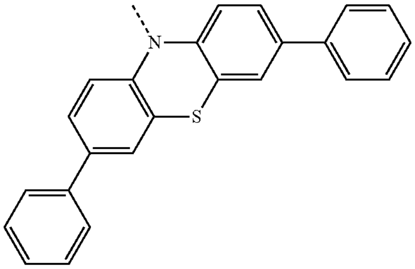
N-17
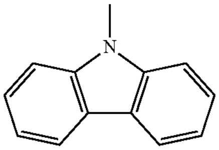
N-18
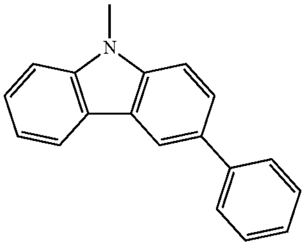
-continued
N-19
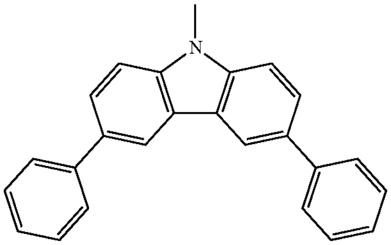
N-20
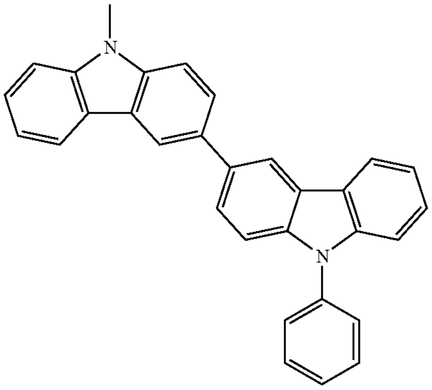
N-21
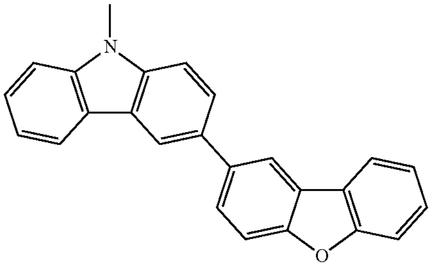
N-22
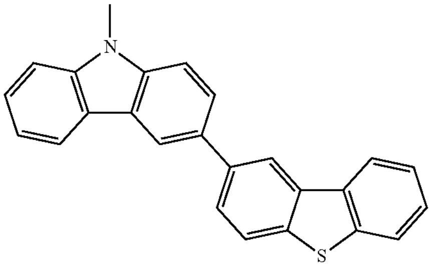
N-23
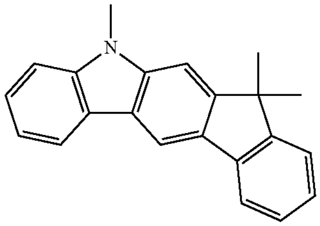

-continued
N-24
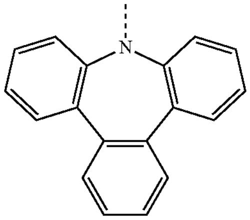
N-25
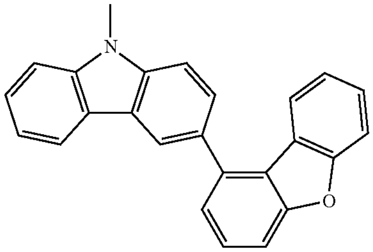
N-26
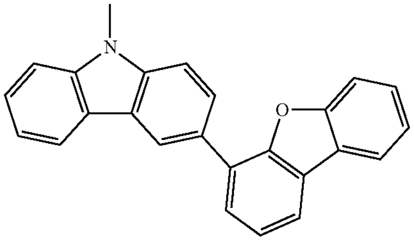
N-27
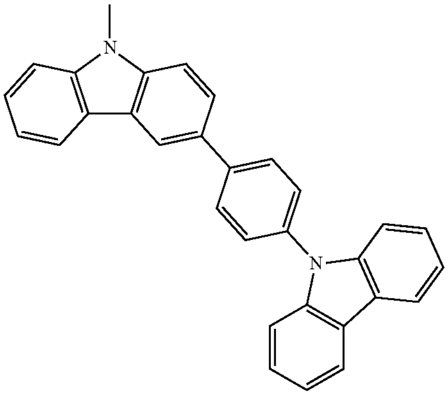
N-28
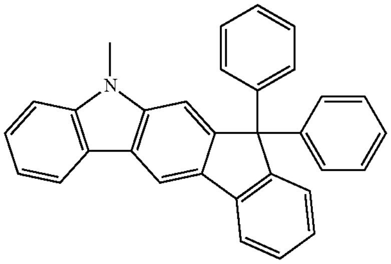
-continued
N-29
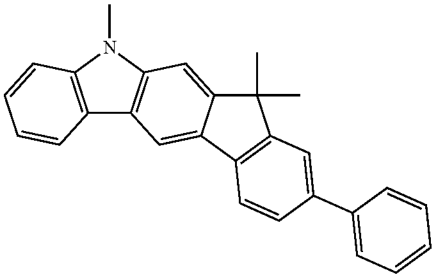
N-30
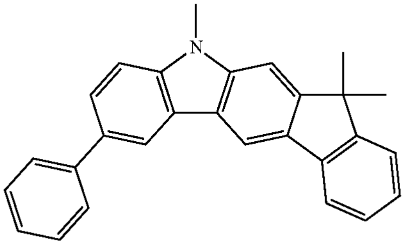
N-31
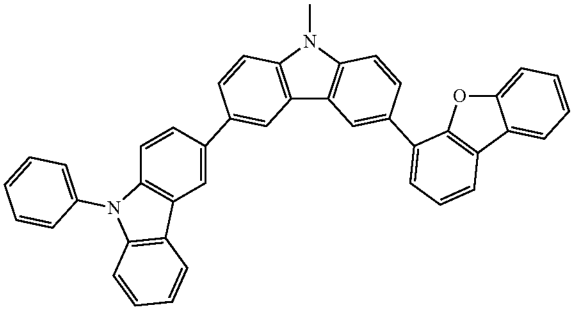
N-32
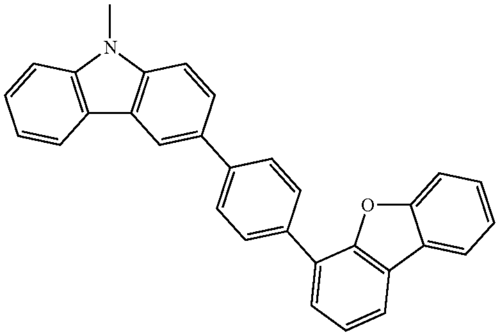
where the groups may each be substituted by an $R^5$ radical at their unoccupied positions, and are preferably unsubstituted in the unoccupied positions, and where the dashed bonds represent the bonds to the rest of the formula.
Preferred embodiments of the group
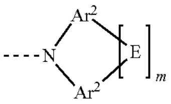

when m=0 are the groups depicted below:
A-1
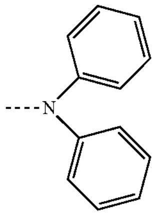
A-2
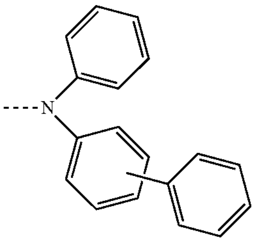
A-3
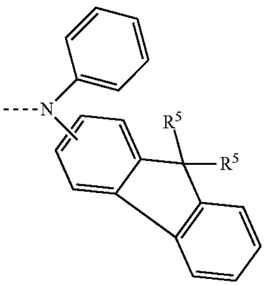
A-4
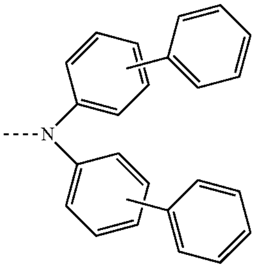
A-5
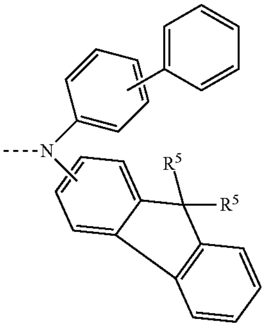
-continued
A-6
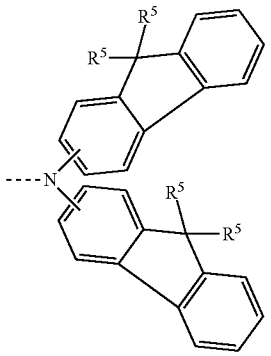
A-7
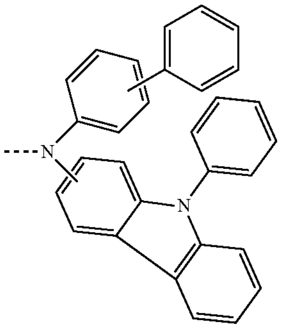
A-8
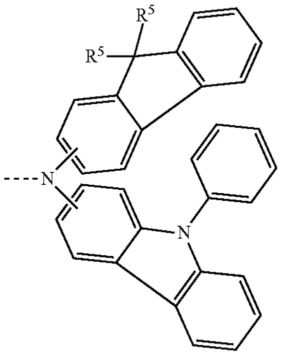
A-9
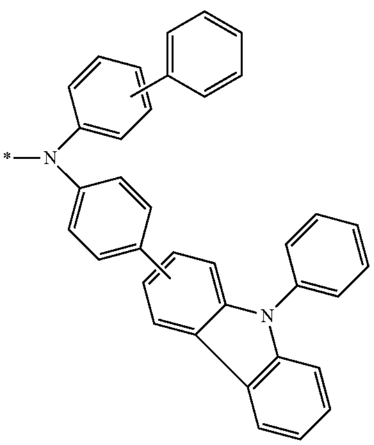

-continued
A-10
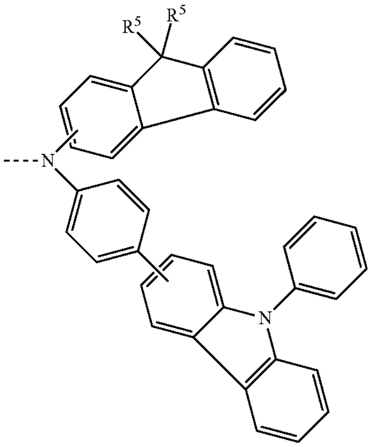
A-11
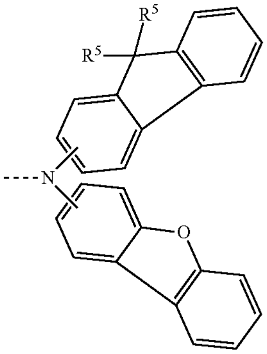
A-12
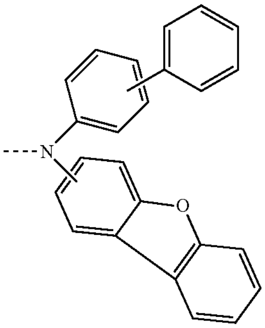
A-13
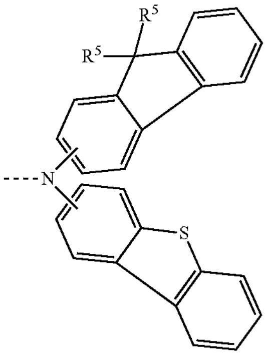
-continued
A-14
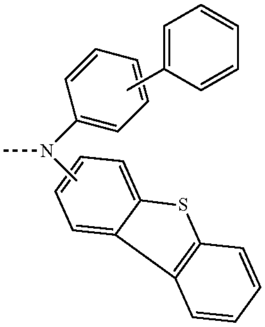
A-15
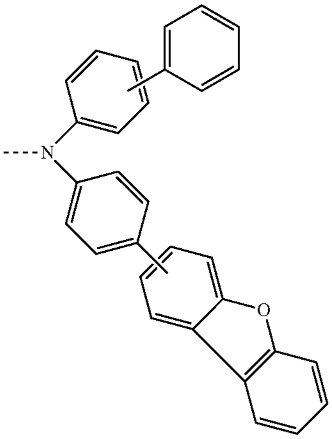
A-16
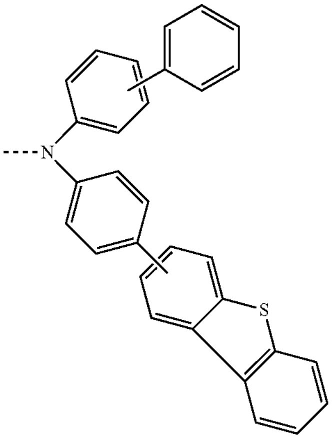
A-17
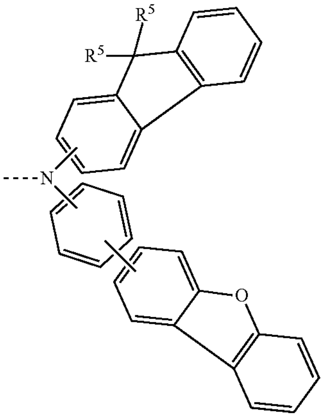

-continued
A-18
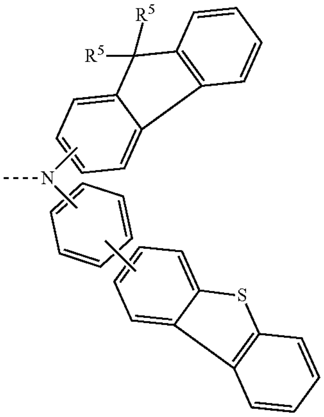
A-19
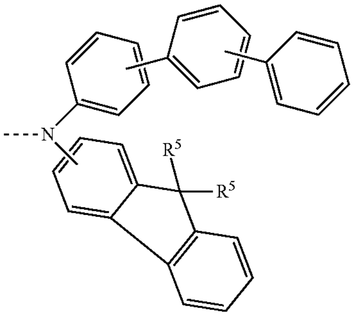
A-20
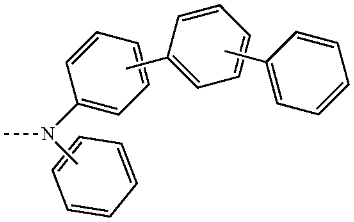
A-21
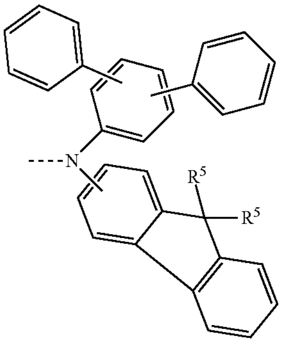
A-22
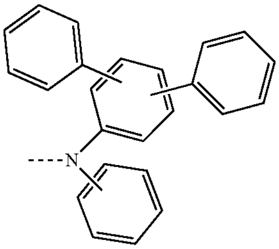
-continued
A-23
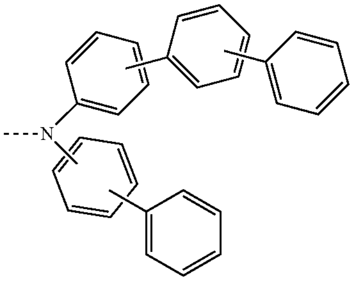
A-24
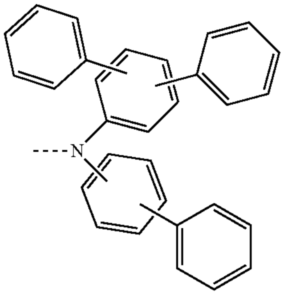
A-25
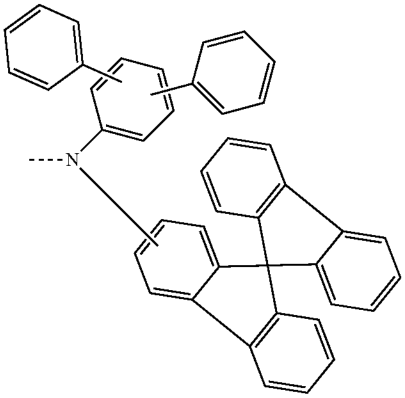
A-26
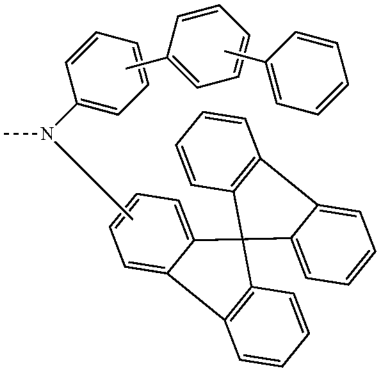

A-27
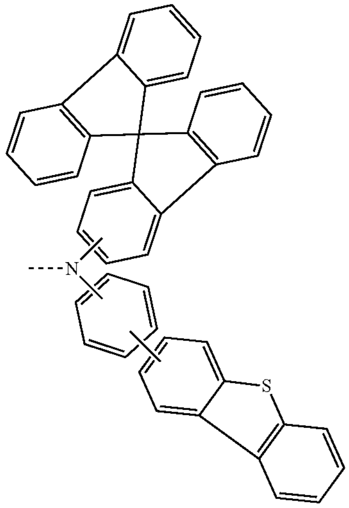
A-28
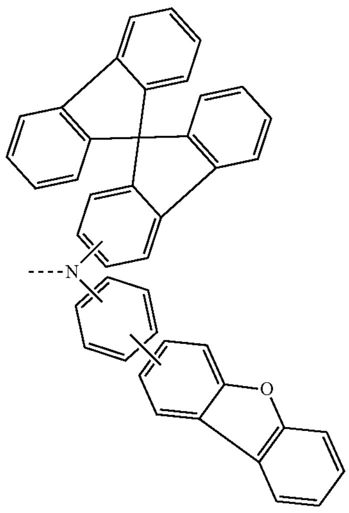
A-29
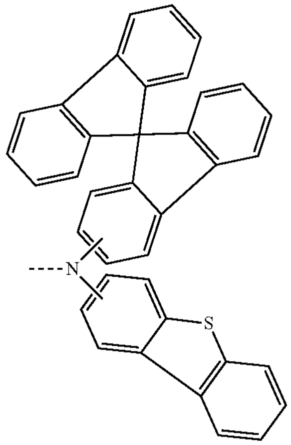
A-30
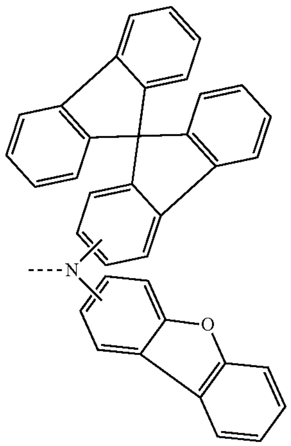
A-31
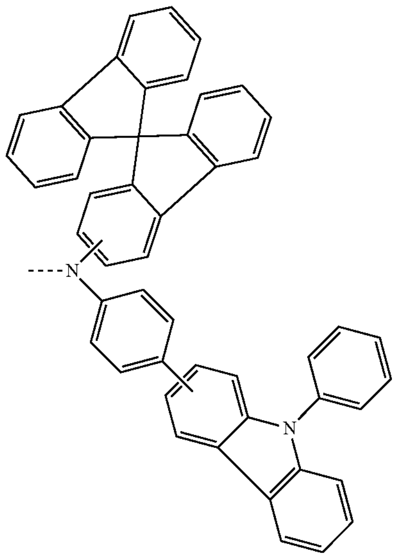
A-32
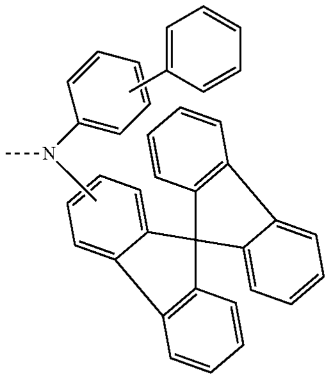

-continued
A-33
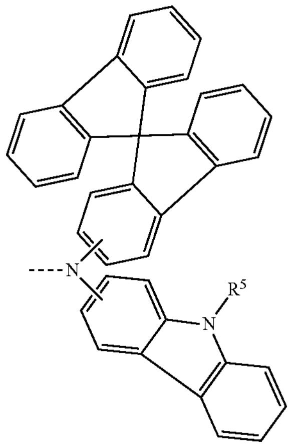
A-34
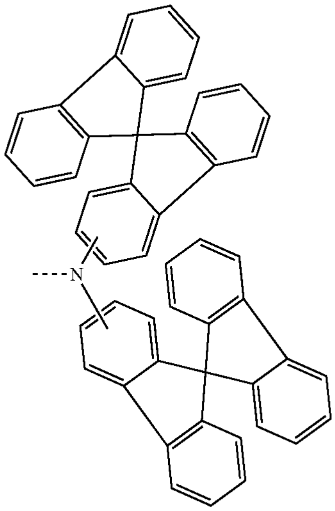
A-35
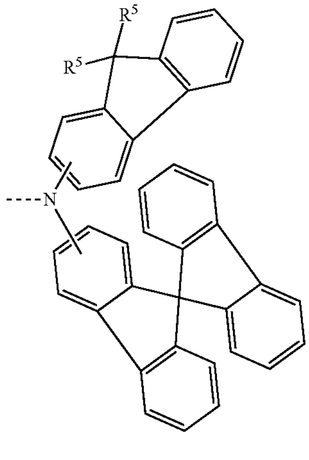
-continued
A-36
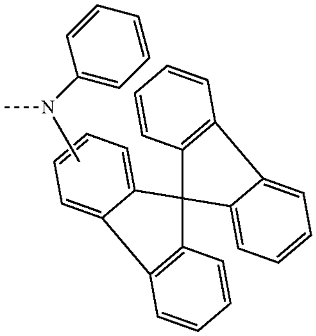
A-37
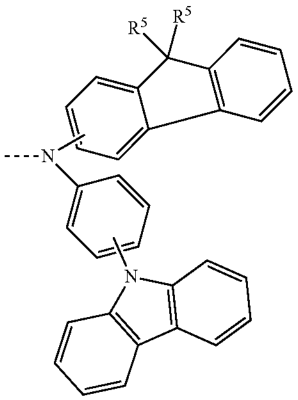
A-38
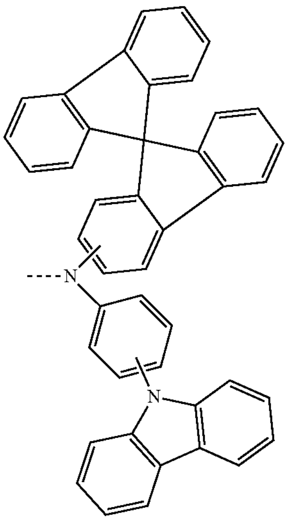

-continued

A-39

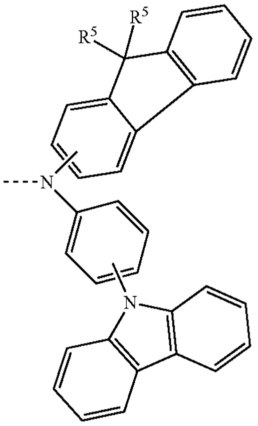

where the groups may each be substituted by an $R^5$ radical at their unoccupied positions, and are preferably unsubstituted in the unoccupied positions, and where the dashed bonds represent the bonds to the rest of the formula.

$R^0$ is preferably H.

$R^1$ is preferably the same or different at each instance and is selected from monovalent groups derived from benzene, biphenyl, terphenyl, quaterphenyl, naphthalene, fluorene, especially 9,9'-dimethylfluorene and 9,9'-diphenylfluorene, benzofluorene, spirobifluorene, indenofluorene, indenocarbazole, dibenzofuran, dibenzothiophene, benzocarbazole, carbazole, benzofuran, benzothiophene, indole, quinoline, pyridine, pyrimidine, pyrazine, pyridazine and triazine, where the monovalent groups may each be substituted by one or more $R^6$ radicals. When $R^6$ radicals are present in the groups, it is preferable when one or two $R^6$ radicals are $N(R^7)_2$ where $R^7$ is selected from aromatic ring systems having 6 to 40 aromatic ring atoms and heteroaromatic ring systems having 5 to 40 aromatic ring atoms. Particularly preferred $R^1$ groups are selected from phenyl, phenyl substituted by one or two-$N(R^7)_2$ groups, biphenyl, N-bonded carbazolyl, C-bonded carbazolyl, naphthyl, dibenzofuranyl and dibenzothiophenyl, each of which may be substituted by one or more $R^6$ radicals and are preferably unsubstituted.

$R^2$ is preferably the same or different at each instance and is selected from H, D, straight-chain alkyl groups having 1 to 20 carbon atoms, branched or cyclic alkyl groups having 3 to 20 carbon atoms, aromatic ring systems having 6 to 40 aromatic ring atoms and heteroaromatic ring systems having 5 to 40 aromatic ring atoms, where said alkyl groups and said aromatic ring systems and heteroaromatic ring systems may each be substituted by one or more $R^6$ radicals. More preferably, $R^2$ is H.

$R^3$ is preferably the same or different at each instance and is selected from H, D, F, CN, $Si(R^6)_3$, straight-chain alkyl groups having 1 to 20 carbon atoms, branched or cyclic alkyl groups having 3 to 20 carbon atoms, aromatic ring systems having 6 to 40 aromatic ring atoms and heteroaromatic ring systems having 5 to 40 aromatic ring atoms; where the alkyl groups mentioned, the aromatic ring systems mentioned and the heteroaromatic ring systems mentioned may each be substituted by one or more $R^6$ radicals; and where one or more $CH_2$ groups in the alkyl groups mentioned may be replaced by —C≡C—, —$R^6C$═$CR^6$—, $Si(R^6)_2$, C═O, C═$NR^6$, —$NR^6$—, —O—, —S—, —C(═O)O— or —C(═O)$NR^6$—. More preferably, $R^3$ is H.

$R^4$, $R^5$ are preferably the same or different at each instance and are selected from H, D, F, CN, $Si(R^6)_3$, $N(R^6)_2$, straight-chain alkyl groups having 1 to 20 carbon atoms, branched or cyclic alkyl groups having 3 to 20 carbon atoms, aromatic ring systems having 6 to 40 aromatic ring atoms and heteroaromatic ring systems having 5 to 40 aromatic ring atoms; where the alkyl groups mentioned, the aromatic ring systems mentioned and the heteroaromatic ring systems mentioned may each be substituted by one or more $R^6$ radicals; and where one or more $CH_2$ groups in the alkyl groups mentioned may be replaced by —C≡C—, —$R^6C$═$CR^6$—, $Si(R^6)_2$, C═O, C═$NR^6$, —$NR^6$—, —O—, —S—, —C(═O)O— or —C(═O)$NR^6$—.

$R^4$ radicals bonded to an $X^1$═$C(R^4)_2$ group are preferably selected from alkyl groups having 1 to 20 carbon atoms, aromatic ring systems having 6 to 20 aromatic ring atoms and heteroaromatic ring systems having 5 to 20 aromatic ring atoms; where said alkyl groups, said aromatic ring systems and said heteroaromatic ring systems may each be substituted by one or more $R^6$ radicals. In a preferred embodiment, the two $R^4$ radicals in an $X^1$═$C(R^4)_2$ group together form a ring, such that the carbon atom of the $X^1$═$C(R^4)_2$ group is a spiro atom. The ring formed in this case is preferably a cycloalkyl ring or a ring of the following structure:

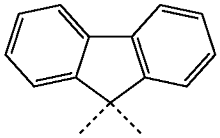

where the dotted bonds indicate the bonds from the $X^1$ group to the rest of the compound.

Preferably, $R^6$ is the same or different at each instance and is selected from H, D, F, CN, $Si(R^7)_3$, $N(R^7)_2$, straight-chain alkyl or alkoxy groups having 1 to 20 carbon atoms, branched or cyclic alkyl or alkoxy groups having 3 to 20 carbon atoms, aromatic ring systems having 6 to 40 aromatic ring atoms and heteroaromatic ring systems having 5 to 40 aromatic ring atoms; where the alkyl and alkoxy groups mentioned, the aromatic ring systems mentioned and the heteroaromatic ring systems mentioned may each be substituted by one or more $R^7$ radicals; and where one or more $CH_2$ groups in the alkyl or alkoxy groups mentioned may be replaced by —C≡C—, —$R^7C$═$CR^7$—, $Si(R^7)_2$, C═O, C═$NR^7$, —$NR^7$—, —O—, —S—, —C(═O)O— or —C(═O)$NR^7$—.

Preferred embodiments of the formula (I) conform to the following formulae:

Formula (I-A)

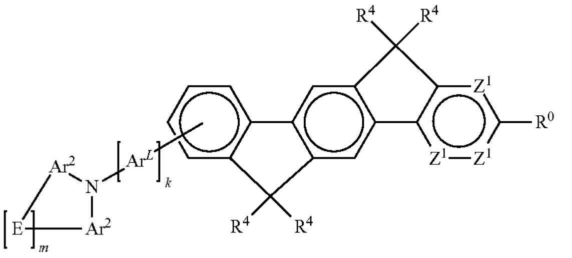

Formula (I-B)

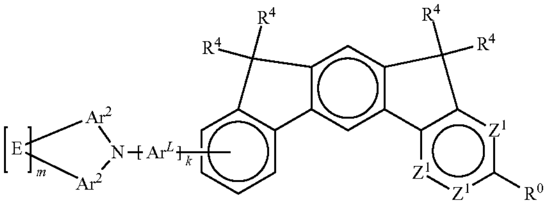

where all positions shown as unsubstituted on the benzene rings may each be substituted by an $R^3$ radical.

Preferably, in the formulae (I-A) and (I-B), the group

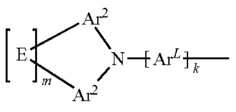

is in each case bonded para to the bond to the adjacent benzene group, which corresponds to formulae (I-A-a) and (I-B-a):

Formula (I-A-a)

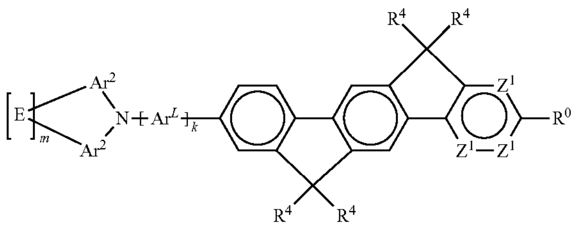

Formula (I-B-a)

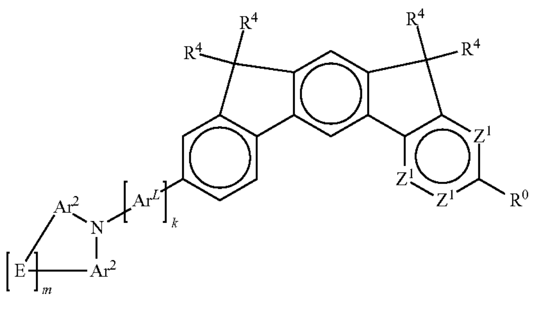

where all positions shown as unsubstituted on the benzene rings may each be substituted by an $R^3$ radical.

Preferred embodiments of the formula (II) conform to the following formulae:

Formula (II-A)

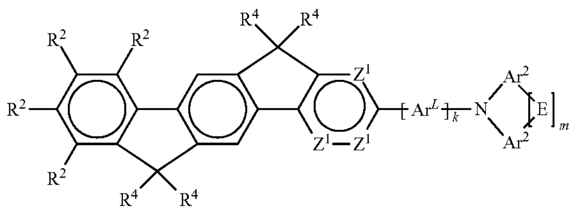

Formula (II-B)

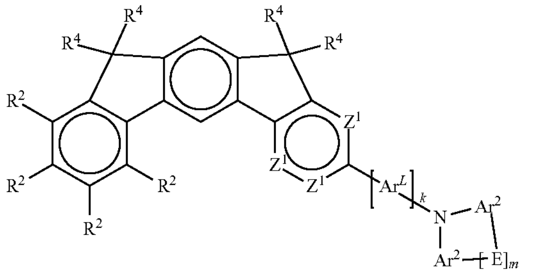

where all positions shown as unsubstituted on the benzene rings may each be substituted by an $R^3$ radical.

Further preferred embodiments of the formula (I) correspond to one of the following formulae:

Formula (I-C)

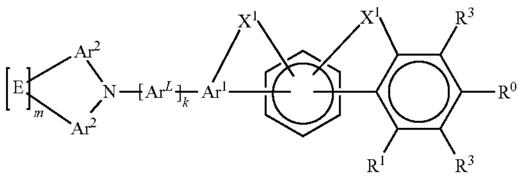

Formula (I-D)

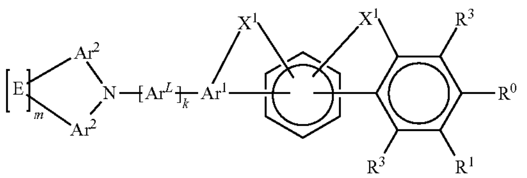

Formula (I-E)

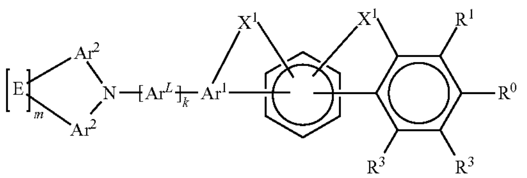

Formula (I-F)

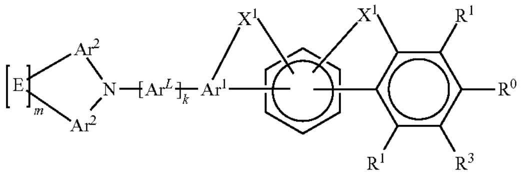

-continued

Formula (I-G)

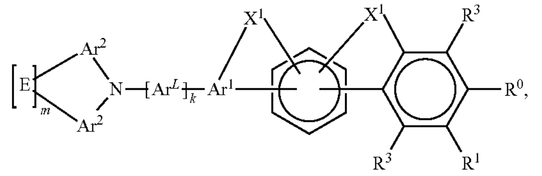

where the variables that occur as are defined above, and where $R^0$ and $R^3$ are preferably H. Further preferably, in these formulae, k=0 and m=0, and $Ar^1$ is a phenyl group which may be substituted by one or more $R^3$ radicals.

Preferred embodiments of the formula (I-A) and (I-B) conform to the following formulae:

Formula (I-A-1)

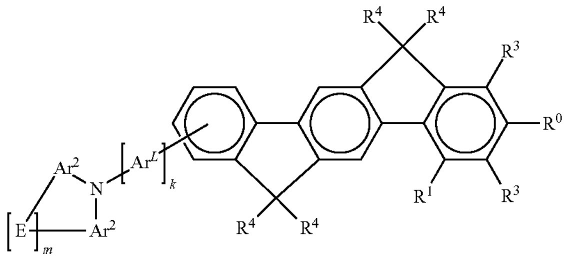

Formula (I-A-2)

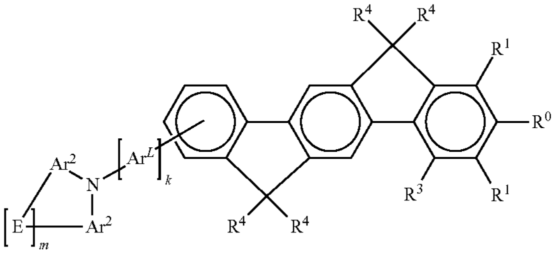

Formula (I-B-1)

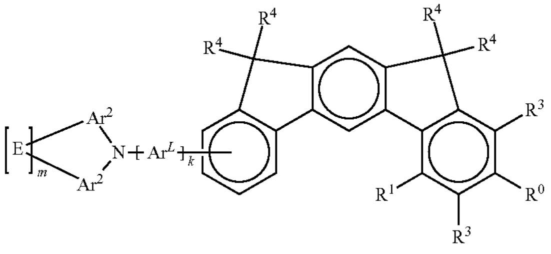

where the variables that occur are as defined above. Preferably, in these formulae, k=0 and m=0. Further preferably, in these formulae, $R^3$ and $R^0$ are H. Preferably, in the formulae (I-A-1), (I-A-2) and (I-B-1), the group

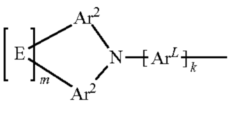

is in each case bonded para to the bond to the adjacent benzene group, which corresponds to the following formulae:

Formula (I-A-1-a)

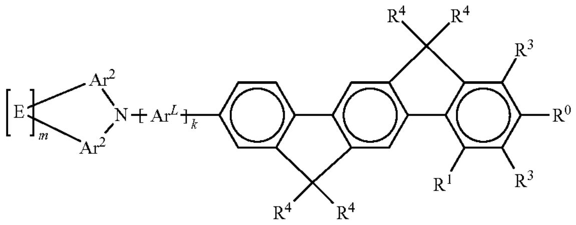

Formula (I-A-2-a)

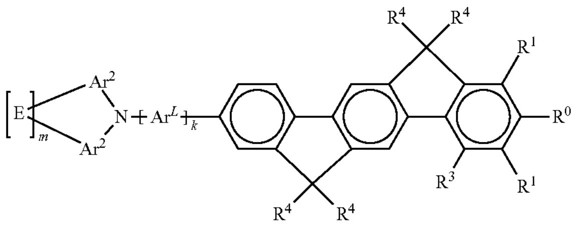

Formula (I-B-1-a)

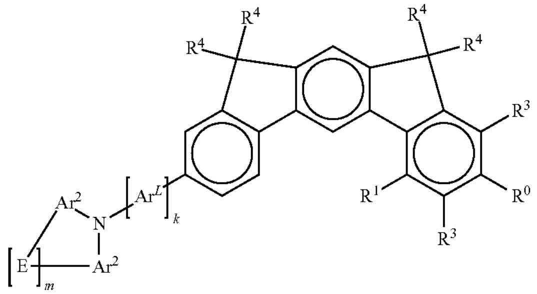

where the variables that occur are as defined above.

Preferred embodiments of the formula (I-A-1), (I-A-2) and (I-B-1) are the following formulae:

Formula (I-A-1-1)

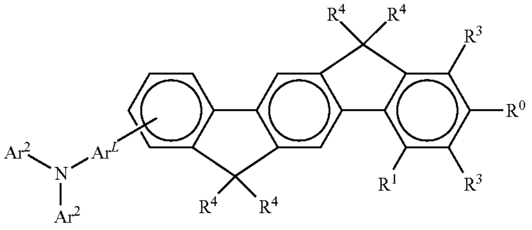

Formula (I-A-1-2)

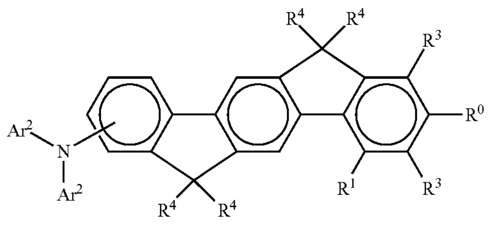

-continued
Formula (I-A-1-3)
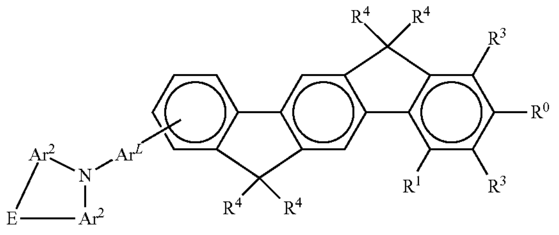
Formula (I-A-1-4)
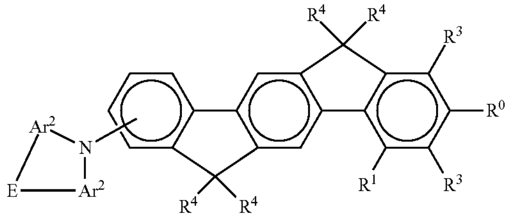
Formula (I-A-1-5)
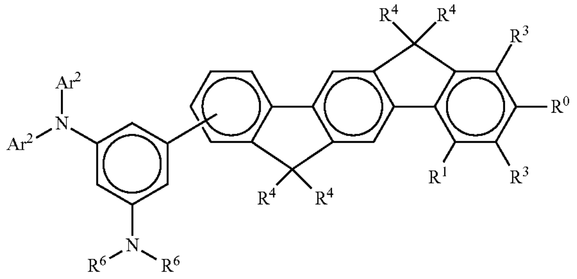
Formula (I-A-1-6)
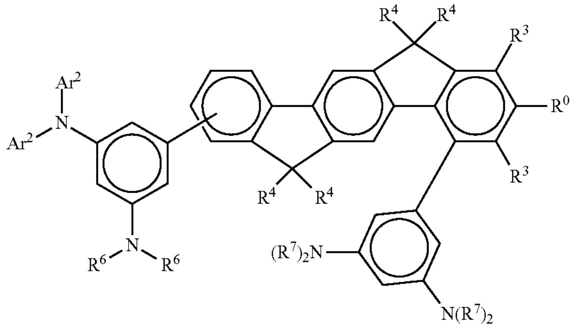
Formula (I-A-1-7)
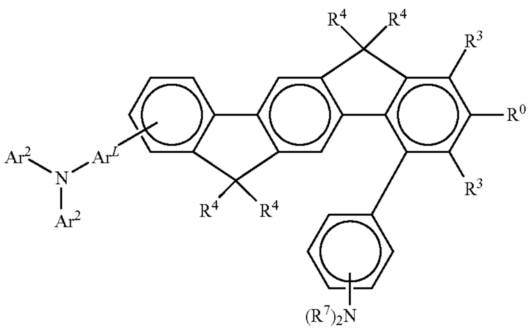
-continued
Formula (I-A-1-8)
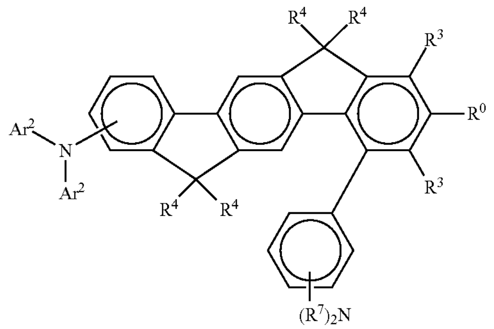
Formula (I-A-2-1)
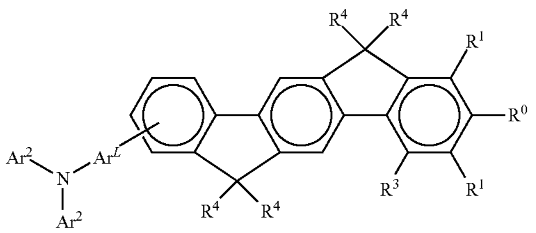
Formula (I-A-2-2)
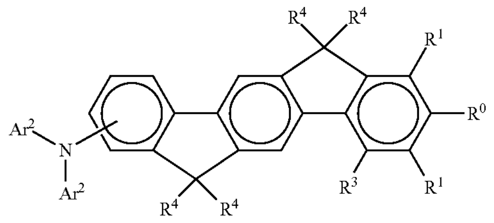
Formula (I-A-2-3)
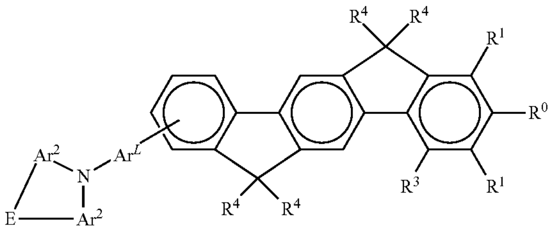
Formula (I-A-2-4)
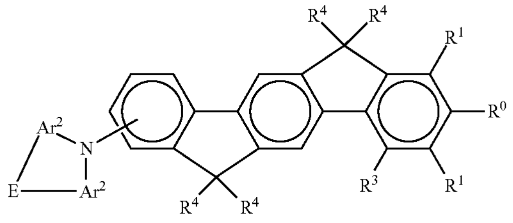

-continued

Formula (I-B-1-1)

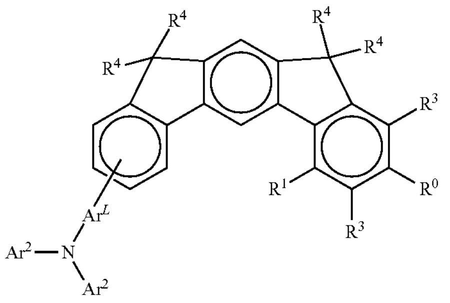

Formula (I-B-1-2)

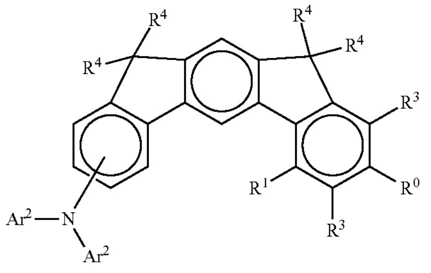

Formula (I-B-1-3)

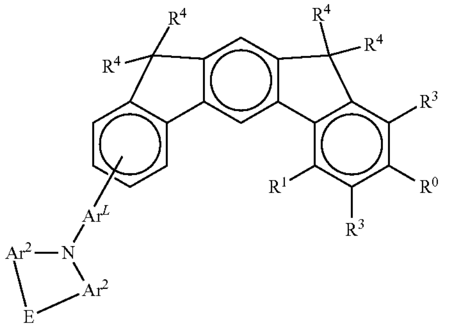

Formula (I-B-1-4)

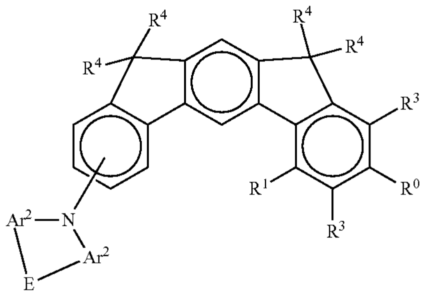

-continued

Formula (I-B-1-5)

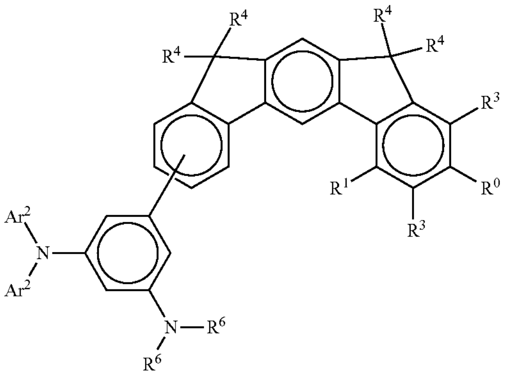

Formula (I-B-1-6)

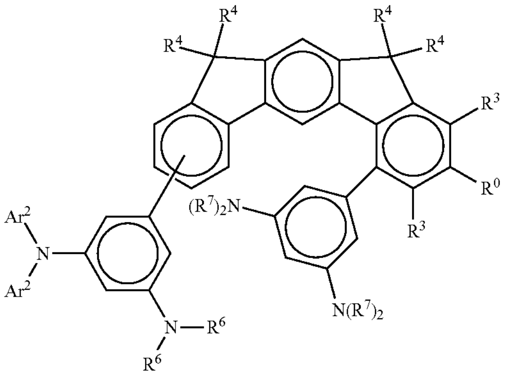

Formula (I-B-1-7)

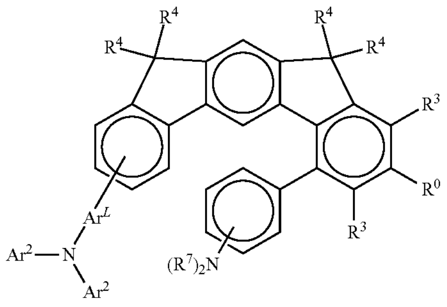

Formula (I-B-1-8)

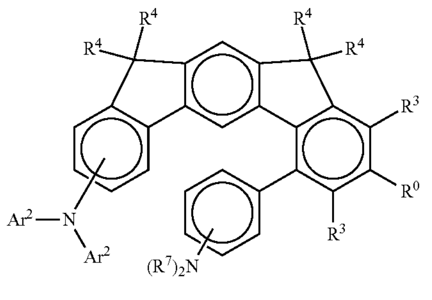

where the variables that occur as are defined above, and where $R^0$ and $R^3$ are preferably H. In formulae (I-A-1-3), (I-A-1-4), (I-A-2-3), (I-A-2-4), (I-B-1-3) and (I-B-1-4), E is preferably selected from single bond and $C(R^4)_2$; more preferably, E is a single bond. $Ar^L$ in formulae (I-A-1-1), (I-A-1-3), (I-A-1-7), (I-A-2-1), (I-A-2-3), (I-B-1-1), (I-B-1-3) and (I-B-1-7) is preferably a phenyl group which may be substituted by one or more $R^5$ radicals. Preferably, in the abovementioned formulae, the group selected from the following groups

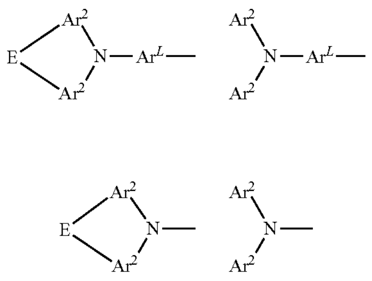

if present is in each case bonded in the position para to the bond to the adjacent benzene group.

Among the abovementioned formulae, particular preference is given to formulae (I-A-1-1), (I-A-1-2), (I-A-2-1), (I-A-2-2), (I-B-1-1) and (I-B-1-2), among these particularly to (I-A-1-1) and (I-A-1-2), and among these very particularly to (I-A-1-2). Very particularly preferred formulae are correspondingly the following embodiments of formula (I-A-1-1) and (I-A-1-2):

Formula (I-A-1-1-a)

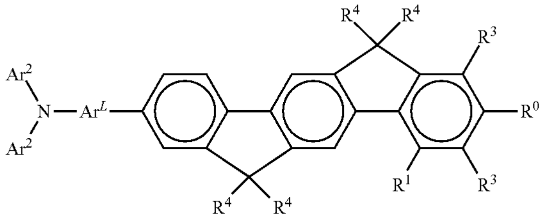

Formula (I-A-1-2-a)

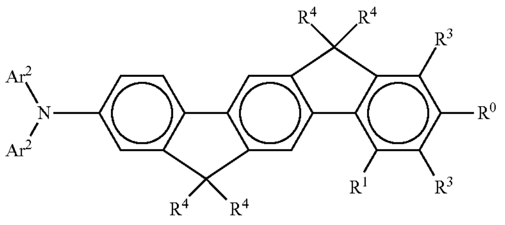

where formula (I-A-1-2-a) is the most preferred.

Preferred embodiments of the formula (II-A) conform to the following formulae:

Formula (II-A-1)

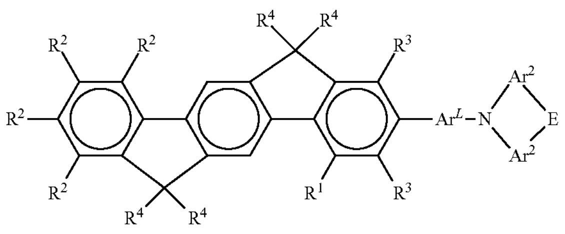

-continued

Formula (II-A-2)

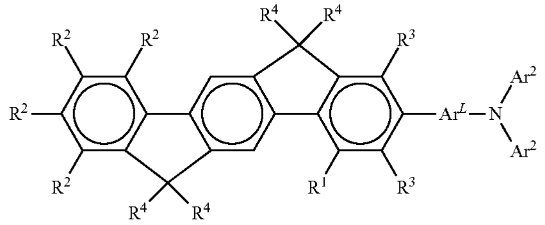

Formula (II-A-3)

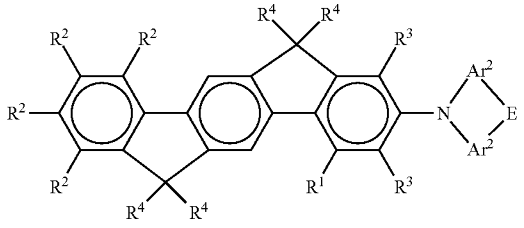

Formula (II-A-4)

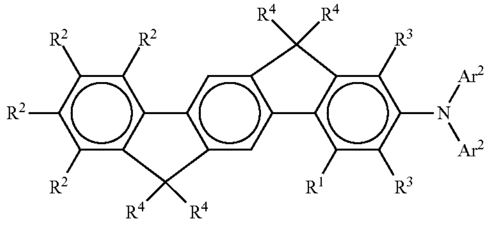

where the variables that occur as are defined above, and where $R^2$ and $R^3$ are preferably H. In formulae (II-A-1) and (II-A-3), E is preferably selected from single bond and $C(R^4)_2$; more preferably, E is a single bond. $Ar^L$ in formulae (II-A-1) and (II-A-2) is preferably a phenyl group which may be substituted by one or more $R^5$ radicals. Among the abovementioned formulae, particular preference is given to formula (II-A-4).

Preferred compounds according to the present invention are depicted below:

1

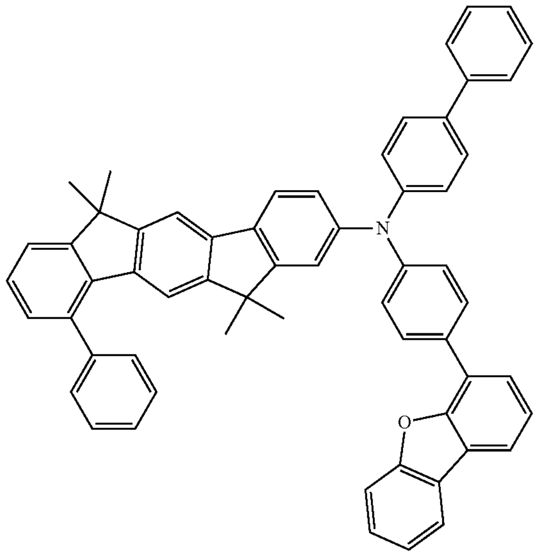

-continued
2
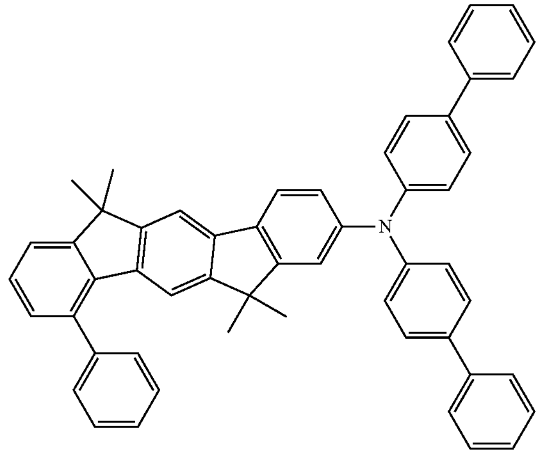
3
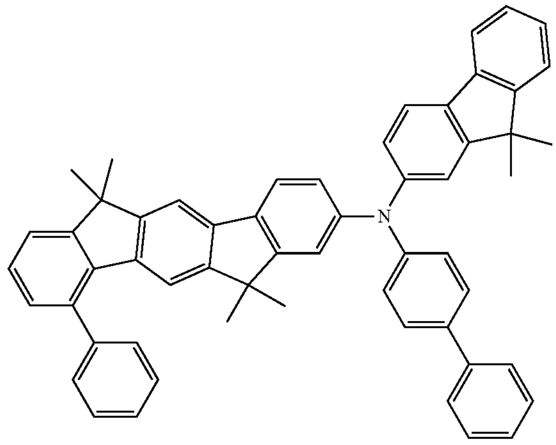
4
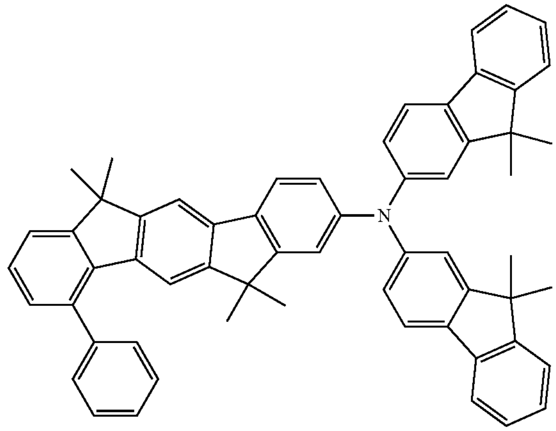
-continued
5
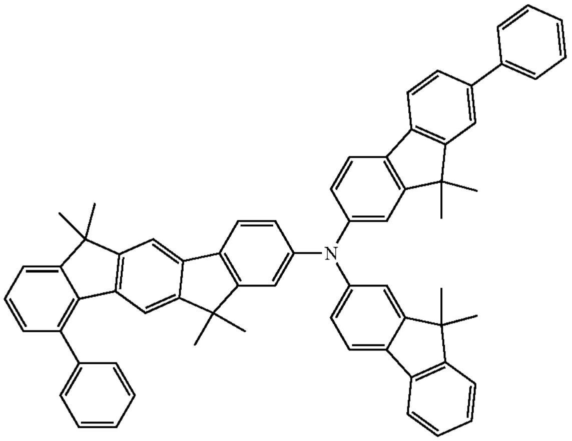
6
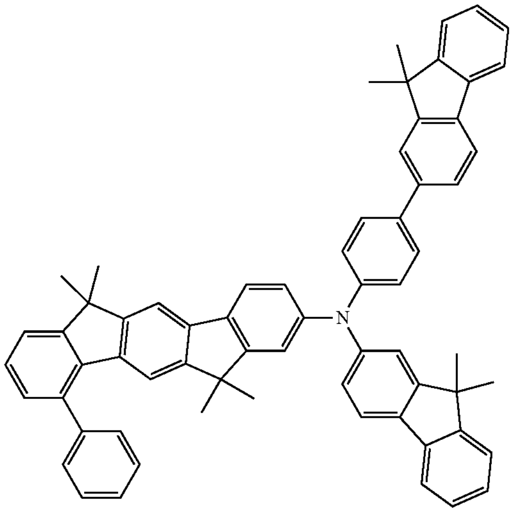
7
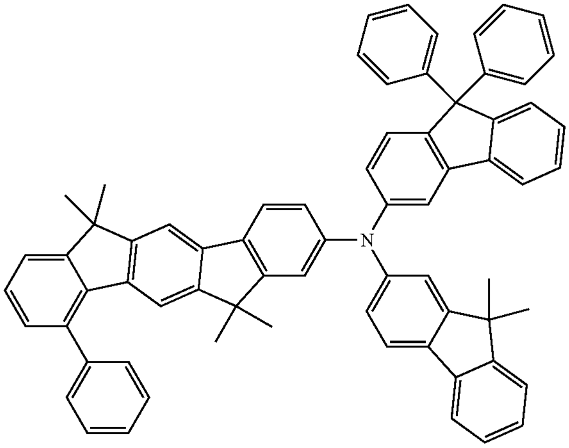

-continued
8
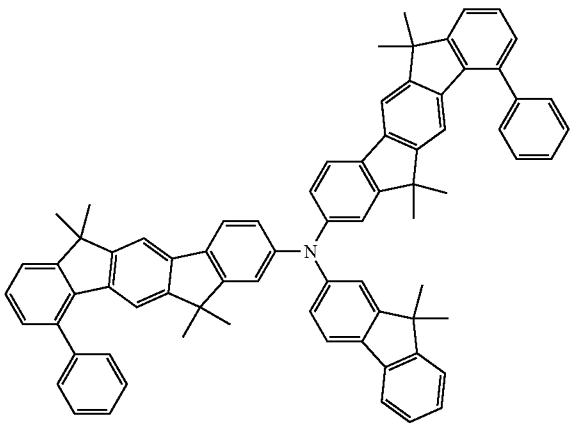
9
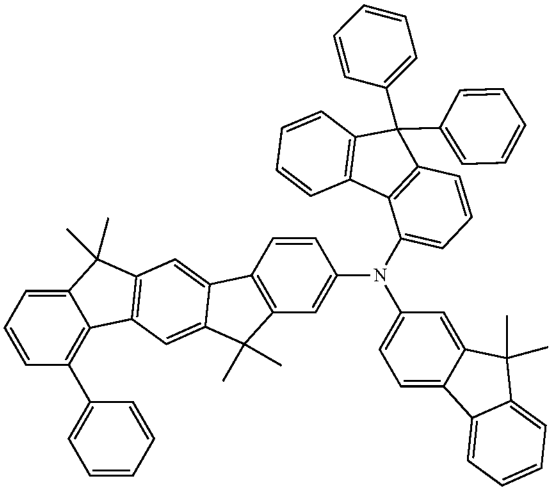
10
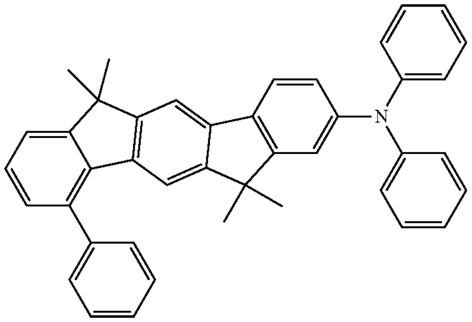
11
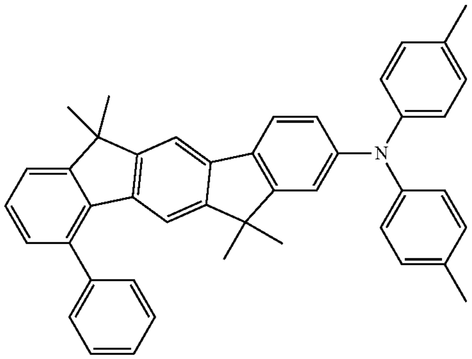
-continued
12
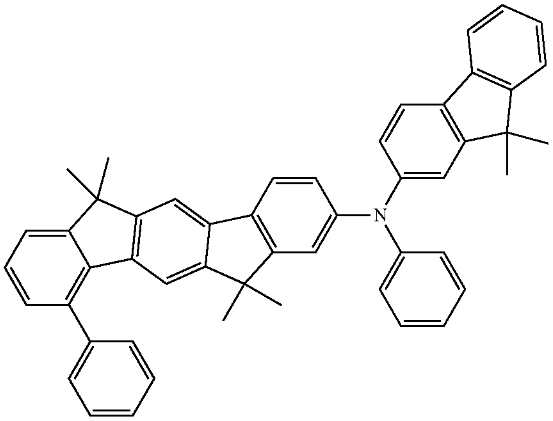
13
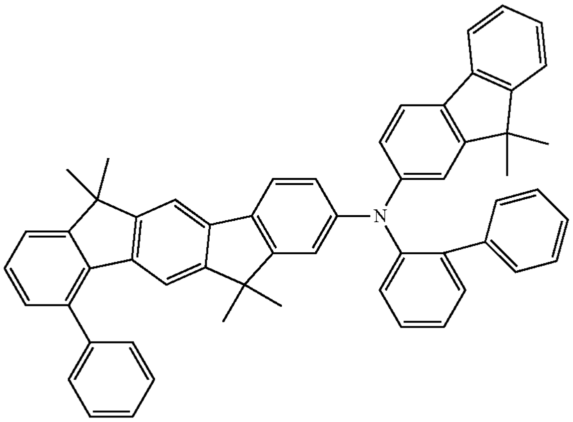
14
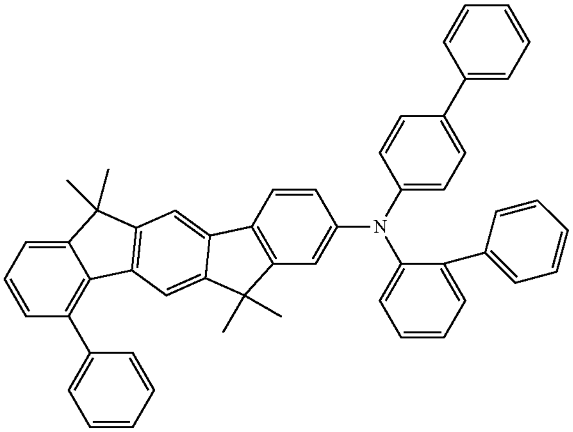

-continued
15
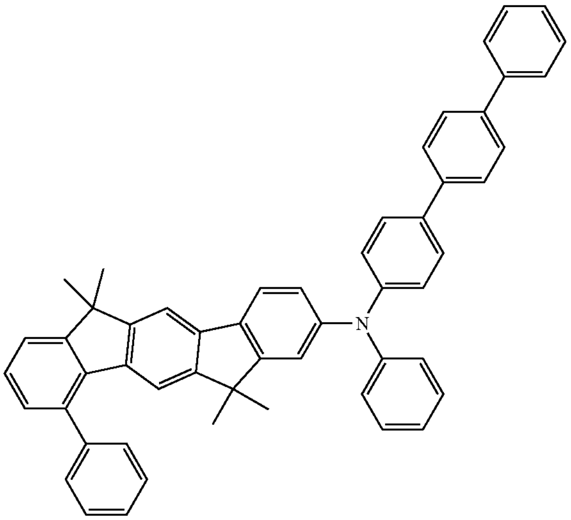
16
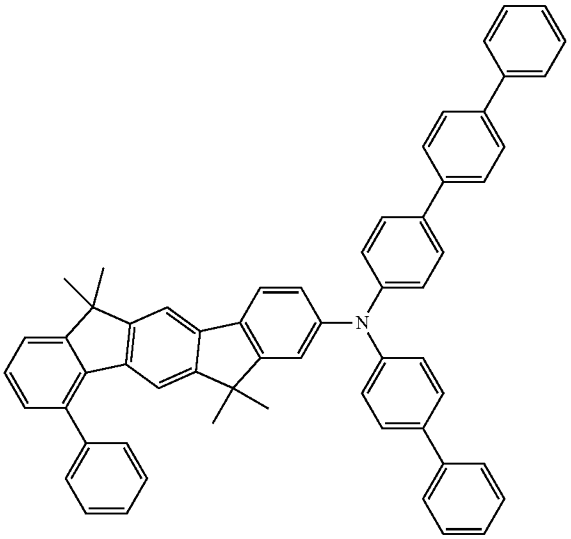
17
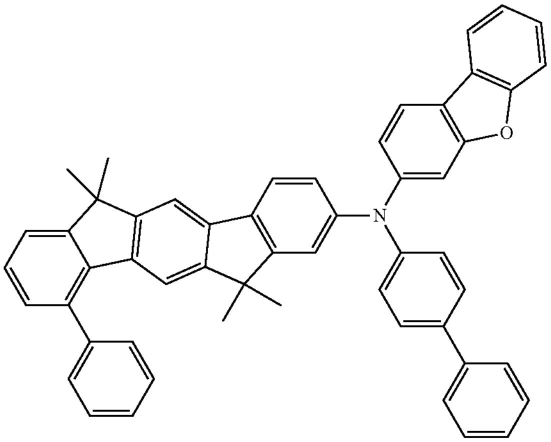
-continued
18
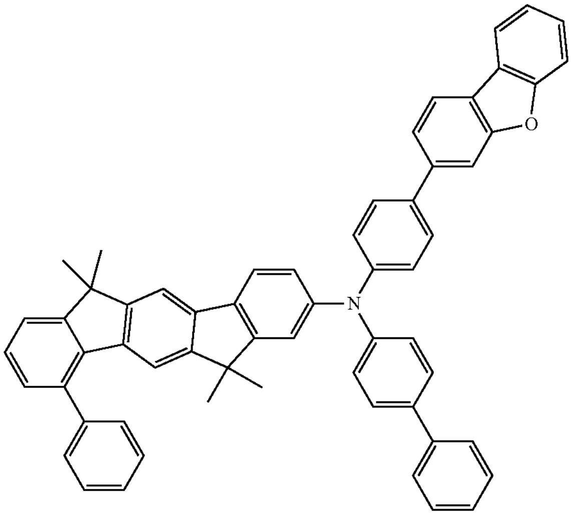
19
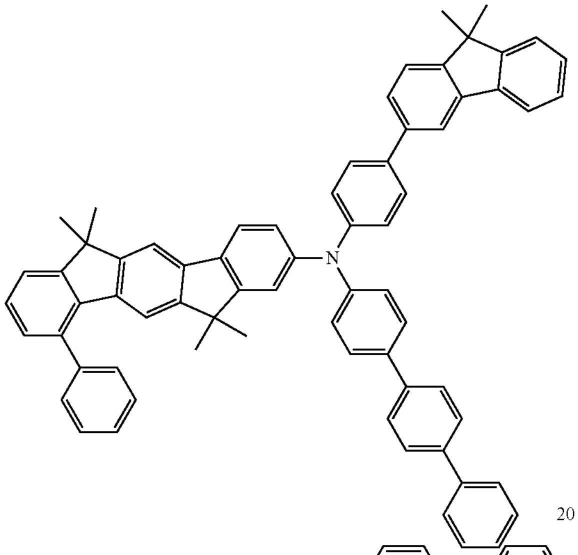
20
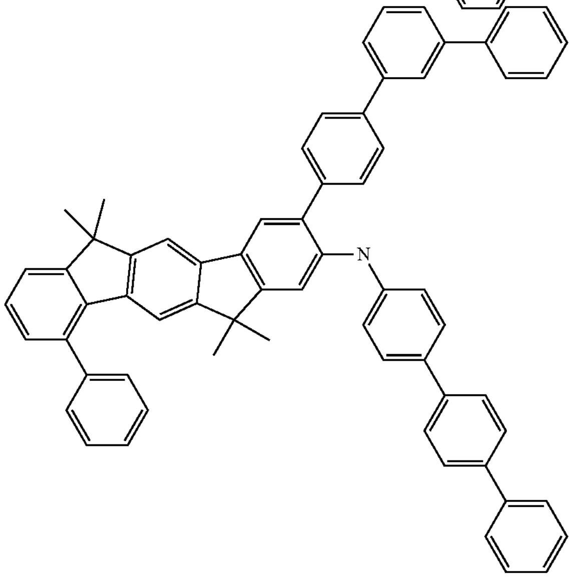

-continued
21
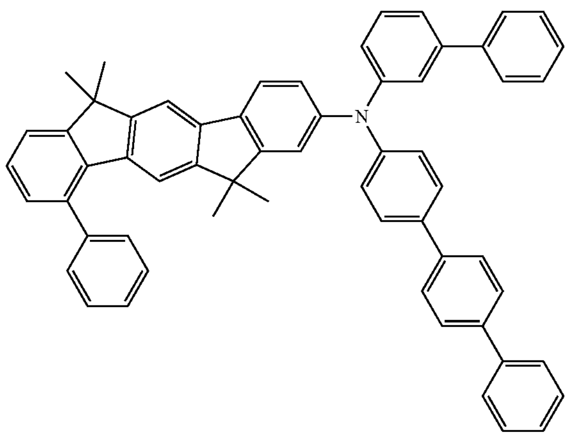
22
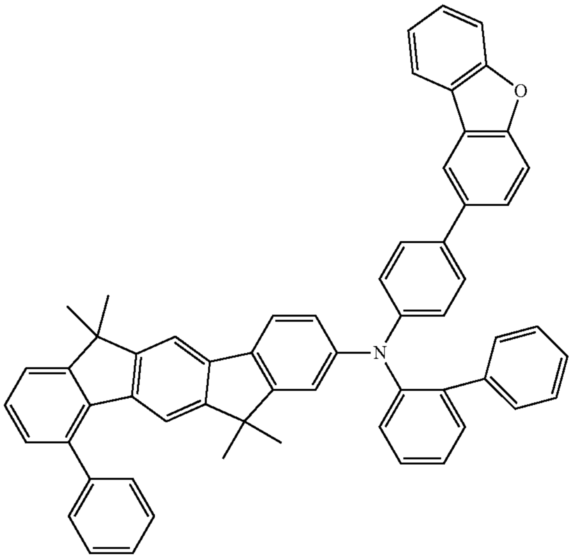
23
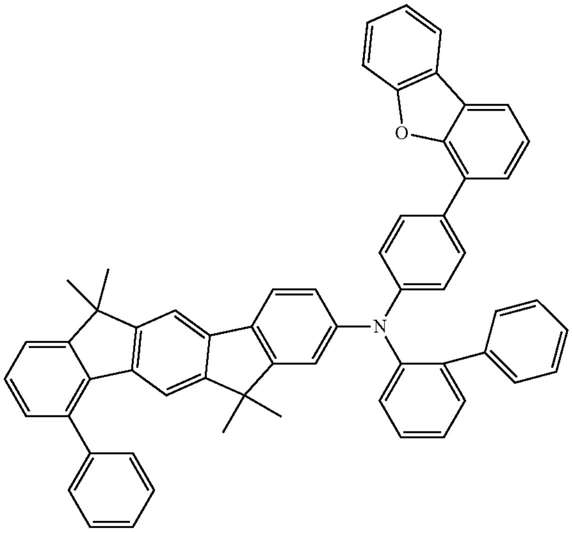
-continued
24
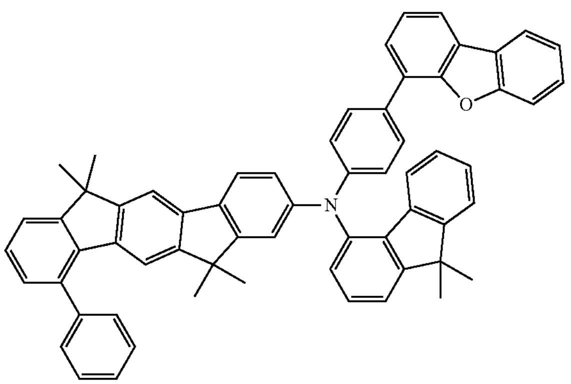
25
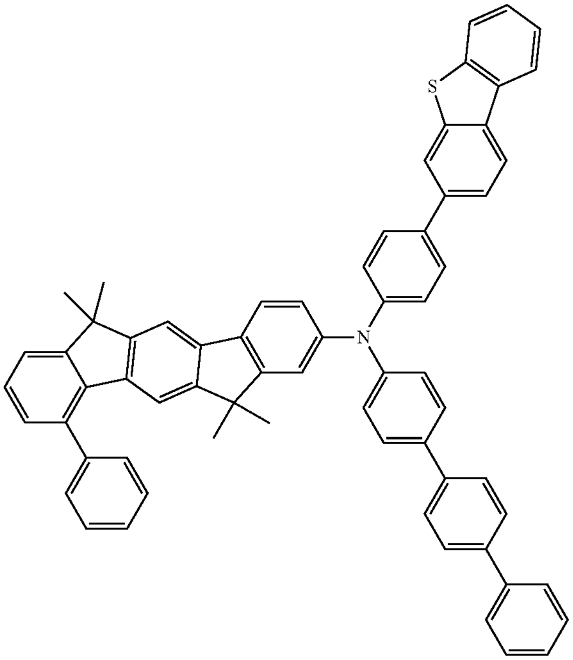
26
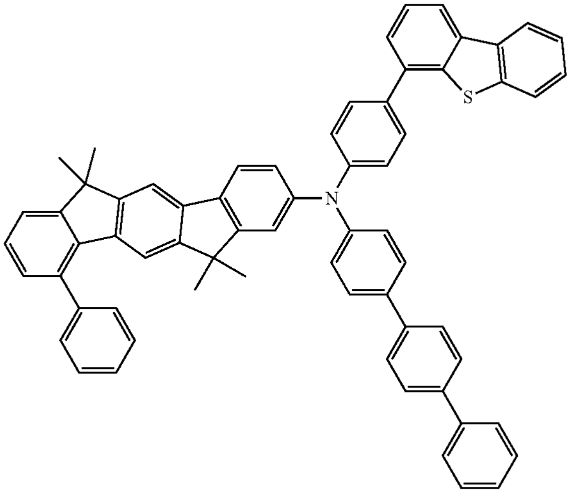

-continued
27
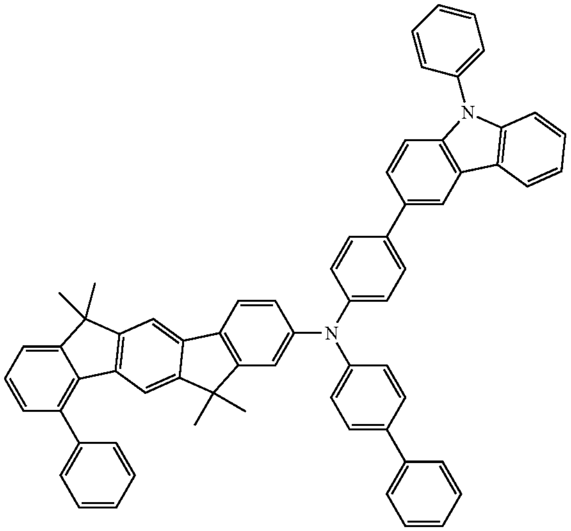
28
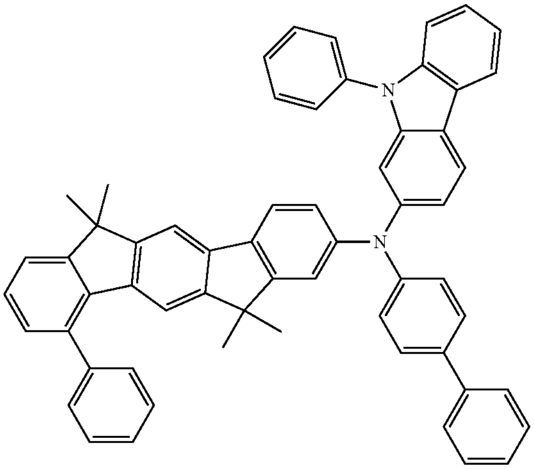
29
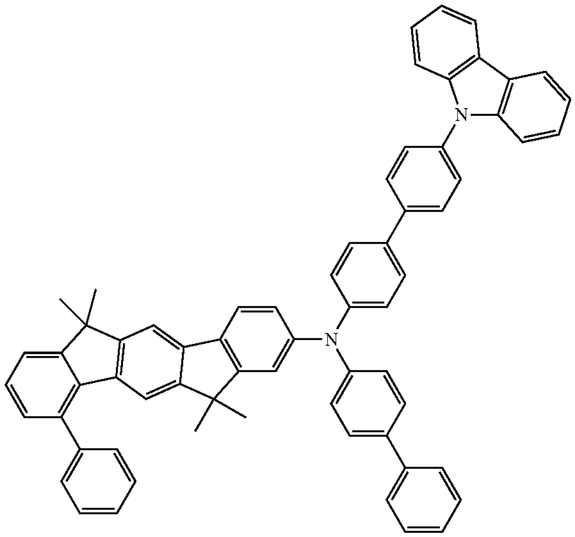
-continued
30
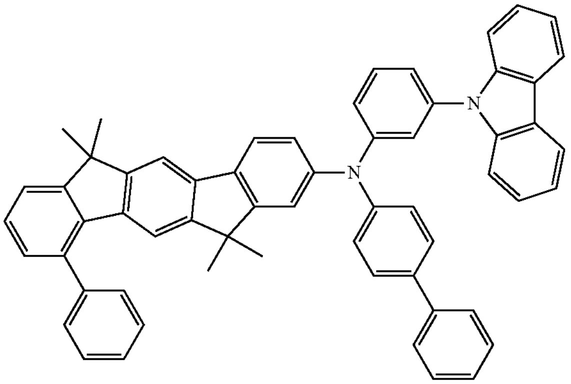
31
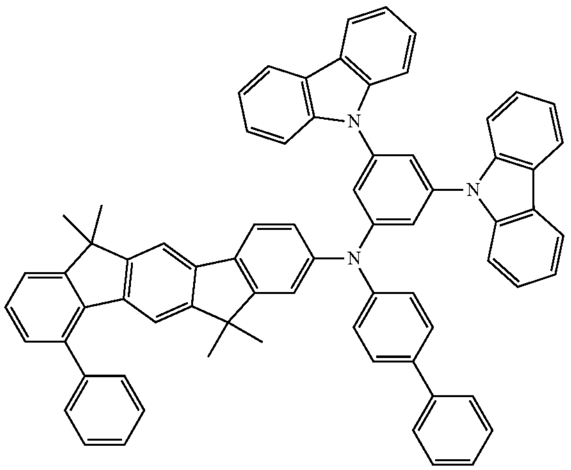
32
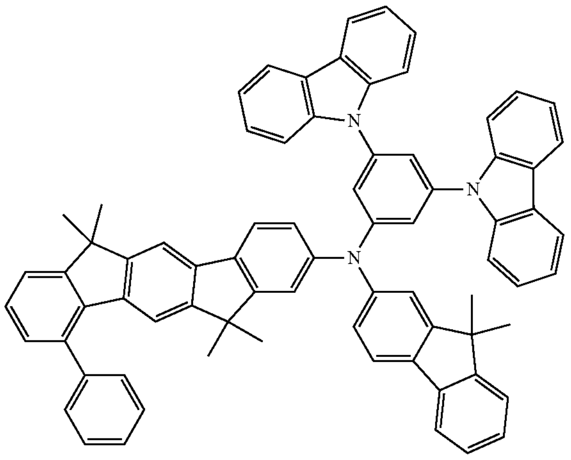

33
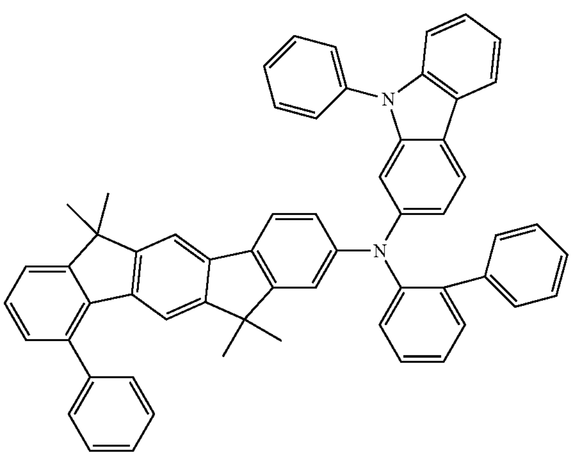
34
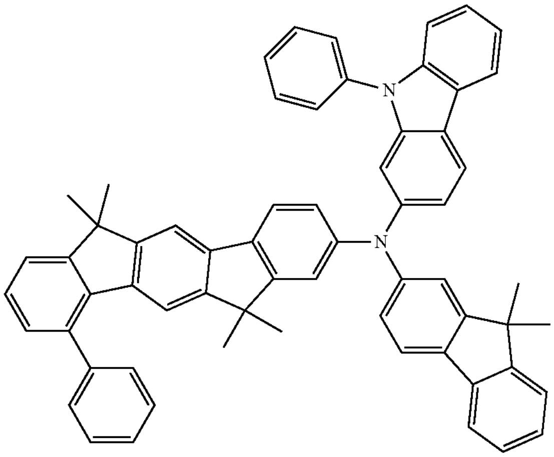
35
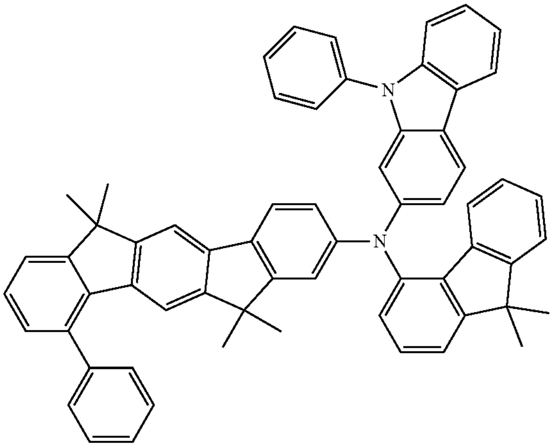
36
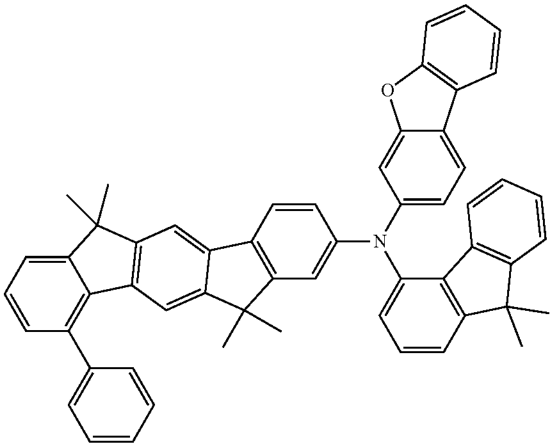
37
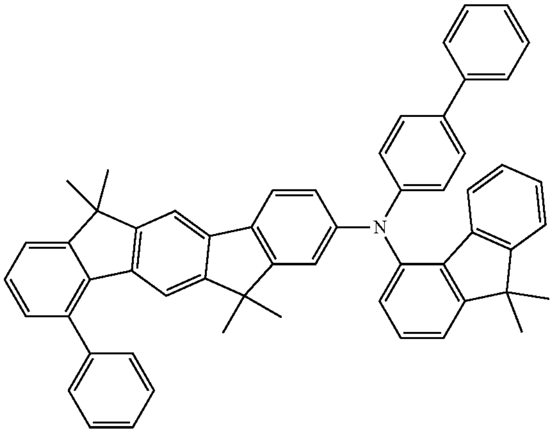
38
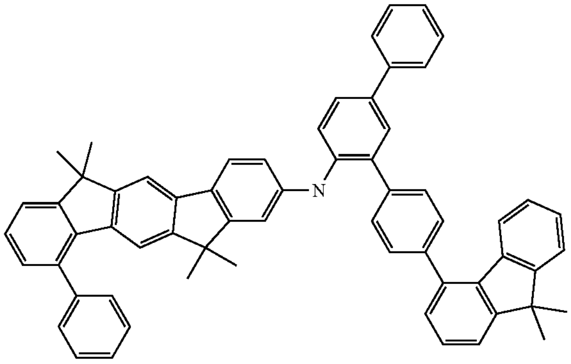

-continued
39
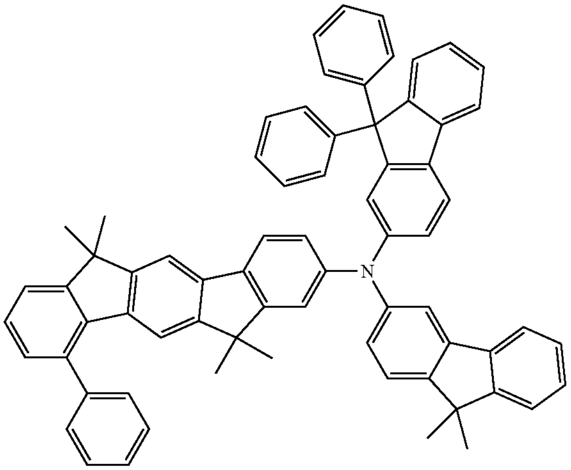
40
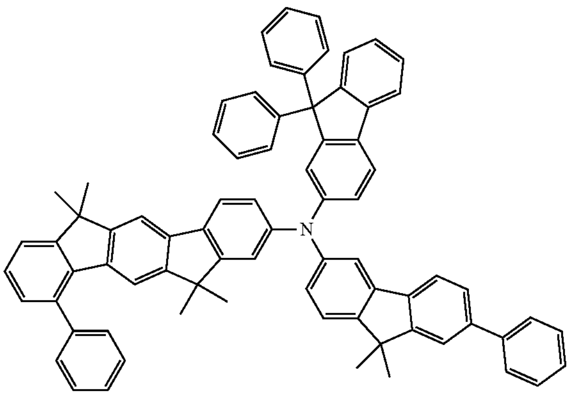
41
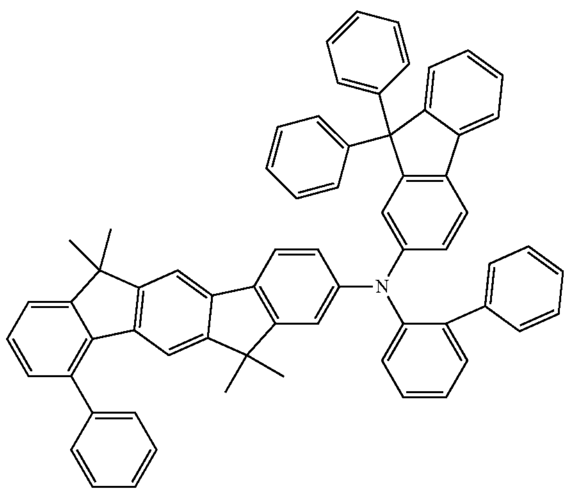
-continued
42
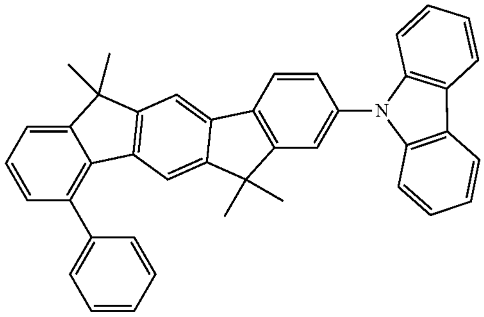
43
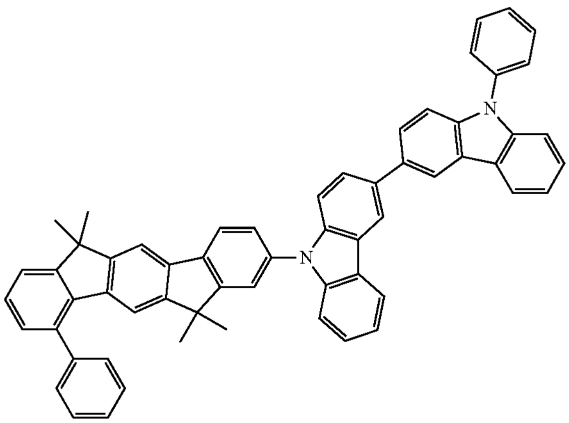
44
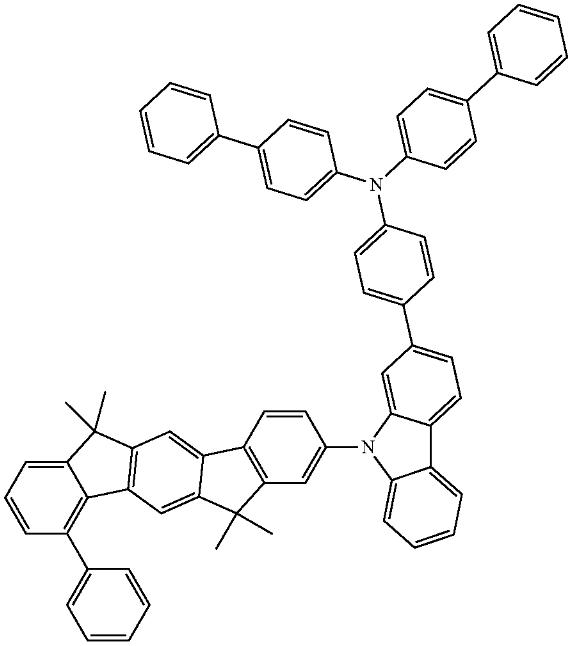

-continued
45
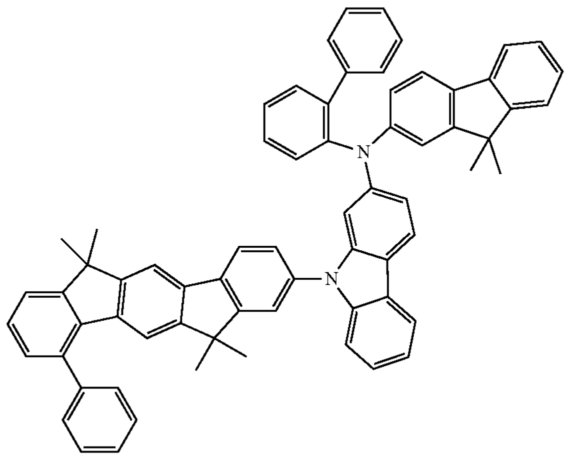
46
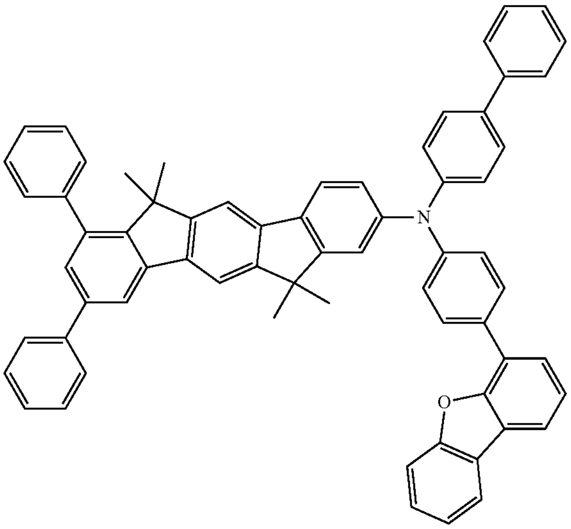
47
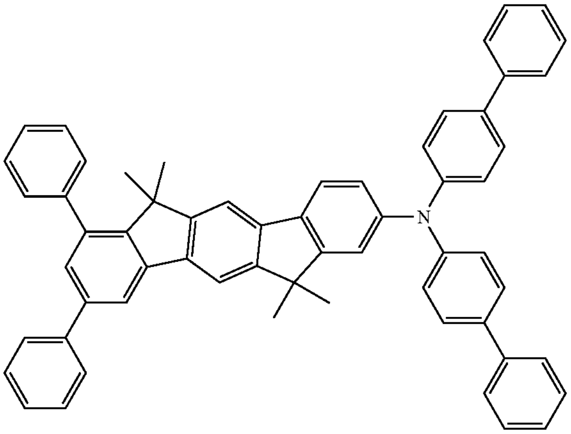
-continued
48
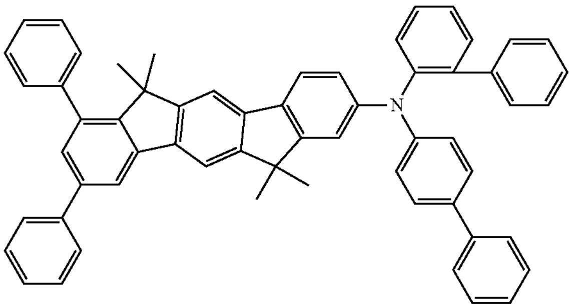
49
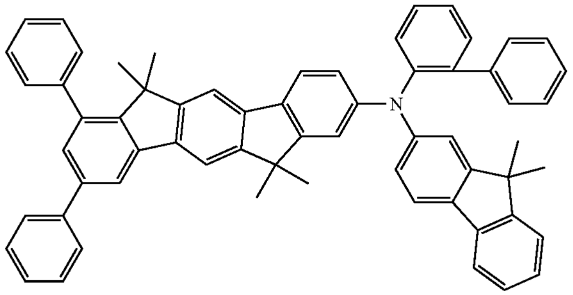
50
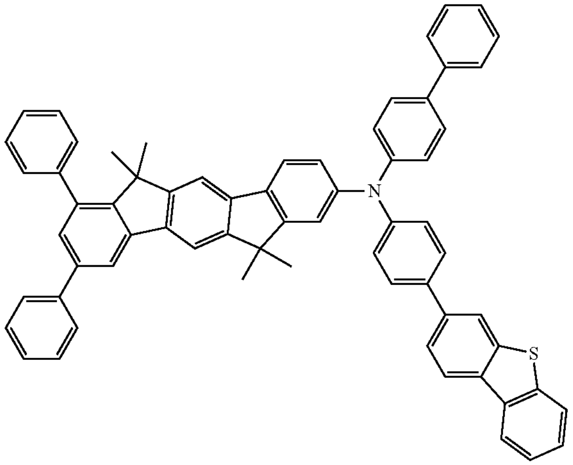
51
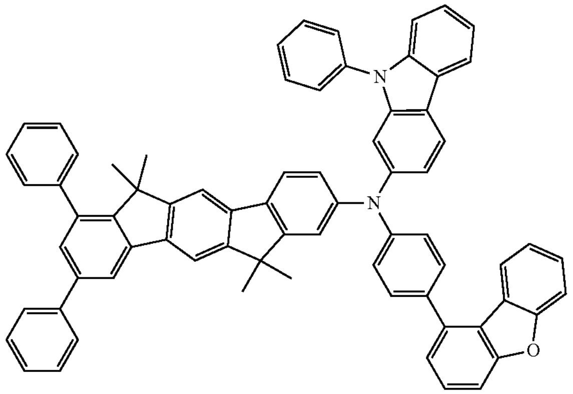

52
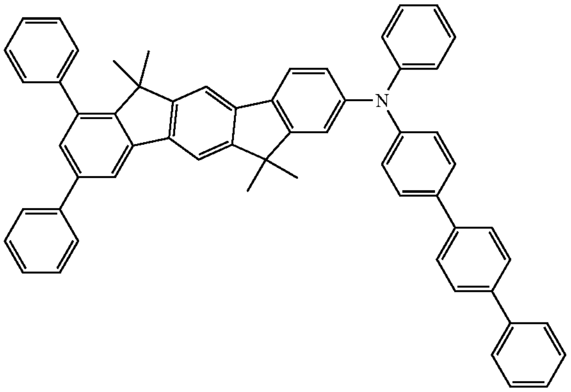
53
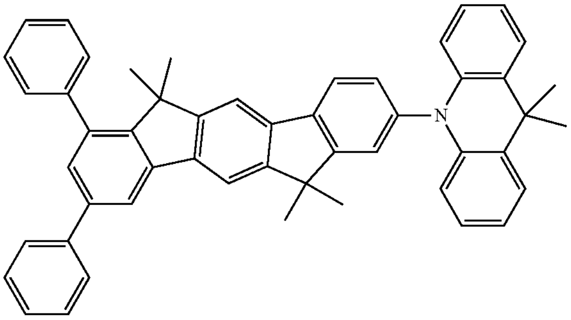
54
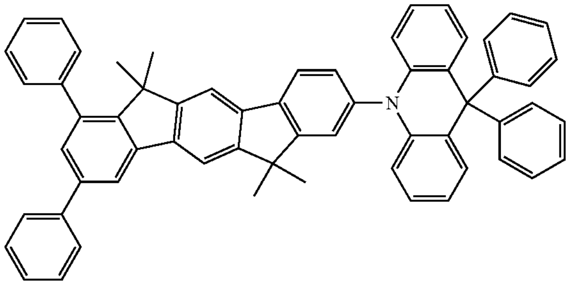
55
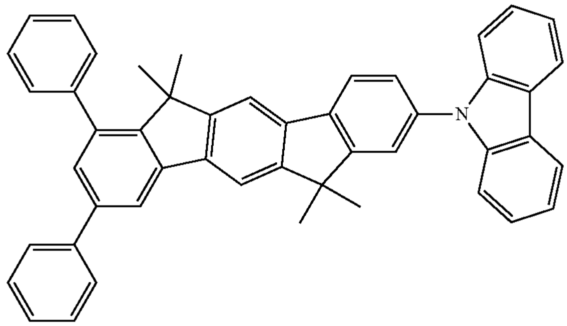
56
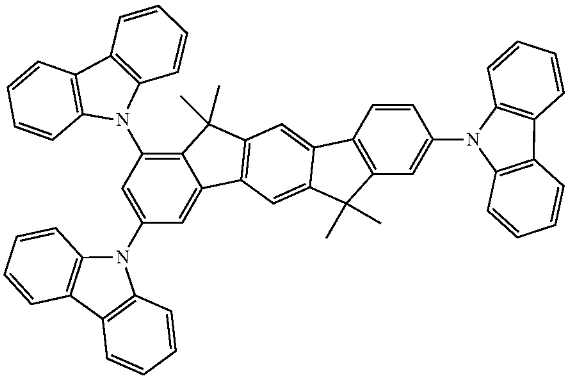
57
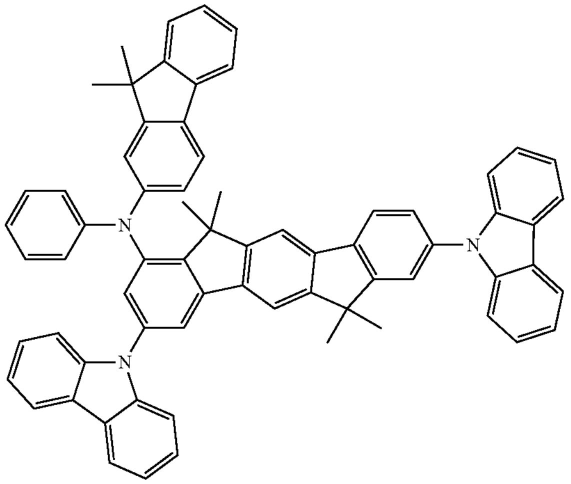
58
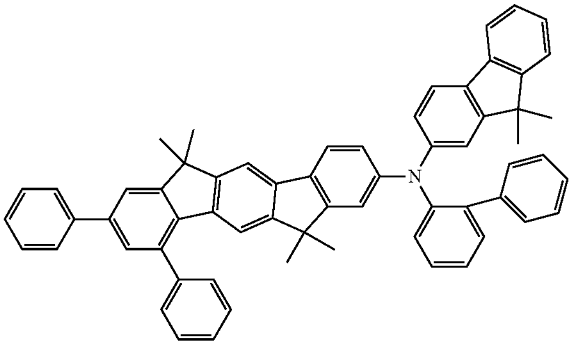
59
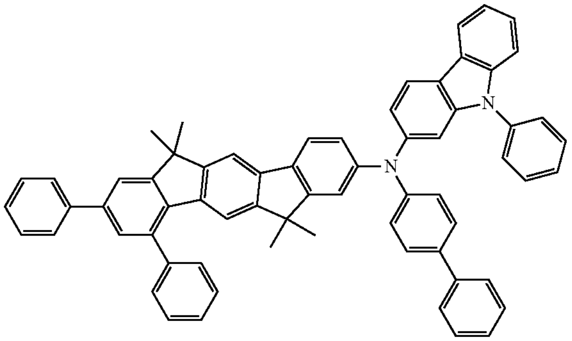

-continued
60
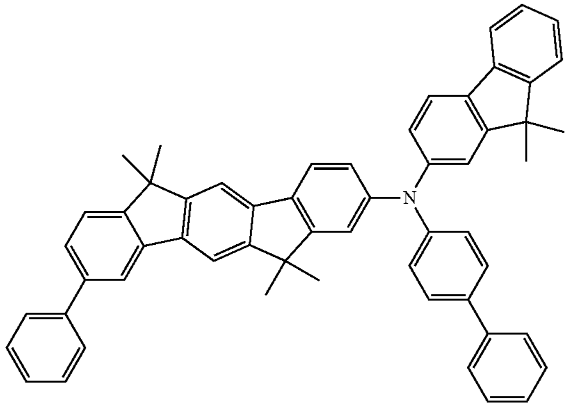
61
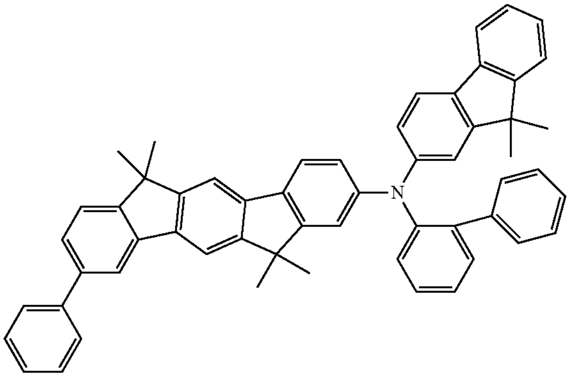
62
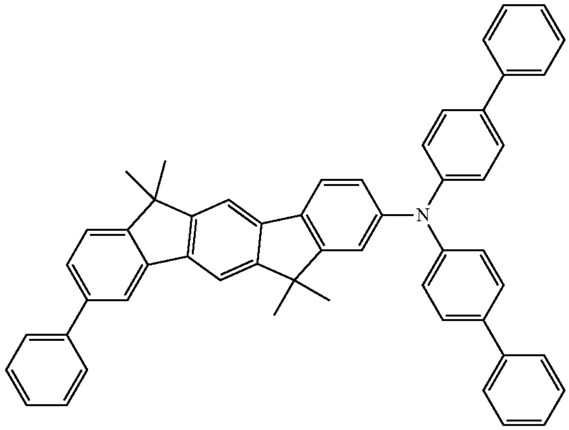
-continued
63
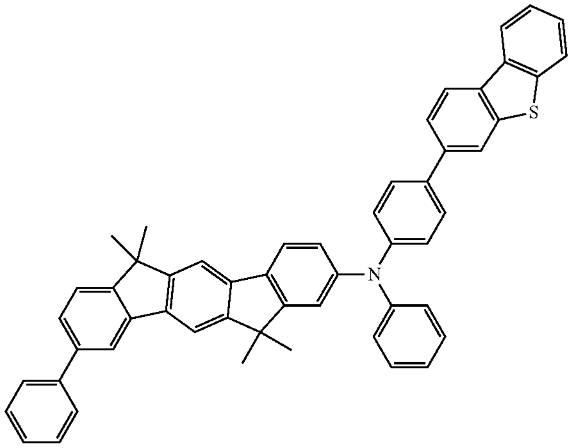
64
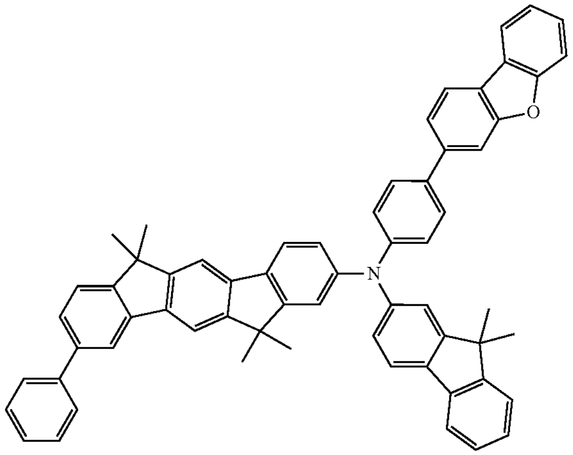
65
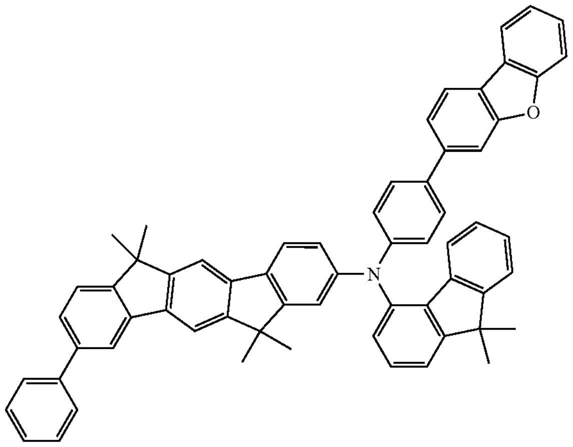

-continued
66
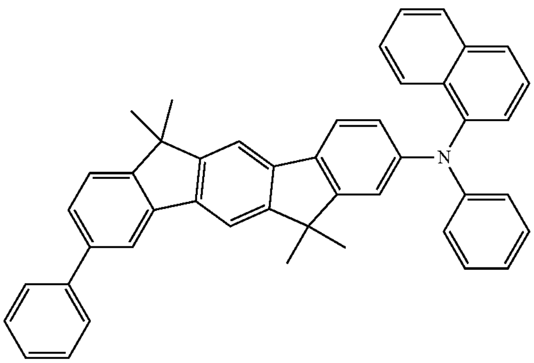
67
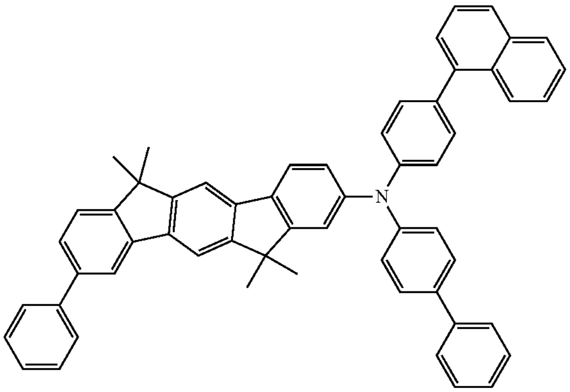
68
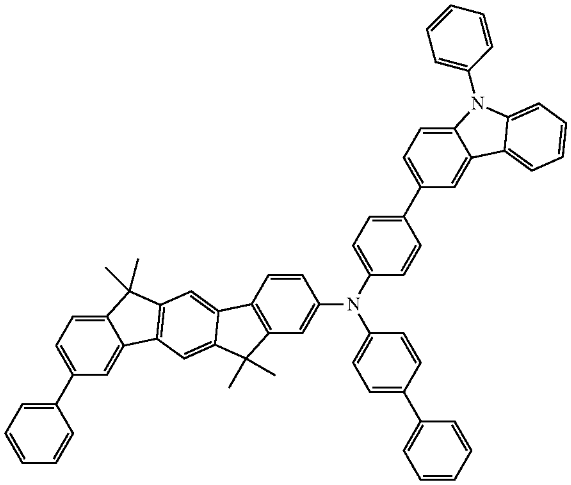
69
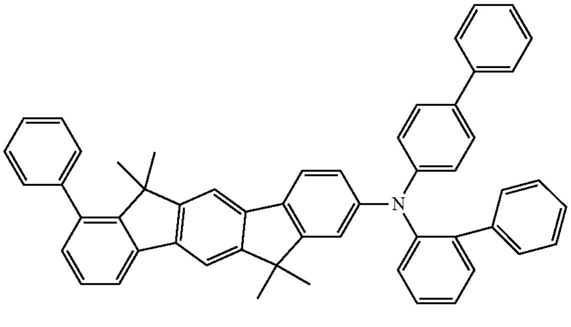
-continued
70
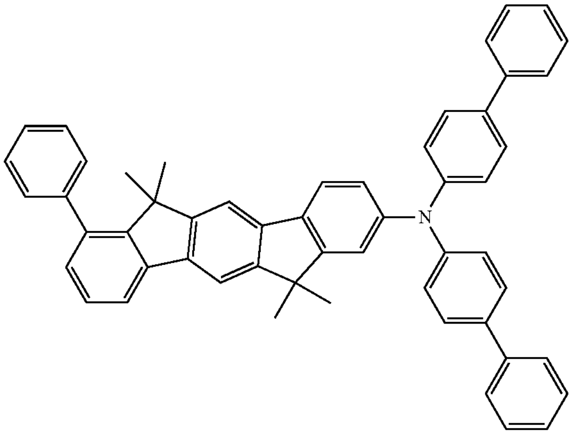
71
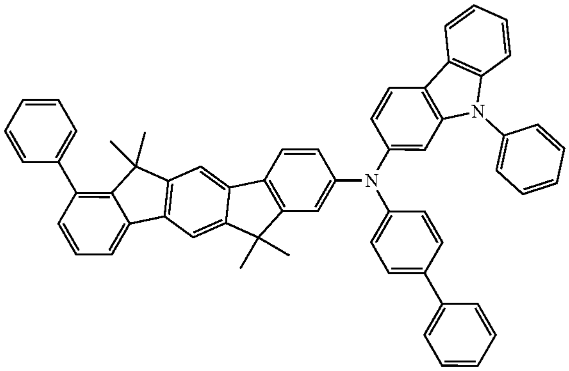
72
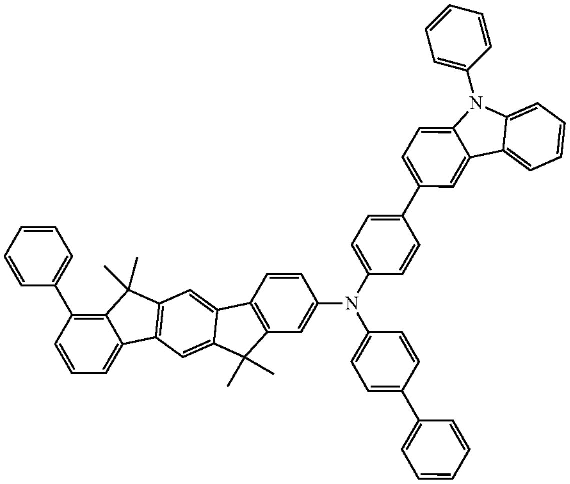

-continued
73
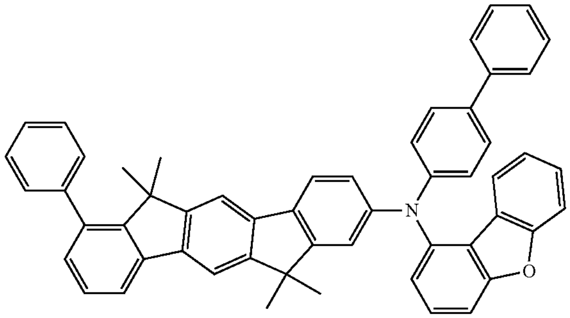
74
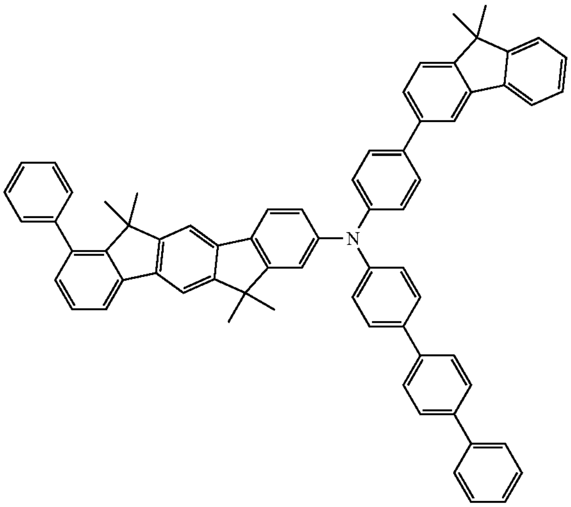
75
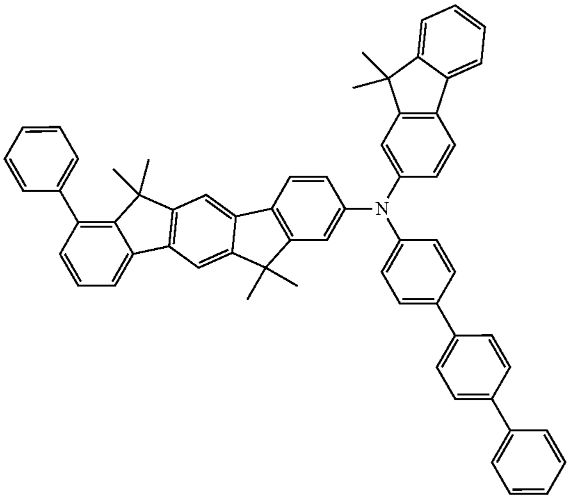
-continued
76
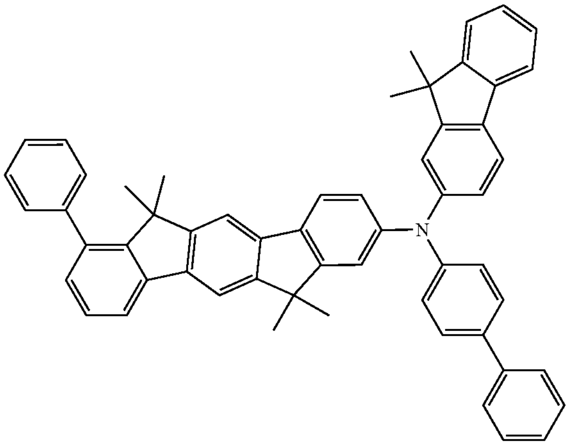
77
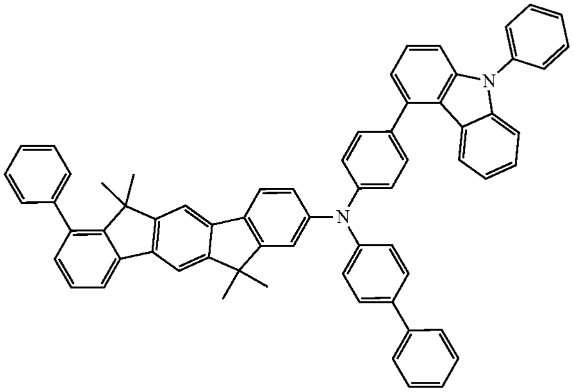
78
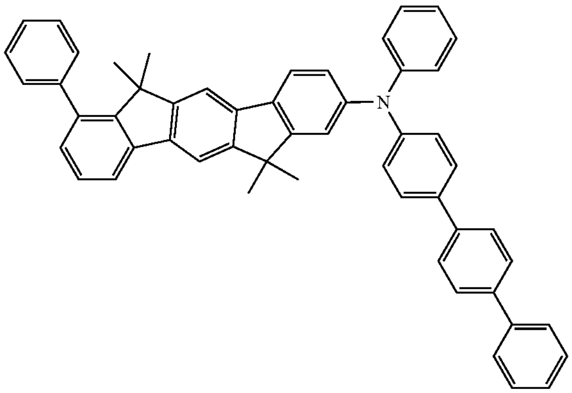

-continued
79
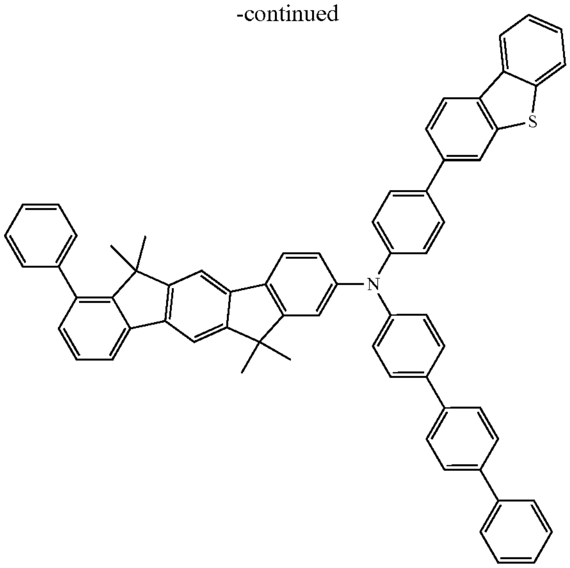
80
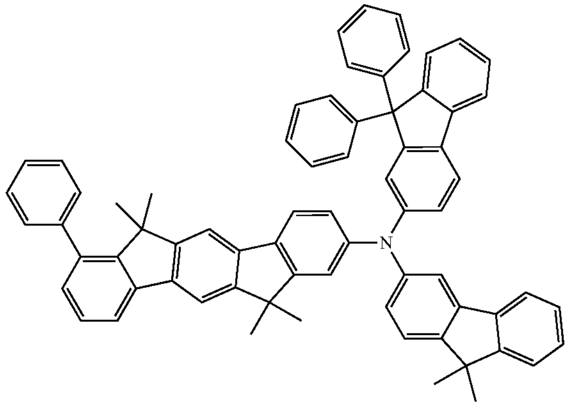
81
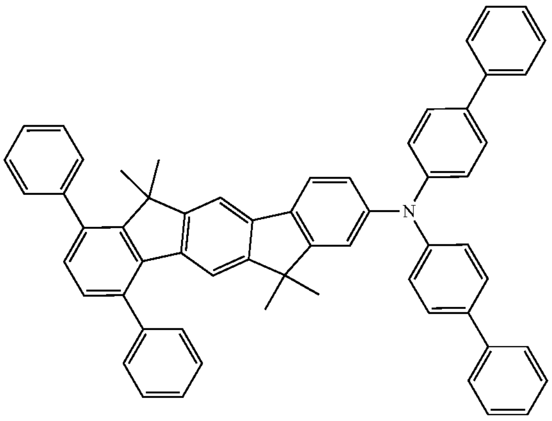
-continued
82
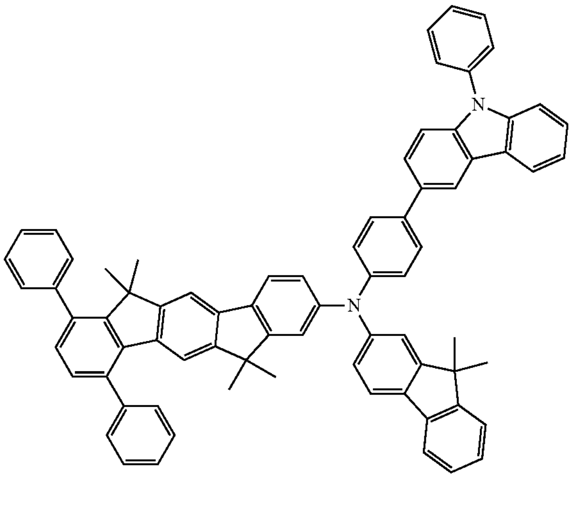
83
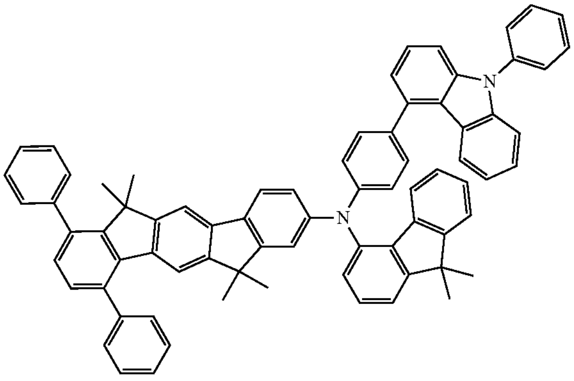

84
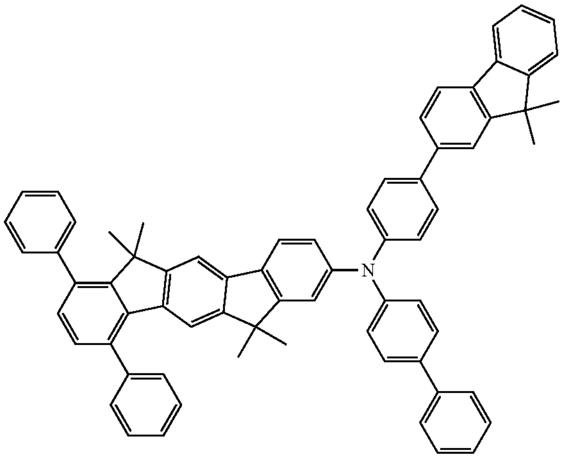
85
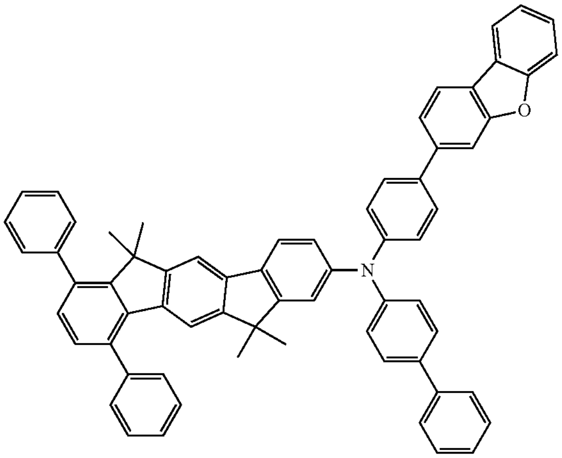
86
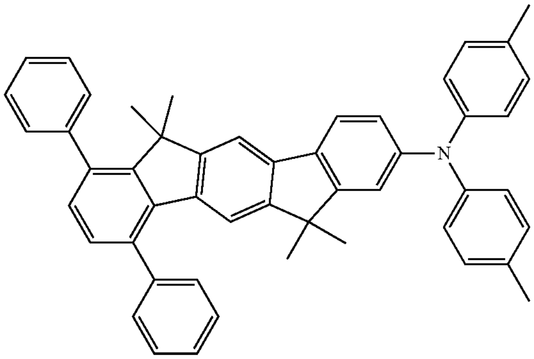
87
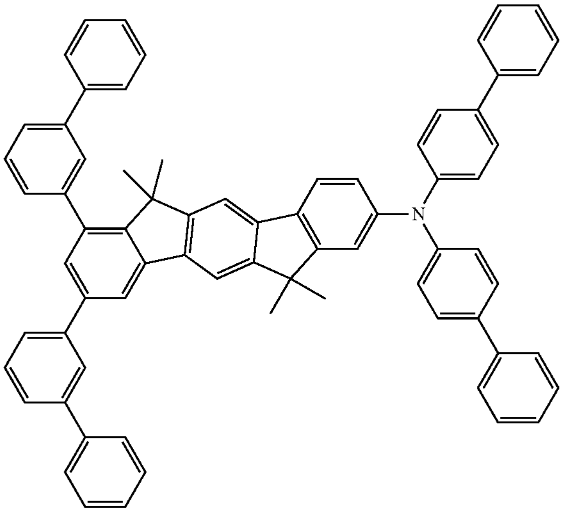
88
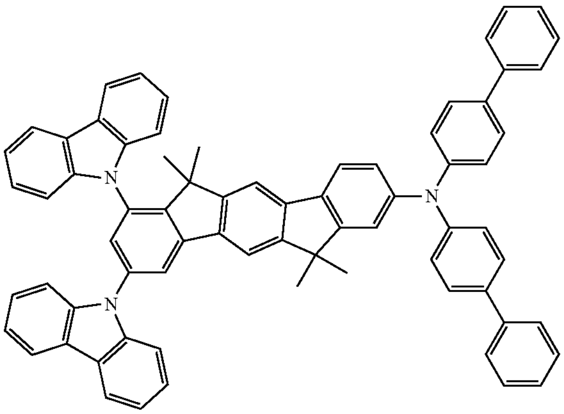
89
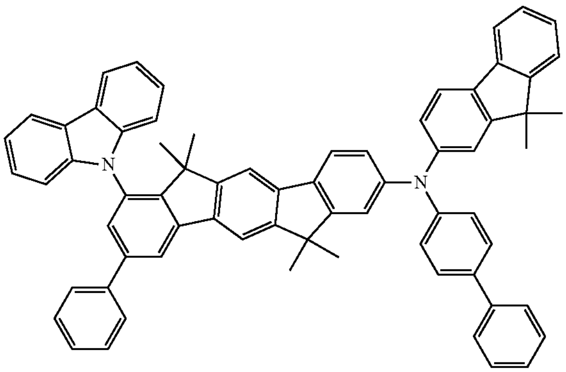

-continued
90
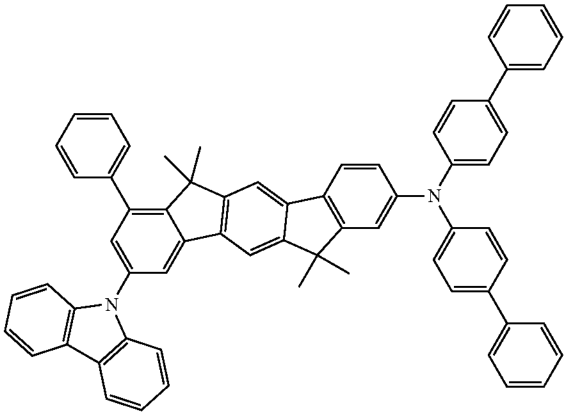
91
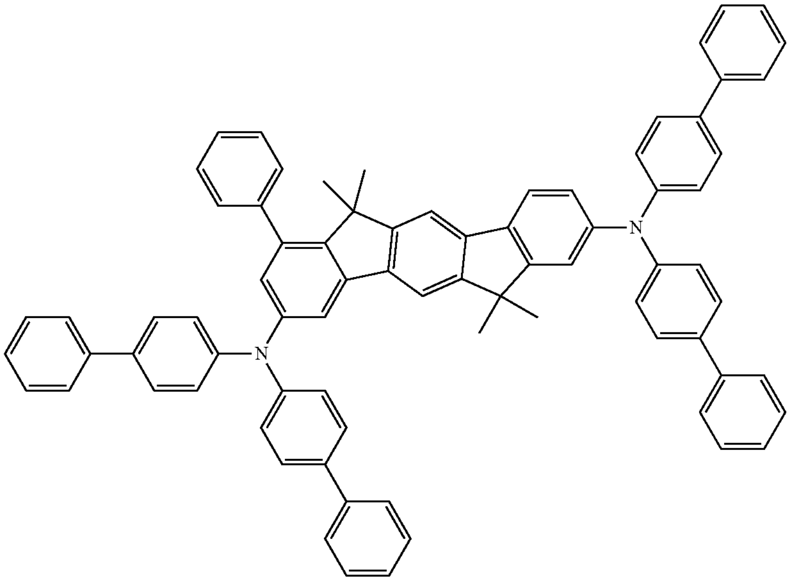
92
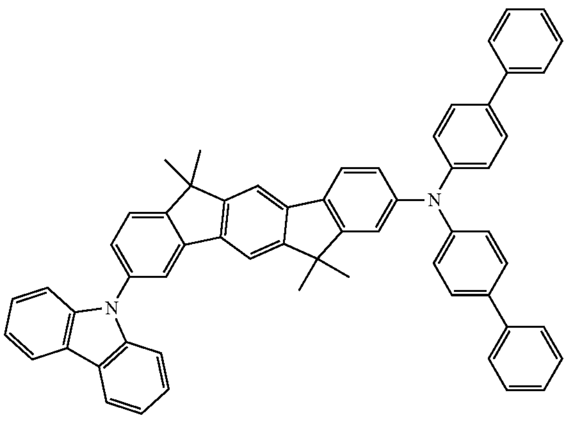
93
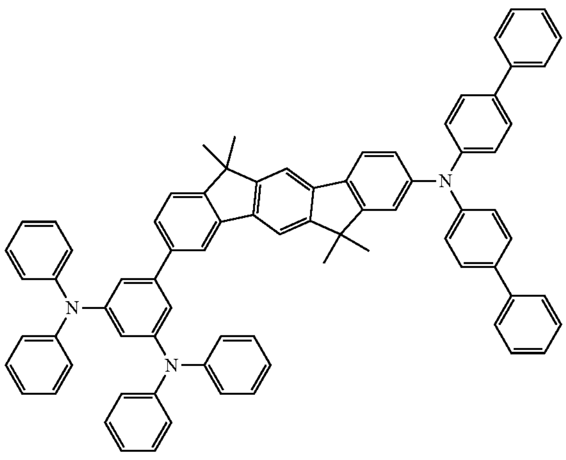

-continued
94
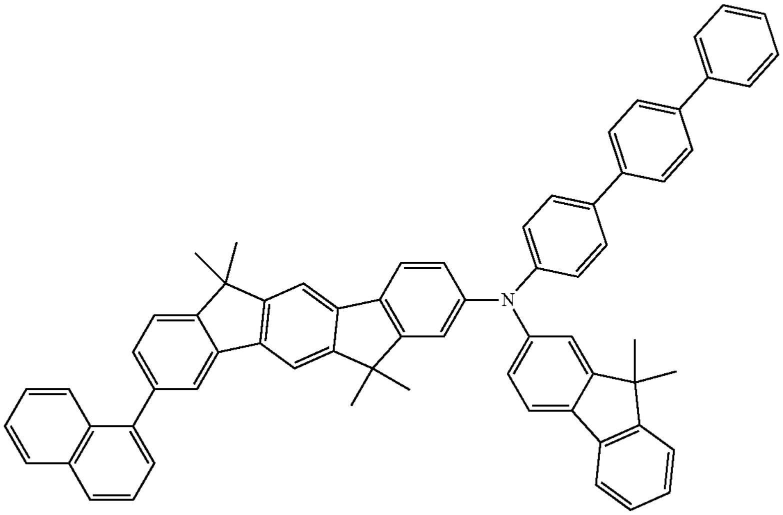
95
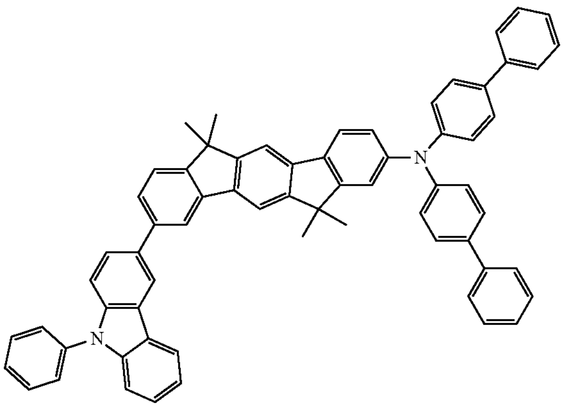
96
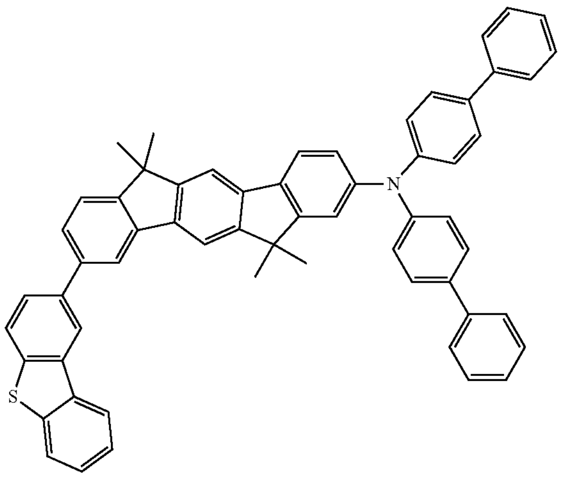
97
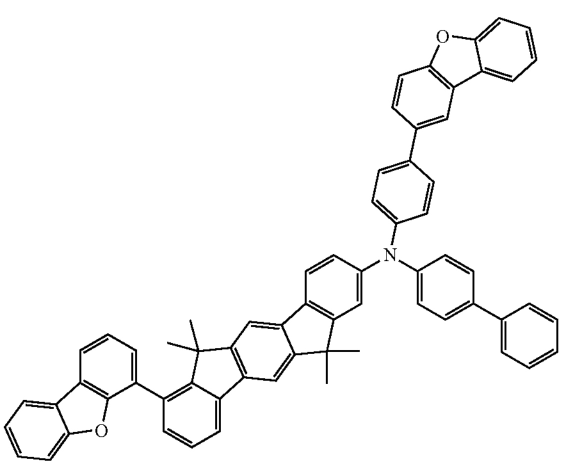
98
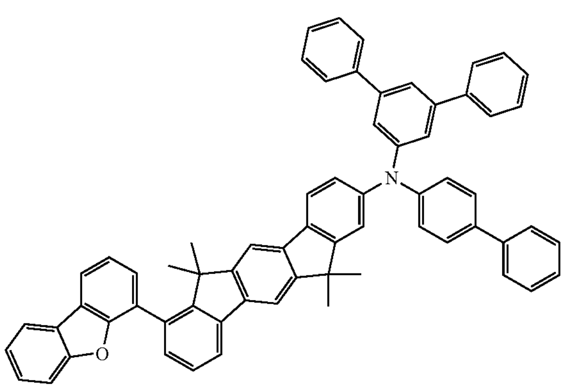

-continued
99
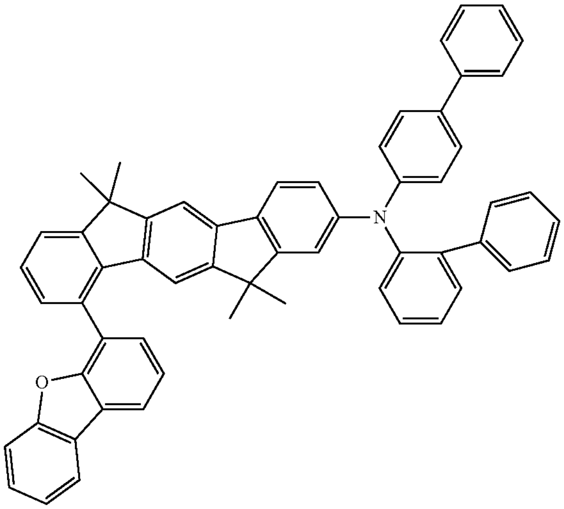
100
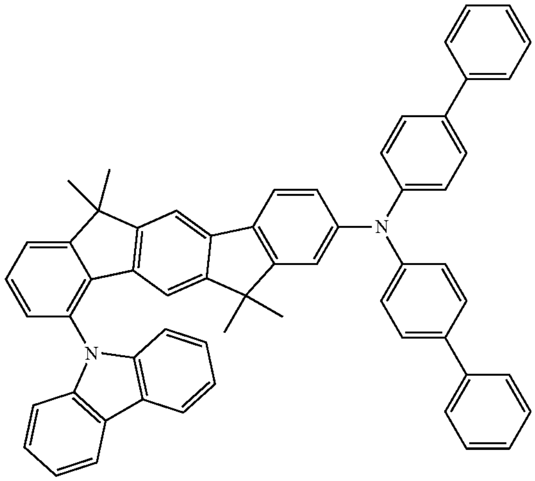
101
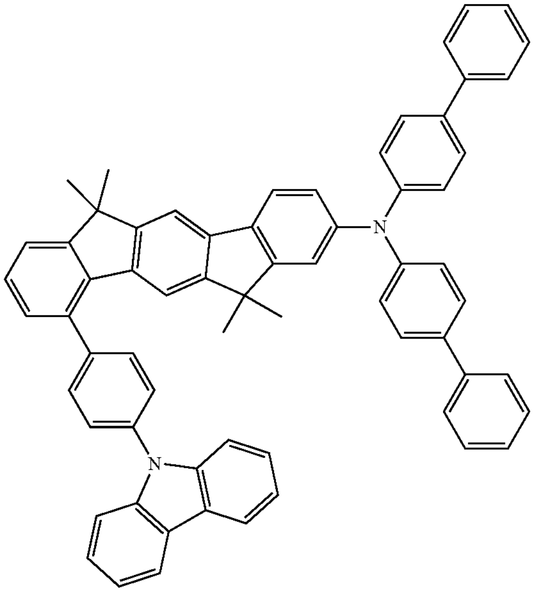
102
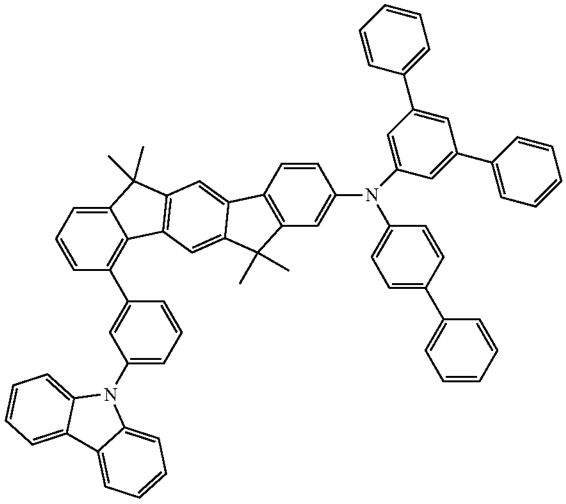

-continued
103
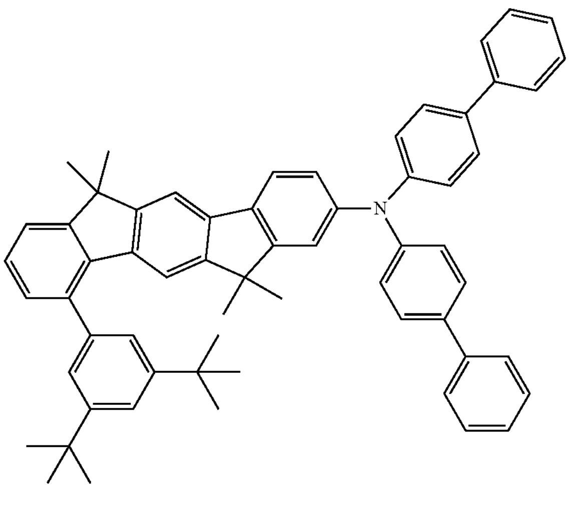
104
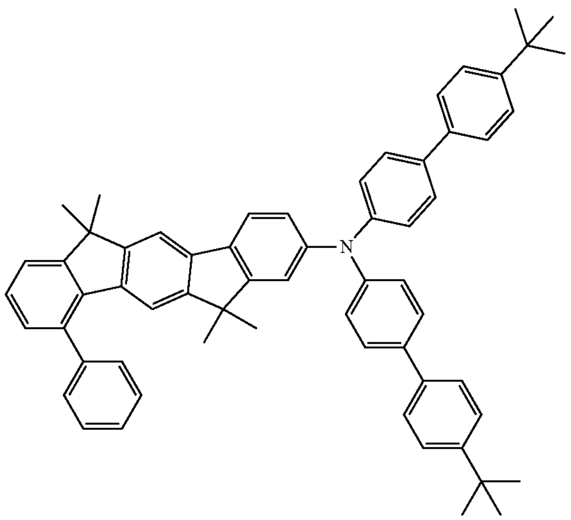
105
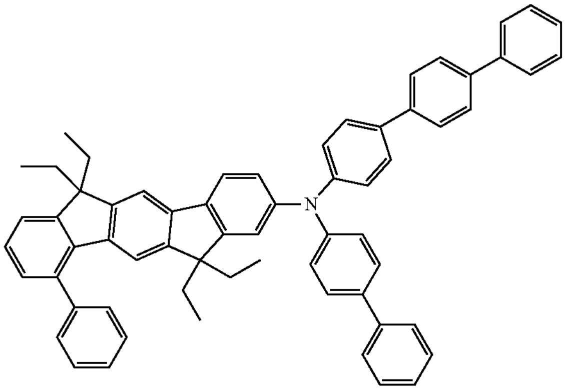
106
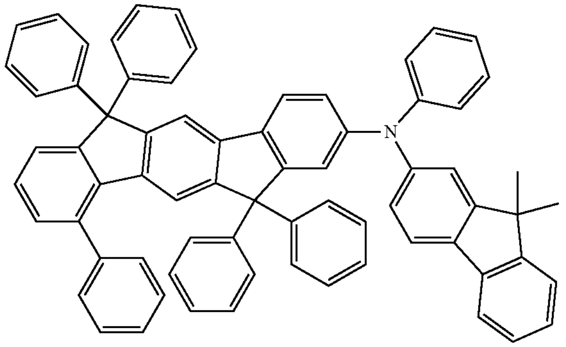
107
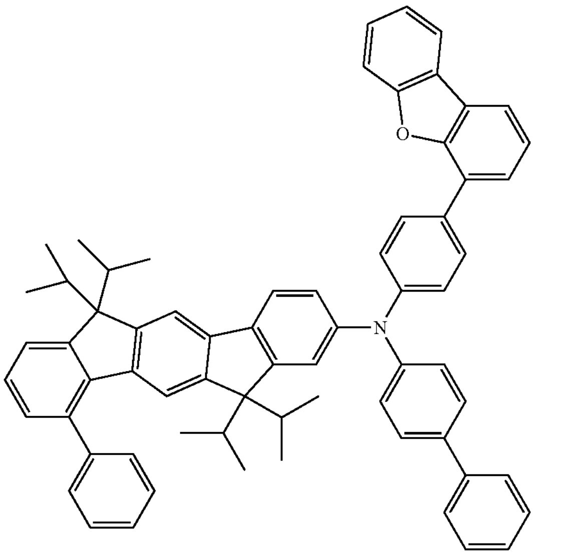
108
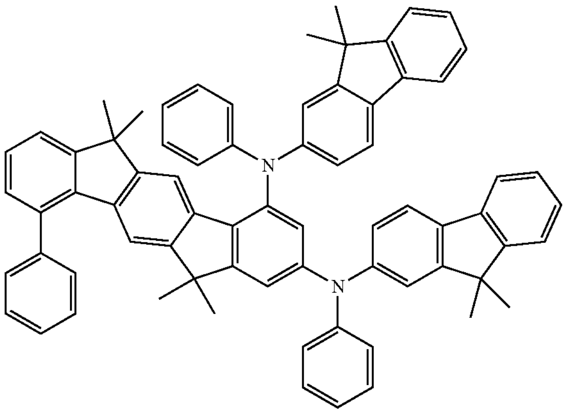

-continued
109
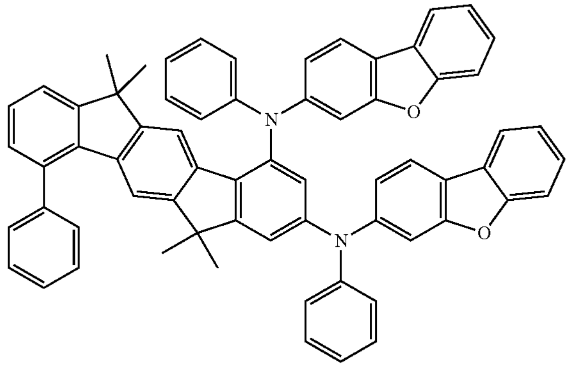
110
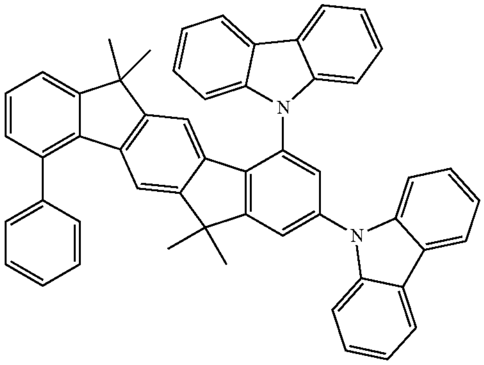
111
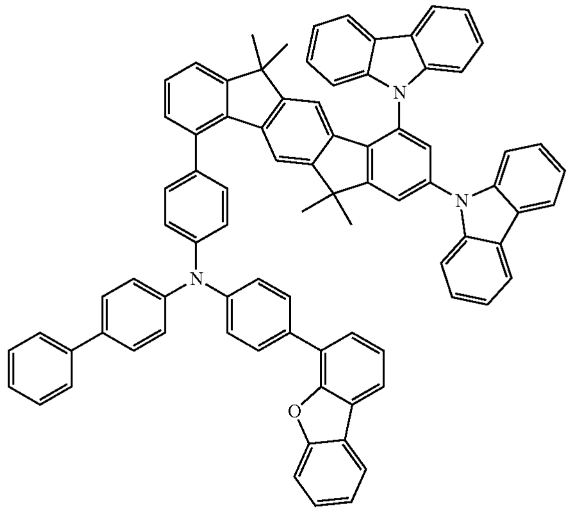
112
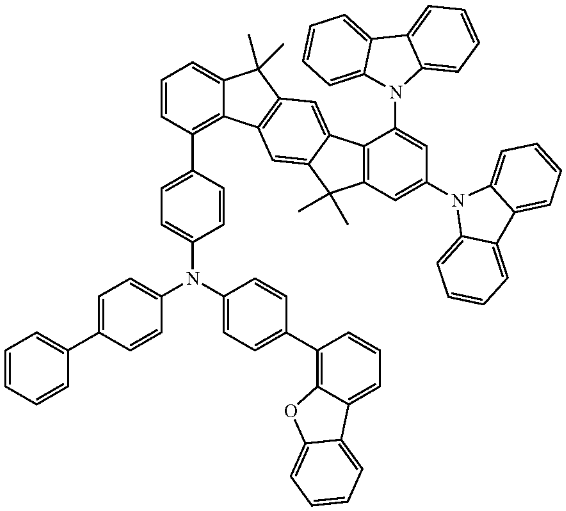
113
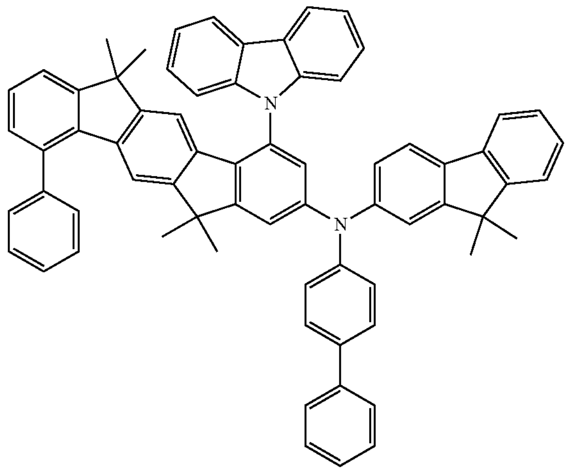
114
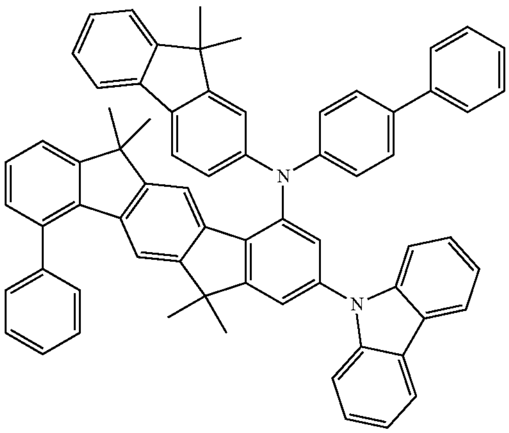

-continued
115
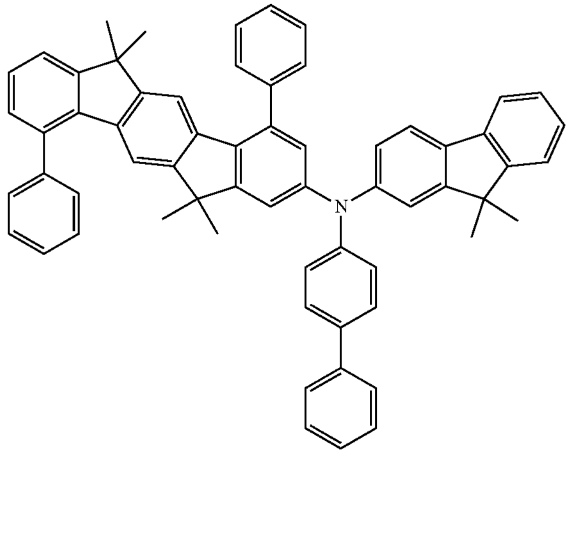
116
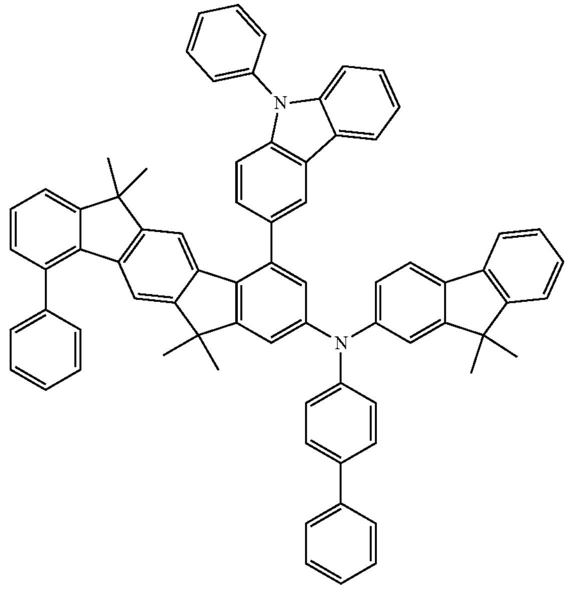
117
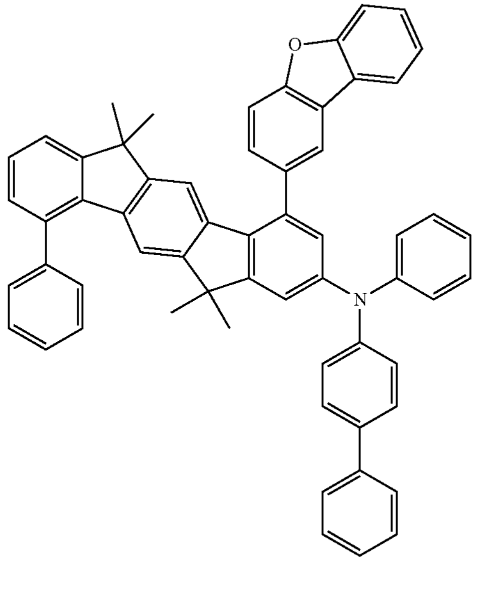
118
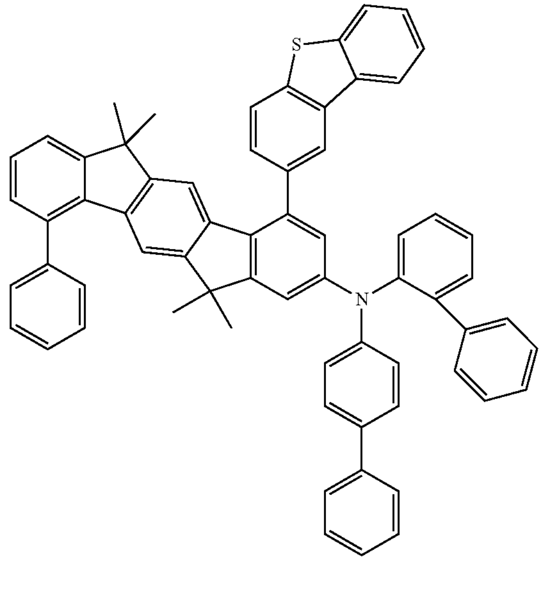

-continued
119
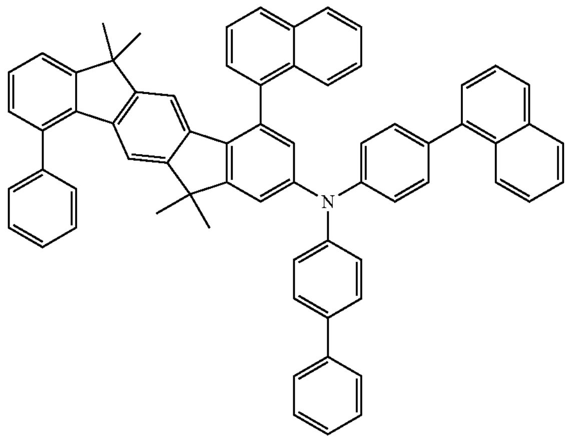
120
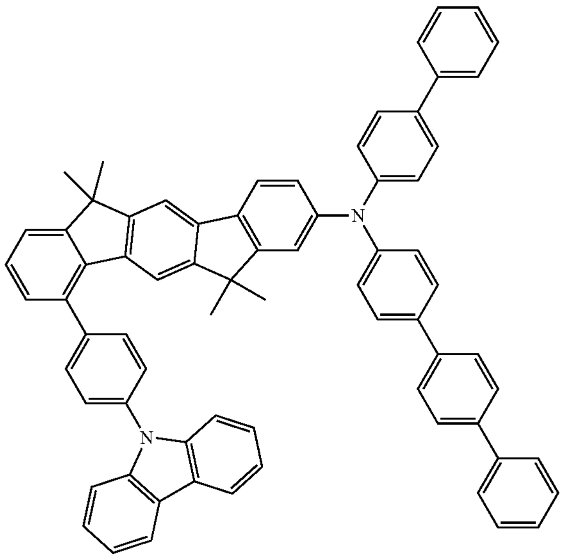
121
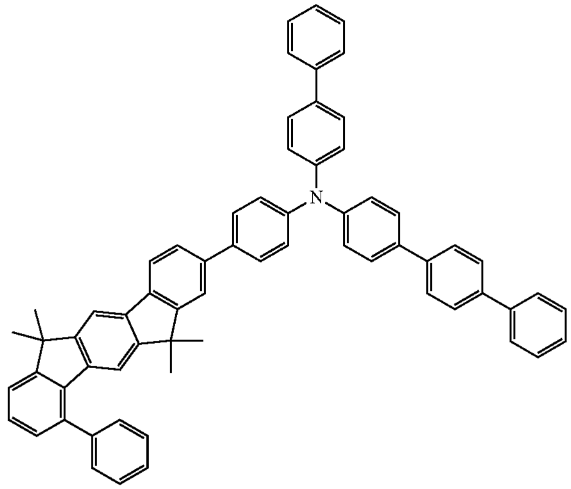
122
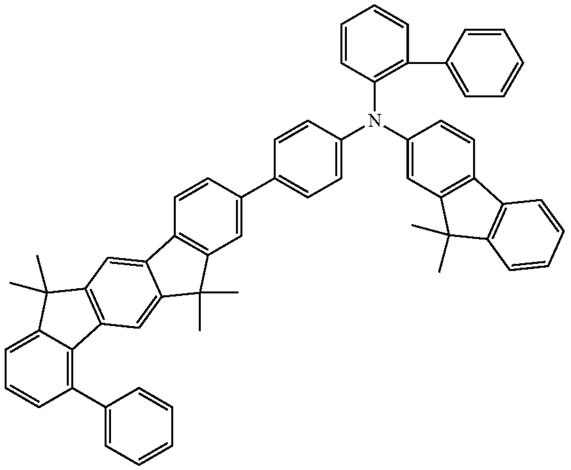
123
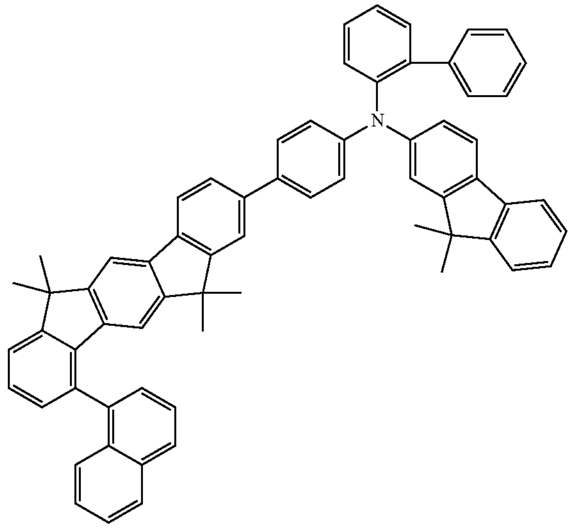
124
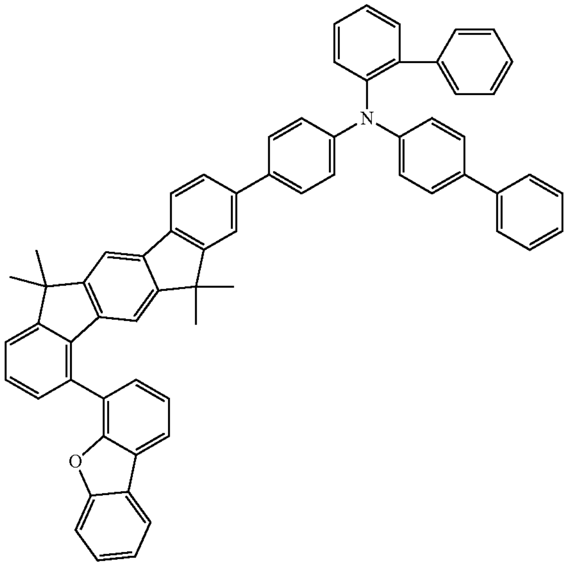

-continued
125
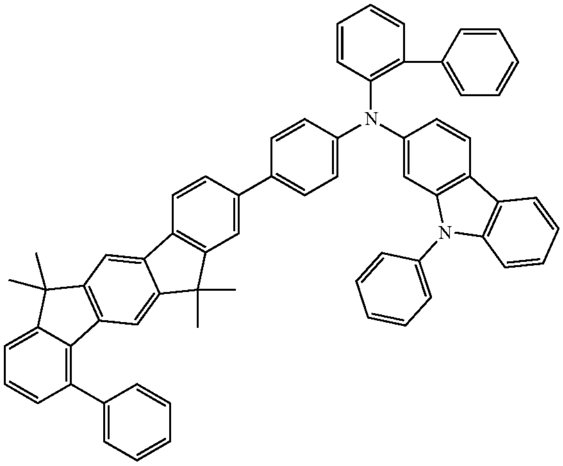
126
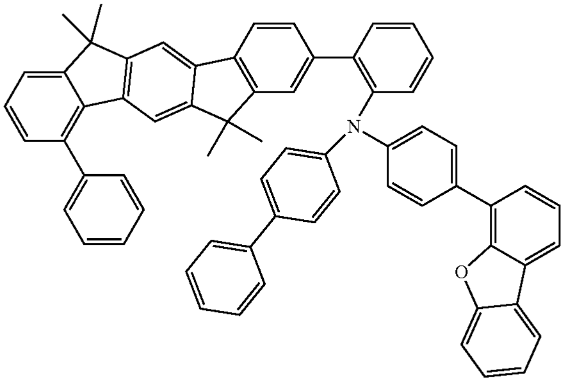
127
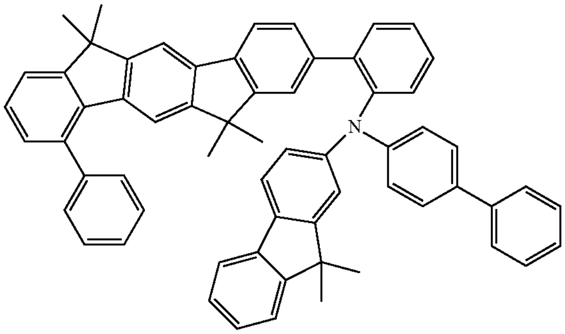
128
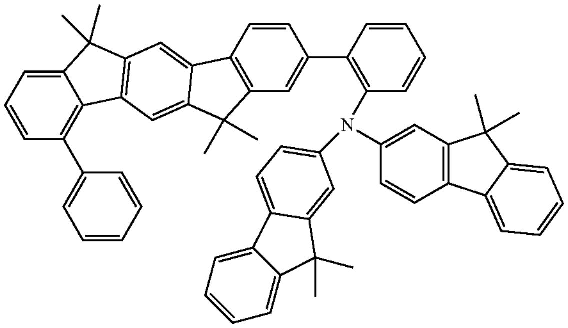
129
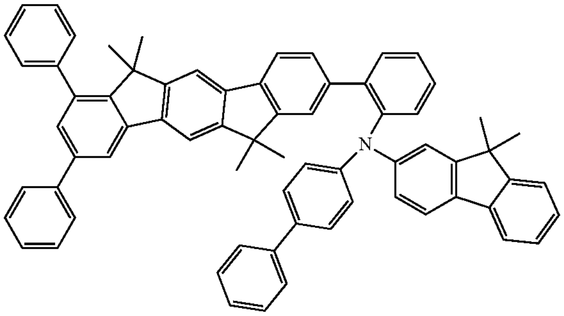
130
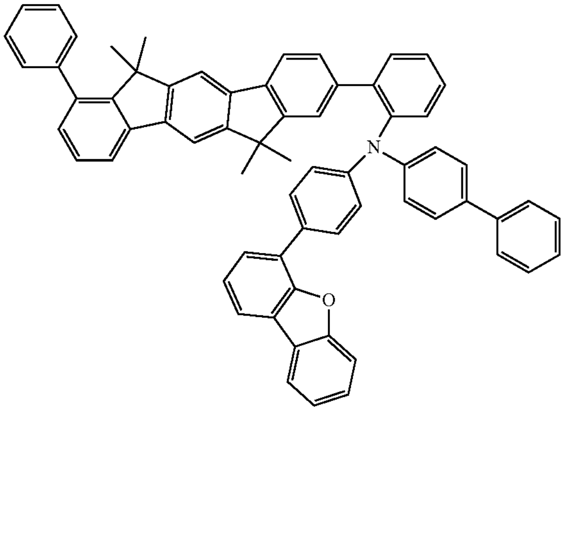

-continued
131
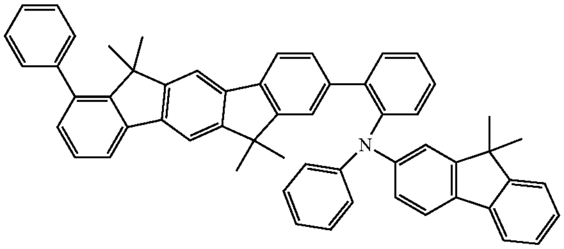
132
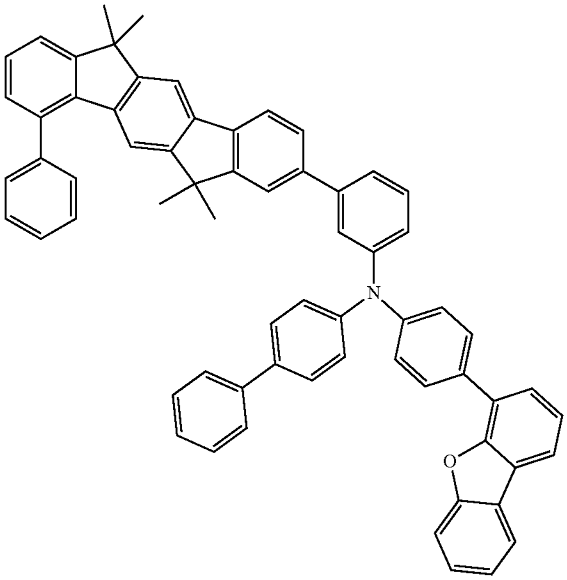
133
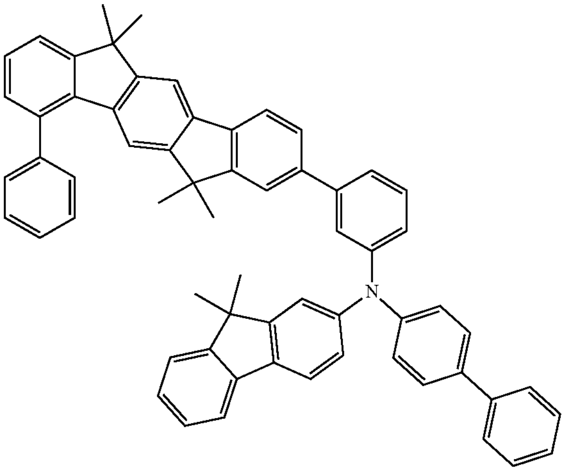
134
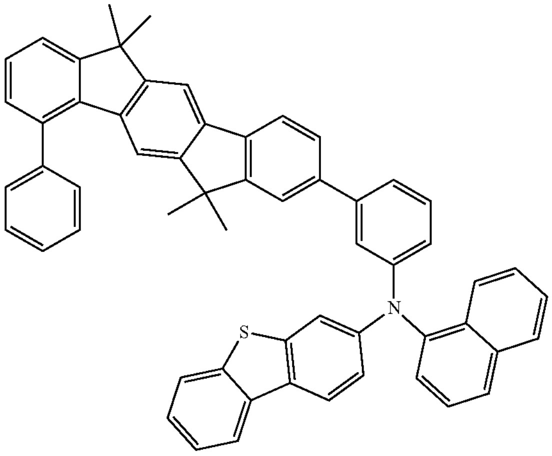
135
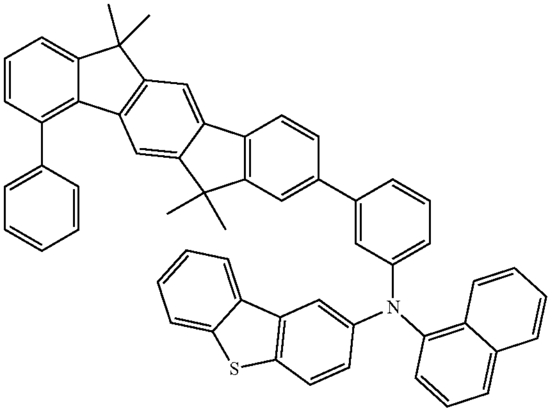
136
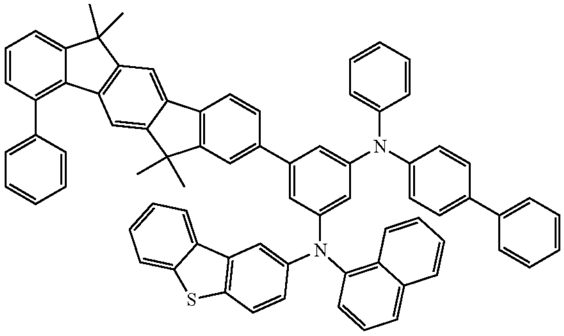

-continued
137
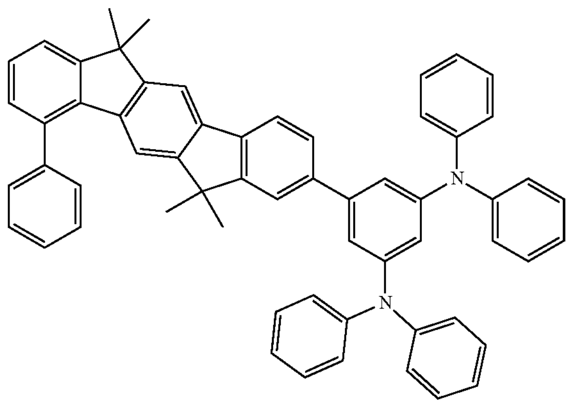
138
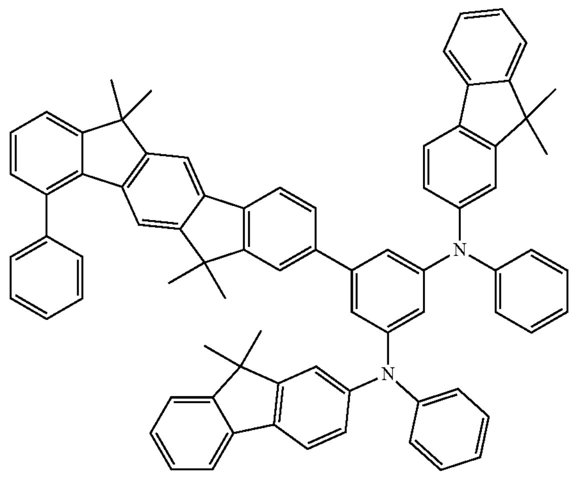
139
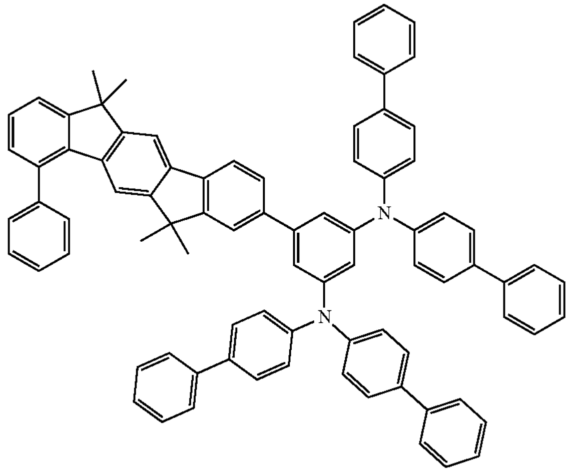
140
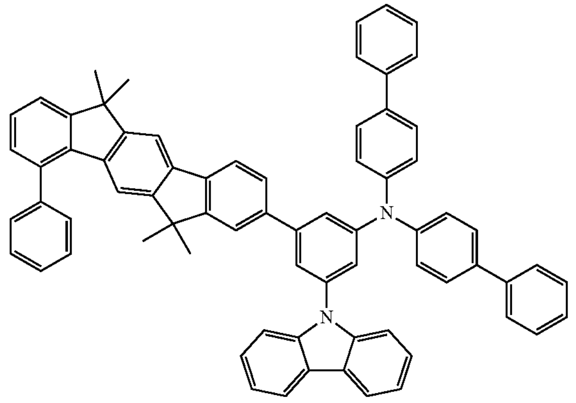
141
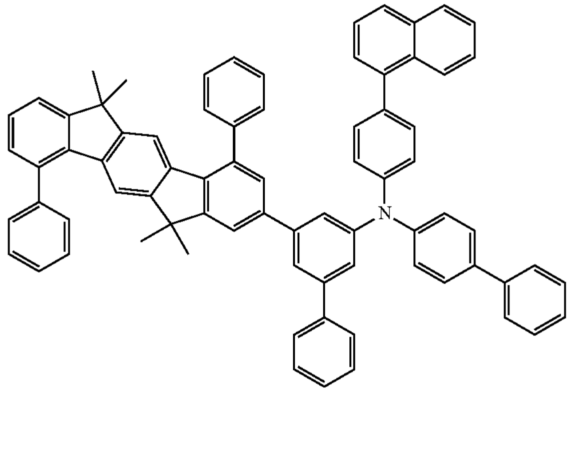
142
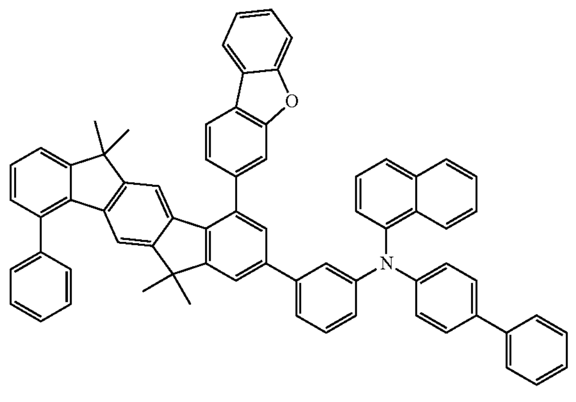

-continued
143
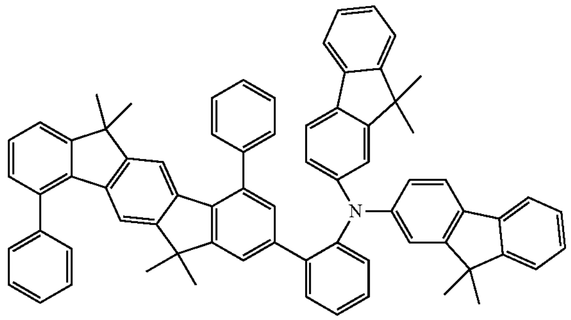
144
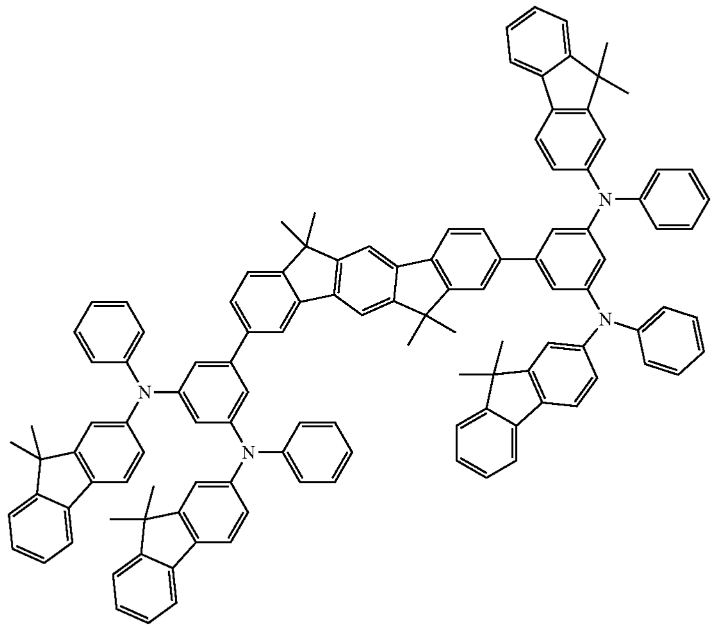
145
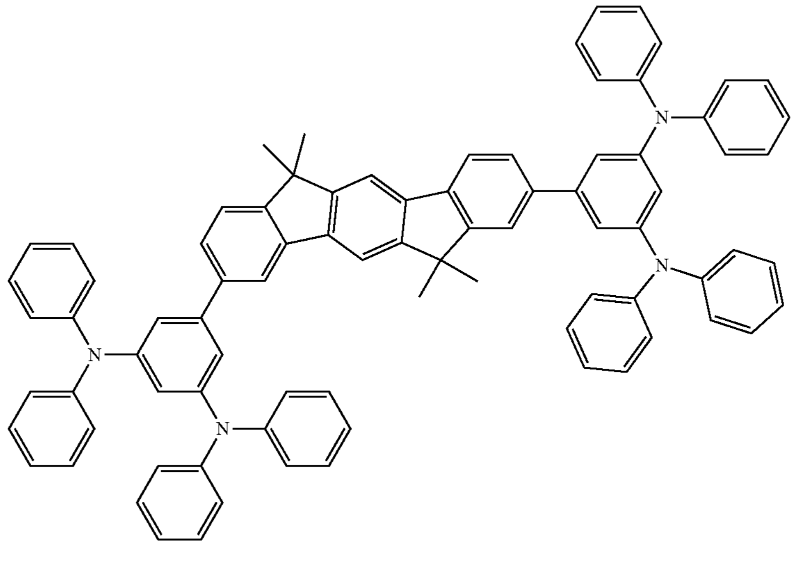

-continued
146
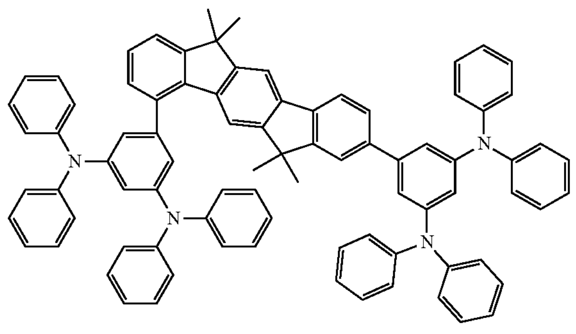
147
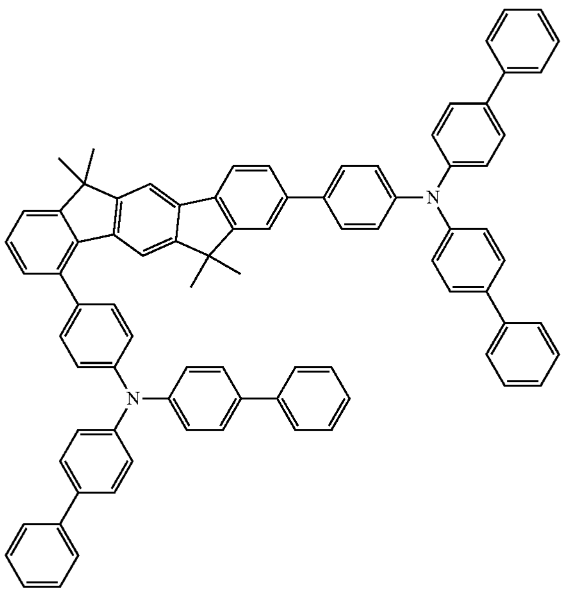
148
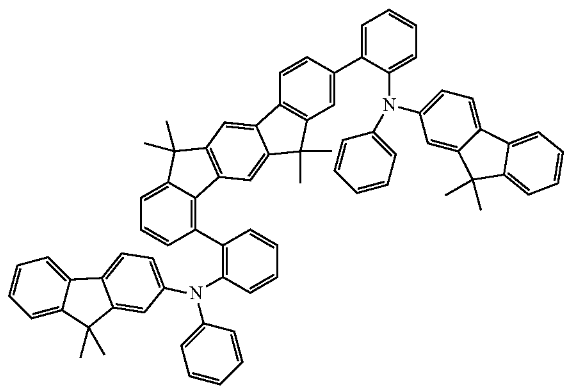
149
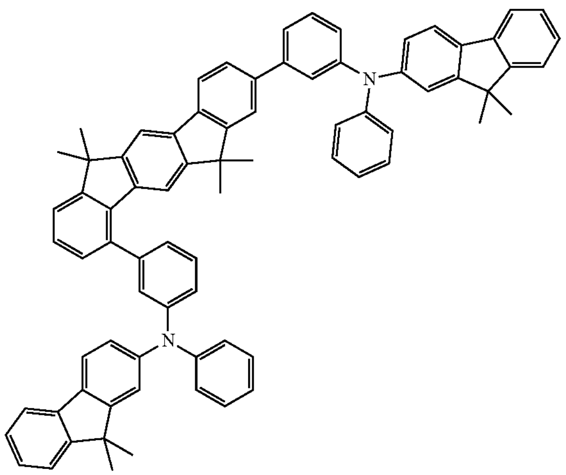
150
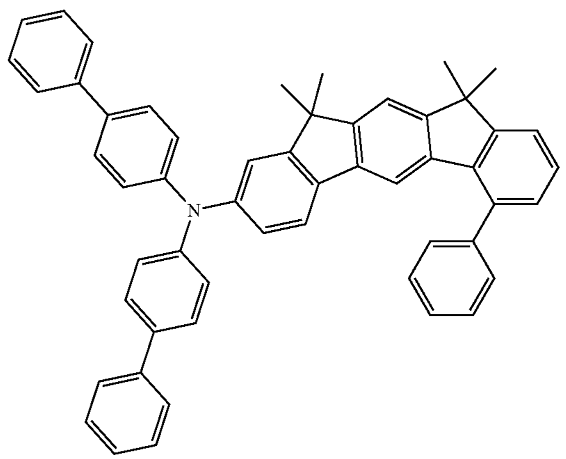
151
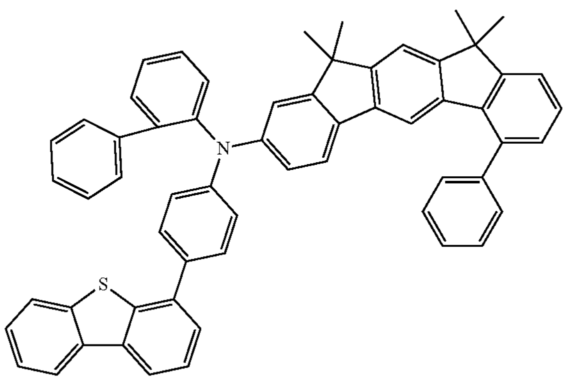

-continued
152
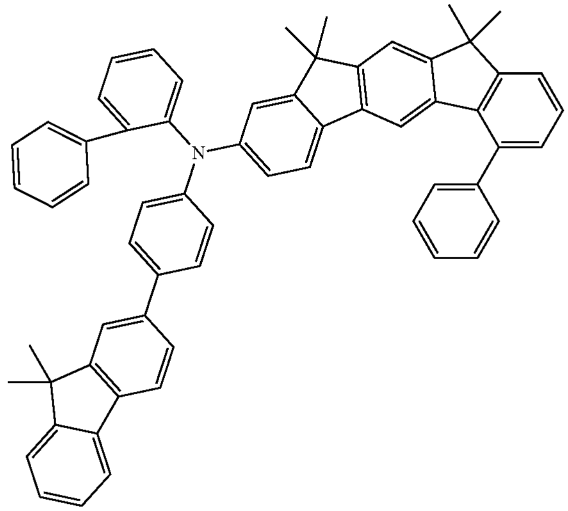
153
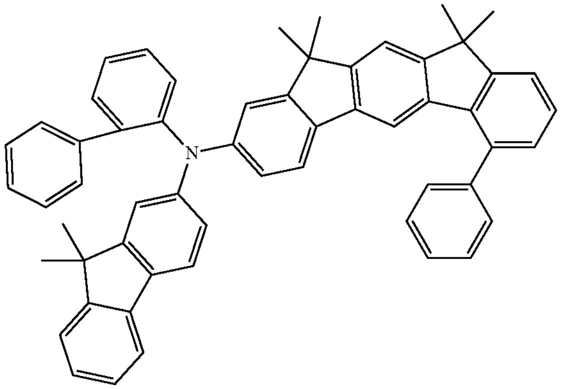
154
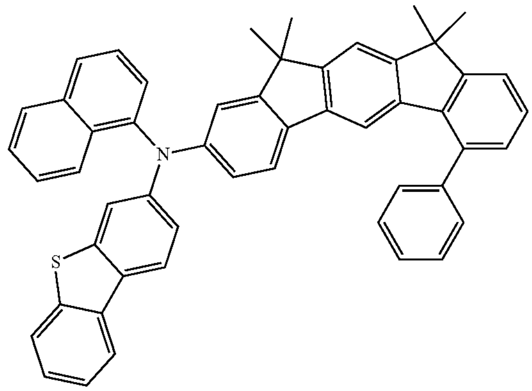
155
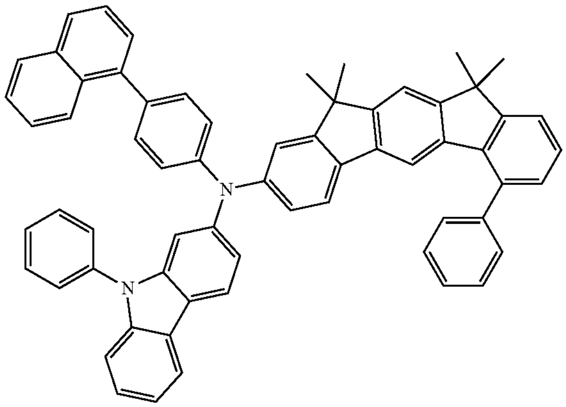
156
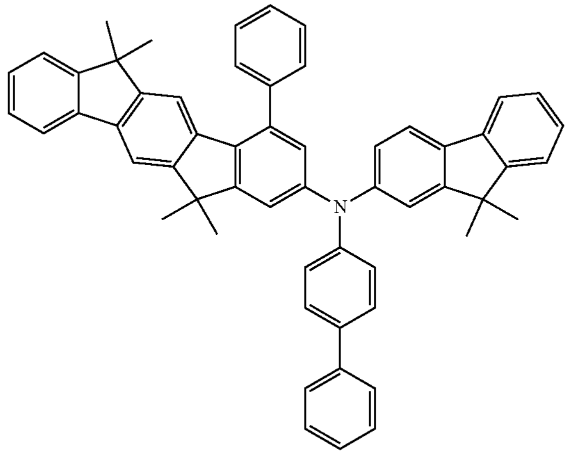
157
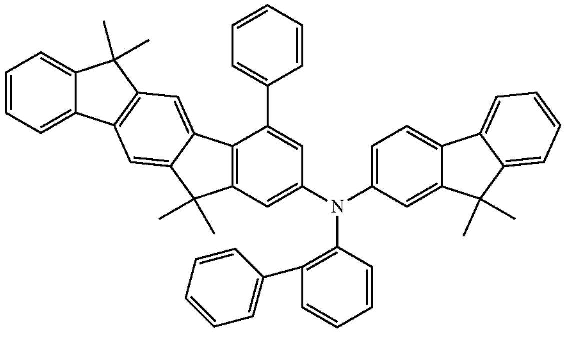

-continued
158
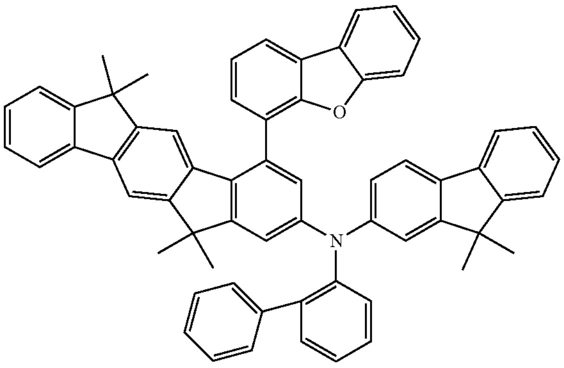
159
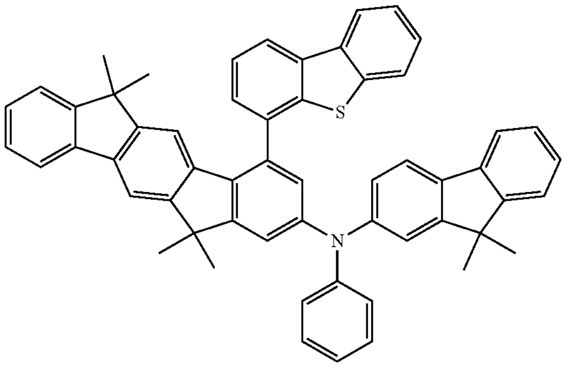
160
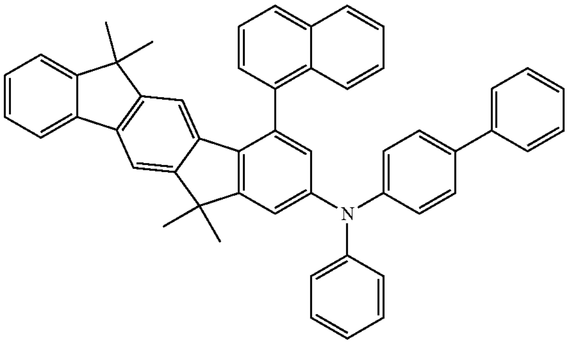
161
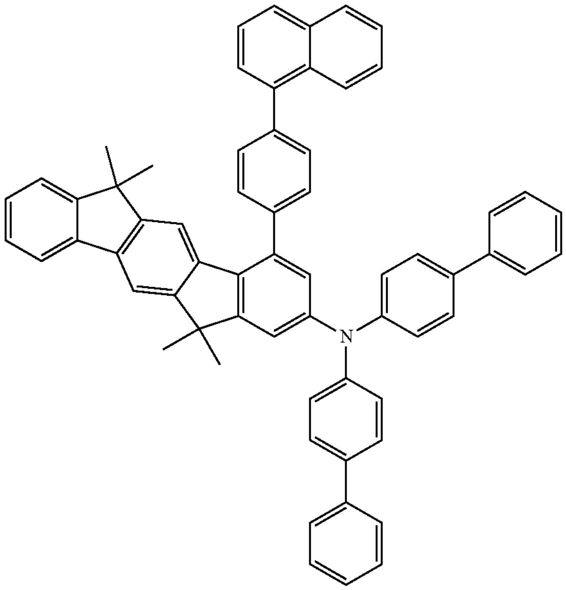
162
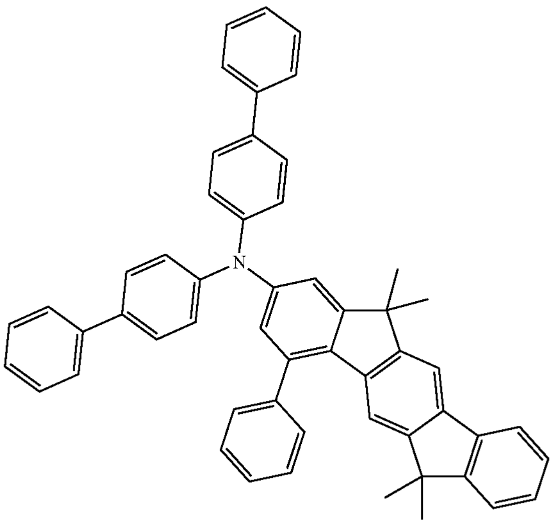
163
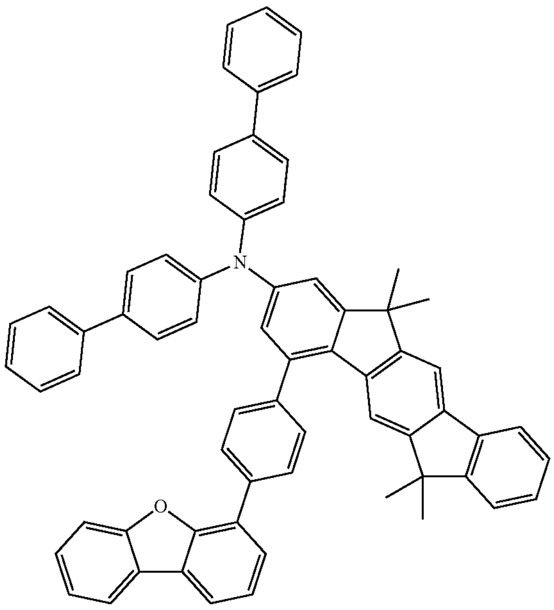

-continued
164
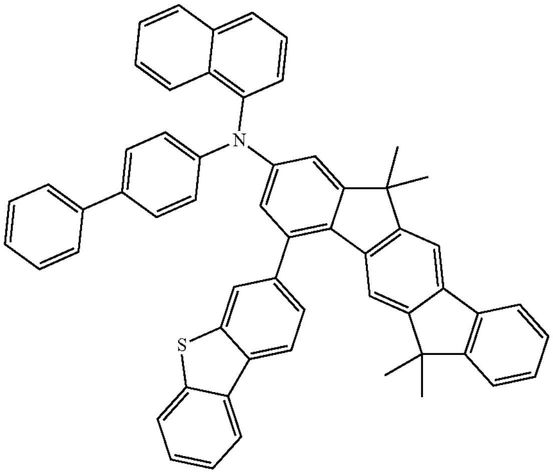
165
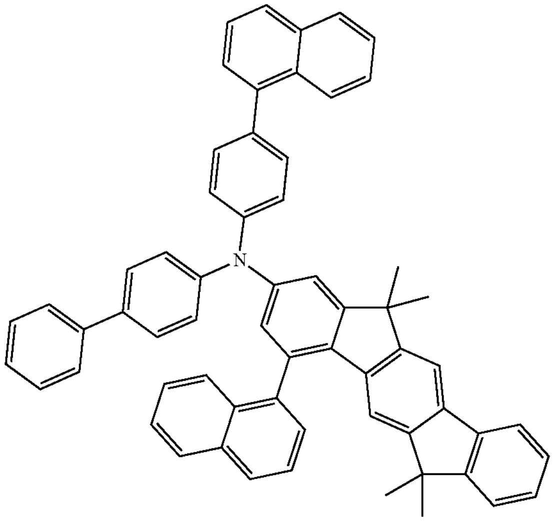
166
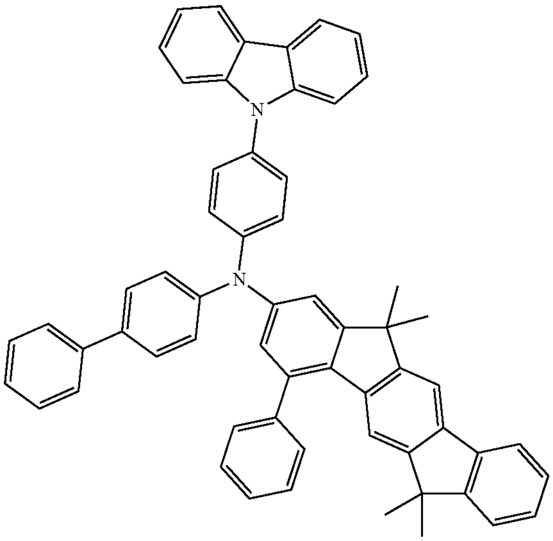
167
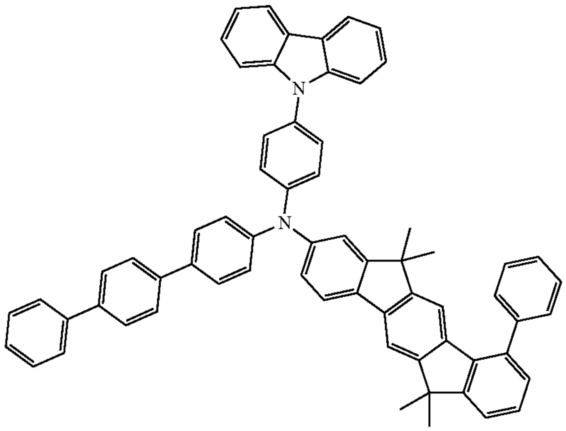

-continued
168
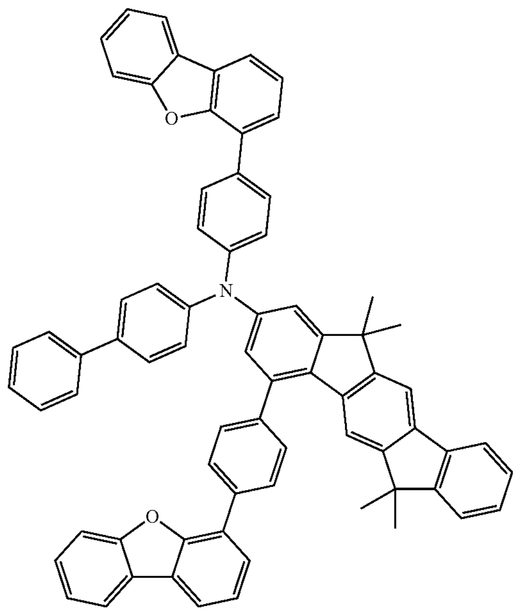
169
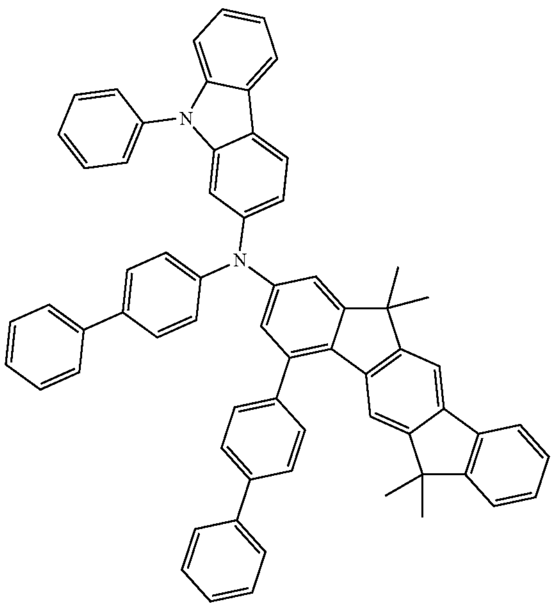
170
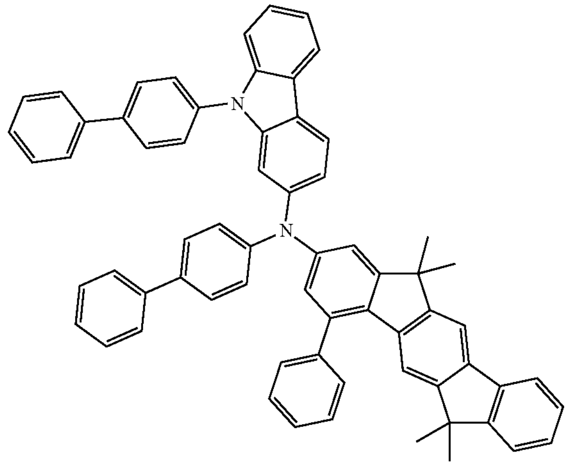
171
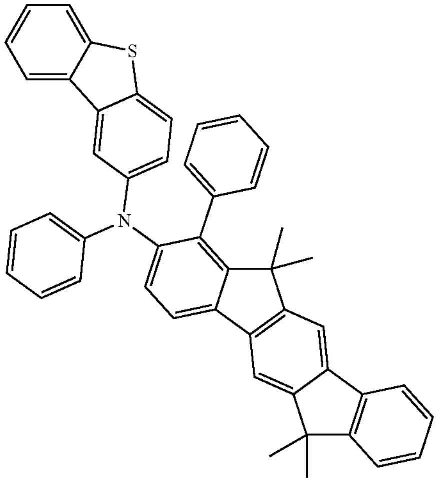
172
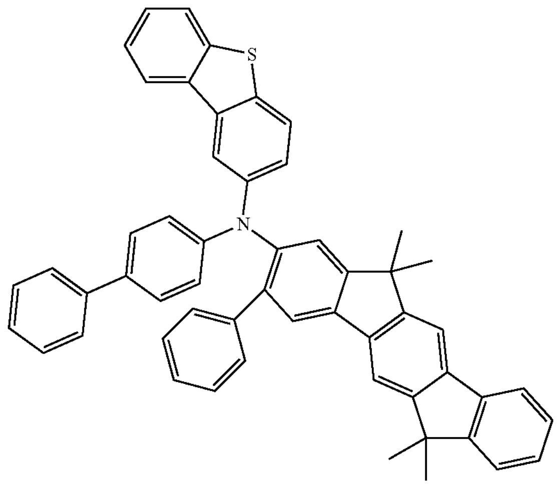
173
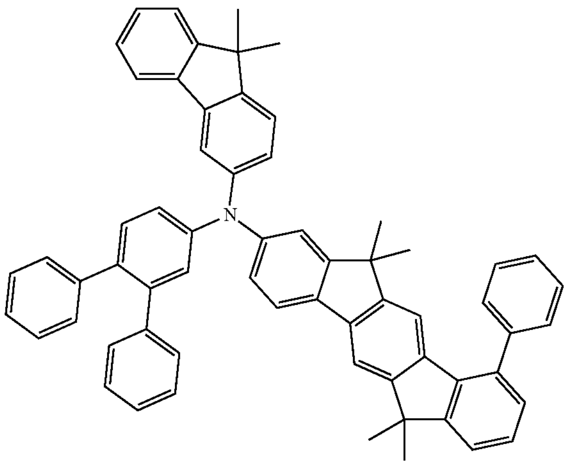

The compounds of formula (I) and (II) can be prepared by means of known organic reactions, especially by means of Suzuki reactions, Hartwig-Buchwald reactions, and cyclization reactions.

In a preferred process (Scheme 1), proceeding from a benzene compound bearing two reactive groups X and two carboxylic ester groups, via two sequential Suzuki couplings, an intermediate in which a benzene group having an amino group A is bonded to the central benzene group on one side and a benzene group having an aromatic Ar substituent is bonded on 10 the other side is prepared. The aromatic substituent is in the ortho or meta position to the bond between the two benzene groups.

Subsequently, the carboxylic ester groups of this compound are converted to tertiary alkoxy groups by reaction with a metal alkyl compound, preferably a lithium alkyl compound or a Grignard alkyl compound. These tertiary alkoxy groups cyclize to form rings under the action of acid, and so the compound of the formula (I) is obtained.

Scheme 1

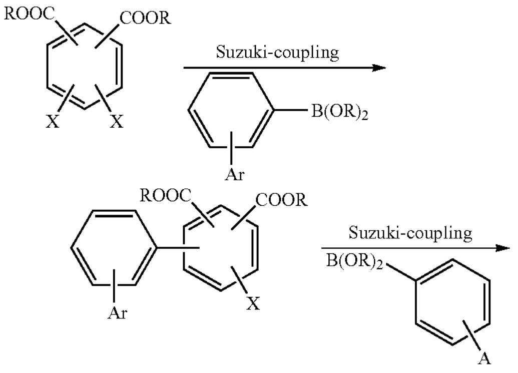

-continued

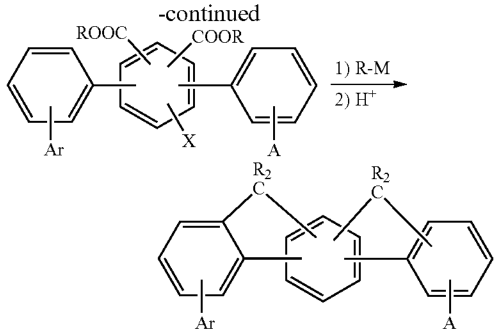

R: organic radical
Ar: aromatic or heteroaromatic ring system
A: $-Ar-NAr_2-$ or $-NAr_2$
M: Metal or metal halide
X: reactive group, preferably Cl, Br, or I In an alternative preferred process (Scheme 2), proceeding from a benzene compound bearing two reactive groups X and two carboxylic ester groups, via two sequential Suzuki couplings, an intermediate in which a benzene group having a reactive group X is bonded to the central benzene group on one side and a benzene group having an aromatic substituent Ar is bonded on the other side is prepared. The aromatic substituent is in the ortho or meta position to the bond between the two benzene groups.

Subsequently, the carboxylic ester groups of this compound are converted to tertiary alkoxy groups by reaction with a metal alkyl compound, preferably a lithium alkyl compound or a Grignard alkyl compound. These tertiary alkoxy groups cyclize to form rings under the action of acid. Finally, an amino group is introduced via a Buchwald coupling, or a diarylaminoaryl or a diarylaminoheteroaryl group is introduced by Suzuki reaction, such that the compound of the formula (I) is obtained.

Scheme 2

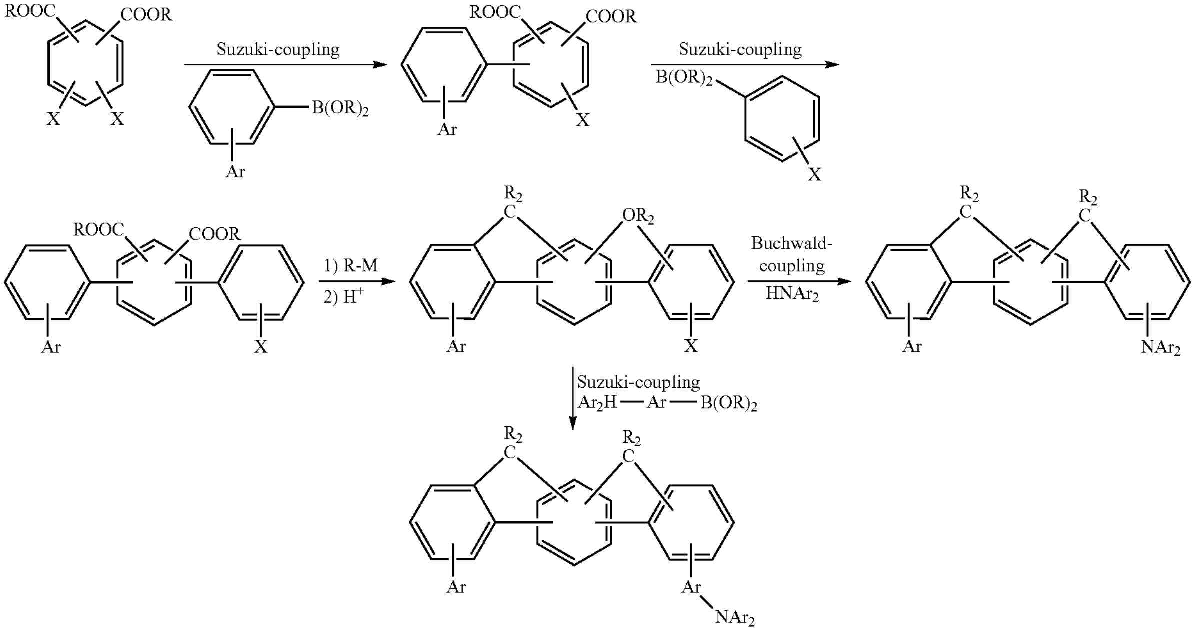

R: organic radical
Ar: aromatic or heteroaromatic ring system
M: Metal or metal halide
X: reactive group, preferably Cl, Br, or I In an alternative preferred process (Scheme 3), proceeding from a benzene compound bearing two reactive groups X and two carboxylic ester groups, via two sequential Suzuki couplings, an intermediate in which a benzene group having a reactive group X is bonded to the central benzene group on one side and a benzene group having an amino group A is bonded on the other side is prepared. The reactive group X is in the ortho or meta position to the bond between the two benzene groups.

Subsequently, the carboxylic ester groups of this compound are converted to tertiary alkoxy groups by reaction with a metal alkyl compound, preferably a lithium alkyl compound or a Grignard alkyl compound. These tertiary alkoxy groups cyclize to form rings under the action of acid. Finally, via a Suzuki reaction, an aromatic substituent Ar is introduced, and so the compound of the formula (I) is obtained.

Scheme 3

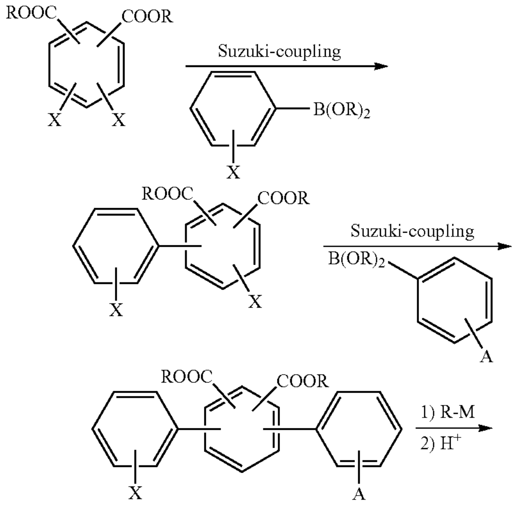

-continued

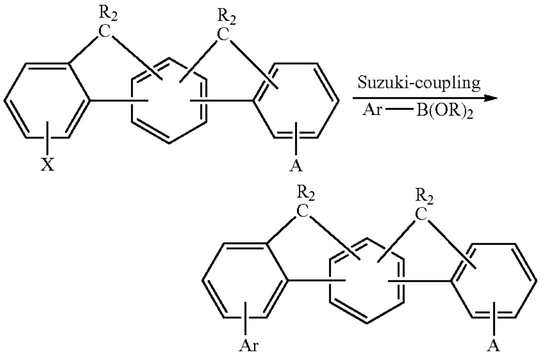

R: organic radical
Ar: aromatic or heteroaromatic ring system
A: —Ar—$NAr_2$— or —$NAr_2$
M: Metal or metal halide
X: reactive group, preferably Cl, Br, or I A preferred process for preparing compounds of formula (II) is shown in Scheme 4 below. In this case, firstly, proceeding from a benzene compound bearing two reactive groups X and two carboxylic ester groups, via two sequential Suzuki couplings, an intermediate in which a benzene group is bonded to the central benzene group on one side and a benzene group having two reactive X groups is bonded on the other side is prepared. At least one of the two reactive groups X is in the ortho or meta position to the bond between the two benzene groups. Subsequently, the carboxylic ester groups of this compound are converted to tertiary alkoxy groups by reaction with a metal alkyl compound, preferably a lithium alkyl compound or a Grignard alkyl compound. These tertiary alkoxy groups cyclize to form rings under the action of acid. Then an amino group is introduced via a Buchwald coupling, or a diarylaminoaryl or a diarylaminoheteroaryl group is introduced by Suzuki reaction. Finally, via a Suzuki reaction, an aromatic substituent Ar is introduced, and so the compound of the formula (II) is obtained.

Scheme 4

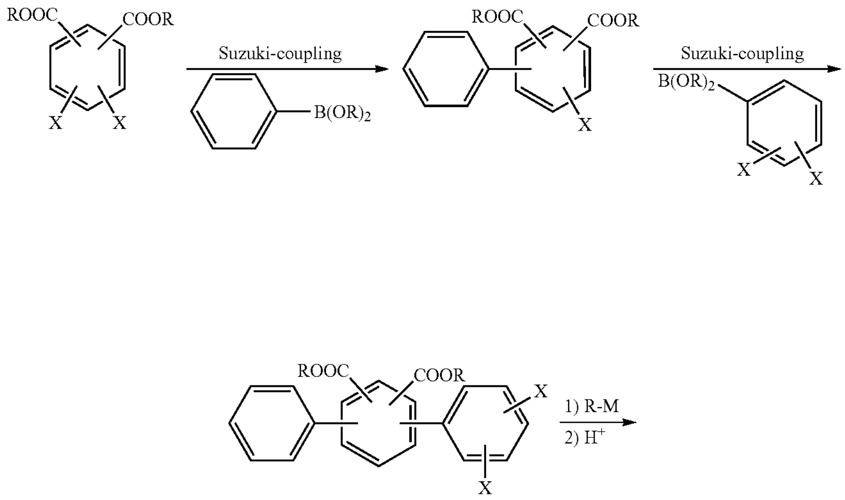

-continued

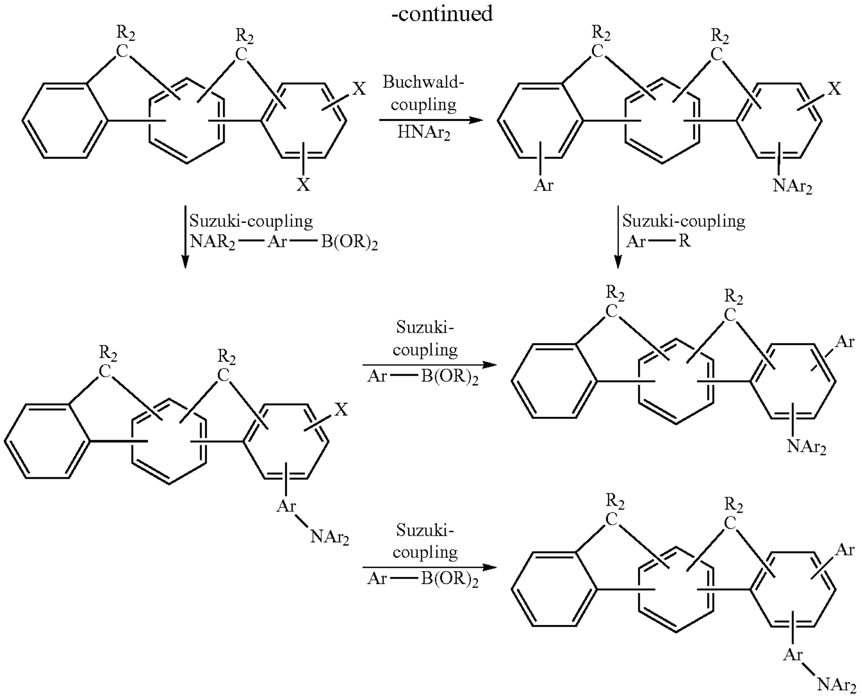

R: organic radical
Ar: aromatic or heteroaromatic ring system
M: Metal or metal halide
X: reactive group, preferably Cl, Br, or I The present application thus further provides a process for preparing a compound of formula (I) or (II), characterized in that a benzene compound that bears two carboxylic ester groups and at least one reactive group is reacted with a benzene compound that contains a boronic acid group and at least one group selected from reactive groups X and aromatic or heteroaromatic groups Ar. In this case, the boronic acid group and the at least one group selected from X and Ar groups are in ortho or meta positions to one another on the benzene ring.

Preferably, the X group is selected from Cl, Br, I, mesylate and tosylate. Preferably, the reaction in which the benzene compound that bears two carboxylic ester groups and two reactive groups is reacted with the benzene compound that contains a boronic acid group and a group selected from reactive groups X and aromatic or heteroaromatic groups Ar is a Suzuki reaction.

The above-described compounds, especially compounds substituted by reactive leaving groups, such as bromine, iodine, chlorine, boronic acid or boronic ester, may find use as monomers for production of corresponding oligomers, dendrimers or polymers. Suitable reactive leaving groups are, for example, bromine, iodine, chlorine, boronic acids, boronic esters, amines, alkenyl or alkynyl groups having a terminal C—C double bond or C—C triple bond, oxiranes, oxetanes, groups which enter into a cycloaddition, for example a 1,3-dipolar cycloaddition, for example dienes or azides, carboxylic acid derivatives, alcohols and silanes.

The invention therefore further provides oligomers, polymers or dendrimers containing one or more compounds of formula (I) or (II), wherein the bond(s) to the polymer, oligomer or dendrimer may be localized at any desired positions substituted by $R^1$, $R^2$, $R^3$, $R^4$ or $R^5$ in formula (I) or (II). According to the linkage of the compound, the compound is part of a side chain of the oligomer or polymer or part of the main chain. An oligomer in the context of this invention is understood to mean a compound formed from at least three monomer units. A polymer in the context of the invention is understood to mean a compound formed from at least ten monomer units. The polymers, oligomers or dendrimers of the invention may be conjugated, partly conjugated or nonconjugated. The oligomers or polymers of the invention may be linear, branched or dendritic. In the structures having linear linkage, the units of formula (I) or (II) may be joined directly to one another, or they may be joined to one another via a bivalent group, for example via a substituted or unsubstituted alkylene group, via a heteroatom or via a bivalent aromatic or heteroaromatic group. In branched and dendritic structures, it is possible, for example, for three or more units of formula (I) or (II) to be joined via a trivalent or higher-valency group, for example via a trivalent or higher-valency aromatic or heteroaromatic group, to give a branched or dendritic oligomer or polymer.

For the repeat units of formula (I) or (II) in oligomers, dendrimers and polymers, the same preferences apply as described above for compounds of formula (I) or (II).

For preparation of the oligomers or polymers, the monomers of the invention are homopolymerized or copolymerized with further monomers. Suitable and preferred comonomers are selected from fluorenes, spirobifluorenes, paraphenylenes, carbazoles, thiophenes, dihydrophenanthrenes, cis- and trans-indenofluorenes, ketones, phenanthrenes or else two or more of these units. The polymers, oligomers and dendrimers typically contain still further units, for example emitting (fluorescent or phosphorescent) units, for example vinyltriarylamines or phosphorescent metal complexes, and/or charge transport units, especially those based on triarylamines.

The polymers and oligomers of the invention are generally prepared by polymerization of one or more monomer types, of which at least one monomer leads to repeat units of the formula (I) or (II) in the polymer. Suitable polymerization reactions are known to those skilled in the art and are described in the literature. Particularly suitable and preferred polymerization reactions which lead to formation of C—C or C—N bonds are the Suzuki polymerization, the Yamamoto polymerization, the Stille polymerization and the Hartwig-Buchwald polymerization.

For the processing of the compounds of the invention from a liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl) ethane or mixtures of these solvents.

The invention therefore further provides a formulation, especially a solution, dispersion or emulsion, comprising at least one compound of formula (I) or (II) and at least one solvent, preferably an organic solvent. The way in which such solutions can be prepared is known to those skilled in the art.

The compounds of the invention are suitable for use in electronic devices, especially in organic electroluminescent devices (OLEDs). Depending on the substitution, the compounds are used in different functions and layers.

The invention therefore further provides for the use of the compound of formula (I) or (II) in an electronic device. This electronic device is preferably selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and more preferably organic electroluminescent devices (OLEDs).

The invention further provides, as already set out above, an electronic device comprising at least one compound of formula (I) or (II). This electronic device is preferably selected from the abovementioned devices.

It is more preferably an organic electroluminescent device (OLED) comprising anode, cathode and at least one emitting layer, characterized in that at least one organic layer, which may be an emitting layer, a hole-transporting layer or another layer, comprises at least one compound of formula (I) or (II).

Apart from the cathode, anode and emitting layer, the organic electroluminescent device may also comprise further layers. These are selected, for example, from in each case one or more hole injection layers, hole transport layers, hole blocker layers, electron transport layers, electron injection layers, electron blocker layers, exciton blocker layers, interlayers, charge generation layers and/or organic or inorganic p/n junctions.

The sequence of the layers of the organic electroluminescent device comprising the compound of the formula (I) or (II) is preferably as follows: anode-hole injection layer-hole transport layer-optionally further hole transport layer(s)-optionally electron blocker layer-emitting layer-optionally hole blocker layer-electron transport layer-electron injection layer-cathode. It is additionally possible for further layers to be present in the OLED.

The organic electroluminescent device of the invention may contain two or more emitting layers. More preferably, these emission layers in this case have several emission maxima between 380 nm and 750 nm overall, such that the overall result is white emission; in other words, various emitting compounds which may fluoresce or phosphoresce and which emit blue, green, yellow, orange or red light are used in the emitting layers. Especially preferred are three-layer systems, i.e. systems having three emitting layers, where the three layers show blue, green and orange or red emission. The compounds of the invention are preferably present here in a hole transport layer, hole injection layer, electron blocker layer, and/or emitting layer, more preferably in an emitting layer as matrix material, and/or in an electron blocker layer.

It is preferable in accordance with the invention when the compound of formula (I) or (II) is used in an electronic device comprising one or more phosphorescent emitting compounds. In this case, the compound may be present in different layers, preferably in a hole transport layer, an electron blocker layer, a hole injection layer and/or an emitting layer. More preferably, it is present in an electron blocker layer or in an emitting layer in combination with a phosphorescent emitting compound. In the latter case, the phosphorescent emitting compound is preferably selected from red- or green-phosphorescent emitting compounds. It is most preferably present in an electron blocker layer.

The term "phosphorescent emitting compounds" typically encompasses compounds where the emission of light is effected through a spin-forbidden transition, for example a transition from an excited triplet state or a state having a higher spin quantum number, for example a quintet state.

Suitable phosphorescent emitting compounds (=triplet emitters) are especially compounds which, when suitably excited, emit light, preferably in the visible region, and also contain at least one atom of atomic number greater than 20, preferably greater than 38, and less than 84, more preferably greater than 56 and less than 80. Preference is given to using, as phosphorescent emitting compounds, compounds containing copper, molybdenum, tungsten, rhenium, ruthenium, osmium, rhodium, iridium, palladium, platinum, silver, gold or europium, especially compounds containing iridium, platinum or copper. In the context of the present invention, all luminescent iridium, platinum or copper complexes are considered to be phosphorescent emitting compounds.

In general, all phosphorescent complexes as used for phosphorescent OLEDs according to the prior art and as known to those skilled in the art in the field of organic electroluminescent devices are suitable. It is also possible for the person skilled in the art, without exercising inventive skill, to use further phosphorescent complexes in combination with the compounds of formula (I) or (II) in organic electroluminescent devices. Further examples are listed in the following table:
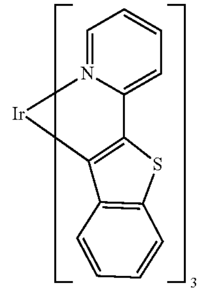
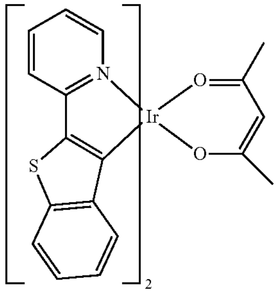
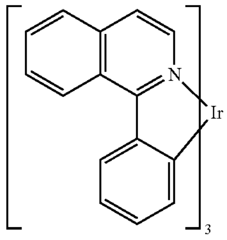
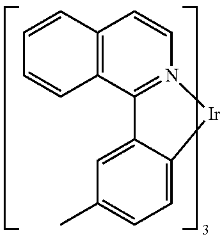
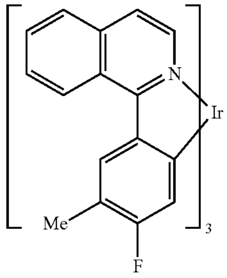
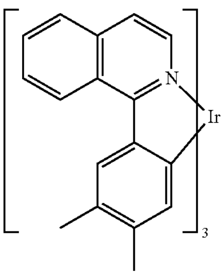
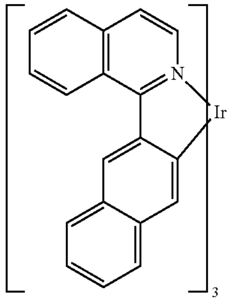
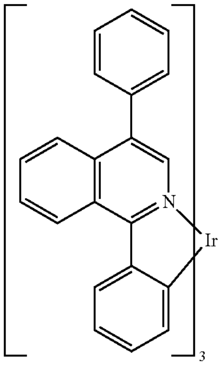
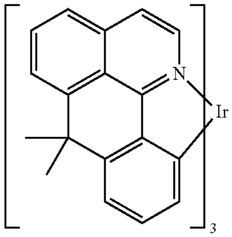
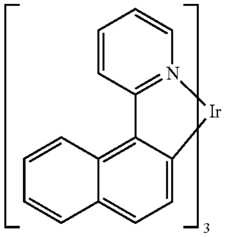
-continued
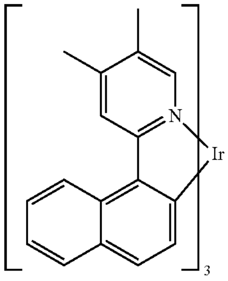
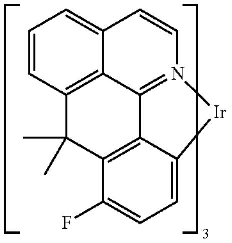
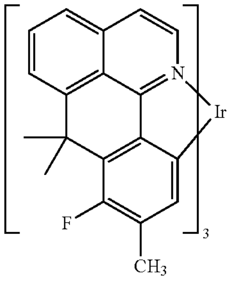
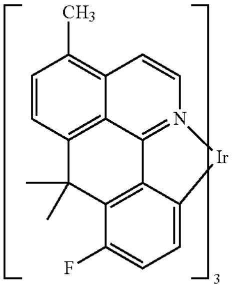
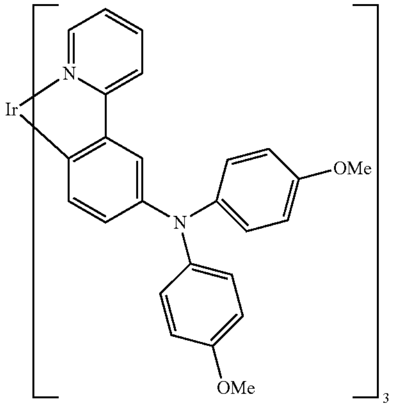
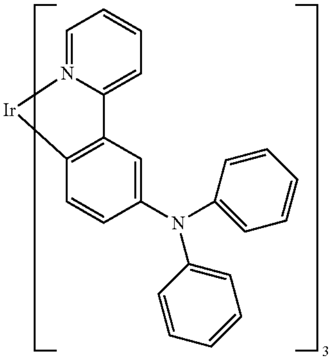

-continued
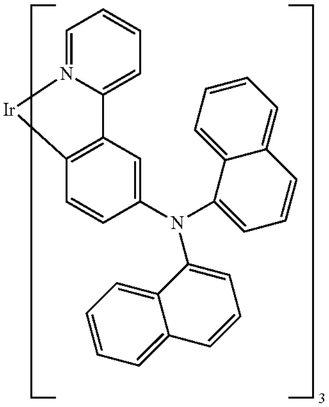
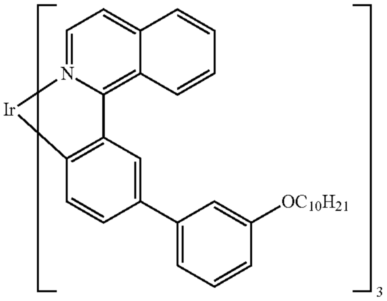
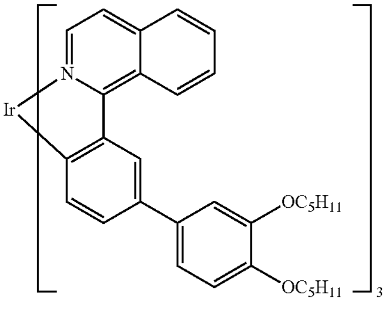
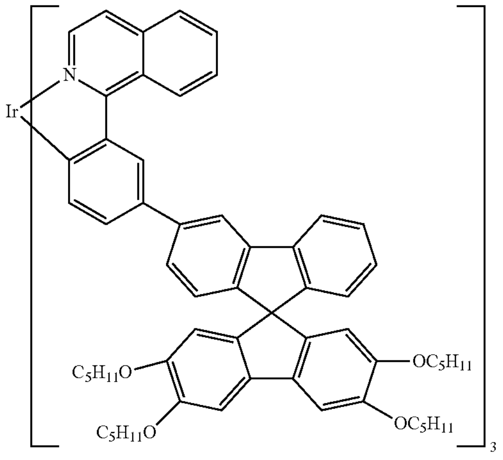
-continued
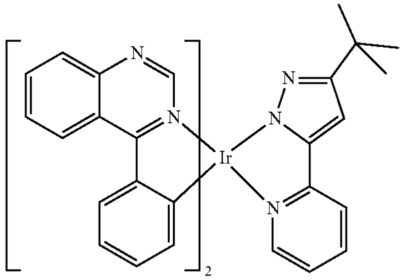
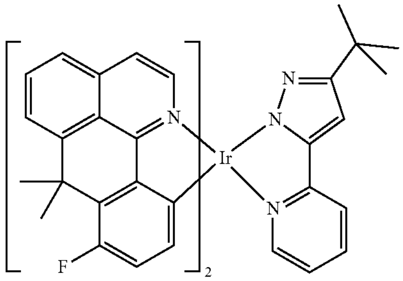
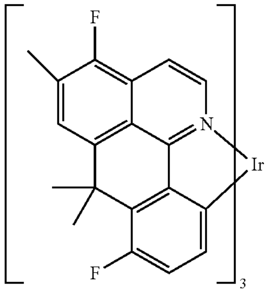
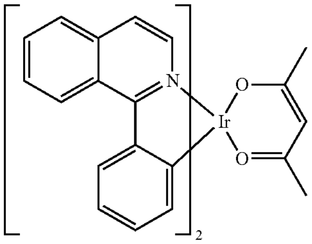
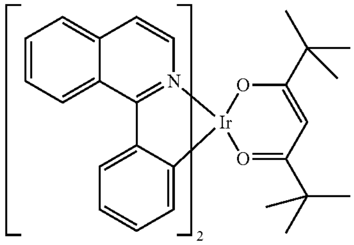
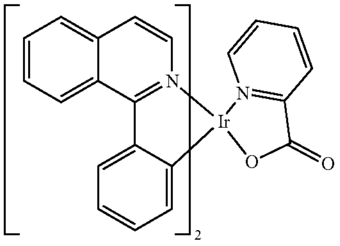

-continued
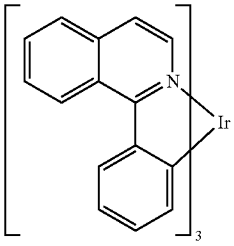
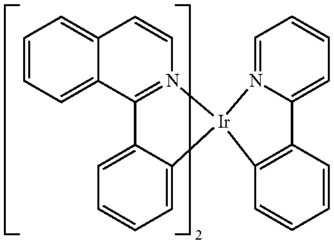
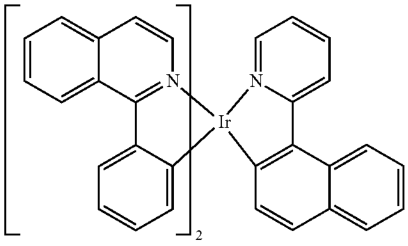
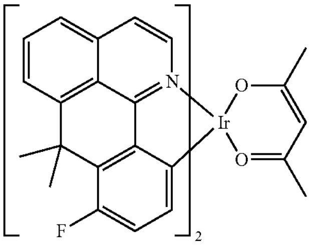
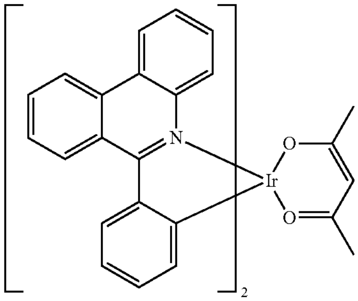
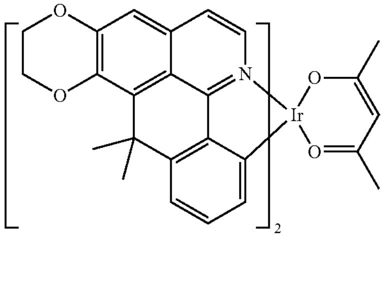
-continued
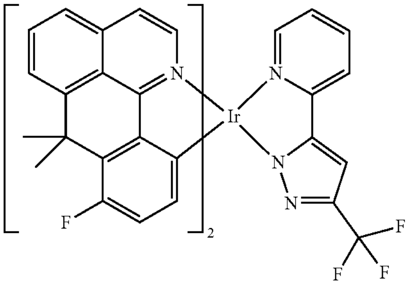
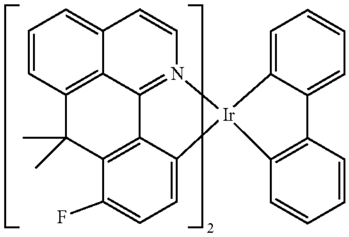
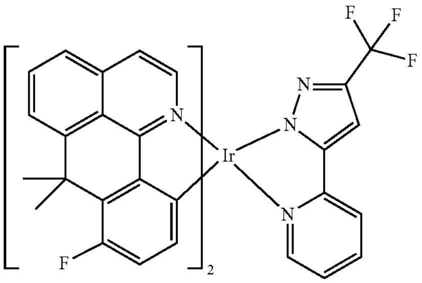
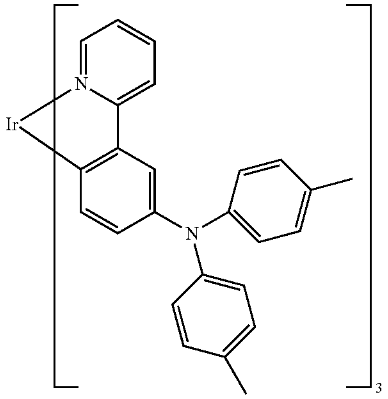
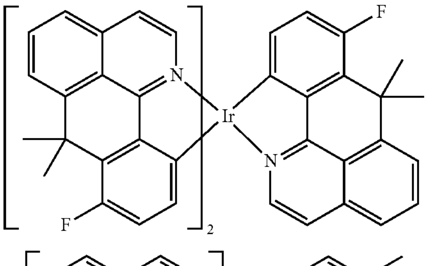
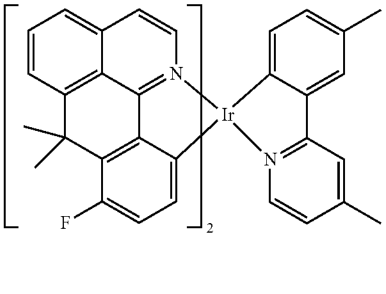

-continued
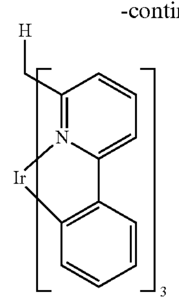
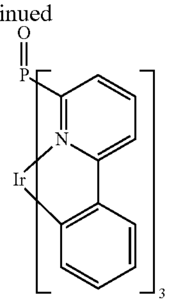
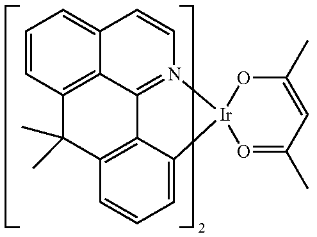
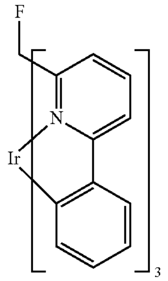
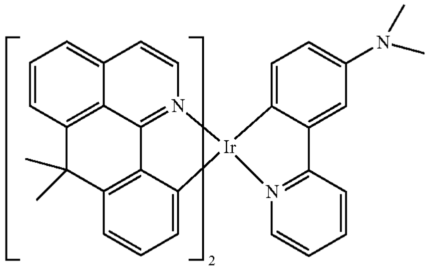
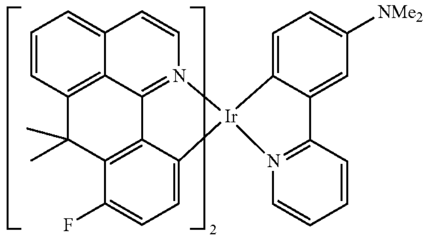
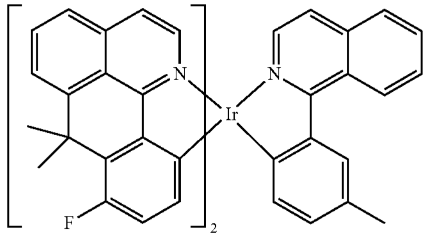
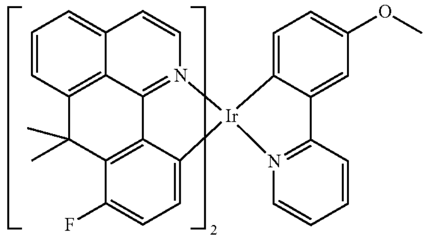
-continued
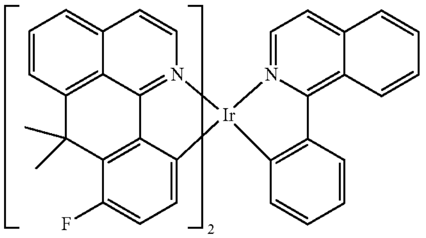
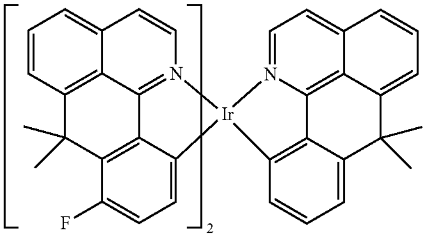
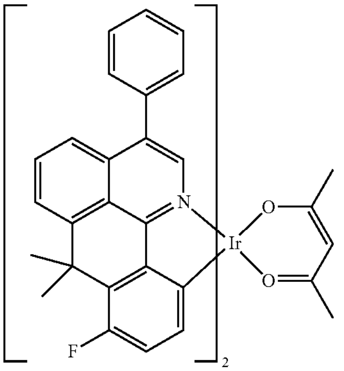
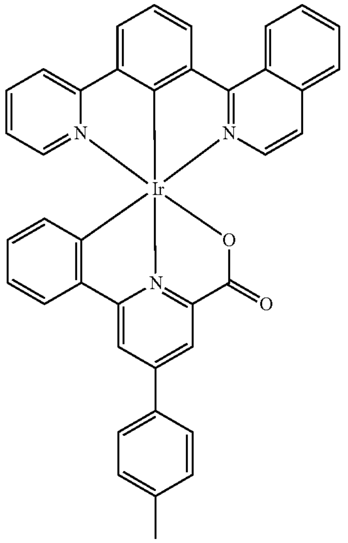
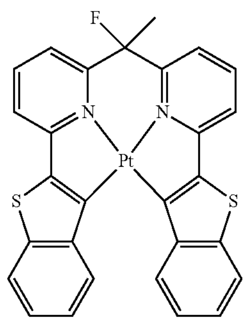

-continued
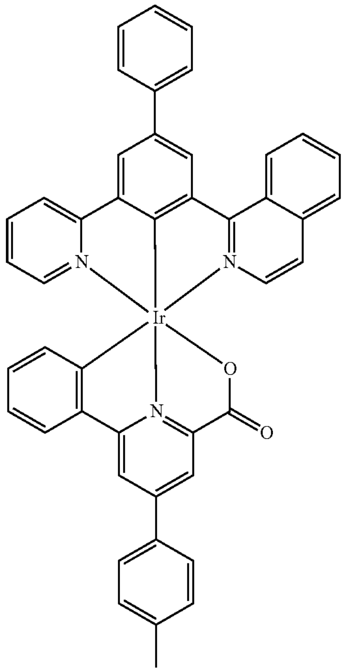
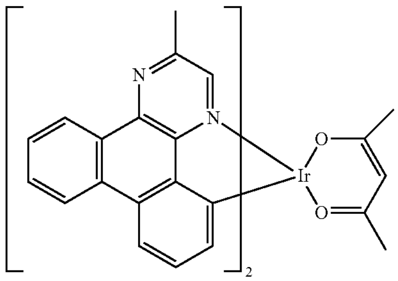
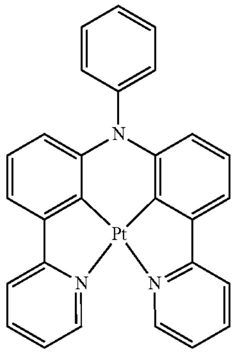
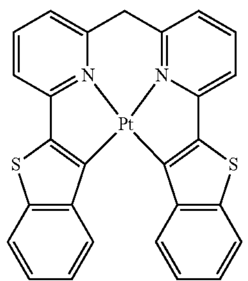
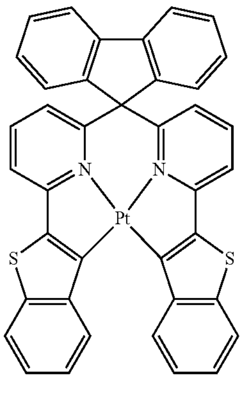
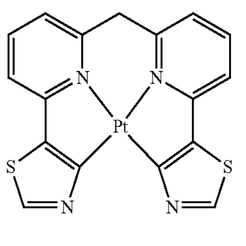
-continued
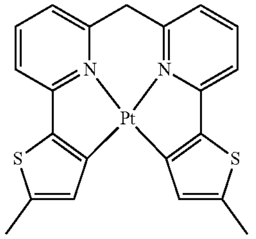
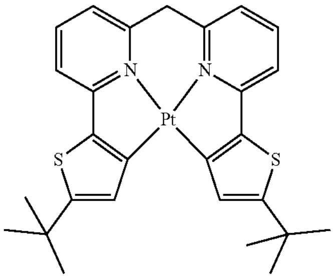
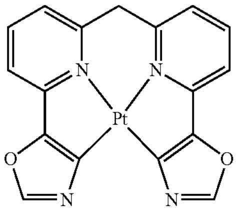
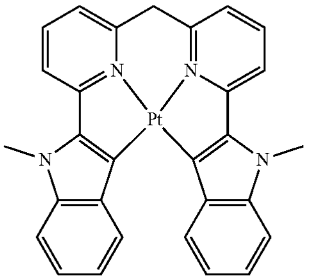
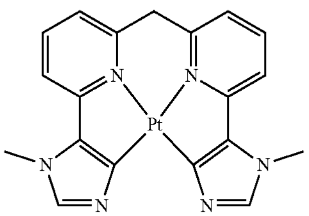
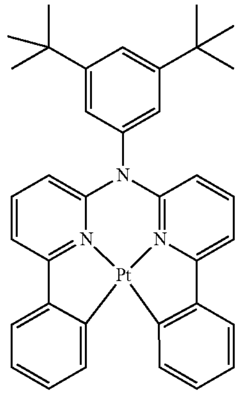
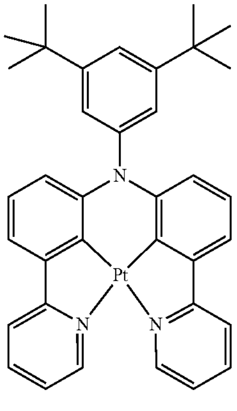
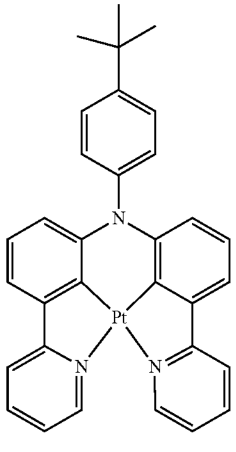

-continued
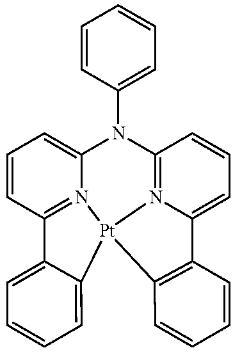
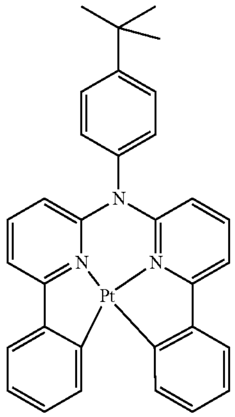
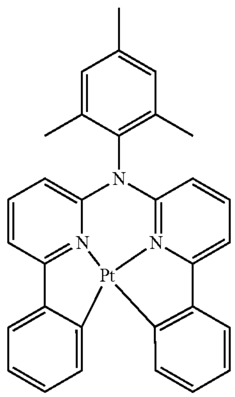
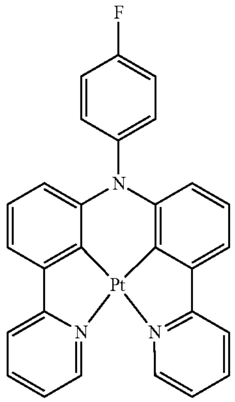
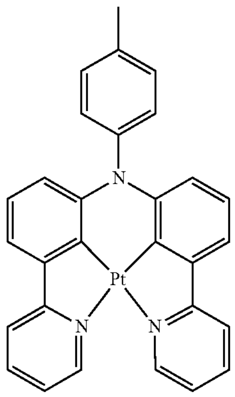
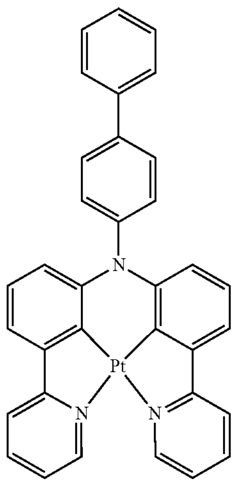
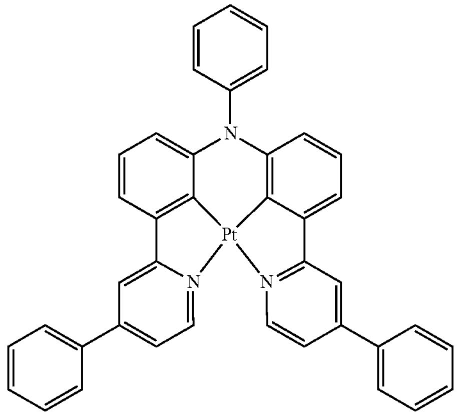
-continued
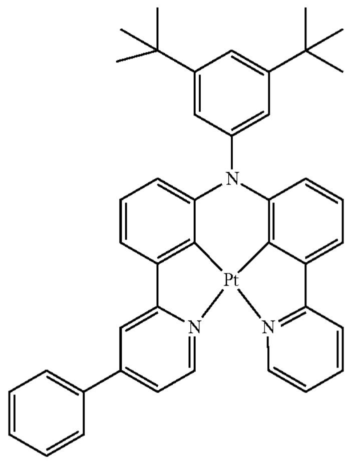
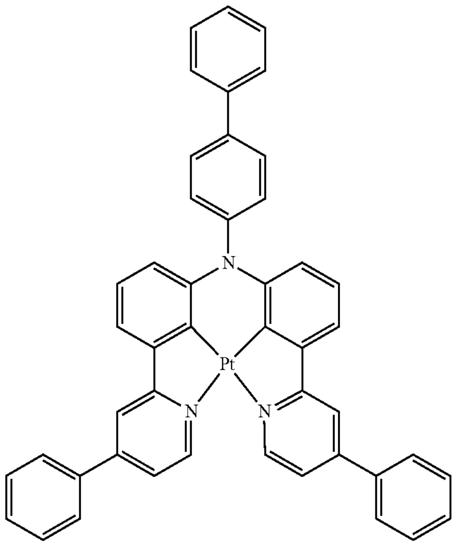
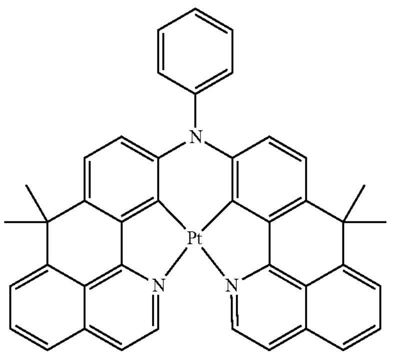

-continued
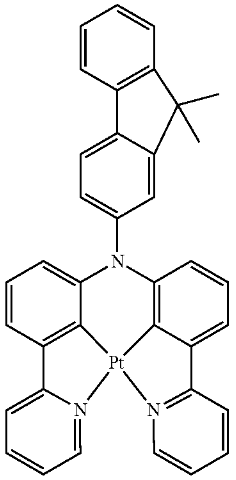
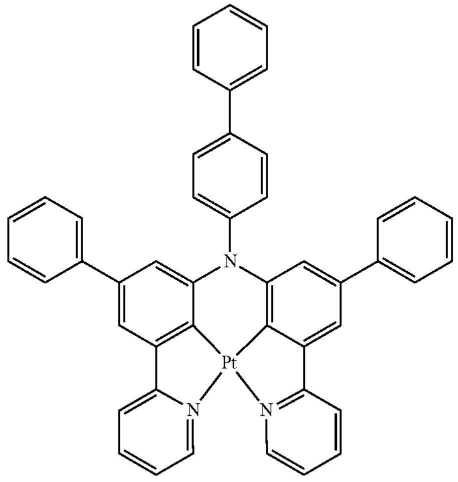
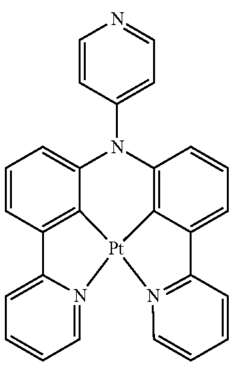
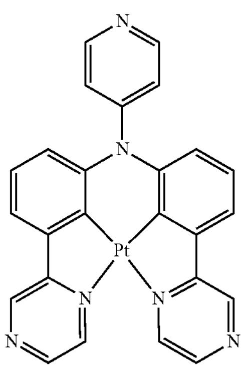
-continued
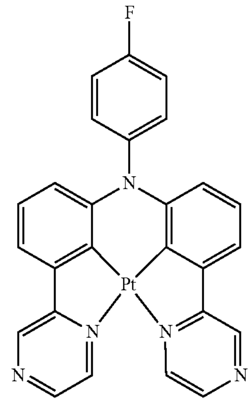
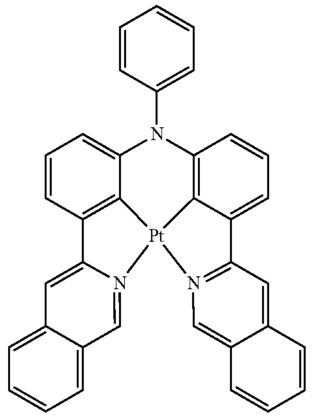
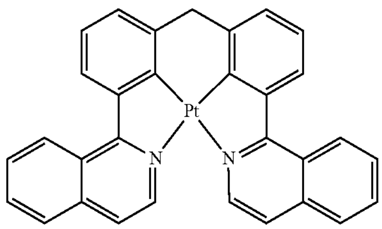
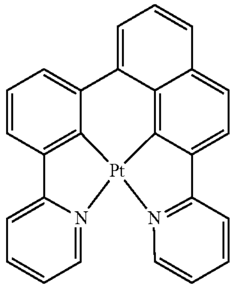
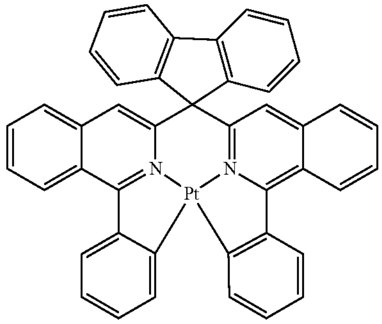
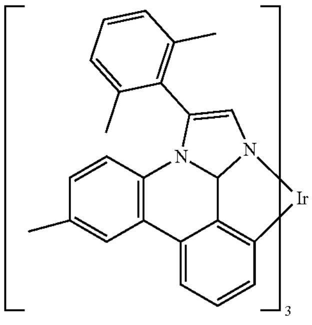

-continued
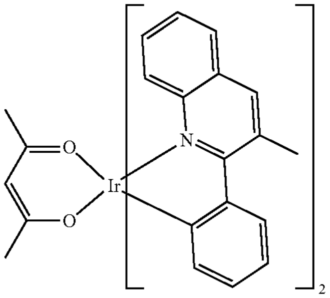
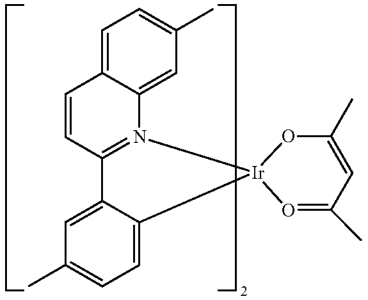
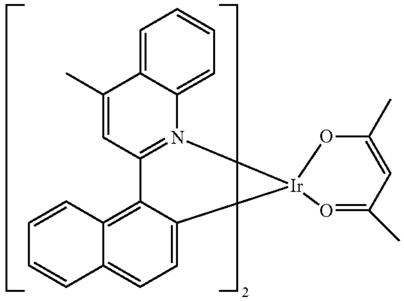
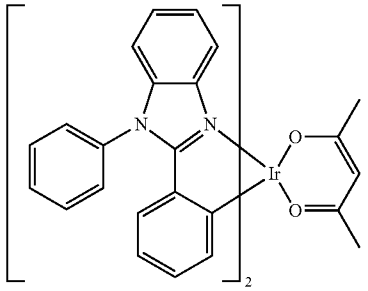
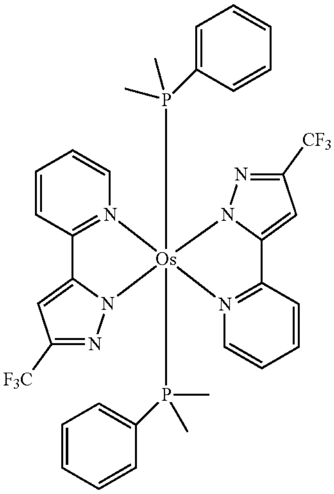
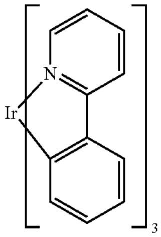
-continued
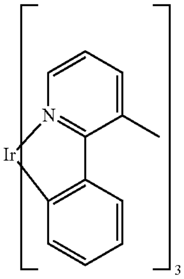
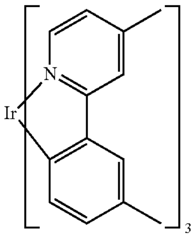
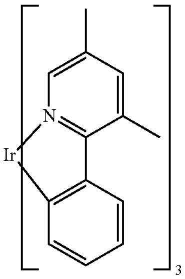
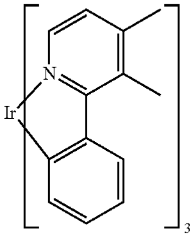
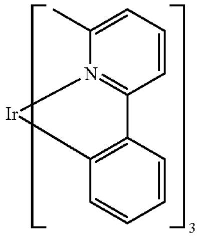
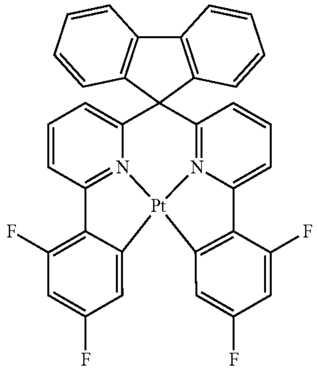
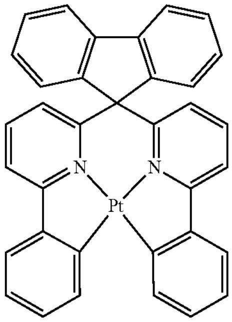
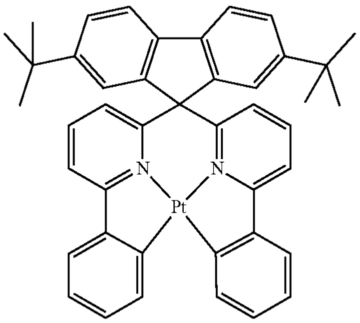

-continued
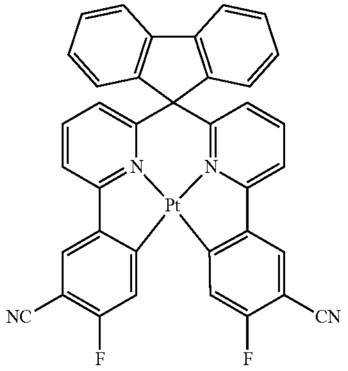
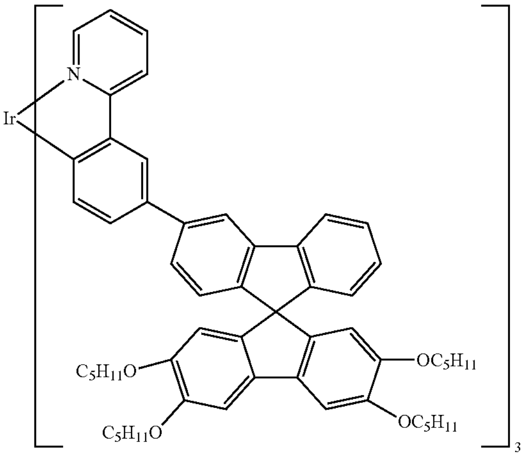
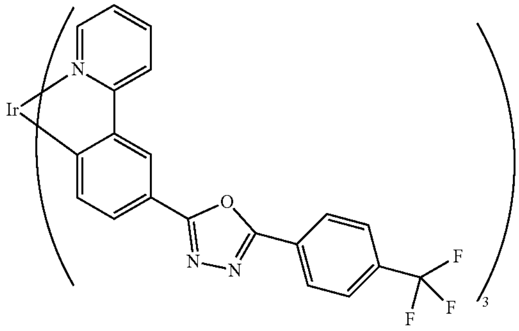
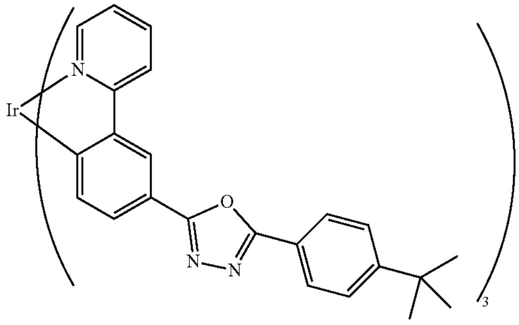
-continued
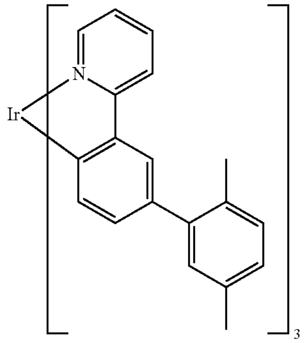
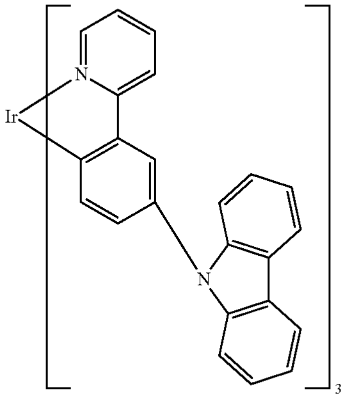
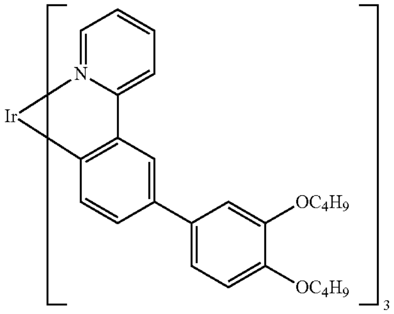
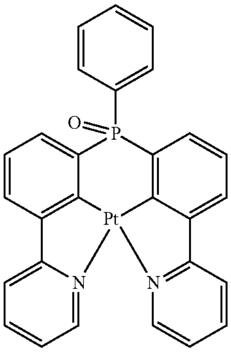
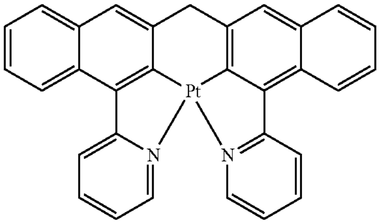

-continued
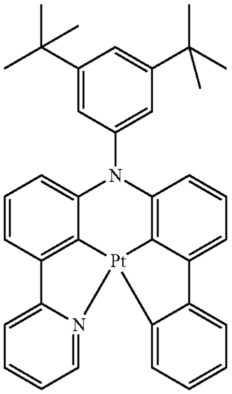
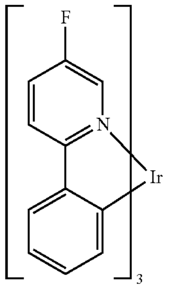
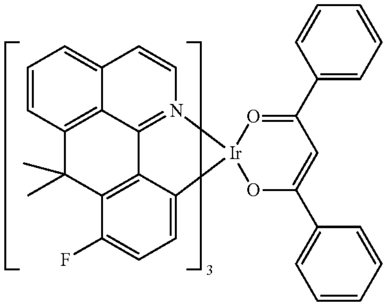
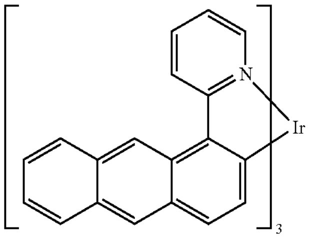
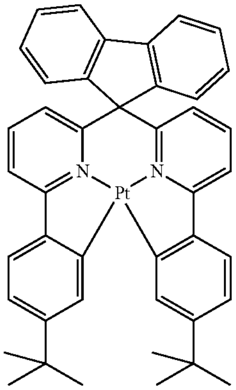
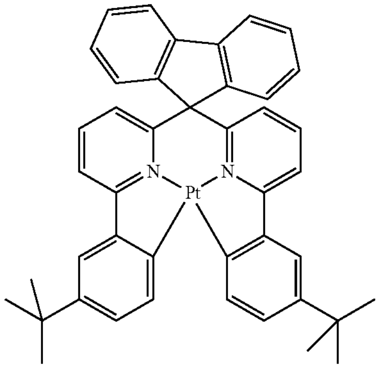
-continued
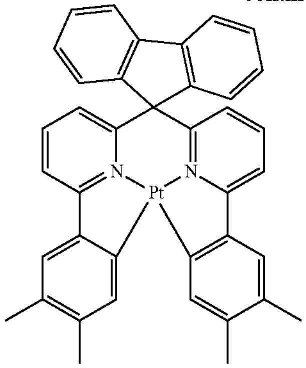
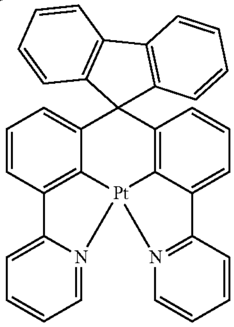
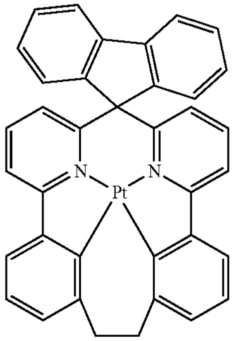
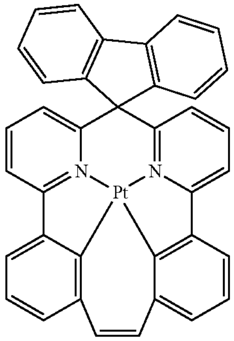
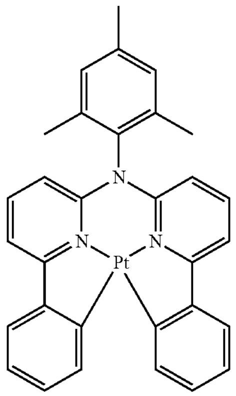
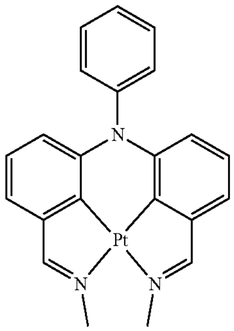
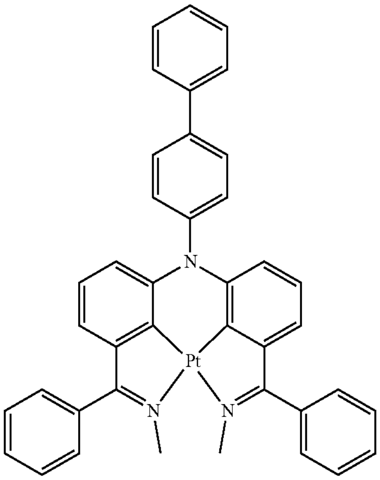

-continued
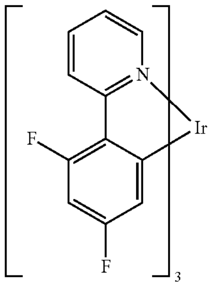
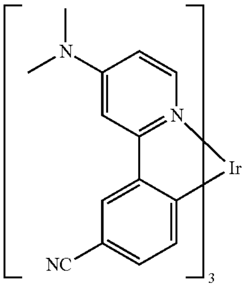
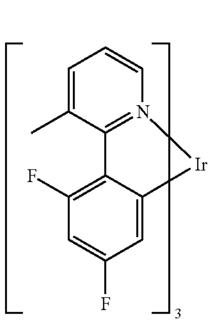
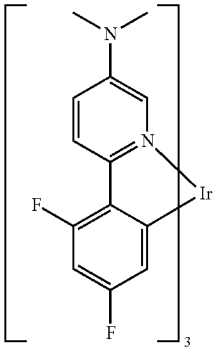
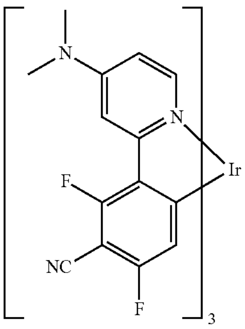
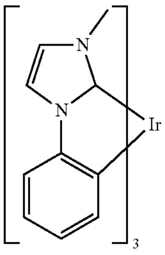
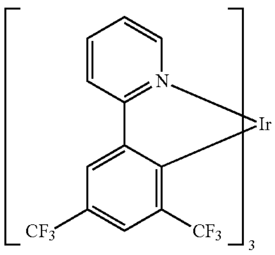
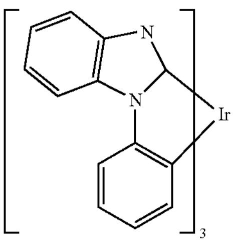
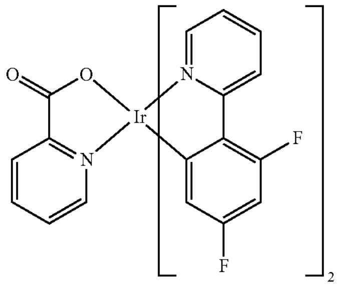
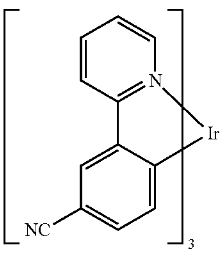
-continued
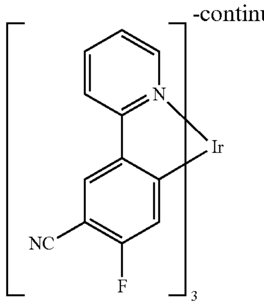
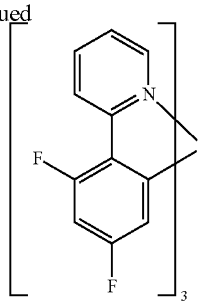
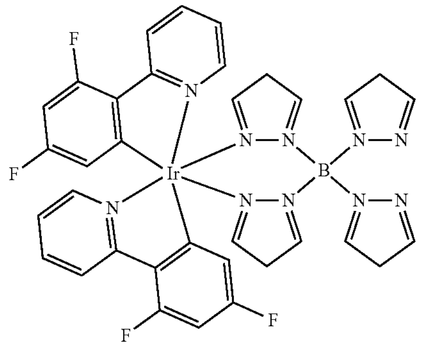
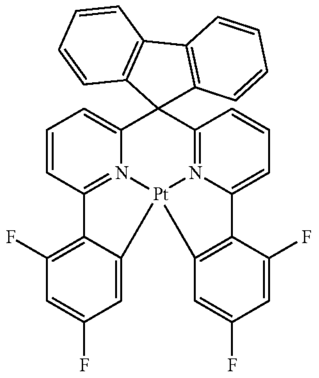
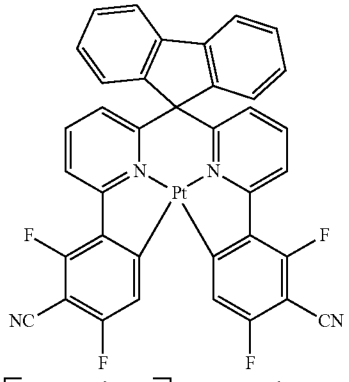
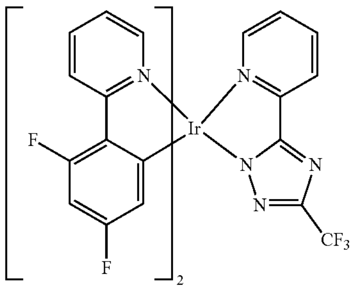

-continued
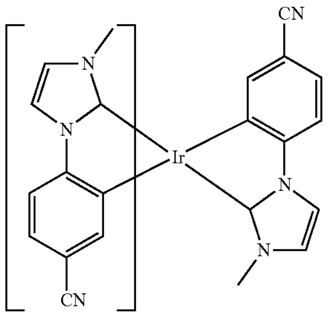
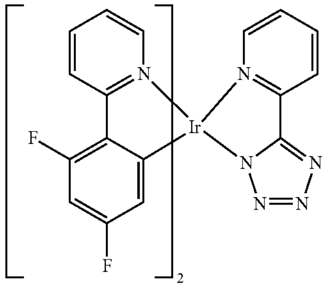
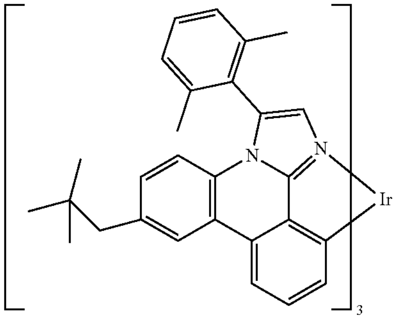
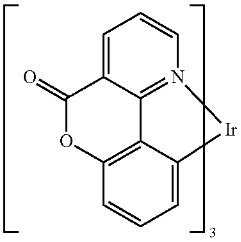
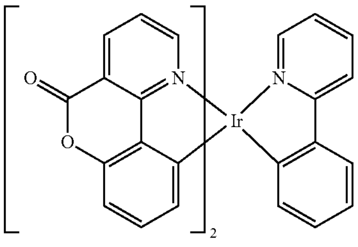
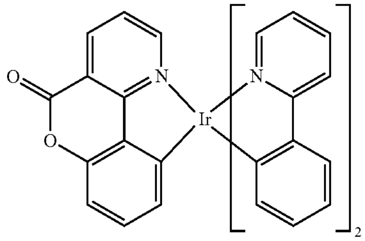
-continued
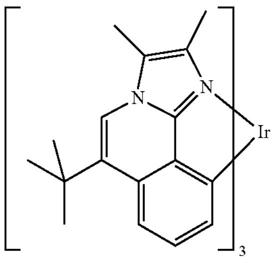
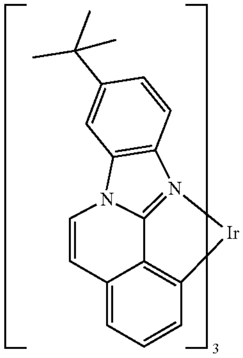
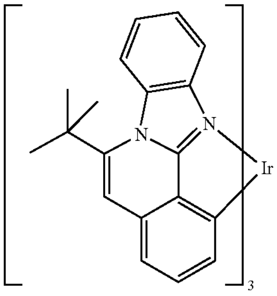
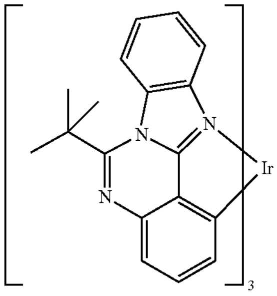
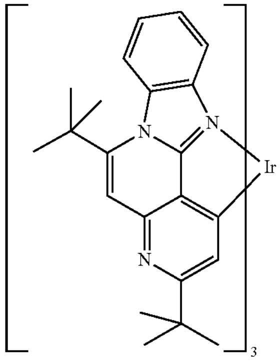
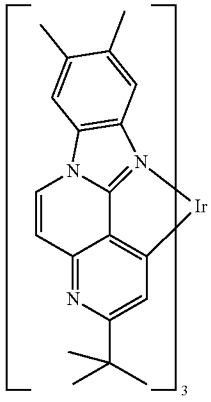
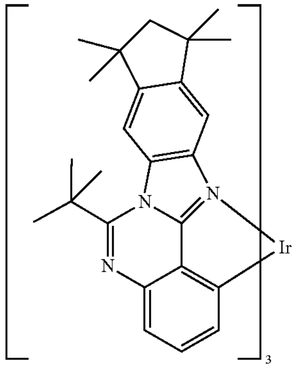
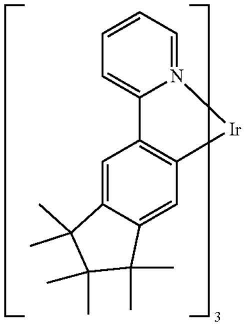

-continued
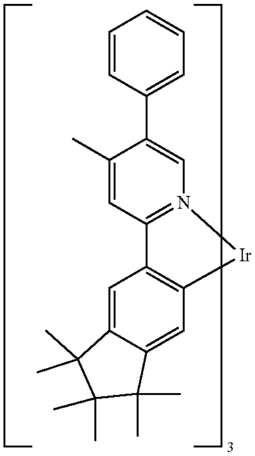
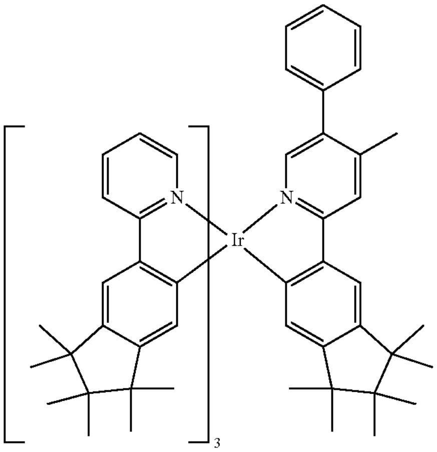
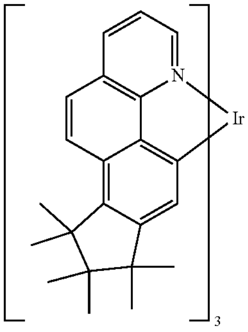
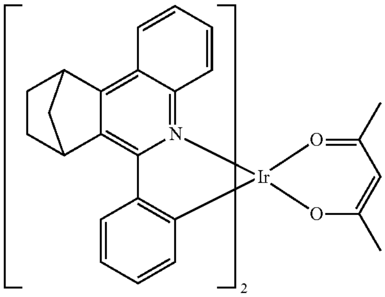
-continued
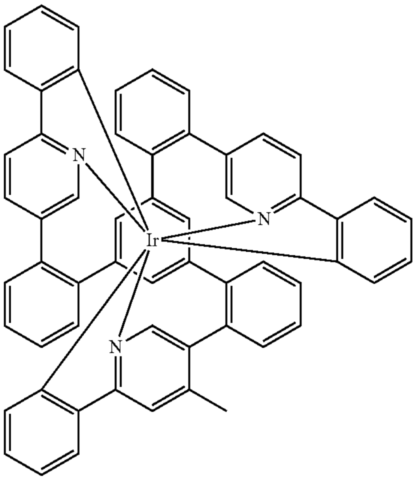
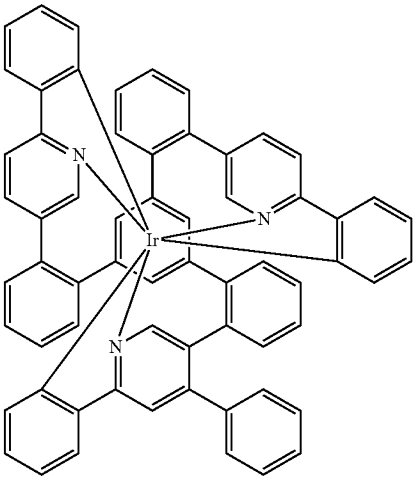
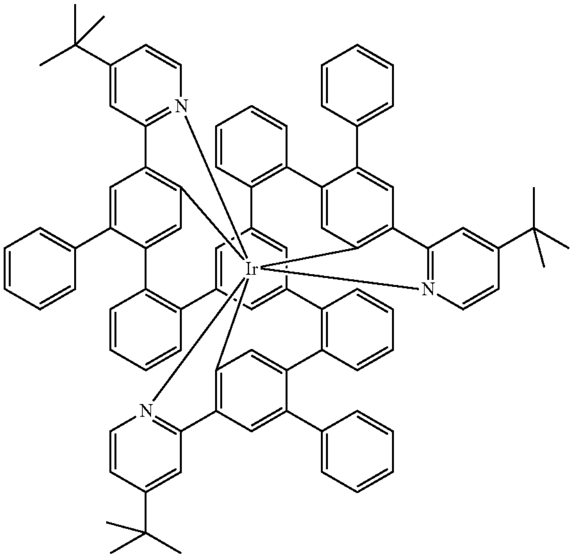

-continued

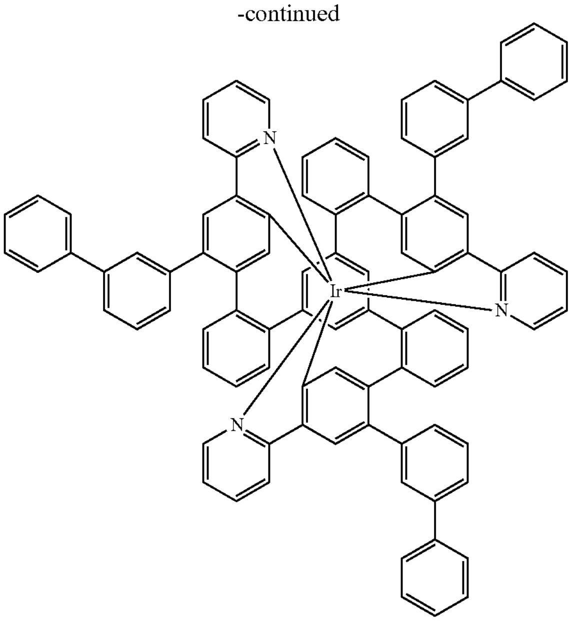

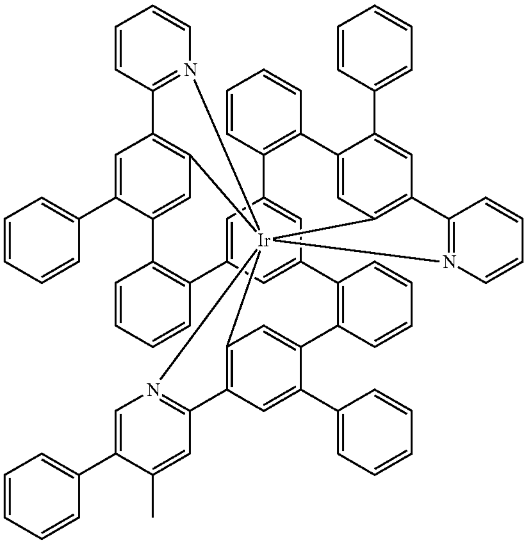

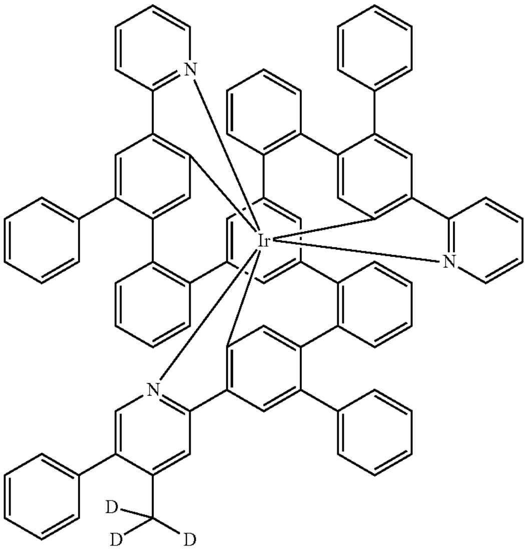

In a preferred embodiment of the invention, the compounds of formula (I) or (II) are used as hole-transporting material. The compounds are then preferably in a hole-transporting layer. Preferred embodiments of hole-transporting layers are hole transport layers, electron blocker layers and hole injection layers. When the compound of the formula (I) or (II) is present in a hole-transporting layer, the latter is preferably an electron-blocking layer. This preferably directly adjoins the emitting layer on the anode side.

A hole transport layer according to the present application is a layer having a hole-transporting function between the anode and emitting layer. More particularly, it is a hole-transporting layer which is not a hole injection layer and not an electron blocker layer.

Hole injection layers and electron blocker layers are understood in the context of the present application to be specific embodiments of hole-transporting layers. A hole injection layer, in the case of a plurality of hole-transporting layers between the anode and emitting layer, is a hole-transporting layer which directly adjoins the anode or is separated therefrom only by a single coating of the anode. An electron blocker layer, in the case of a plurality of hole-transporting layers between the anode and emitting layer, is that hole-transporting layer which directly adjoins the emitting layer on the anode side. Preferably, the OLED of the invention comprises two, three or four hole-transporting layers between the anode and emitting layer, at least one of which preferably contains a compound of formula (I) or (II), and more preferably exactly one or two contain a compound of formula (I) or (II).

If the compound of formula (I) or (II) is used as hole transport material in a hole transport layer, a hole injection layer or an electron blocker layer, the compound can be used as pure material, i.e. in a proportion of 100%, in the hole transport layer, or it can be used in combination with one or more further compounds. In a preferred embodiment, the organic layer comprising the compound of the formula (I) or (II) then additionally contains one or more p-dopants. p-Dopants used according to the present invention are preferably those organic electron acceptor compounds capable of oxidizing one or more of the other compounds in the mixture.

Particularly preferred p-dopants are quinodimethane compounds, azaindenofluorenediones, azaphenalenes, azatriphenylenes, 12, metal halides, preferably transition metal halides, metal oxides, preferably metal oxides containing at least one transition metal or a metal of main group 3, and transition metal complexes, preferably complexes of Cu, Co, Ni, Pd and Pt with ligands containing at least one oxygen atom as bonding site. Preference is further given to transition metal oxides as dopants, preferably oxides of rhenium, molybdenum and tungsten, more preferably $Re_2O_7$, $MoO_3$, $WO_3$ and $ReO_3$.

The p-dopants are preferably in substantially homogeneous distribution in the p-doped layers. This can be achieved, for example, by coevaporation of the p-dopant and the hole transport material matrix.

Preferred p-dopants are especially the following compounds:
(D-1)
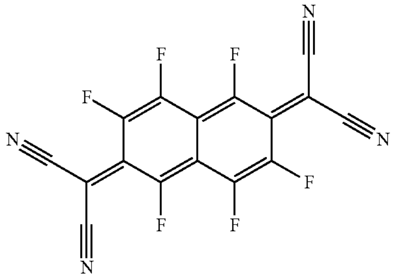
(D-2)
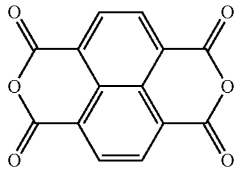
(D-3)
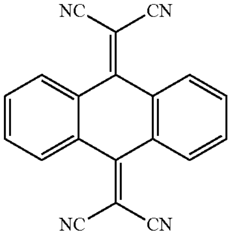
(D-4)
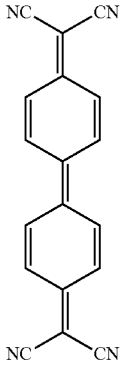
(D-5)
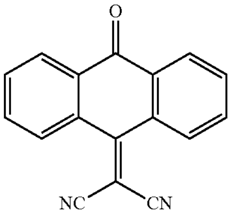
(D-6)
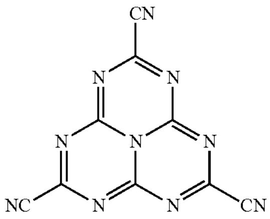
-continued
(D-7)
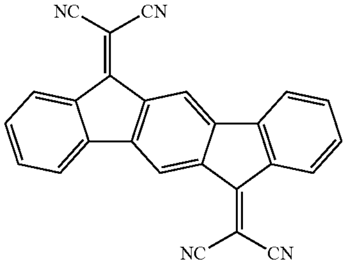
(D-8)
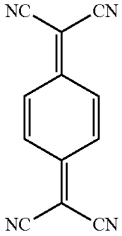
(D-9)
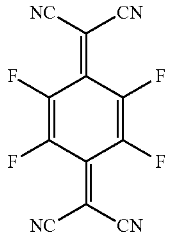
(D-10)
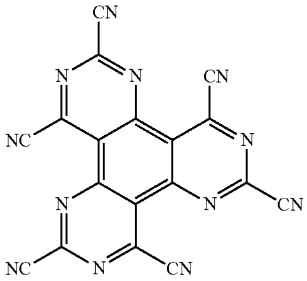
(D-11)
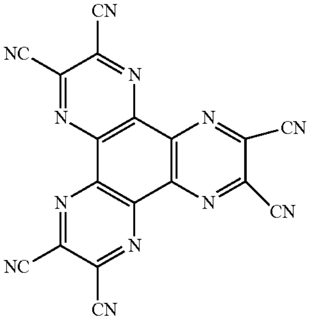

-continued (D-12)

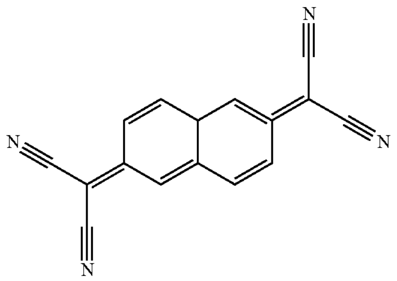

(D-13)

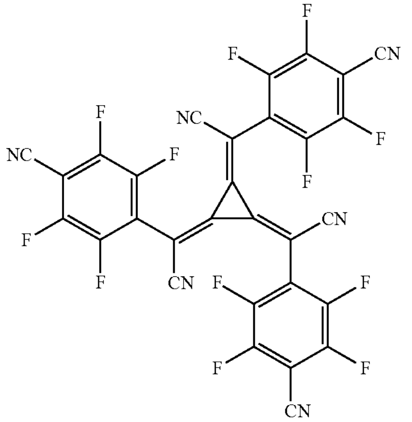

In a further preferred embodiment of the invention, the compound of formula (I) or (II) is used as hole transport material in combination with a hexaazatriphenylene derivative in an OLED. Particular preference is given here to using the hexaazatriphenylene derivative in a separate layer.

In a preferred embodiment of the present invention, the compound of the formula (I) or (II) is used in an emitting layer as matrix material in combination with one or more emitting compounds, preferably phosphorescent emitting compounds. The phosphorescent emitting compounds here are preferably selected from red-phosphorescent and green-phosphorescent compounds.

The proportion of the matrix material in the emitting layer in this case is between 50.0% and 99.9% by volume, preferably between 80.0% and 99.5% by volume, and more preferably between 85.0% and 97.0% by volume.

Correspondingly, the proportion of the emitting compound is between 0.1% and 50.0% by volume, preferably between 0.5% and 20.0% by volume, and more preferably between 3.0% and 15.0% by volume.

An emitting layer of an organic electroluminescent device may also comprise systems comprising a plurality of matrix materials (mixed matrix systems) and/or a plurality of emitting compounds. In this case too, the emitting compounds are generally those compounds having the smaller proportion in the system and the matrix materials are those compounds having the greater proportion in the system. In individual cases, however, the proportion of a single matrix material in the system may be less than the proportion of a single emitting compound.

It is preferable that the compounds of formula (I) or (II) are used as a component of mixed matrix systems, preferably for phosphorescent emitters. The mixed matrix systems preferably comprise two or three different matrix materials, more preferably two different matrix materials. Preferably, in this case, one of the two materials is a material having hole-transporting properties and the other material is a material having electron-transporting properties. The compound of the formula (I) or (II) is preferably the matrix material having hole-transporting properties. Correspondingly, when the compound of the formula (I) or (II) is used as matrix material for a phosphorescent emitter in the emitting layer of an OLED, a second matrix compound having electron-transporting properties is present in the emitting layer. The two different matrix materials may be present in a ratio of 1:50 to 1:1, preferably 1:20 to 1:1, more preferably 1:10 to 1:1 and most preferably 1:4 to 1:1.

The desired electron-transporting and hole-transporting properties of the mixed matrix components may, however, also be combined mainly or entirely in a single mixed matrix component, in which case the further mixed matrix component(s) fulfil(s) other functions.

The mixed matrix systems may comprise one or more emitting compounds, preferably one or more phosphorescent emitting compounds. In general, mixed matrix systems are preferably used in phosphorescent organic electroluminescent devices.

Particularly suitable matrix materials which can be used in combination with the inventive compounds as matrix components of a mixed matrix system are selected from the preferred matrix materials specified below for phosphorescent emitting compounds, and among these especially from those having electron-transporting properties.

Preferred embodiments of the different functional materials in the electronic device are listed hereinafter.

Preferred fluorescent emitting compounds are selected from the class of the arylamines. An arylamine or an aromatic amine in the context of this invention is understood to mean a compound containing three substituted or unsubstituted aromatic or heteroaromatic ring systems bonded directly to the nitrogen. Preferably, at least one of these aromatic or heteroaromatic ring systems is a fused ring system, more preferably having at least 14 aromatic ring atoms. Preferred examples of these are aromatic anthraceneamines, aromatic anthracenediamines, aromatic pyreneamines, aromatic pyrenediamines, aromatic chryseneamines or aromatic chrysenediamines. An aromatic anthraceneamine is understood to mean a compound in which a diarylamino group is bonded directly to an anthracene group, preferably in the 9 position. An aromatic anthracenediamine is understood to mean a compound in which two diarylamino groups are bonded directly to an anthracene group, preferably in the 9,10 positions. Aromatic pyreneamines, pyrenediamines, chryseneamines and chrysenediamines are defined analogously, where the diarylamino groups are bonded to the pyrene preferably in the 1 position or 1,6 positions. Further preferred emitting compounds are indenofluoreneamines or—diamines, benzoindenofluoreneamines or—diamines, and dibenzoindenofluoreneamines or—diamines, and indenofluorene derivatives having fused aryl groups. Likewise preferred are pyrenearylamines, benzoindenofluoreneamines, benzofluoreneamines, extended benzoindenofluorenes, phenoxazines, and fluorene derivatives substituted by furan units or by thiophene units.

Useful matrix materials, preferably for fluorescent emitting compounds, include materials of various substance classes. Preferred matrix materials are selected from the classes of the oligoarylenes (e.g. 2,2',7,7'-tetraphenylspirobifluorene or dinaphthylanthracene), especially the oligoarylenes containing fused aromatic groups, the oligoarylenevinylenes (e.g. DPVBi or spiro-DPVBi), the polypodal metal complexes, the hole-conducting compounds, the electron-conducting compounds, especially ketones, phosphine oxides and sulfur oxides, the atropisomers, the boronic acid derivatives or the benzanthracenes. Particularly preferred matrix materials are selected from the classes of the oligoarylenes comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes comprising anthracene, benzanthracene, benzophenanthrene and/or pyrene or atropisomers of these compounds. An oligoarylene in the context of this invention shall be understood to mean a compound in which at least three aryl or arylene groups are bonded to one another.

Preferred matrix materials for phosphorescent emitting compounds are, as well as the compounds of the formula (I) or (II), aromatic ketones, aromatic phosphine oxides or aromatic sulfoxides or sulfones, triarylamines, carbazole derivatives, indolocarbazole derivatives, indenocarbazole derivatives, azacarbazole derivatives, bipolar matrix materials, silanes, azaboroles or boronic esters, triazine derivatives, zinc complexes, diazasilole or tetraazasilole derivatives, diazaphosphole derivatives, bridged carbazole derivatives, triphenylene derivatives and lactams.

Suitable charge transport materials as usable in the hole injection or hole transport layer or electron blocker layer or in the electron transport layer of the electronic device of the invention are, as well as the compounds of the formula (I) or (II), for example, the compounds disclosed in Y. Shirota et al., Chem. Rev. 2007, 107 (4), 953-1010, or other materials as used in these layers according to the prior art.

Preferred materials for hole-transporting layers of the OLEDs are the following materials:

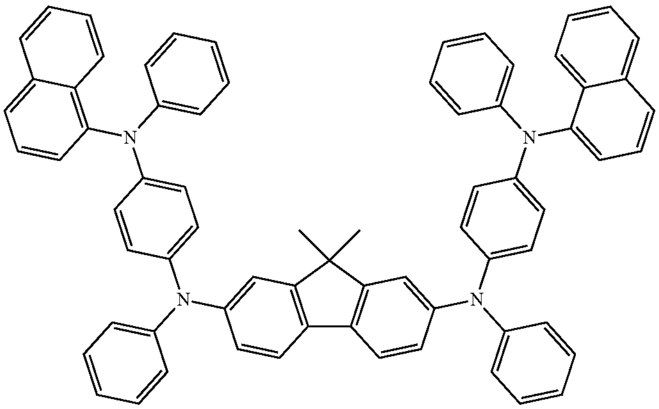

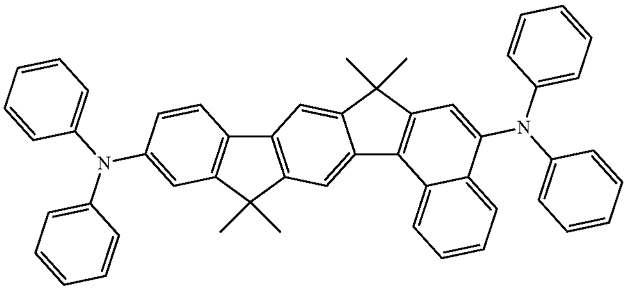

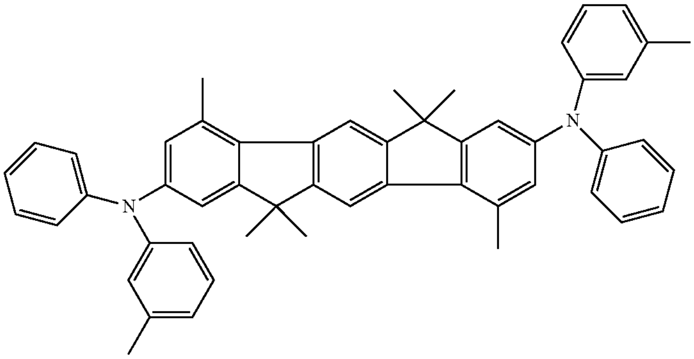

-continued
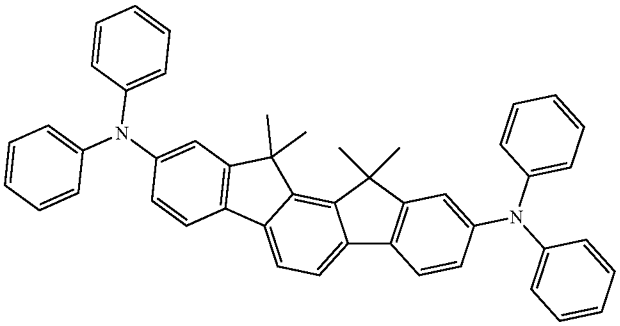
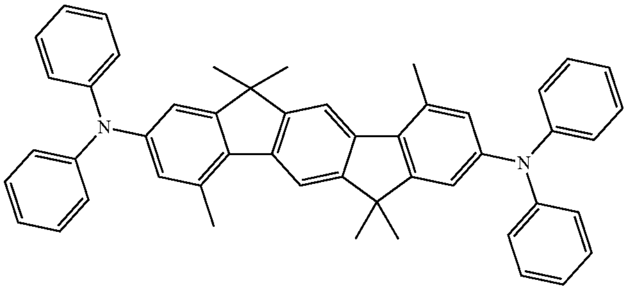
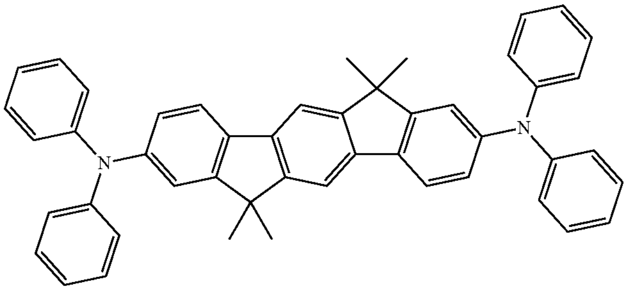
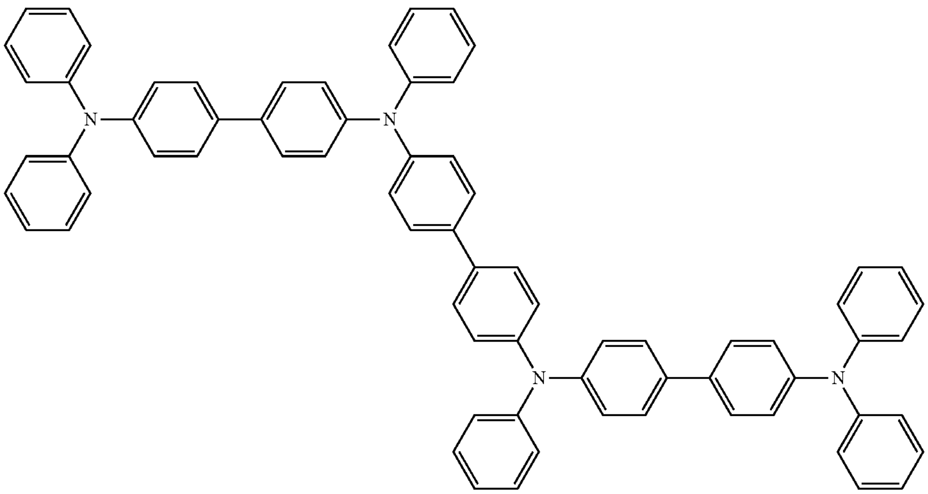

-continued
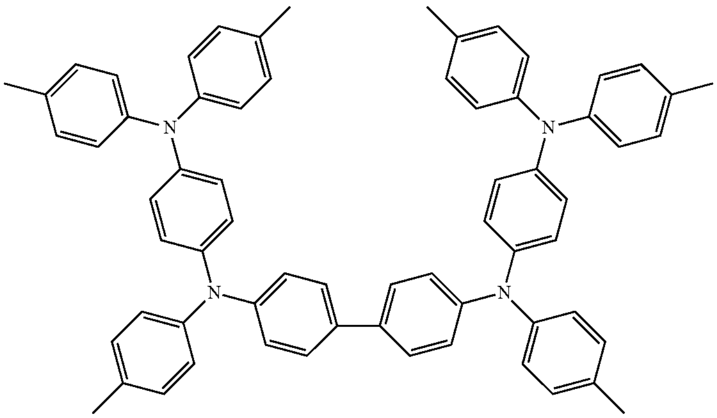
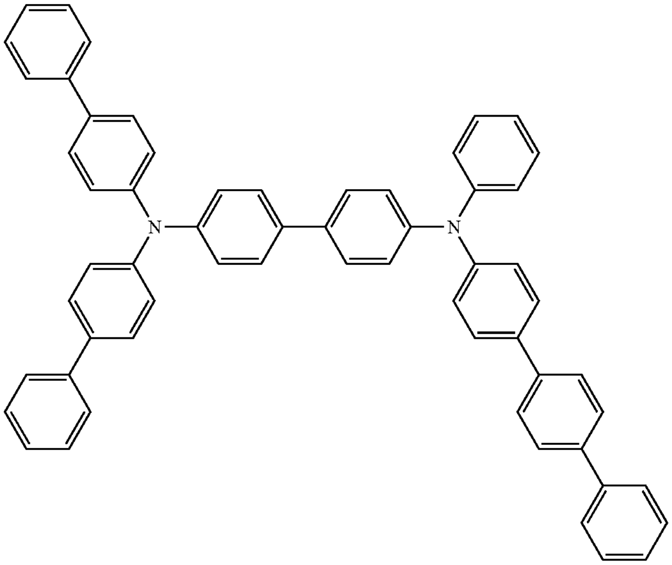
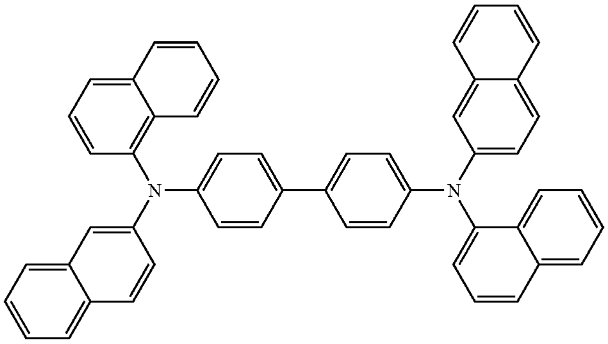
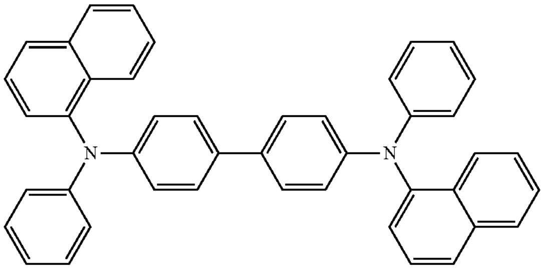

-continued
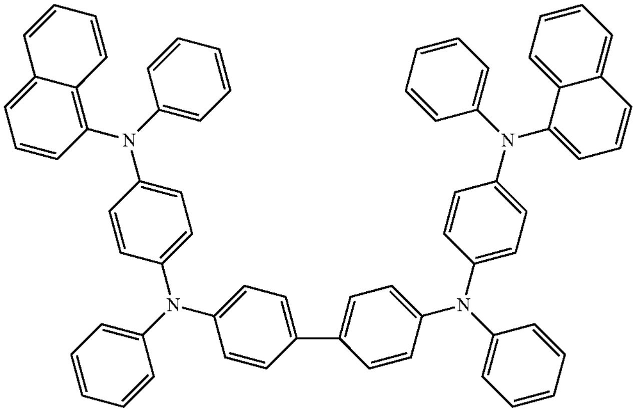
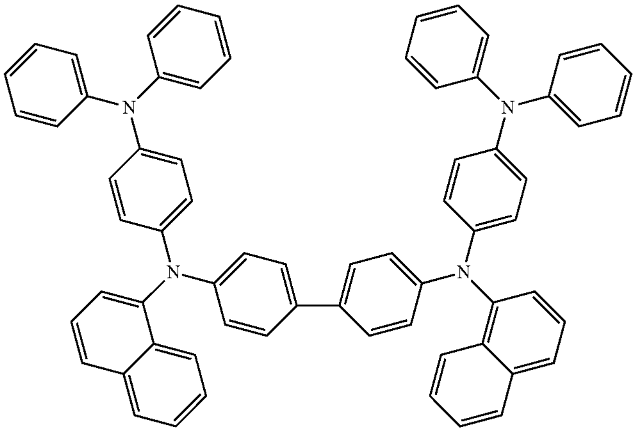
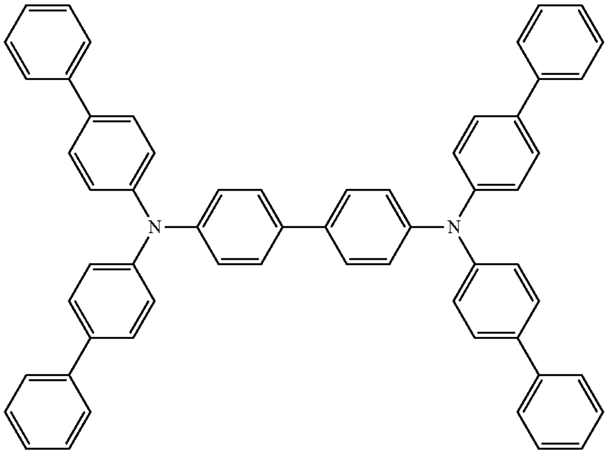
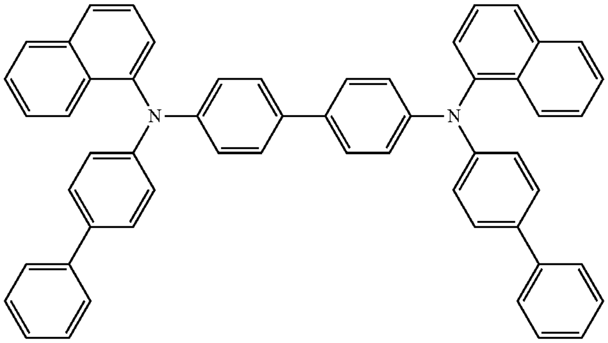

-continued
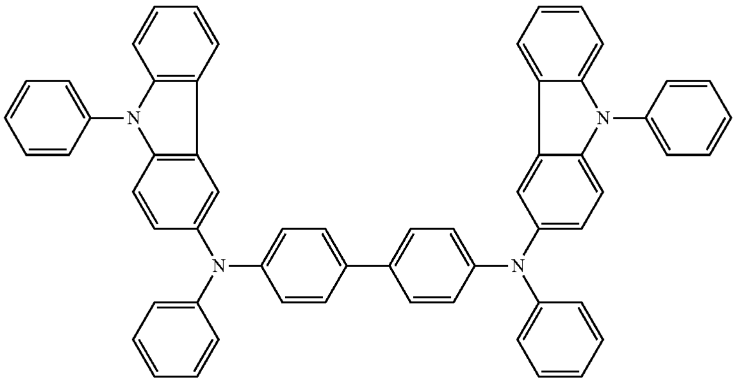
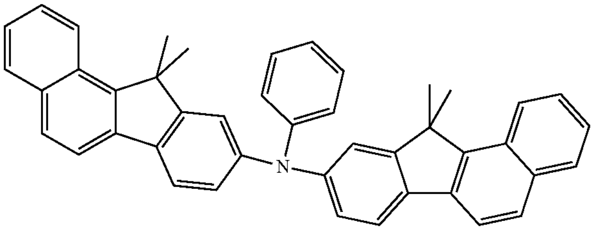
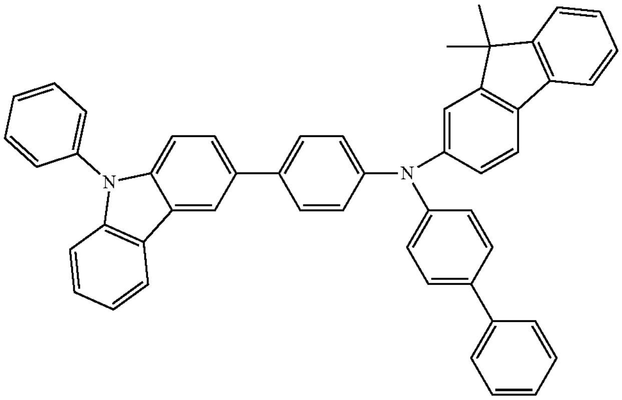
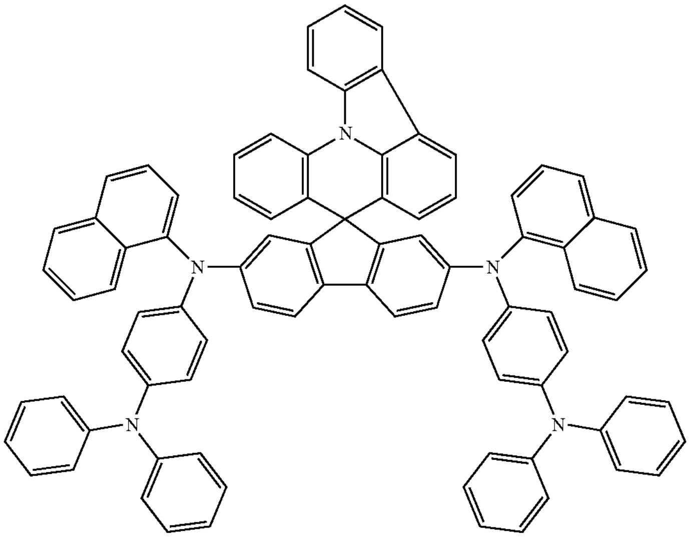

-continued

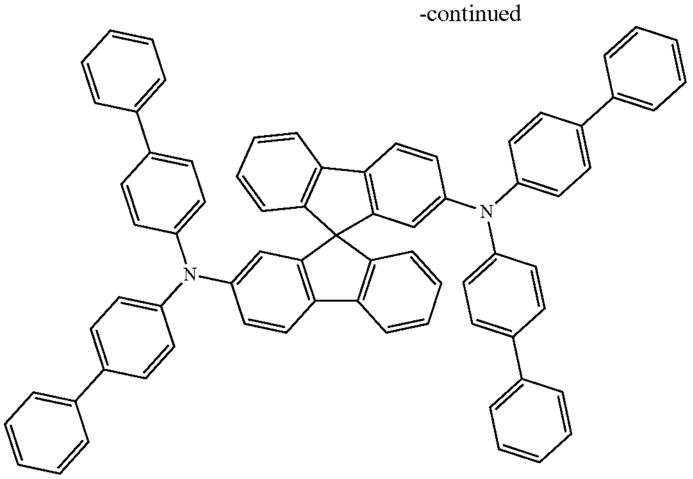

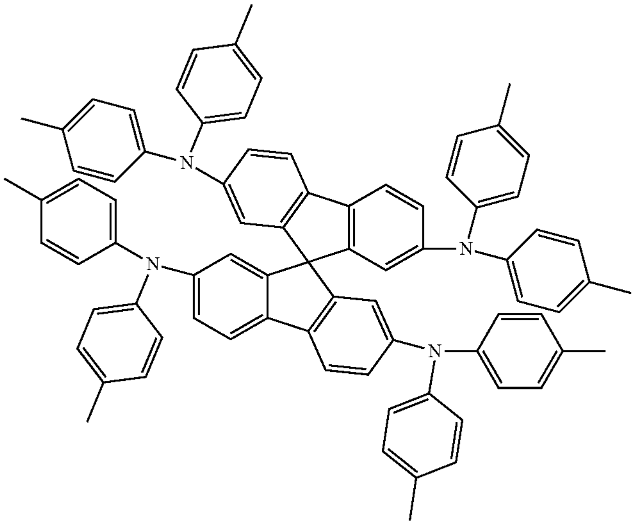

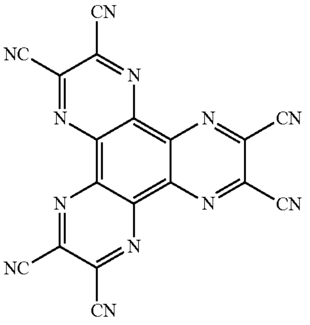

Preferably, the inventive OLED comprises two or more different hole-transporting layers. The compound of the formula (I) or (II) may be used here in one or more of or in all the hole-transporting layers. In a preferred embodiment, the compound of the formula (I) or (II) is used in exactly one or exactly two hole-transporting layers, and other compounds, preferably aromatic amine compounds, are used in the further hole-transporting layers present. Further compounds which, as well as the compounds of the formula (I) or (II), are preferably used in hole-transporting layers of the OLEDs of the invention are especially indenofluoreneamine derivatives, amine derivatives, hexaazatriphenylene derivatives, amine derivatives with fused aromatic systems, monobenzoindenofluoreneamines, dibenzoindenofluoreneamines, spirobifluoreneamines, fluoreneamines, spirodibenzopyranamines, dihydroacridine derivatives, spirodibenzofurans and spirodibenzothiophenes, phenanthrenediarylamines, spirotribenzotropolones, spirobifluorenes having meta-phenyldiamine groups, spirobisacridines, xanthenediarylamines, and 9,10-dihydroanthracene spiro compounds having diarylamino groups.

Materials used for the electron transport layer may be any materials as used according to the prior art as electron transport materials in the electron transport layer. Especially suitable are aluminium complexes, for example $Alq_3$, zirconium complexes, for example $Zrq_4$, lithium complexes, for example Liq, benzimidazole derivatives, triazine derivatives, pyrimidine derivatives, pyridine derivatives, pyrazine derivatives, quinoxaline derivatives, quinoline derivatives, oxadiazole derivatives, aromatic ketones, lactams, boranes, diazaphosphole derivatives and phosphine oxide derivatives. Particular preference is given to the compounds shown in the following table:
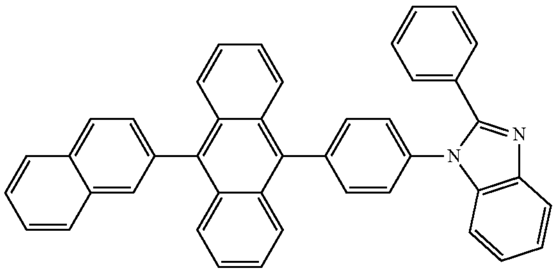
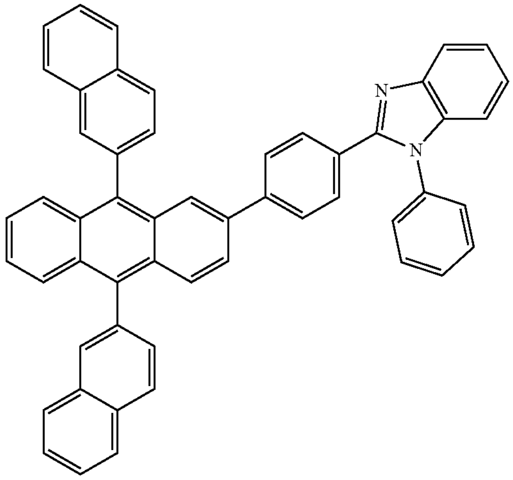
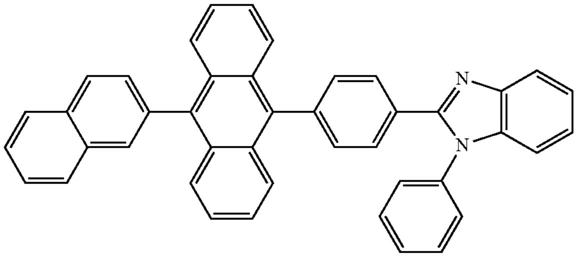
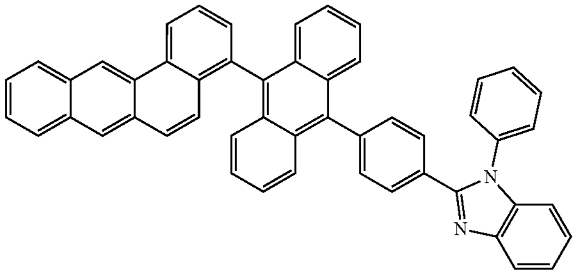
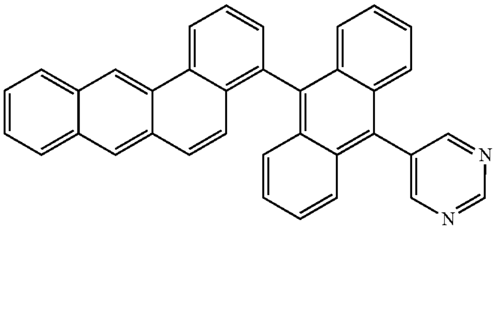
-continued
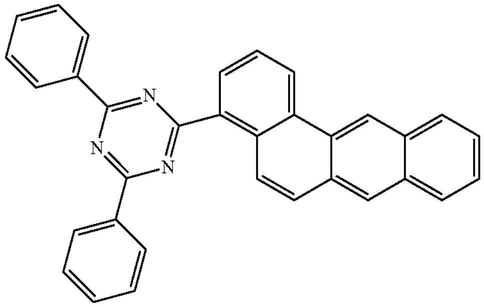
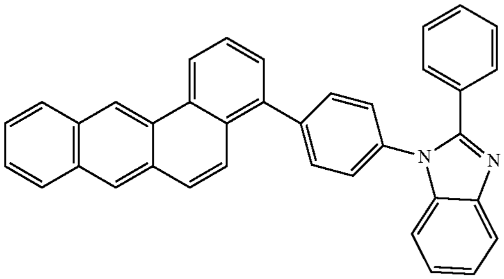
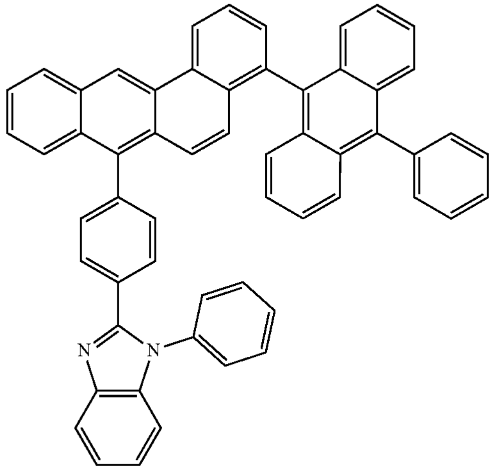
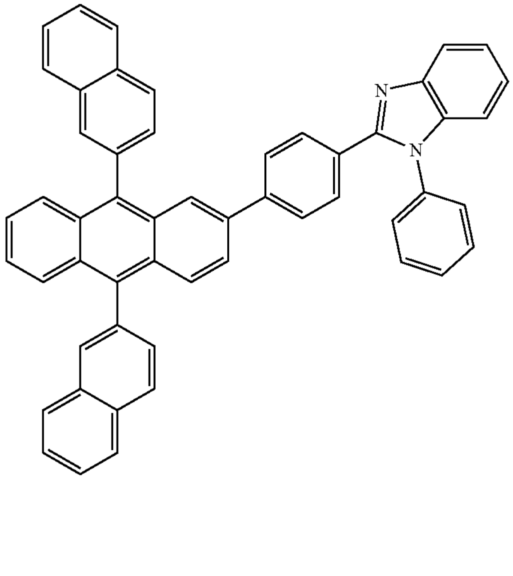

-continued
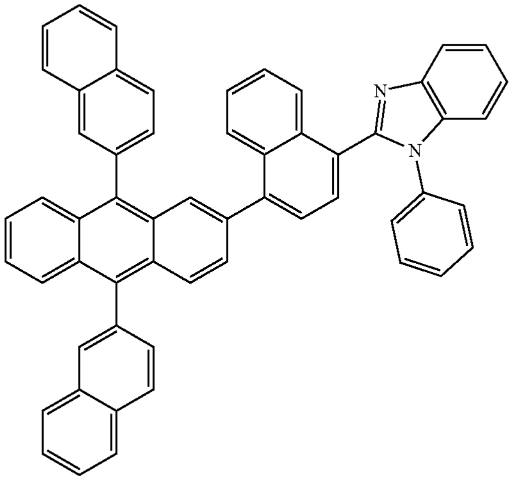
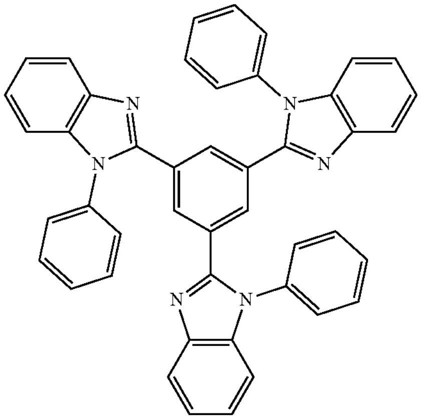
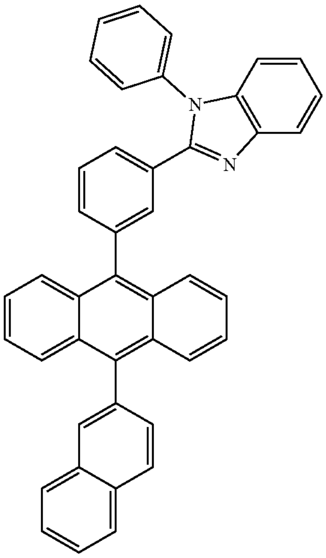
-continued
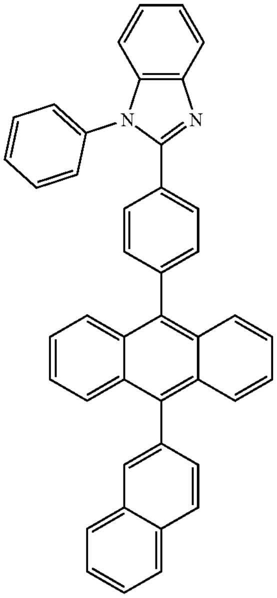
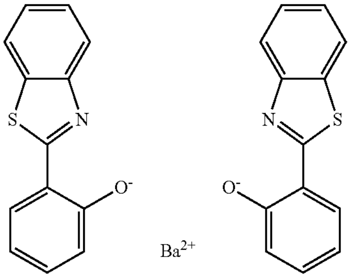
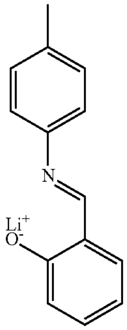
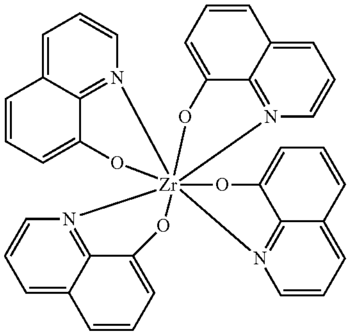

-continued
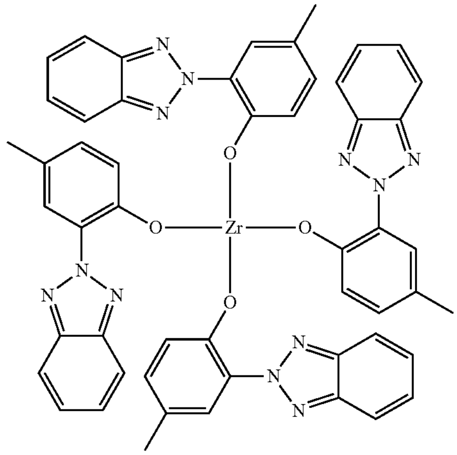
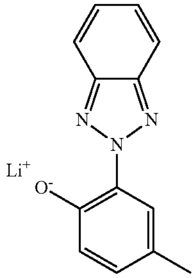
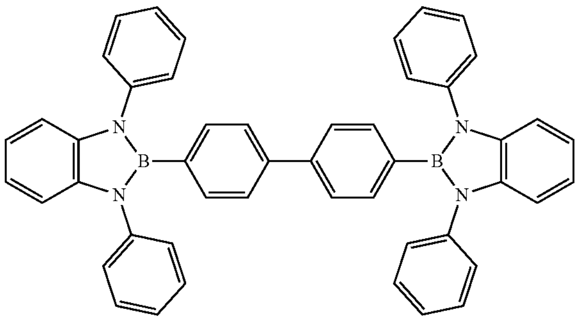
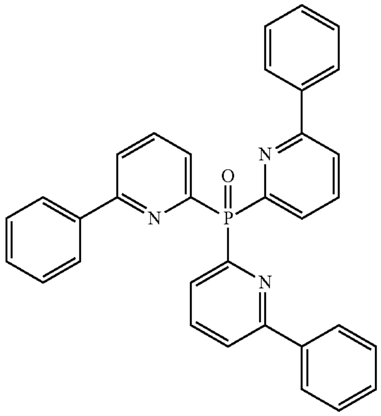
-continued
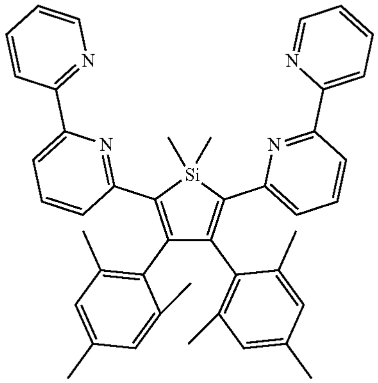
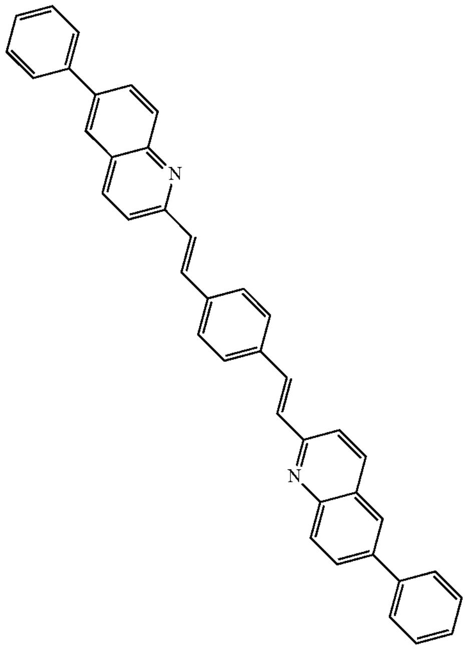
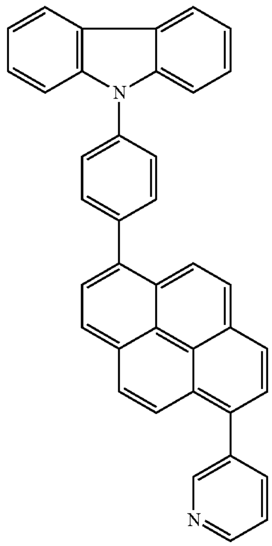

-continued

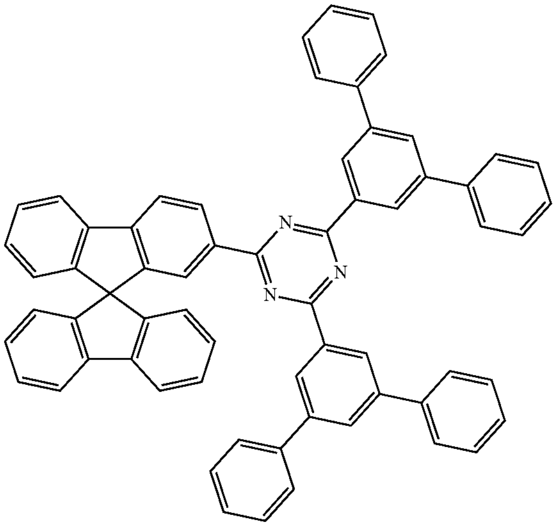

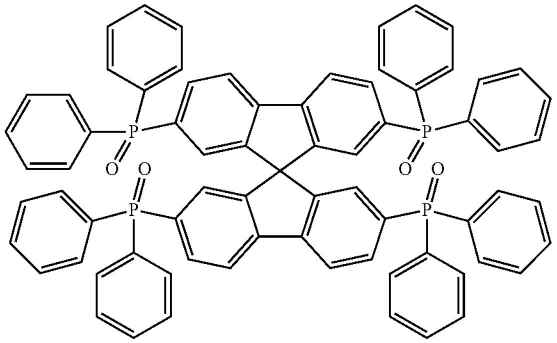

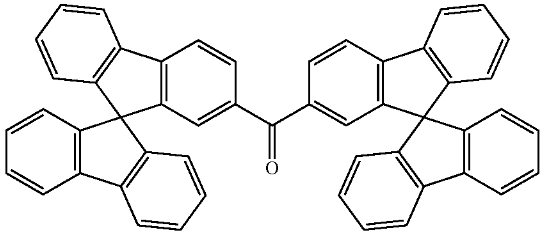

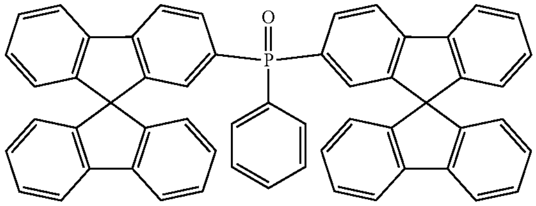

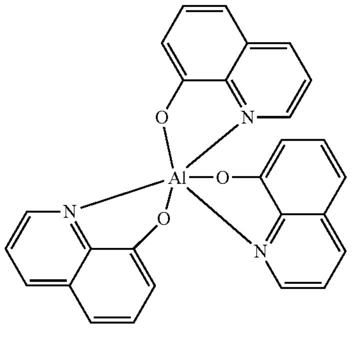

Preferred cathodes of the electronic device are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag or Al, in which case combinations of the metals such as Ca/Ag, Mg/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). It is also possible to use lithium quinolinate (LiQ) for this purpose. The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/$NiO_x$, Al/$PtO_x$) may also be preferred. For some applications, at least one of the electrodes has to be transparent or partly transparent in order to enable either the irradiation of the organic material (organic solar cell) or the emission of light (OLED, O-LASER). Preferred anode materials here are conductive mixed metal oxides. Particular preference is given to indium tin oxide (ITO) or indium zinc oxide (IZO). Preference is further given to conductive doped organic materials, especially conductive doped polymers. In addition, the anode may also consist of two or more layers, for example of an inner layer of ITO and an outer layer of a metal oxide, preferably tungsten oxide, molybdenum oxide or vanadium oxide.

The device is structured appropriately (according to the application), contact-connected and finally sealed, in order to rule out damaging effects by water and air.

In a preferred embodiment, the electronic device is characterized in that one or more layers are coated by a sublimation process. In this case, the materials are applied by vapour deposition in vacuum sublimation systems at an initial pressure of less than 10-5 mbar, preferably less than 10-6 mbar. In this case, however, it is also possible that the initial pressure is even lower, for example less than 10-7 mbar.

Preference is likewise given to an electronic device, characterized in that one or more layers are coated by the OVPD (organic vapour phase deposition) method or with the aid of a carrier gas sublimation. In this case, the materials are applied at a pressure between 10-5 mbar and 1 bar. A special case of this method is the OVJP (organic vapour jet printing) method, in which the materials are applied directly by a nozzle and thus structured (for example M. S. Arnold et al., Appl. Phys. Lett. 2008, 92, 053301).

Preference is additionally given to an electronic device, characterized in that one or more layers are produced from solution, for example by spin-coating, or by any printing method, for example screen printing, flexographic printing, nozzle printing or offset printing, but more preferably LITI (light-induced thermal imaging, thermal transfer printing) or inkjet printing. For this purpose, soluble compounds of formula (I) or (II) are needed. High solubility can be achieved by suitable substitution of the compounds.

It is further preferable that an electronic device of the invention is produced by applying one or more layers from solution and one or more layers by a sublimation method.

According to the invention, the electronic devices comprising one or more compounds of formula (I) or (II) can be used in displays, as light sources in lighting applications and as light sources in medical and/or cosmetic applications.

EXAMPLES

A) Synthesis Examples

Example 1-1

Synthesis of the Inventive Compound 1-1 and Variants

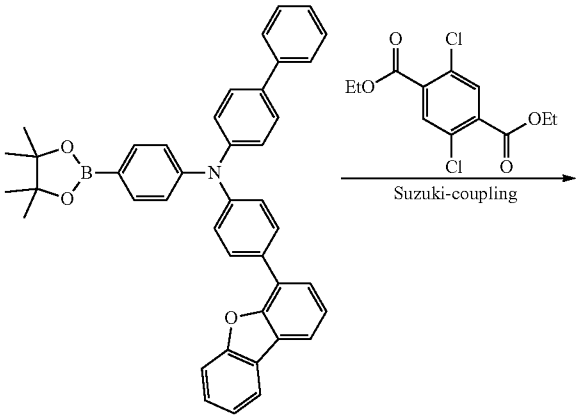

0-1

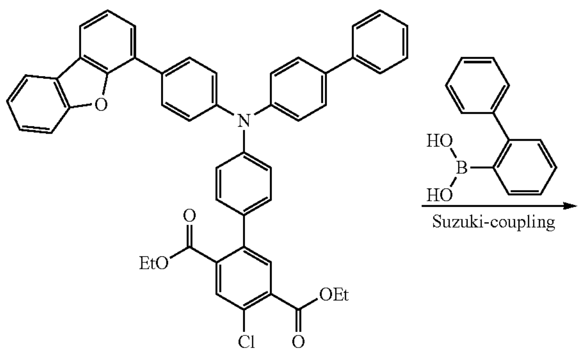

I-1

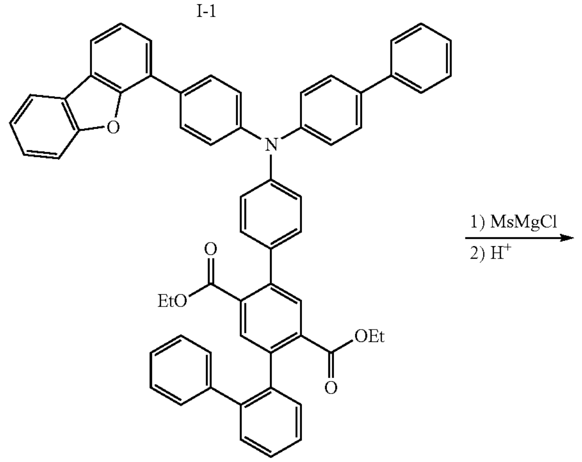

II-1

-continued

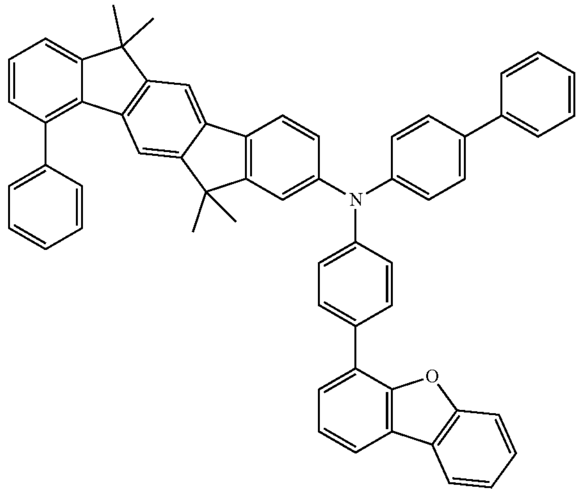

1-1

Intermediate I-1

22 g of the boronic ester derivative 0-1 (34.8 mmol) and 11.7 g of bromochlorodicarboxylic ester derivatives (34.8 mmol) are suspended in 200 ml of toluene, 100 ml of ethanol and 50 ml of water. 7.4 g of sodium carbonate are added. The reaction solution is degassed and saturated with $N_2$. Thereafter, 0.6 g (0.51 mmol) of $Pd(Ph_3P)_4$ are added. The reaction mixture is heated to boiling under a protective atmosphere for 16 h. The mixture is subsequently partitioned between toluene and water, and the organic phase is washed three times with water and dried over $Na_2SO_4$ and concentrated by rotary evaporation. The remaining residue is extracted by stirring in heptane. The yield is 23 g (87% of theory).

Intermediate II-1

6.3 g of (2-phenylphenyl) boronic acid (31.6 mmol) and 23 g of the chlorine derivative I-1 (30 mmol) are suspended in 260 ml of toluene and 100 ml of water. 8.3 g of potassium carbonate are added thereto. The solution is degassed and saturated with $N_2$. Thereafter, 276 mg (0.3 mmol) of $Pd_2(dba)_3$ and 250 mg of SPhos (0.3 mmol) are added. The reaction mixture is heated to boiling under a protective atmosphere for 12 h. The mixture is subsequently partitioned between toluene and water, and the organic phase is washed three times with water and dried over $Na_2SO_4$ and concentrated by rotary evaporation. After the crude product has been filtered through silica gel with toluene, the remaining residue is recrystallized from EtOH. The yield is 20.7 g (80% of theory).

The following compounds are prepared in an analogous manner:
| | | Boronic acid derivative 2 | Product |
|---|---|---|---|
| II-2 | Reactant 1<br>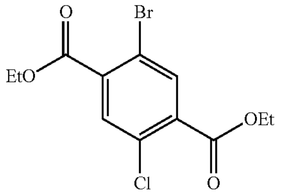 [SMILES: CCOC(=O)c1cc(Br)c(C(=O)OCC)cc1Cl]<br>Boronic acid derivative 1<br>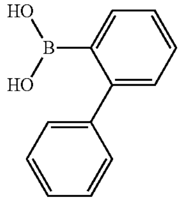 | 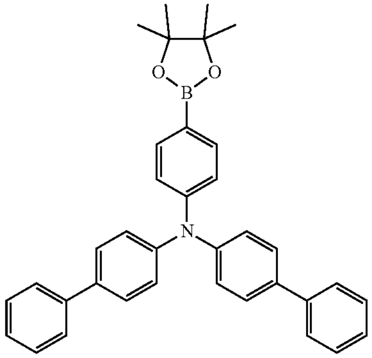 [SMILES: CC1(C)OB(c2ccc(N(c3ccc(-c4ccccc4)cc3)c3ccc(-c4ccccc4)cc3)cc2)OC1(C)C] | 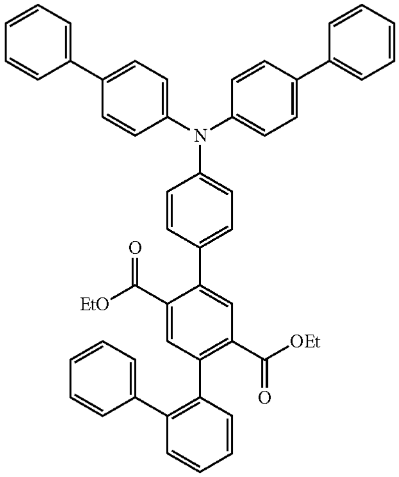 [SMILES: CCOC(=O)c1cc(-c2ccccc2-c2ccccc2)c(C(=O)OCC)cc1-c1ccc(N(c2ccc(-c3ccccc3)cc2)c2ccc(-c3ccccc3)cc2)cc1] |
| II-3 | Reactant 1<br>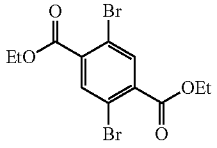 [SMILES: CCOC(=O)c1cc(Br)c(C(=O)OCC)cc1Br]<br>Boronic acid derivative 1<br>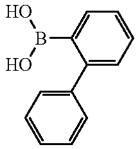 | 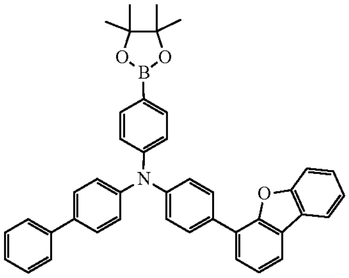 [SMILES: CC1(C)OB(c2ccc(N(c3ccc(-c4ccccc4)cc3)c3ccc(-c4cccc5c4oc4ccccc45)cc3)cc2)OC1(C)C] | 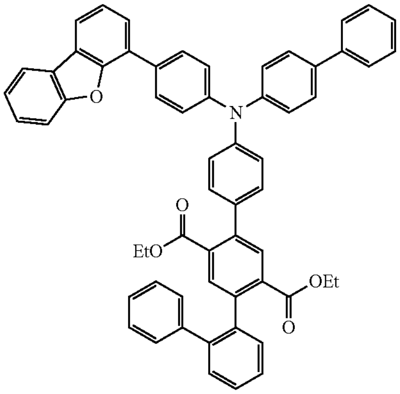 [SMILES: CCOC(=O)c1cc(-c2ccccc2-c2ccccc2)c(C(=O)OCC)cc1-c1ccc(N(c2ccc(-c3ccccc3)cc2)c2ccc(-c3cccc4c3oc3ccccc34)cc2)cc1] |

-continued
| | | Boronic acid derivative 2 | Product |
|---|---|---|---|
| II-4 | Reactant 1<br>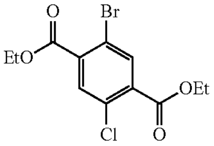 [SMILES: CCOC(=O)c1cc(Br)c(C(=O)OCC)cc1Cl] | 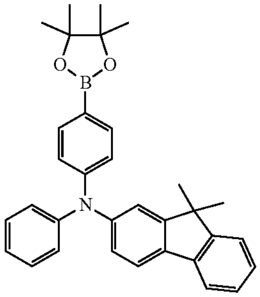 [SMILES: CC1(C)c2ccccc2-c2ccc(N(c3ccccc3)c3ccc(B4OC(C)(C)C(C)(C)O4)cc3)cc21] | 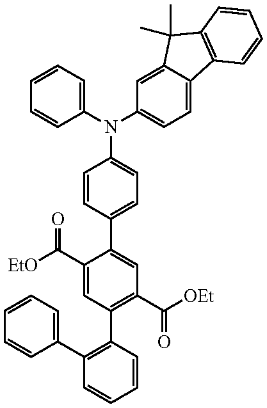 [SMILES: CCOC(=O)c1cc(-c2ccccc2-c2ccccc2)c(C(=O)OCC)cc1-c1ccc(N(c2ccccc2)c2ccc3c(c2)C(C)(C)c2ccccc2-3)cc1] |
| | Boronic acid derivative 1<br>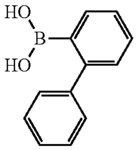 [SMILES: OB(O)c1ccccc1-c1ccccc1] | | |
| II-5 | Reactant 1<br>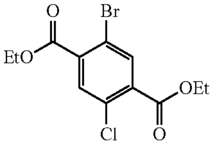 [SMILES: CCOC(=O)c1cc(Br)c(C(=O)OCC)cc1Cl] | 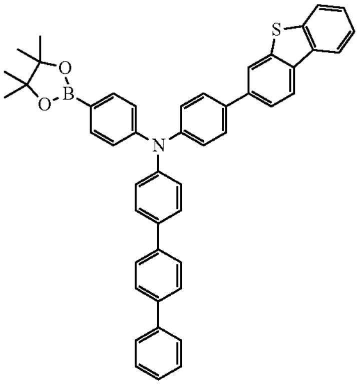 [SMILES: CC1(C)OB(c2ccc(N(c3ccc(-c4ccc(-c5ccccc5)cc4)cc3)c3ccc(-c4ccc5c(c4)sc4ccccc45)cc3)cc2)OC1(C)C] | 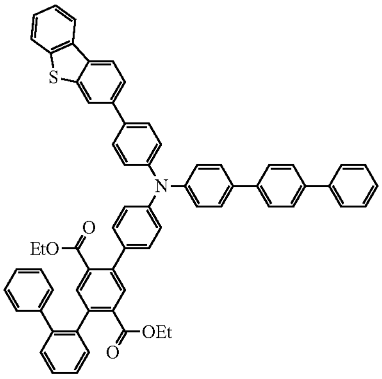 [SMILES: CCOC(=O)c1cc(-c2ccccc2-c2ccccc2)c(C(=O)OCC)cc1-c1ccc(N(c2ccc(-c3ccc(-c4ccccc4)cc3)cc2)c2ccc(-c3ccc4c(c3)sc3ccccc34)cc2)cc1] |
| | Boronic acid derivative 1<br>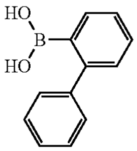 [SMILES: OB(O)c1ccccc1-c1ccccc1] | | |
| II-6 | Reactant 1<br>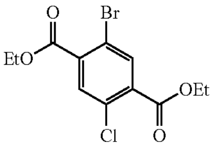 | 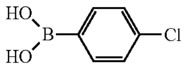 | 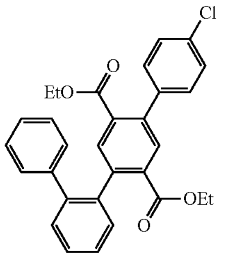 [SMILES: CCOC(=O)c1cc(-c2ccccc2-c2ccccc2)c(C(=O)OCC)cc1-c1ccc(Cl)cc1] |

-continued
| | | Boronic acid derivative 2 | Product |
|---|---|---|---|
| | Boronic acid derivative 1 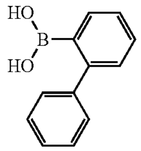 [SMILES: OB(O)c1ccccc1-c1ccccc1] | | |
| II-7 | Reactant 1 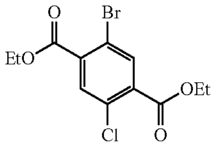 [SMILES: CCOC(=O)c1cc(Br)c(C(=O)OCC)cc1Cl] | 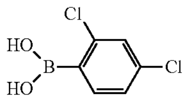 | 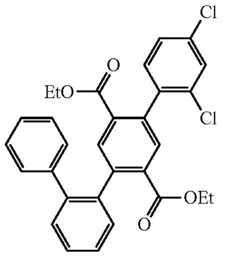 [SMILES: CCOC(=O)c1cc(-c2ccccc2-c2ccccc2)c(C(=O)OCC)cc1-c1ccc(Cl)cc1Cl] |
| | Boronic acid derivative 1 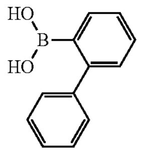 [SMILES: OB(O)c1ccccc1-c1ccccc1] | | |
| II-8 | Reactant 1 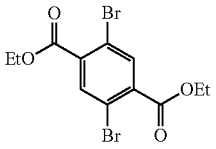 | 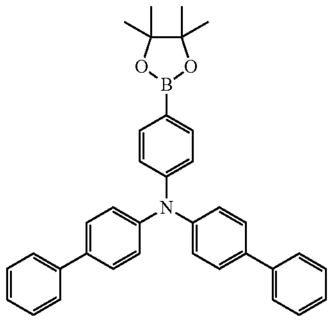 [SMILES: CC1(C)OB(c2ccc(N(c3ccc(-c4ccccc4)cc3)c3ccc(-c4ccccc4)cc3)cc2)OC1(C)C] | 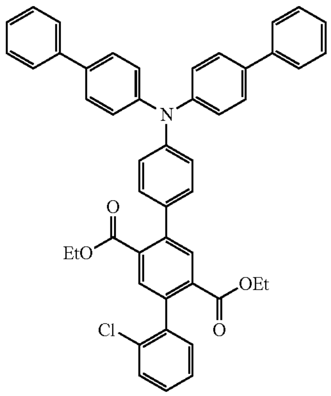 [SMILES: CCOC(=O)c1cc(-c2ccccc2Cl)c(C(=O)OCC)cc1-c1ccc(N(c2ccc(-c3ccccc3)cc2)c2ccc(-c3ccccc3)cc2)cc1] |
| | Boronic acid derivative 1 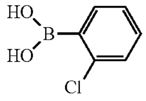 | | |

-continued
| | | Boronic acid derivative 2 | Product |
|---|---|---|---|
| II-9 | Reactant 1<br>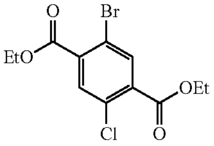<br>Boronic acid derivative 1<br>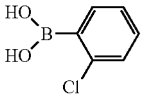 | 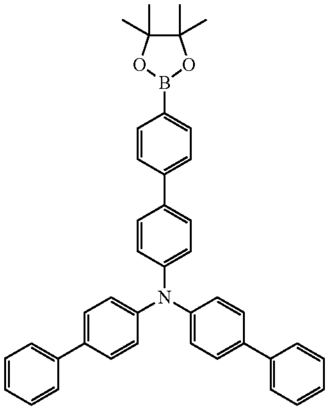 [SMILES: CC1(C)OB(c2ccc(-c3ccc(N(c4ccc(-c5ccccc5)cc4)c4ccc(-c5ccccc5)cc4)cc3)cc2)OC1(C)C] | 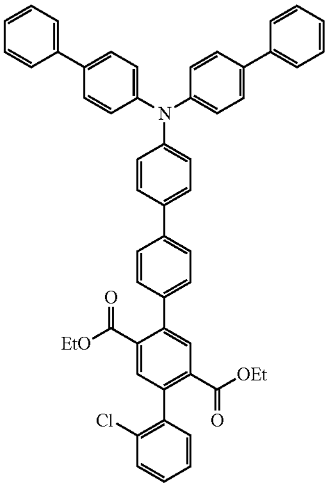 [SMILES: CCOC(=O)c1cc(-c2ccccc2Cl)c(C(=O)OCC)cc1-c1ccc(-c2ccc(N(c3ccc(-c4ccccc4)cc3)c3ccc(-c4ccccc4)cc3)cc2)cc1] |
| II-10 | Reactant 1<br>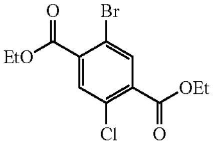 [SMILES: CCOC(=O)c1cc(Br)c(C(=O)OCC)cc1Cl]<br>Boronic acid derivative 1<br>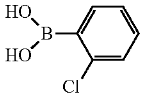 | 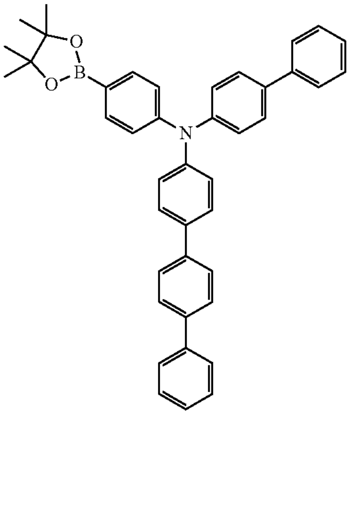 [SMILES: CC1(C)OB(c2ccc(N(c3ccc(-c4ccccc4)cc3)c3ccc(-c4ccc(-c5ccccc5)cc4)cc3)cc2)OC1(C)C] | 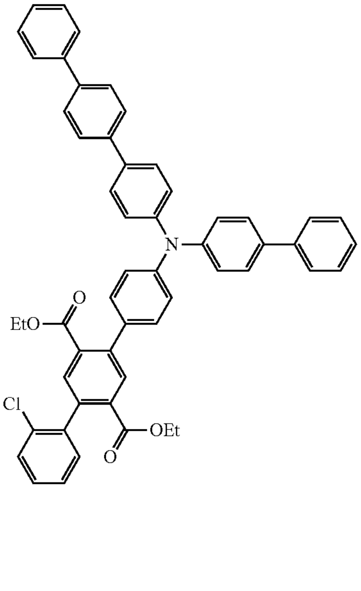 [SMILES: CCOC(=O)c1cc(-c2ccccc2Cl)c(C(=O)OCC)cc1-c1ccc(N(c2ccc(-c3ccccc3)cc2)c2ccc(-c3ccc(-c4ccccc4)cc3)cc2)cc1] |

-continued
| | | Boronic acid derivative 2 | Product |
| --- | --- | --- | --- |
| II-11 | Reactant 1<br>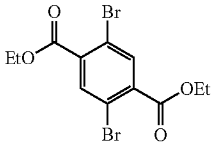<br>Boronic acid derivative 1<br>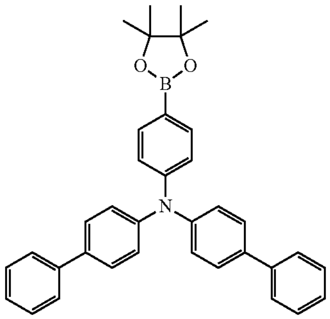 | 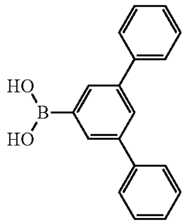 [SMILES: OB(O)c1cc(-c2ccccc2)cc(-c2ccccc2)c1] | 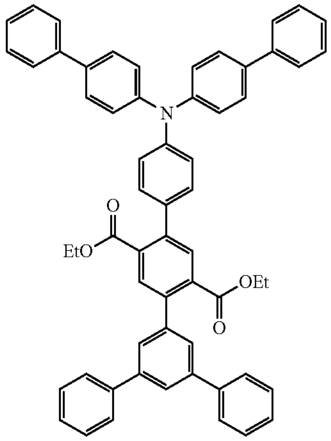 [SMILES: CCOC(=O)c1cc(-c2cc(-c3ccccc3)cc(-c3ccccc3)c2)c(C(=O)OCC)cc1-c1ccc(N(c2ccc(-c3ccccc3)cc2)c2ccc(-c3ccccc3)cc2)cc1] |
| II-12 | Reactant 1<br>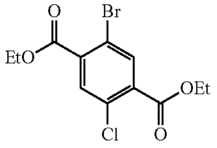<br>Boronic acid derivative 1<br>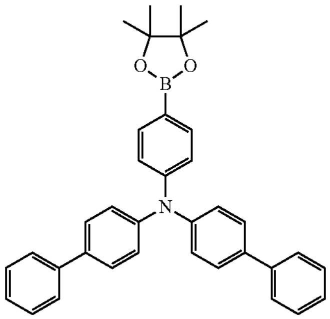 [SMILES: CC1(C)OB(c2ccc(N(c3ccc(-c4ccccc4)cc3)c3ccc(-c4ccccc4)cc3)cc2)OC1(C)C] | 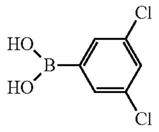 [SMILES: OB(O)c1cc(Cl)cc(Cl)c1] | 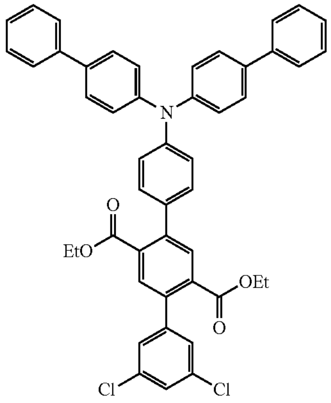 [SMILES: CCOC(=O)c1cc(-c2cc(Cl)cc(Cl)c2)c(C(=O)OCC)cc1-c1ccc(N(c2ccc(-c3ccccc3)cc2)c2ccc(-c3ccccc3)cc2)cc1] |

-continued
| | | Boronic acid derivative 2 | Product |
|---|---|---|---|
| II-13 | Reactant 1<br>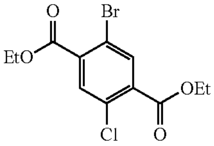 [SMILES: CCOC(=O)c1cc(Br)c(C(=O)OCC)cc1Cl]<br>Boronic acid derivative 1<br>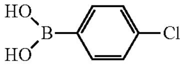 | 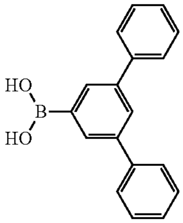 [SMILES: OB(O)c1cc(-c2ccccc2)cc(-c2ccccc2)c1] | 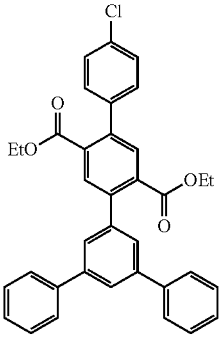 [SMILES: CCOC(=O)c1cc(-c2cc(-c3ccccc3)cc(-c3ccccc3)c2)c(C(=O)OCC)cc1-c1ccc(Cl)cc1] |
| II-14 | Reactant 1<br>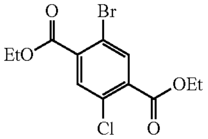 [SMILES: CCOC(=O)c1cc(Br)c(C(=O)OCC)cc1Cl]<br>Boronic acid derivative 1<br>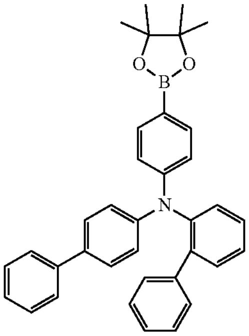 | 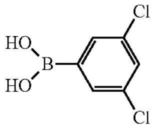 [SMILES: OB(O)c1cc(Cl)cc(Cl)c1] | 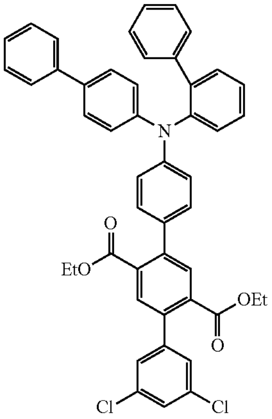 [SMILES: CCOC(=O)c1cc(-c2cc(Cl)cc(Cl)c2)c(C(=O)OCC)cc1-c1ccc(N(c2ccc(-c3ccccc3)cc2)c2ccccc2-c2ccccc2)cc1] |

-continued
| | | Boronic acid derivative 2 | Product |
|---|---|---|---|
| II-15 | Reactant 1 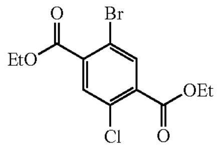 [SMILES: CCOC(=O)c1cc(Br)c(C(=O)OCC)cc1Cl] Boronic acid derivative 1 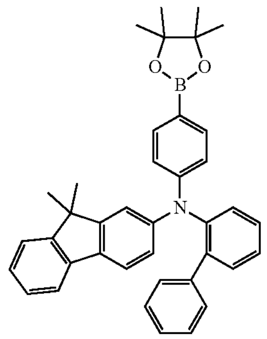 | 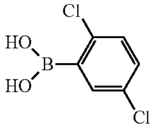 [SMILES: OB(O)c1cc(Cl)ccc1Cl] | 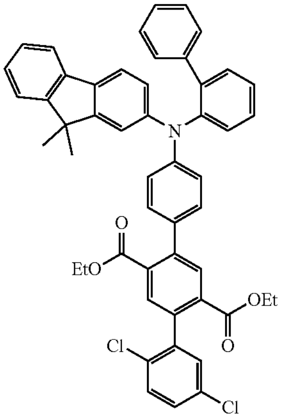 [SMILES: CCOC(=O)c1cc(-c2cc(Cl)ccc2Cl)c(C(=O)OCC)cc1-c1ccc(N(c2ccc3c(c2)C(C)(C)c2ccccc2-3)c2ccccc2-c2ccccc2)cc1] |
| II-16 | Reactant 1 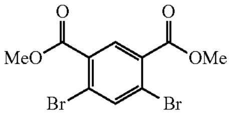 [SMILES: COC(=O)c1cc(C(=O)OC)c(Br)cc1Br] Boronic acid derivative 1 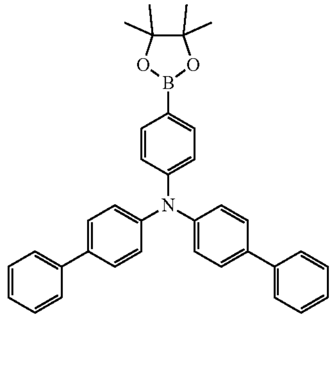 | 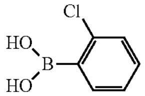 | 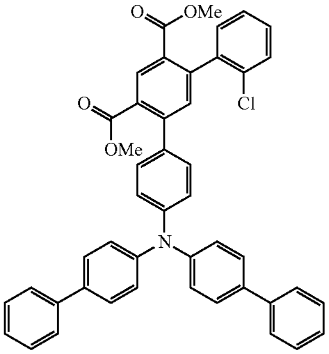 [SMILES: COC(=O)c1cc(C(=O)OC)c(-c2ccccc2Cl)cc1-c1ccc(N(c2ccc(-c3ccccc3)cc2)c2ccc(-c3ccccc3)cc2)cc1] |

-continued
| | | Boronic acid derivative 2 | Product |
|---|---|---|---|
| II-17 | Reactant 1<br>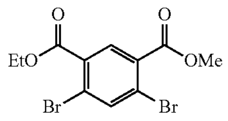<br>Boronic acid derivative 1<br>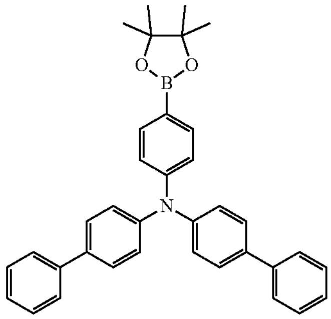 [SMILES: CC1(C)OB(c2ccc(N(c3ccc(-c4ccccc4)cc3)c3ccc(-c4ccccc4)cc3)cc2)OC1(C)C] | 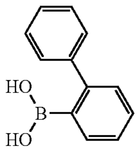 [SMILES: OB(O)c1ccccc1-c1ccccc1] | 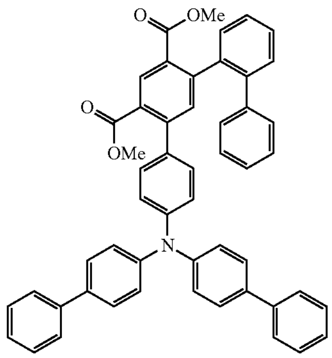 [SMILES: COC(=O)c1cc(C(=O)OC)c(-c2ccccc2-c2ccccc2)cc1-c1ccc(N(c2ccc(-c3ccccc3)cc2)c2ccc(-c3ccccc3)cc2)cc1] |
| II-18 | Reactant 1<br>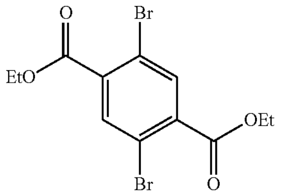 [SMILES: CCOC(=O)c1cc(Br)c(C(=O)OCC)cc1Br] | 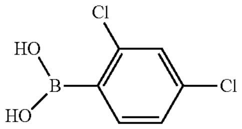 | 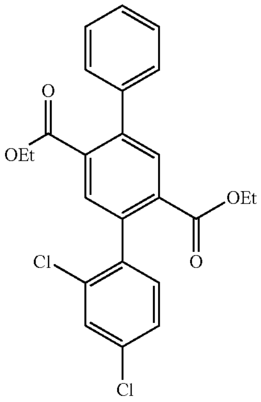 [SMILES: CCOC(=O)c1cc(-c2ccc(Cl)cc2Cl)c(C(=O)OCC)cc1-c1ccccc1] |

-continued

| | | Boronic acid derivative 2 | Product |
|---|---|---|---|
| | Boronic acid derivative 1 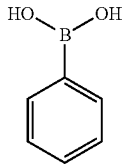 | | |
| II-19 | Reactant 1 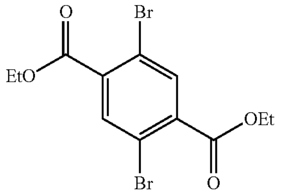 [SMILES: CCOC(=O)c1cc(Br)c(C(=O)OCC)cc1Br] | 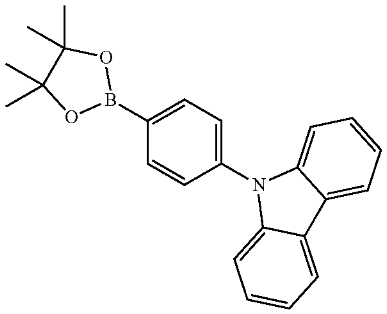 [SMILES: CC1(C)OB(c2ccc(-n3c4ccccc4c4ccccc43)cc2)OC1(C)C] | 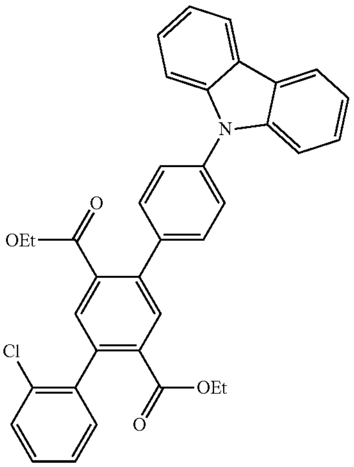 [SMILES: CCOC(=O)c1cc(-c2ccccc2Cl)c(C(=O)OCC)cc1-c1ccc(-n2c3ccccc3c3ccccc32)cc1] |
| | Boronic acid derivative 1 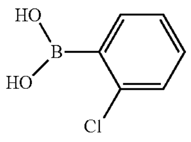 | | |

Compound 1-1

15.0 g (17.4 mmol) of intermediate II-1 are dissolved in a baked-out flask in 150 ml of dried THF. The solution is saturated with $N_2$. The clear solution is cooled down to −5° C. and then 35 ml (105 mmol) of a 3M methylmagnesium chloride solution are added. The reaction mixture is gradually warmed to room temperature and then quenched with ammonium chloride. The mixture is subsequently partitioned between ethyl acetate and water, and the organic phase is washed three times with water, dried over $Na_2SO_4$ and concentrated by rotary evaporation. The solution that has been concentrated by rotary evaporation is dissolved in toluene, and 8 g of Amberlyst 15 are added. The mixture is heated to 110° C. and kept at this temperature for 4 h. During this time, a white solid precipitates out. The mixture is then cooled to room temperature, and the precipitated solid is filtered off with suction and washed with heptane. The residue is dried at 40° C. under reduced pressure. After the crude product has been filtered through silica gel with heptane:ethyl acetate, 1:1, 13 g (90% of theory) of the product are obtained. Finally, the material is sublimed under high vacuum. Purity is 99.9%.

The following compounds are prepared in an analogous manner:
| | | Product |
|---|---|---|
| 1-2 | Reactant 1<br>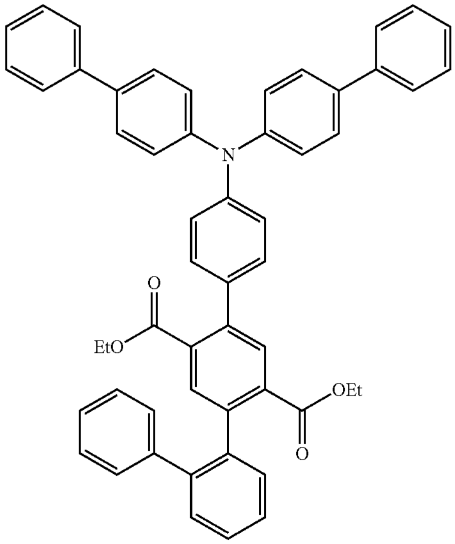 [SMILES: CCOC(=O)c1cc(-c2ccccc2-c2ccccc2)c(C(=O)OCC)cc1-c1ccc(N(c2ccc(-c3ccccc3)cc2)c2ccc(-c3ccccc3)cc2)cc1]<br>Reactant 2<br>MeMgBr | 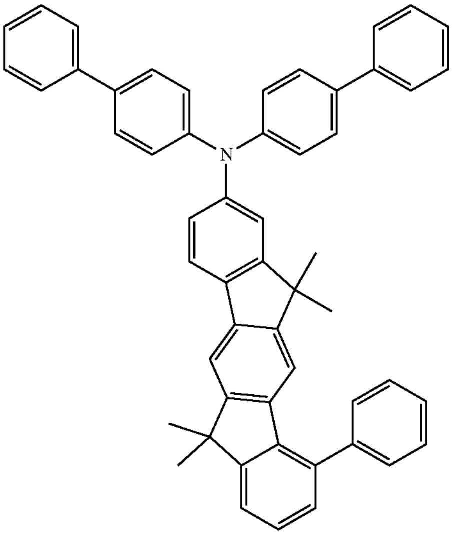 [SMILES: CC1(C)c2cc(N(c3ccc(-c4ccccc4)cc3)c3ccc(-c4ccccc4)cc3)ccc2-c2cc3c(cc21)-c1c(-c2ccccc2)cccc1C3(C)C] |
| 1-3 | Reactant 1<br>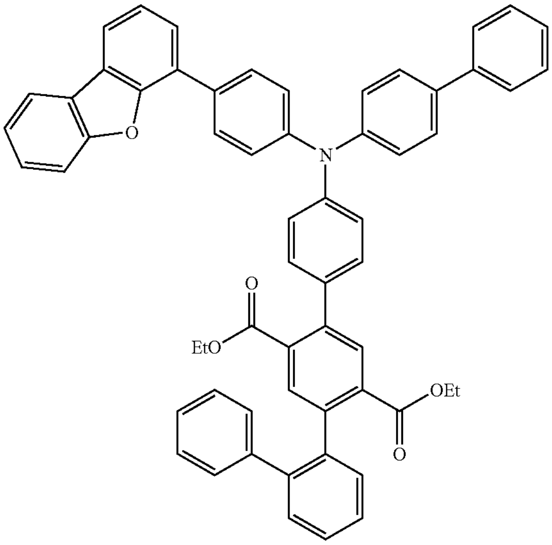 [SMILES: CCOC(=O)c1cc(-c2ccccc2-c2ccccc2)c(C(=O)OCC)cc1-c1ccc(N(c2ccc(-c3ccccc3)cc2)c2ccc(-c3cccc4c3oc3ccccc34)cc2)cc1]<br>Reactant 2<br>iPrMgBr | 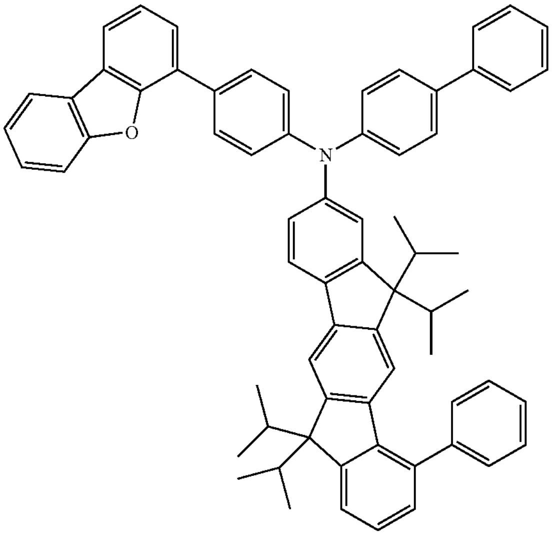 [SMILES: CC(C)C1(C(C)C)c2cc(N(c3ccc(-c4ccccc4)cc3)c3ccc(-c4cccc5c4oc4ccccc45)cc3)ccc2-c2cc3c(cc21)-c1c(-c2ccccc2)cccc1C3(C(C)C)C(C)C] |

-continued
| | | Product |
|---|---|---|
| 1-4 | Reactant 1<br>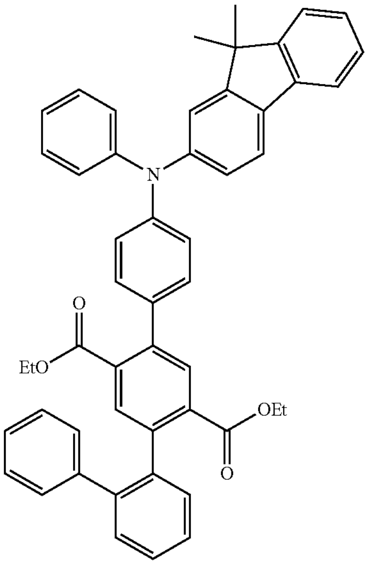 [SMILES: CCOC(=O)c1cc(-c2ccccc2-c2ccccc2)c(C(=O)OCC)cc1-c1ccc(N(c2ccccc2)c2ccc3c(c2)C(C)(C)c2ccccc2-3)cc1]<br>Reactant 2<br>MeMgBr | 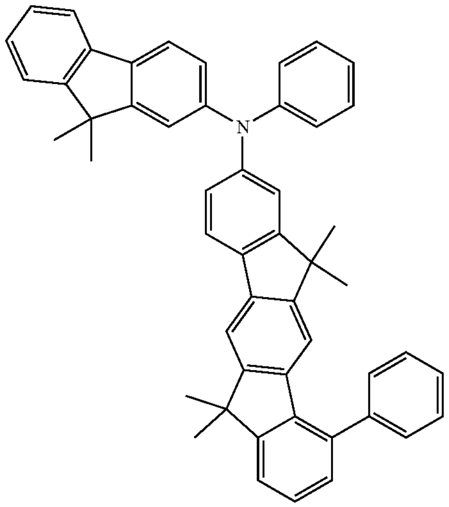 [SMILES: CC1(C)c2ccccc2-c2ccc(N(c3ccccc3)c3ccc4c(c3)C(C)(C)c3cc5c(cc3-4)C(C)(C)c3cccc(-c4ccccc4)c3-5)cc21] |
| 1-5 | Reactant 1<br>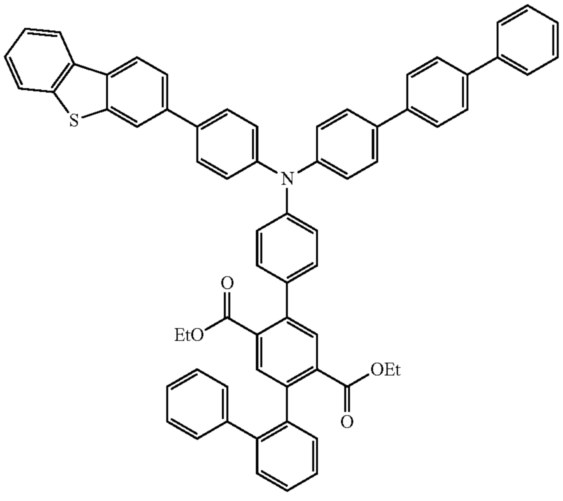 [SMILES: CCOC(=O)c1cc(-c2ccccc2-c2ccccc2)c(C(=O)OCC)cc1-c1ccc(N(c2ccc(-c3ccc(-c4ccccc4)cc3)cc2)c2ccc(-c3ccc4c(c3)sc3ccccc34)cc2)cc1]<br>Reactant 2<br>MeMgBr | 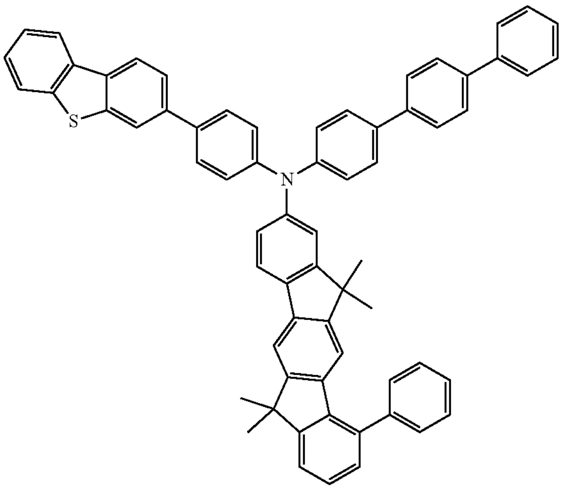 [SMILES: CC1(C)c2cc(N(c3ccc(-c4ccc(-c5ccccc5)cc4)cc3)c3ccc(-c4ccc5c(c4)sc4ccccc45)cc3)ccc2-c2cc3c(cc21)-c1c(-c2ccccc2)cccc1C3(C)C] |

-continued
| | | Product |
|---|---|---|
| 1-6 | Reactant 1<br>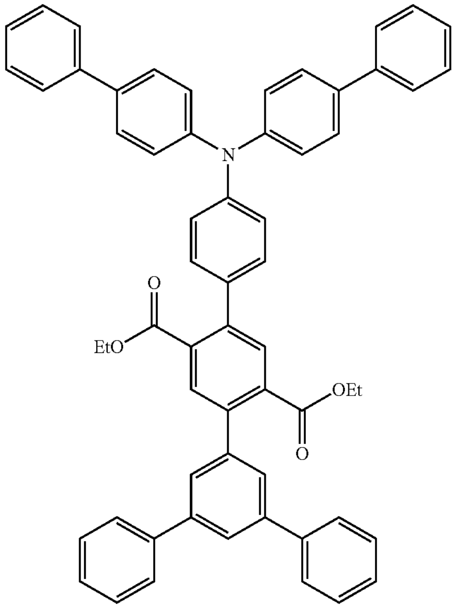 [SMILES: CCOC(=O)c1cc(-c2cc(-c3ccccc3)cc(-c3ccccc3)c2)c(C(=O)OCC)cc1-c1ccc(N(c2ccc(-c3ccccc3)cc2)c2ccc(-c3ccccc3)cc2)cc1]<br>Reactant 2<br>MeMgCl | 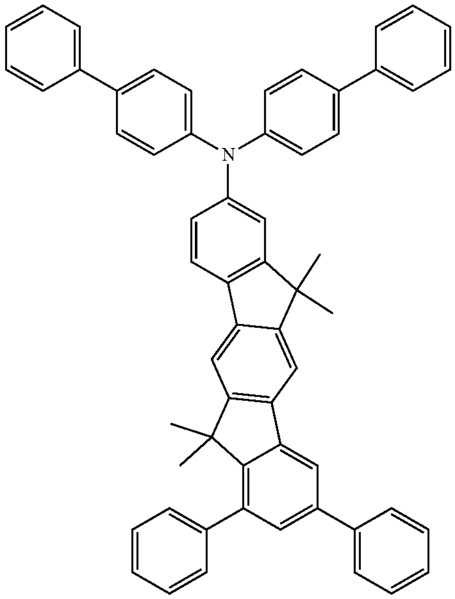 [SMILES: CC1(C)c2cc(N(c3ccc(-c4ccccc4)cc3)c3ccc(-c4ccccc4)cc3)ccc2-c2cc3c(cc21)-c1cc(-c2ccccc2)cc(-c2ccccc2)c1C3(C)C] |
| 1-7 | Reactant 1<br>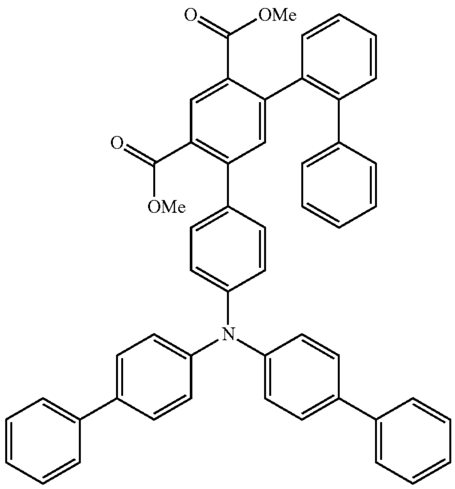 [SMILES: COC(=O)c1cc(C(=O)OC)c(-c2ccccc2-c2ccccc2)cc1-c1ccc(N(c2ccc(-c3ccccc3)cc2)c2ccc(-c3ccccc3)cc2)cc1]<br>Reactant 2<br>MeMgBr | 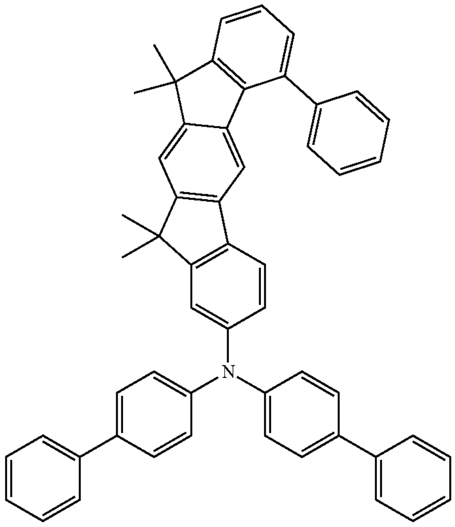 [SMILES: CC1(C)c2cc(N(c3ccc(-c4ccccc4)cc3)c3ccc(-c4ccccc4)cc3)ccc2-c2cc3c(cc21)C(C)(C)c1cccc(-c2ccccc2)c1-3] |

-continued
| | | Product |
|---|---|---|
| III-1 | Reactant 1<br>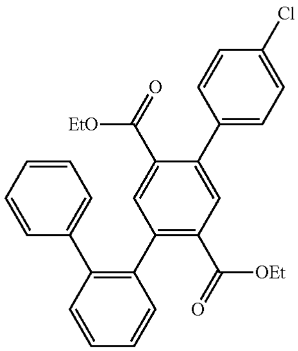 [SMILES: CCOC(=O)c1cc(-c2ccccc2-c2ccccc2)c(C(=O)OCC)cc1-c1ccc(Cl)cc1]<br>Reactant 2<br>MeLi | 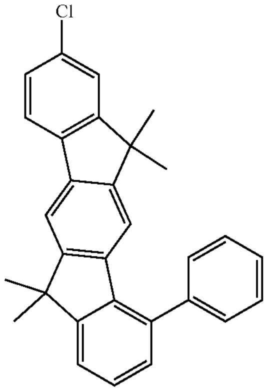 [SMILES: CC1(C)c2cc(Cl)ccc2-c2cc3c(cc21)-c1c(-c2ccccc2)cccc1C3(C)C] |
| III-2 | Reactant 1<br>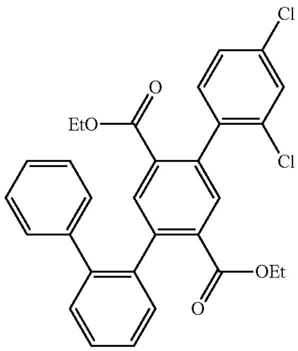 [SMILES: CCOC(=O)c1cc(-c2ccccc2-c2ccccc2)c(C(=O)OCC)cc1-c1ccc(Cl)cc1Cl]<br>Reactant 2<br>MeMgBr | 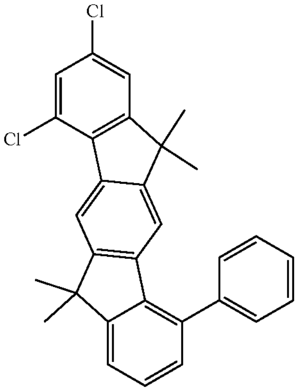 [SMILES: CC1(C)c2cc3c(cc2-c2c(Cl)cc(Cl)cc21)C(C)(C)c1cccc(-c2ccccc2)c1-3] |
| III-3 | Reactant 1<br>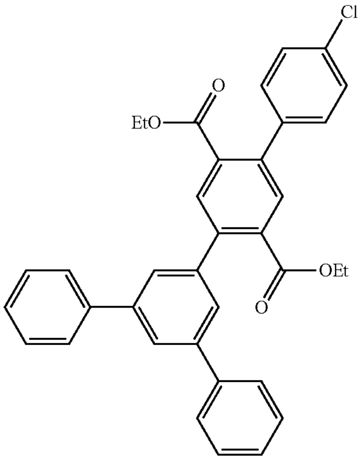 [SMILES: CCOC(=O)c1cc(-c2cc(-c3ccccc3)cc(-c3ccccc3)c2)c(C(=O)OCC)cc1-c1ccc(Cl)cc1]<br>Reactant 2<br>MeMgBr | 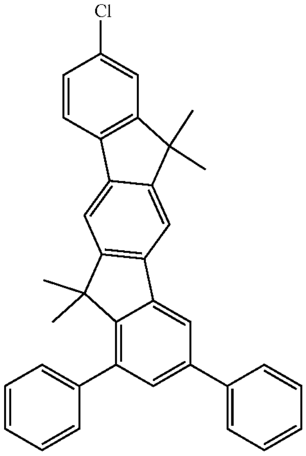 [SMILES: CC1(C)c2cc(Cl)ccc2-c2cc3c(cc21)-c1cc(-c2ccccc2)cc(-c2ccccc2)c1C3(C)C] |

-continued
| | | Product |
|---|---|---|
| III-4 | Reactant 1<br>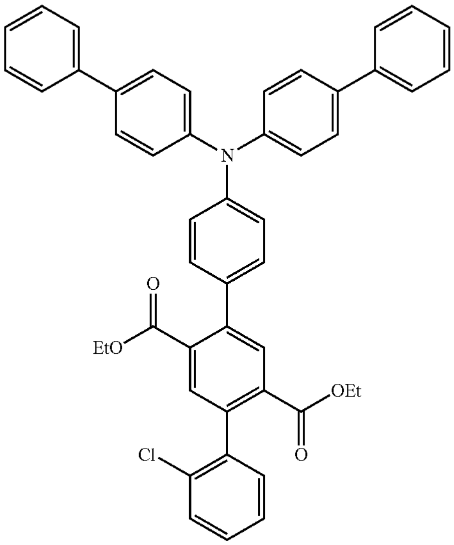 [SMILES: CCOC(=O)c1cc(-c2ccccc2Cl)c(C(=O)OCC)cc1-c1ccc(N(c2ccc(-c3ccccc3)cc2)c2ccc(-c3ccccc3)cc2)cc1]<br>Reactant 2<br>MeMgBr | 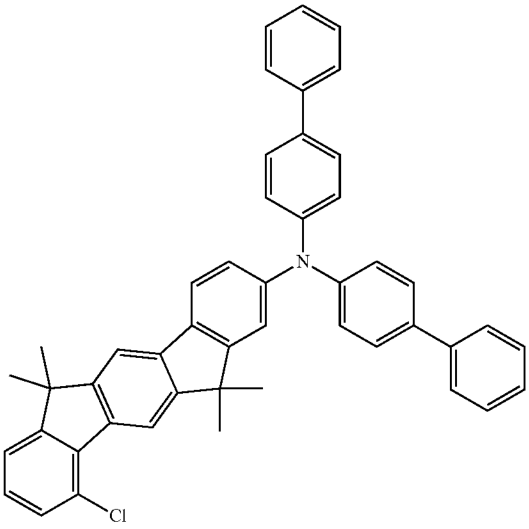 [SMILES: CC1(C)c2cc(N(c3ccc(-c4ccccc4)cc3)c3ccc(-c4ccccc4)cc3)ccc2-c2cc3c(cc21)-c1c(Cl)cccc1C3(C)C] |
| III-5 | Reactant 1<br>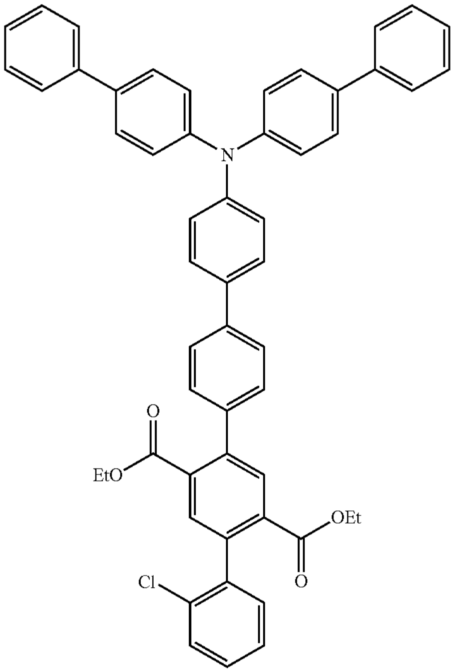 [SMILES: CCOC(=O)c1cc(-c2ccccc2Cl)c(C(=O)OCC)cc1-c1ccc(-c2ccc(N(c3ccc(-c4ccccc4)cc3)c3ccc(-c4ccccc4)cc3)cc2)cc1]<br>Reactant 2<br>MeMgCl | 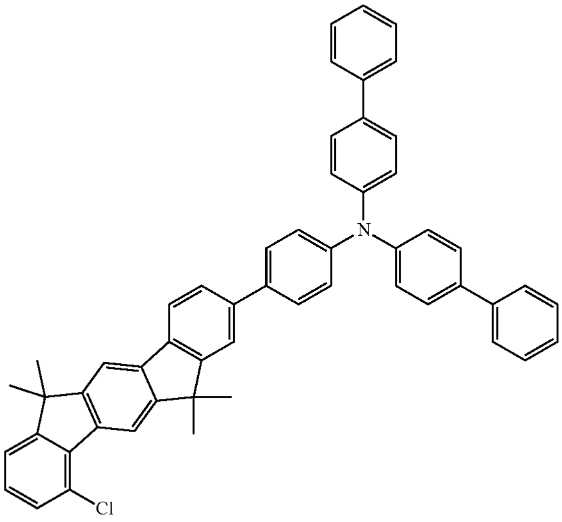 [SMILES: CC1(C)c2cc(-c3ccc(N(c4ccc(-c5ccccc5)cc4)c4ccc(-c5ccccc5)cc4)cc3)ccc2-c2cc3c(cc21)-c1c(Cl)cccc1C3(C)C] |

-continued
| | Product |
|---|---|
| III-6 Reactant 1 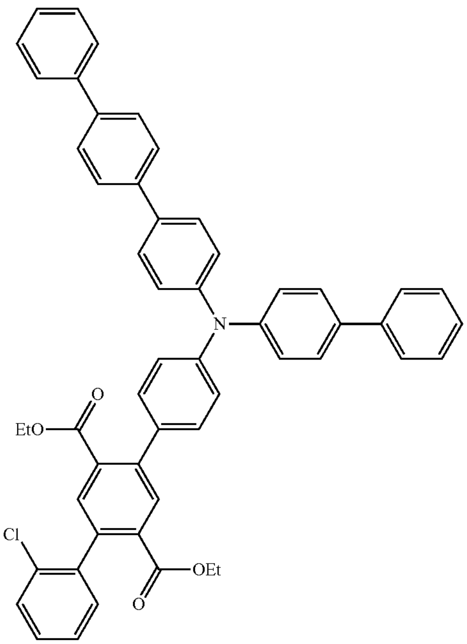 [SMILES: CCOC(=O)c1cc(-c2ccccc2Cl)c(C(=O)OCC)cc1-c1ccc(N(c2ccc(-c3ccccc3)cc2)c2ccc(-c3ccc(-c4ccccc4)cc3)cc2)cc1] Reactant 2 MeLi | 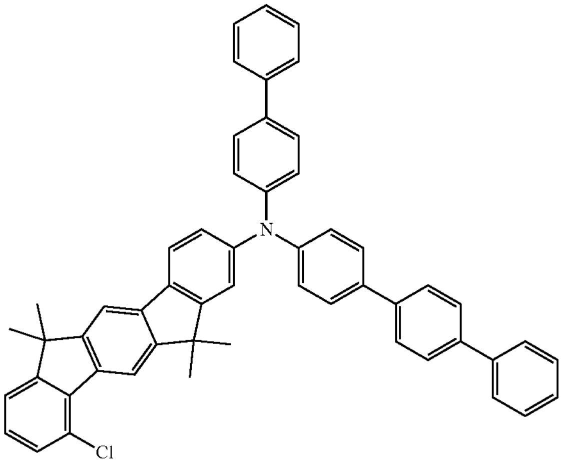 [SMILES: CC1(C)c2cc(N(c3ccc(-c4ccccc4)cc3)c3ccc(-c4ccc(-c5ccccc5)cc4)cc3)ccc2-c2cc3c(cc21)-c1c(Cl)cccc1C3(C)C] |
| III-7 Reactant 1 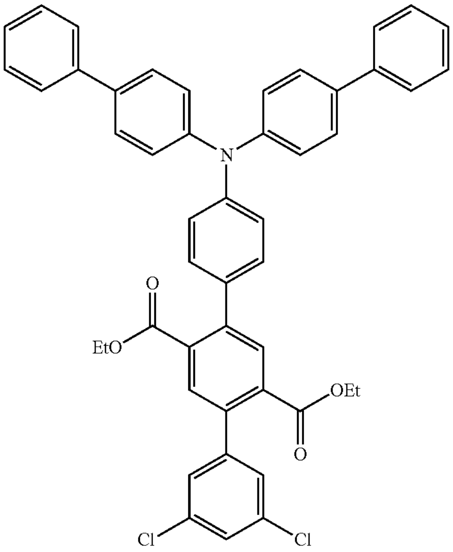 [SMILES: CCOC(=O)c1cc(-c2cc(Cl)cc(Cl)c2)c(C(=O)OCC)cc1-c1ccc(N(c2ccc(-c3ccccc3)cc2)c2ccc(-c3ccccc3)cc2)cc1] Reactant 2 MeMgBr | 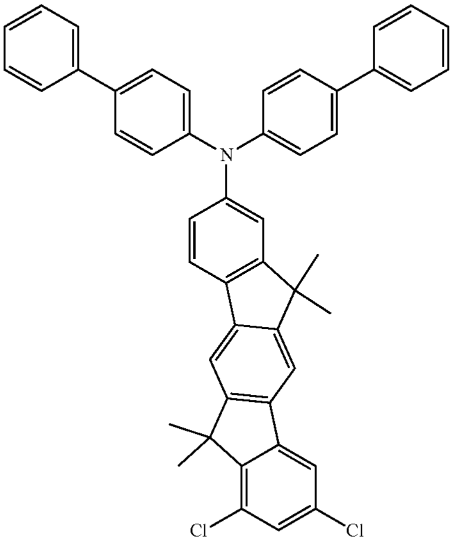 [SMILES: CC1(C)c2cc(N(c3ccc(-c4ccccc4)cc3)c3ccc(-c4ccccc4)cc3)ccc2-c2cc3c(cc21)-c1cc(Cl)cc(Cl)c1C3(C)C] |

-continued
| | | Product |
|---|---|---|
| III-8 | Reactant 1<br>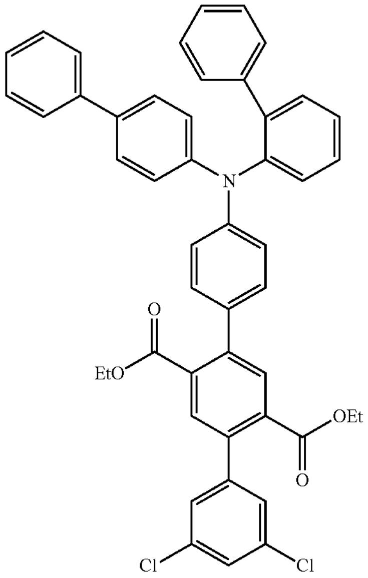 [SMILES: CCOC(=O)c1cc(-c2cc(Cl)cc(Cl)c2)c(C(=O)OCC)cc1-c1ccc(N(c2ccc(-c3ccccc3)cc2)c2ccccc2-c2ccccc2)cc1]<br>Reactant 2<br>MeMgCl | 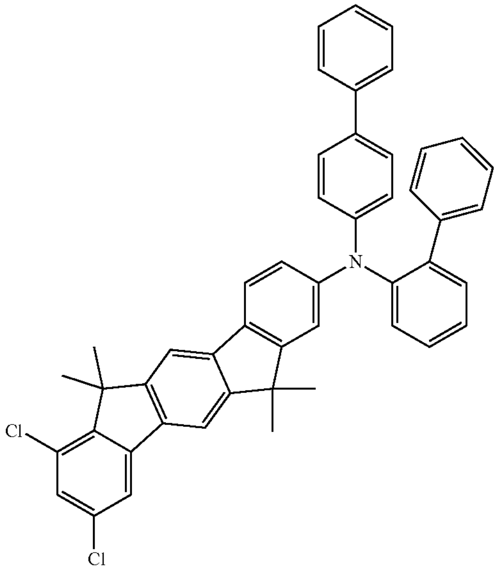 [SMILES: CC1(C)c2cc(N(c3ccc(-c4ccccc4)cc3)c3ccccc3-c3ccccc3)ccc2-c2cc3c(cc21)-c1cc(Cl)cc(Cl)c1C3(C)C] |
| III-9 | Reactant 1<br>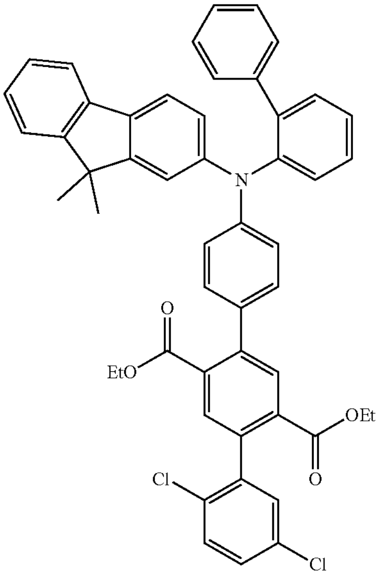 [SMILES: CCOC(=O)c1cc(-c2cc(Cl)ccc2Cl)c(C(=O)OCC)cc1-c1ccc(N(c2ccc3c(c2)C(C)(C)c2ccccc2-3)c2ccccc2-c2ccccc2)cc1]<br>Reactant 2<br>MeMgBr | 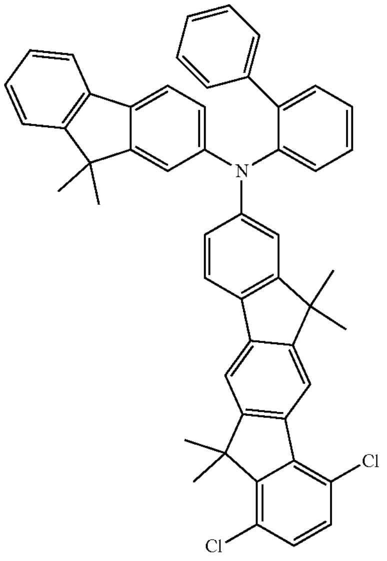 [SMILES: CC1(C)c2ccccc2-c2ccc(N(c3ccc4c(c3)C(C)(C)c3cc5c(cc3-4)C(C)(C)c3c(Cl)ccc(Cl)c3-5)c3ccccc3-c3ccccc3)cc21] |

-continued
| | | Product |
|---|---|---|
| III-10 | Reactant 1<br>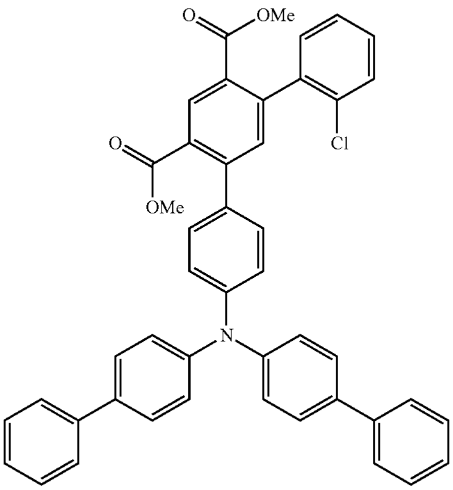 [SMILES: COC(=O)c1cc(C(=O)OC)c(-c2ccccc2Cl)cc1-c1ccc(N(c2ccc(-c3ccccc3)cc2)c2ccc(-c3ccccc3)cc2)cc1]<br>Reactant 2<br>MeMgBr | 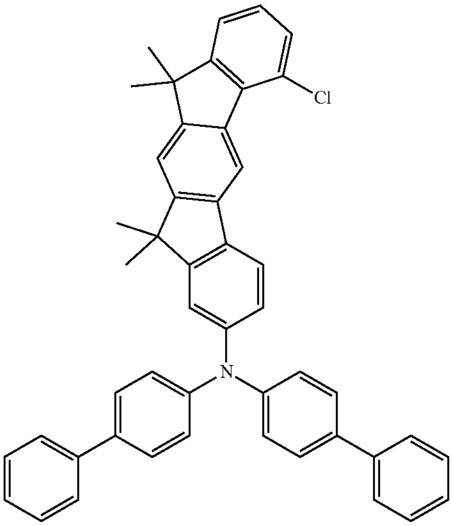 [SMILES: CC1(C)c2cc(N(c3ccc(-c4ccccc4)cc3)c3ccc(-c4ccccc4)cc3)ccc2-c2cc3c(cc21)C(C)(C)c1cccc(Cl)c1-3] |
| III-11 | Reactant 1<br>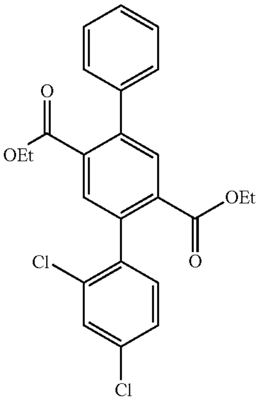 [SMILES: CCOC(=O)c1cc(-c2ccc(Cl)cc2Cl)c(C(=O)OCC)cc1-c1ccccc1]<br>Reactant 2<br>MeMgCl | 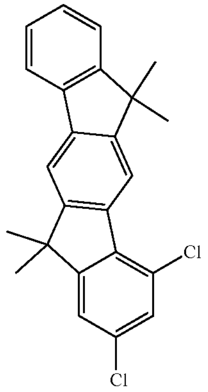 [SMILES: CC1(C)c2ccccc2-c2cc3c(cc21)-c1c(Cl)cc(Cl)cc1C3(C)C] |

-continued

| | | Product |
|---|---|---|
| III-12 | Reactant 1<br>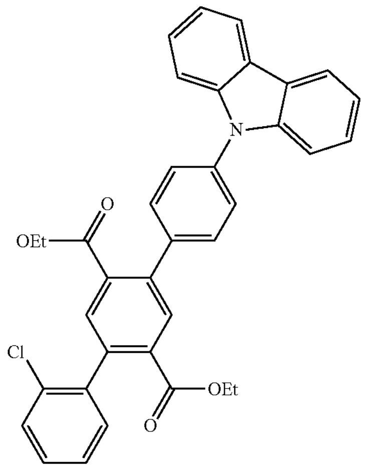 [SMILES: CCOC(=O)c1cc(-c2ccccc2Cl)c(C(=O)OCC)cc1-c1ccc(-n2c3ccccc3c3ccccc32)cc1]<br>Reactant 2<br>MeMgCl | 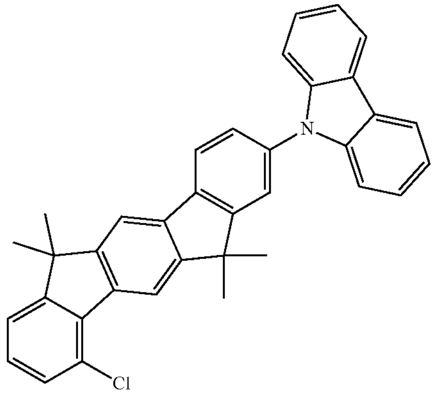 [SMILES: CC1(C)c2cc(-n3c4ccccc4c4ccccc43)ccc2-c2cc3c(cc21)-c1c(Cl)cccc1C3(C)C] |

Compound 2-1

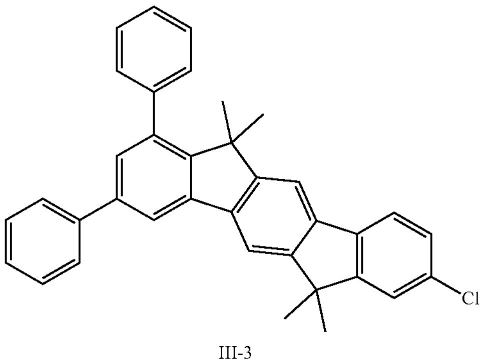

III-3

+

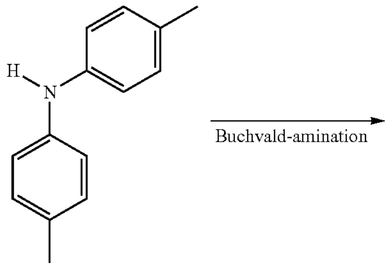

-continued

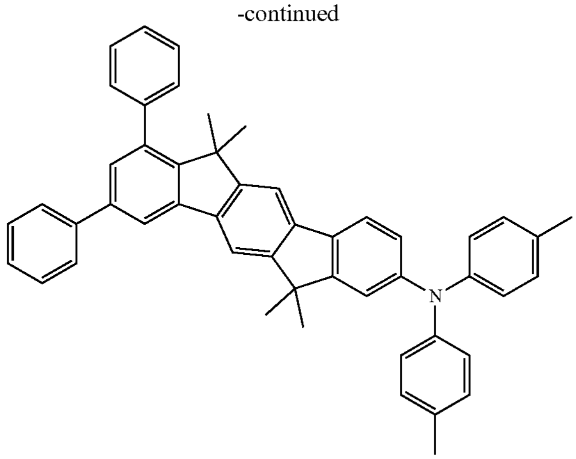

2-1

5.95 g of bis-p-tolylamine (30.2 mmol) and 15 g of the intermediate III-1 (30.2 mmol) are dissolved in 300 ml of toluene. The solution is degassed and saturated with $N_2$. Thereafter, 0.28 g (0.302 mmol) of $Pd_2(dba)_3$ and 0.6 ml of a 1M solution of $(tBu)_3P$ are added thereto, and then 4.3 g of sodium tert-butoxide (45.3 mol) are added. The reaction mixture is heated to boiling under a protective atmosphere for 6 h. The mixture is subsequently partitioned between toluene and water, and the organic phase is washed three times with water and dried over $Na_2SO_4$ and concentrated by rotary evaporation. After the crude product has been filtered through silica gel with toluene, the remaining residue is recrystallized from heptane/toluene. The yield is 14.3 g (72% of theory). Finally, the material is sublimed under high vacuum. Purity is 99.9%.

The following compounds are prepared in an analogous manner:
| | | Product |
|---|---|---|
| 2-2 | Reactant 1<br>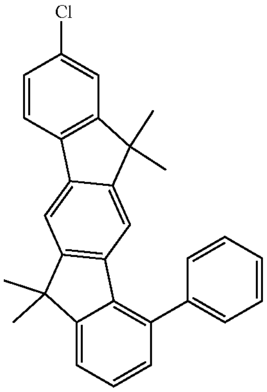 [SMILES: CC1(C)c2cc(Cl)ccc2-c2cc3c(cc21)-c1c(-c2ccccc2)cccc1C3(C)C]<br>Reactant 2<br>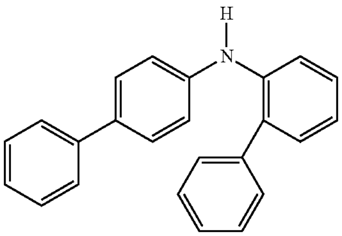 | 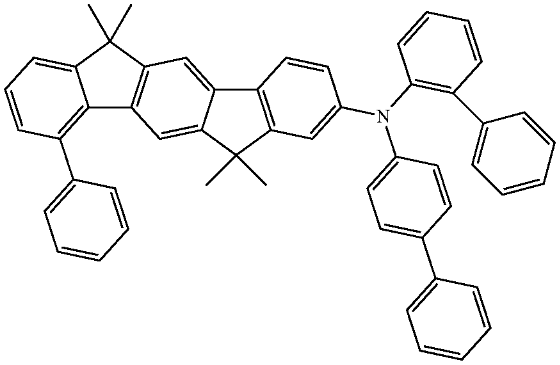 [SMILES: CC1(C)c2cc(N(c3ccc(-c4ccccc4)cc3)c3ccccc3-c3ccccc3)ccc2-c2cc3c(cc21)-c1c(-c2ccccc2)cccc1C3(C)C] |
| 2-3 | Reactant 1<br>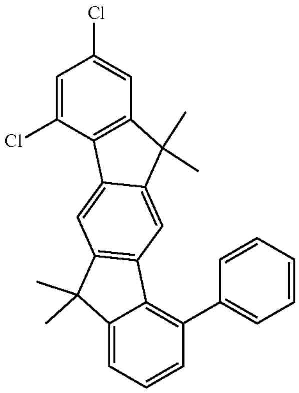 [SMILES: CC1(C)c2cc3c(cc2-c2c(Cl)cc(Cl)cc21)C(C)(C)c1cccc(-c2ccccc2)c1-3]<br>Reactant 2<br>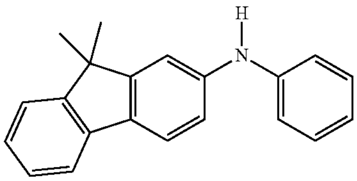<br>2 eq. | 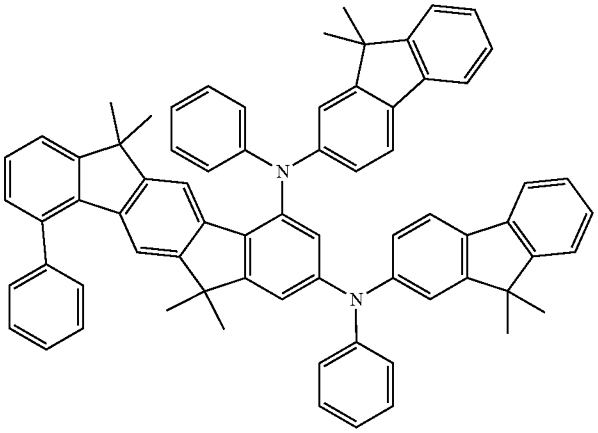 [SMILES: CC1(C)c2ccccc2-c2ccc(N(c3ccccc3)c3cc(N(c4ccccc4)c4ccc5c(c4)C(C)(C)c4ccccc4-5)c4c(c3)C(C)(C)c3cc5c(cc3-4)C(C)(C)c3cccc(-c4ccccc4)c3-5)cc21] |

-continued
| | | Product |
|---|---|---|
| 2-4 | Reactant 1 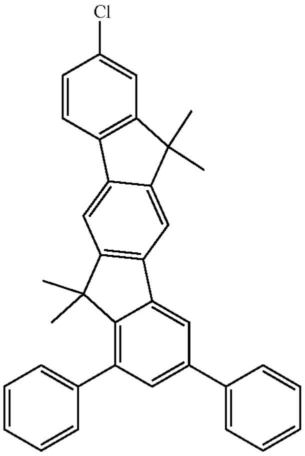 [SMILES: CC1(C)c2cc(Cl)ccc2-c2cc3c(cc21)-c1cc(-c2ccccc2)cc(-c2ccccc2)c1C3(C)C] Reactant 2 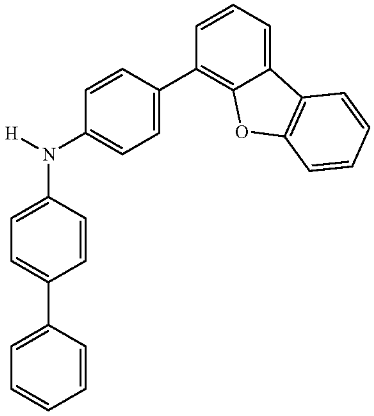 | 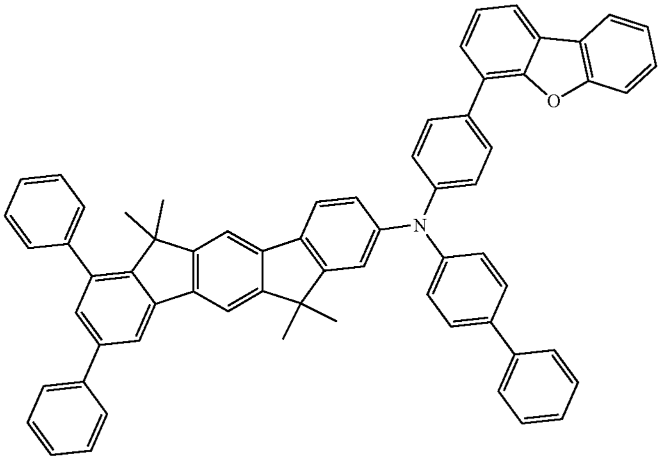 [SMILES: CC1(C)c2cc(N(c3ccc(-c4ccccc4)cc3)c3ccc(-c4cccc5c4oc4ccccc45)cc3)ccc2-c2cc3c(cc21)-c1cc(-c2ccccc2)cc(-c2ccccc2)c1C3(C)C] |
| 2-5 | Reactant 1 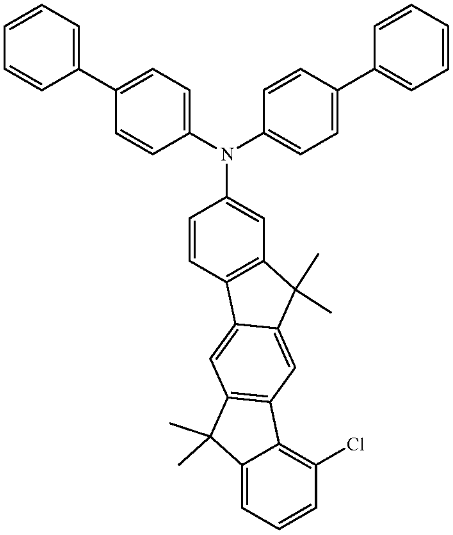 [SMILES: CC1(C)c2cc(N(c3ccc(-c4ccccc4)cc3)c3ccc(-c4ccccc4)cc3)ccc2-c2cc3c(cc21)-c1c(Cl)cccc1C3(C)C] | 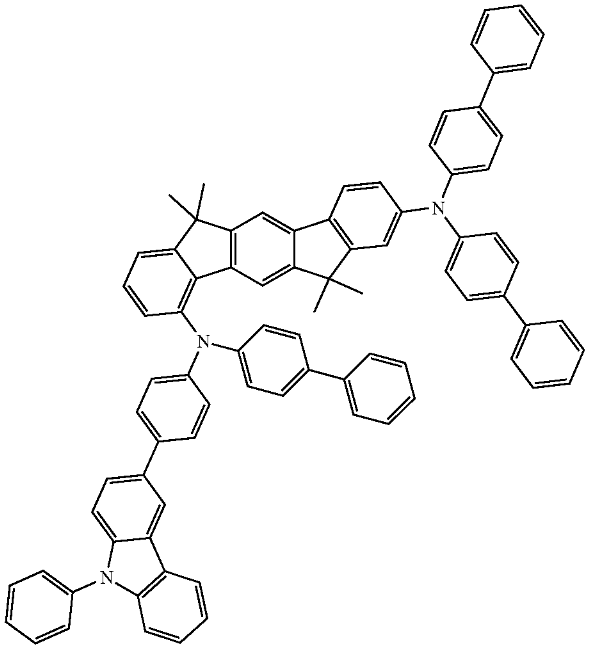 [SMILES: CC1(C)c2cc(N(c3ccc(-c4ccccc4)cc3)c3ccc(-c4ccccc4)cc3)ccc2-c2cc3c(cc21)-c1c(N(c2ccc(-c4ccccc4)cc2)c2ccc(-c4ccc5c(c4)c4ccccc4n5-c4ccccc4)cc2)cccc1C3(C)C] |

-continued
| | | Product |
|---|---|---|
| | Reactant 2<br>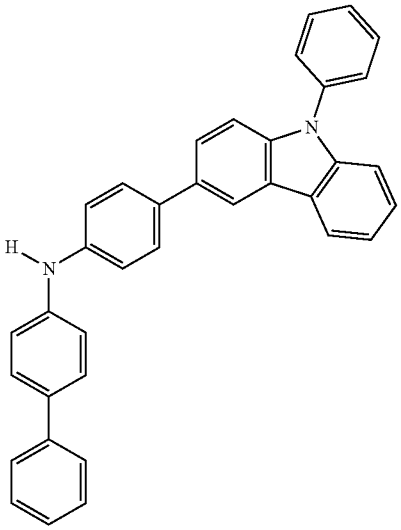 [SMILES: c1ccc(-c2ccc(Nc3ccc(-c4ccc5c(c4)c4ccccc4n5-c4ccccc4)cc3)cc2)cc1] | |
| 2-6 | Reactant 1<br>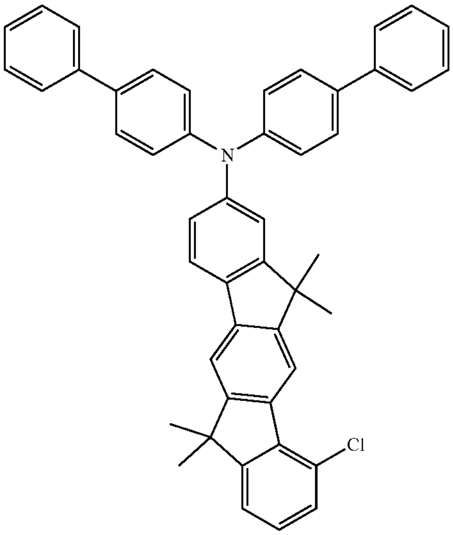 [SMILES: CC1(C)c2cc(N(c3ccc(-c4ccccc4)cc3)c3ccc(-c4ccccc4)cc3)ccc2-c2cc3c(cc21)-c1c(Cl)cccc1C3(C)C]<br>Reactant 2<br>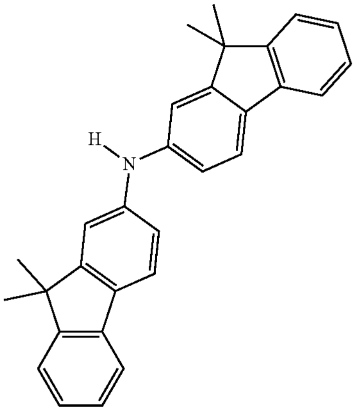 | 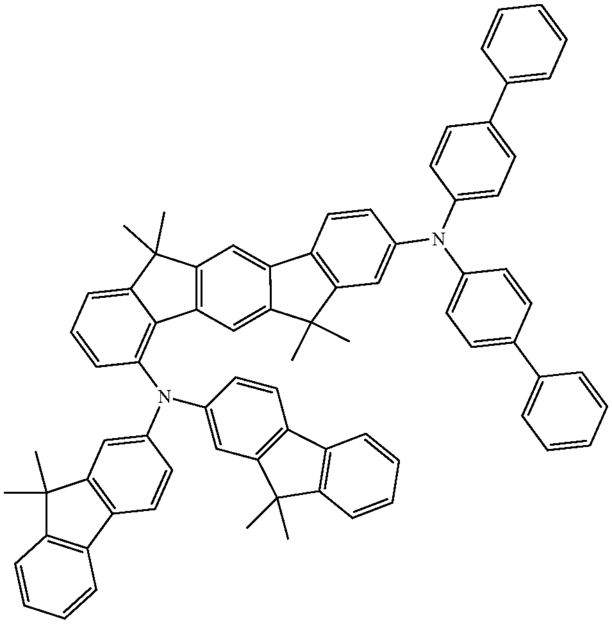 [SMILES: CC1(C)c2ccccc2-c2ccc(N(c3ccc4c(c3)C(C)(C)c3ccccc3-4)c3cccc4c3-c3cc5c(cc3C4(C)C)-c3ccc(N(c4ccc(-c6ccccc6)cc4)c4ccc(-c6ccccc6)cc4)cc3C5(C)C)cc21] |

-continued
| | | Product |
|---|---|---|
| 2-7 | Reactant 1 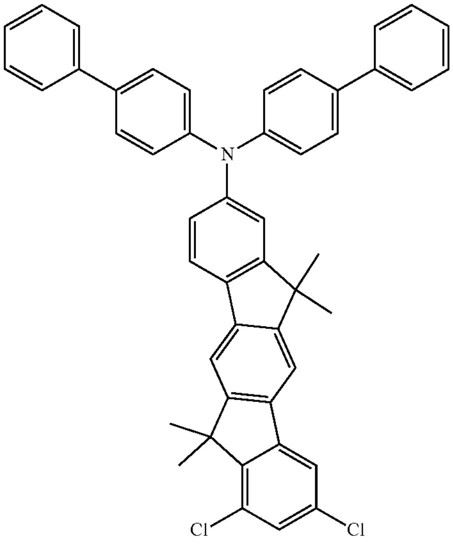 [SMILES: CC1(C)c2cc(N(c3ccc(-c4ccccc4)cc3)c3ccc(-c4ccccc4)cc3)ccc2-c2cc3c(cc21)-c1cc(Cl)cc(Cl)c1C3(C)C] Reactant 2 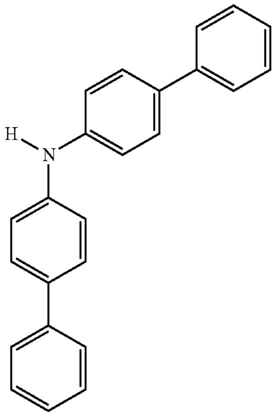 | 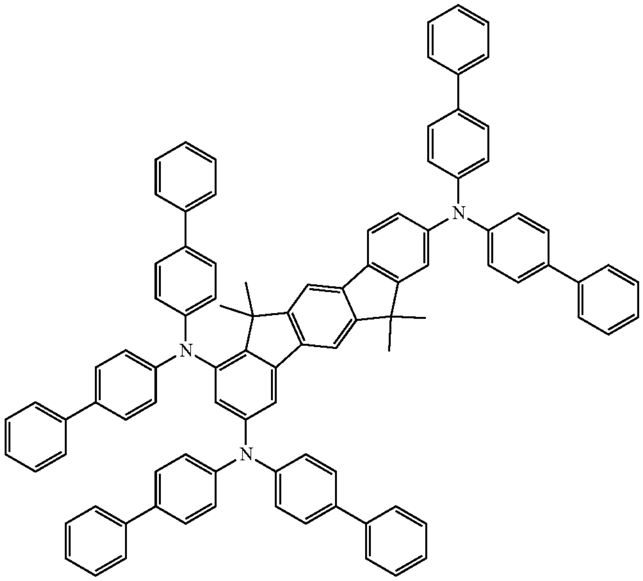 [SMILES: CC1(C)c2cc(N(c3ccc(-c4ccccc4)cc3)c3ccc(-c4ccccc4)cc3)ccc2-c2cc3c(cc21)-c1cc(N(c2ccc(-c4ccccc4)cc2)c2ccc(-c4ccccc4)cc2)cc(N(c2ccc(-c4ccccc4)cc2)c2ccc(-c4ccccc4)cc2)c1C3(C)C] |
| 2-8 | Reactant 1 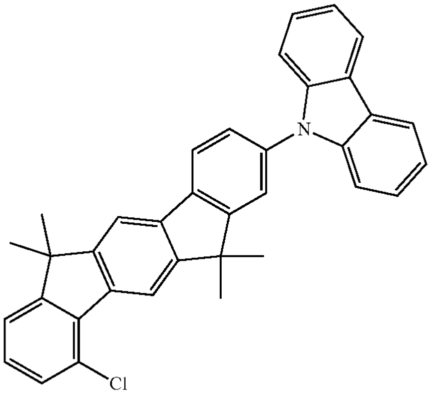 [SMILES: CC1(C)c2cc(-n3c4ccccc4c4ccccc43)ccc2-c2cc3c(cc21)-c1c(Cl)cccc1C3(C)C] | 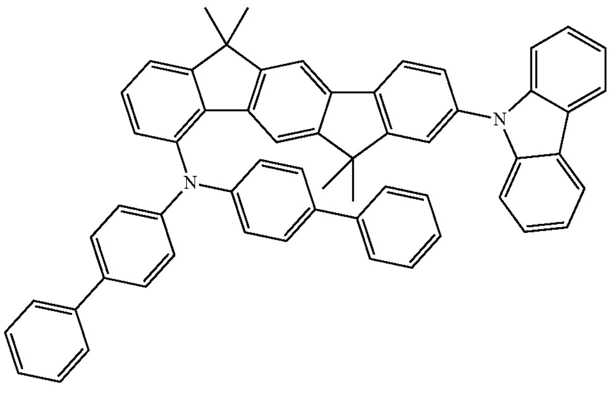 [SMILES: CC1(C)c2cc(-n3c4ccccc4c4ccccc43)ccc2-c2cc3c(cc21)-c1c(N(c2ccc(-c4ccccc4)cc2)c2ccc(-c4ccccc4)cc2)cccc1C3(C)C] |

-continued
| | | Product |
|---|---|---|
| | Reactant 2<br>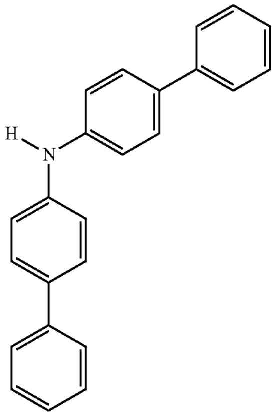 [SMILES: c1ccc(-c2ccc(Nc3ccc(-c4ccccc4)cc3)cc2)cc1] | |
| 2-9 | Reactant 1<br>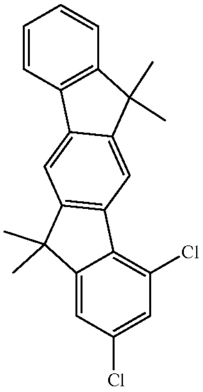 [SMILES: CC1(C)c2ccccc2-c2cc3c(cc21)-c1c(Cl)cc(Cl)cc1C3(C)C]<br>Reactant 2<br>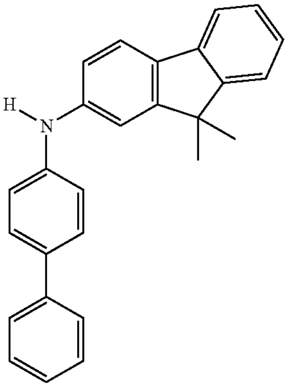 | 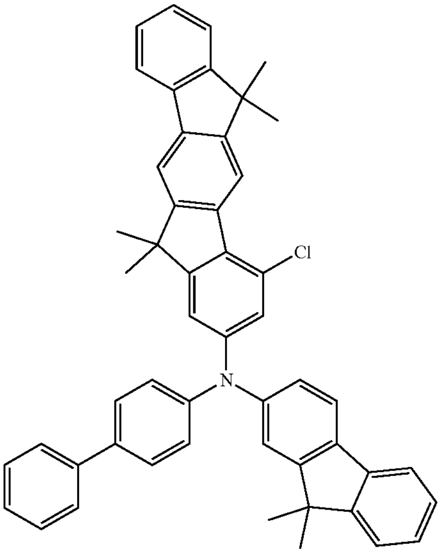 [SMILES: CC1(C)c2ccccc2-c2ccc(N(c3ccc(-c4ccccc4)cc3)c3cc(Cl)c4c(c3)C(C)(C)c3cc5c(cc3-4)C(C)(C)c3ccccc3-5)cc21] |

-continued
| | Product |
|---|---|
| 2-10<br>Reactant 1<br>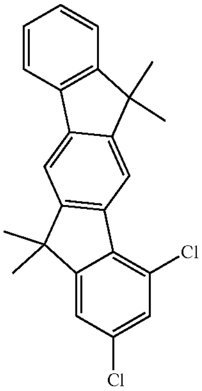 [SMILES: CC1(C)c2ccccc2-c2cc3c(cc21)-c1c(Cl)cc(Cl)cc1C3(C)C]<br>Reactant 2<br>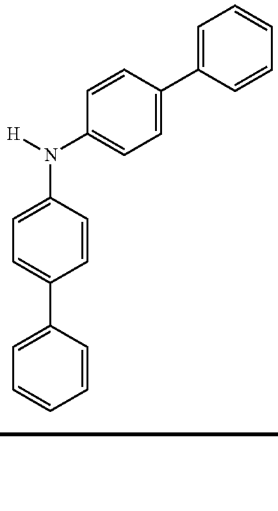 | 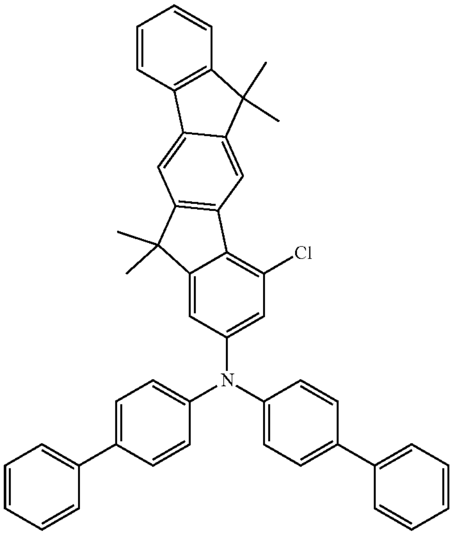 [SMILES: CC1(C)c2ccccc2-c2cc3c(cc21)-c1c(Cl)cc(N(c2ccc(-c4ccccc4)cc2)c2ccc(-c4ccccc4)cc2)cc1C3(C)C] |

Compound 3-1

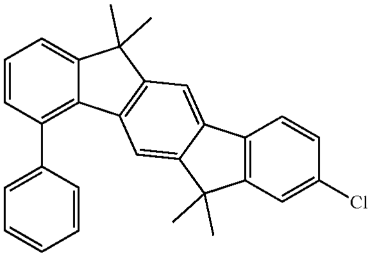

+

III-1

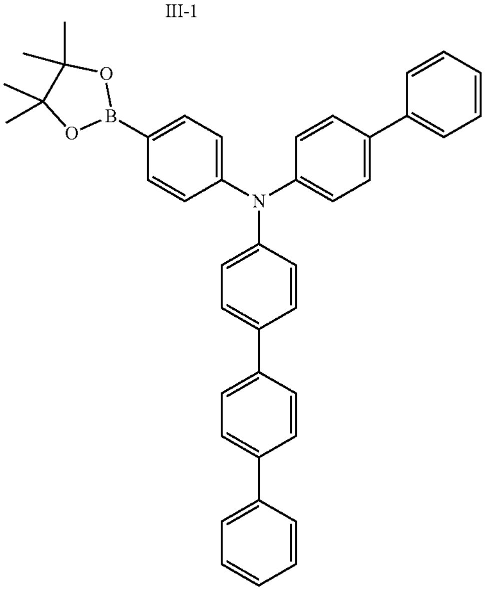

IV-1

-continued

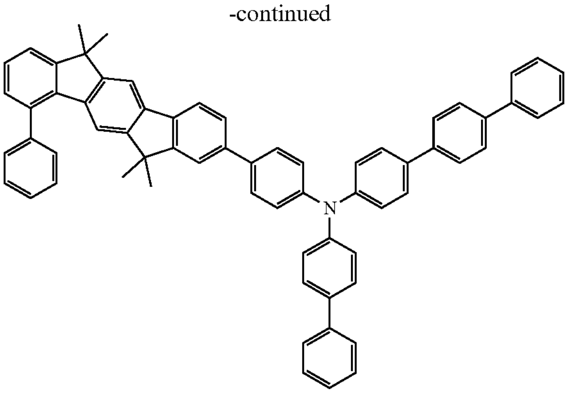

3-1

17.1 g (28.51 mmol) of the pinacolboronic ester derivative IV-1 and 12 g (28.51 mmol) of intermediate III-1 are suspended in 350 ml of toluene and 4.1 g of sodium tert-butoxide (42.8 mmol). 0.26 g (0.285 mmol) of $Pd_2(dba)_2$ is added to this suspension, and the reaction mixture is heated under reflux for 12 h. After cooling, the organic phase is removed, filtered through silica gel, washed three times with 80 ml of water and then concentrated to dryness. After the crude product has been filtered through silica gel with toluene, the remaining residue is recrystallized from heptane/toluene. The yield is 18 g (75% of theory). Finally, the material is sublimed under high vacuum. Purity is 99.9%.

The following compounds are prepared in an analogous manner:

| | Reactant 1 | Reactant 2 |
|---|---|---|
| 3-2 | 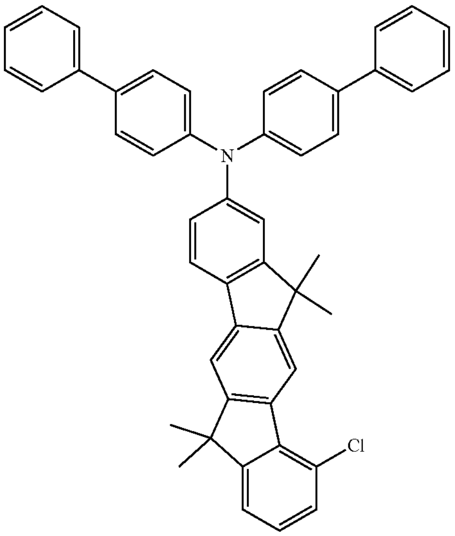 [SMILES: CC1(C)c2cc(N(c3ccc(-c4ccccc4)cc3)c3ccc(-c4ccccc4)cc3)ccc2-c2cc3c(cc21)-c1c(Cl)cccc1C3(C)C] | 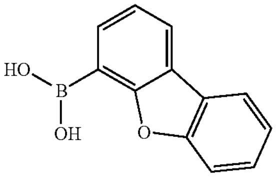 [SMILES: OB(O)c1cccc2c1oc1ccccc12] |

-continued
| | Reactant 1 | Reactant 2 |
|---|---|---|
| 3-3 | 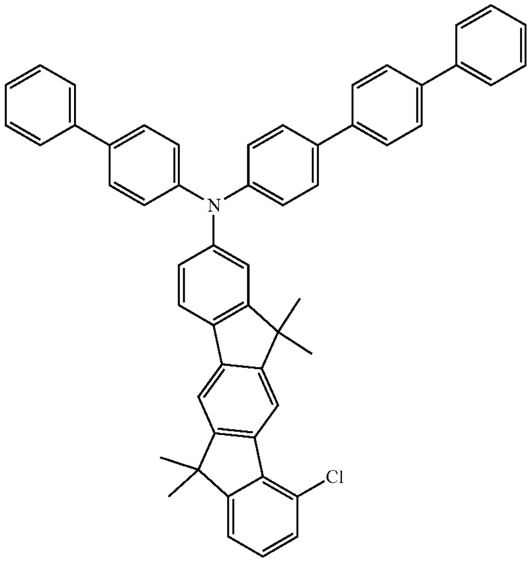 [SMILES: CC1(C)c2cc(N(c3ccc(-c4ccccc4)cc3)c3ccc(-c4ccc(-c5ccccc5)cc4)cc3)ccc2-c2cc3c(cc21)-c1c(Cl)cccc1C3(C)C] | 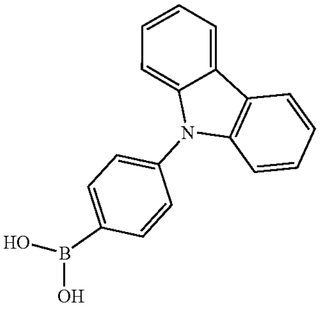 [SMILES: OB(O)c1ccc(-n2c3ccccc3c3ccccc32)cc1] |
| 3-4 | 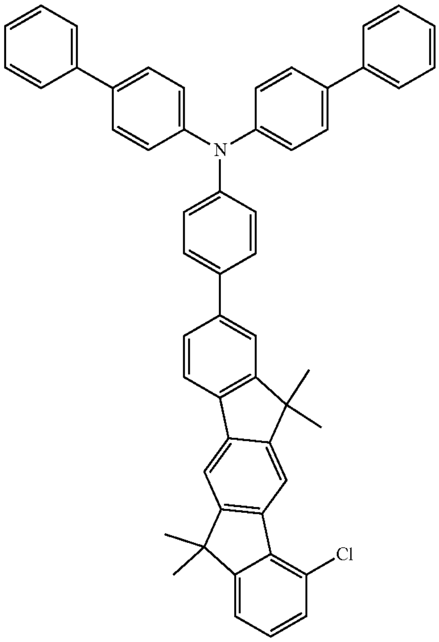 [SMILES: CC1(C)c2cc(-c3ccc(N(c4ccc(-c5ccccc5)cc4)c4ccc(-c5ccccc5)cc4)cc3)ccc2-c2cc3c(cc21)-c1c(Cl)cccc1C3(C)C] | 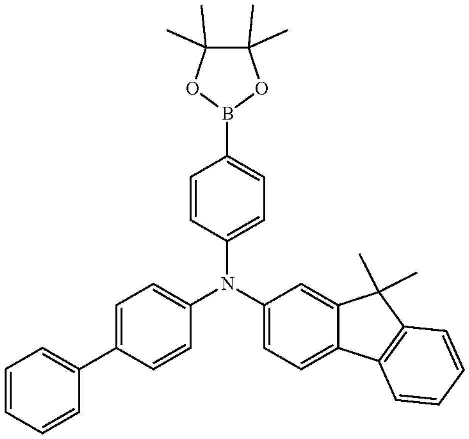 [SMILES: CC1(C)c2ccccc2-c2ccc(N(c3ccc(B4OC(C)(C)C(C)(C)O4)cc3)c3ccc(-c4ccccc4)cc3)cc21] |
| 3-5 | 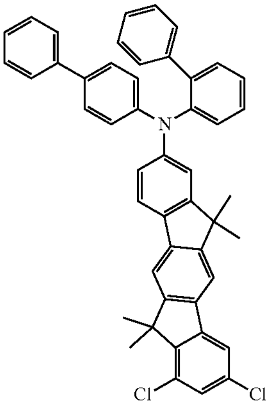 [SMILES: CC1(C)c2cc(N(c3ccc(-c4ccccc4)cc3)c3ccccc3-c3ccccc3)ccc2-c2cc3c(cc21)-c1cc(Cl)cc(Cl)c1C3(C)C] | 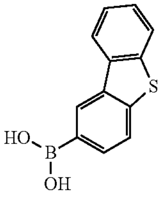 [SMILES: OB(O)c1ccc2sc3ccccc3c2c1] |

-continued
| | Reactant 1 | Reactant 2 |
|---|---|---|
| 3-6 | 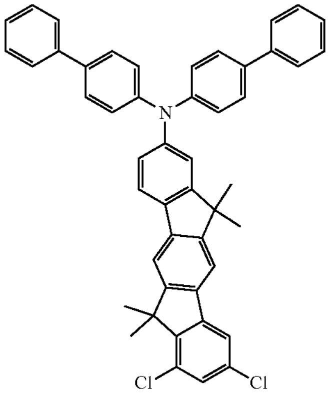 [SMILES: CC1(C)c2cc(N(c3ccc(-c4ccccc4)cc3)c3ccc(-c4ccccc4)cc3)ccc2-c2cc3c(cc21)-c1cc(Cl)cc(Cl)c1C3(C)C] | 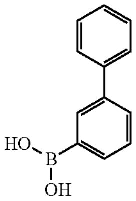 [SMILES: OB(O)c1cccc(-c2ccccc2)c1] |
| 3-7 | 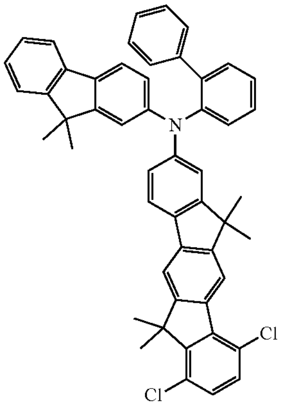 [SMILES: CC1(C)c2ccccc2-c2ccc(N(c3ccc4c(c3)C(C)(C)c3cc5c(cc3-4)C(C)(C)c3c(Cl)ccc(Cl)c3-5)c3ccccc3-c3ccccc3)cc21] | 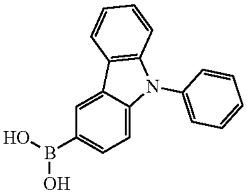 [SMILES: OB(O)c1ccc2c(c1)c1ccccc1n2-c1ccccc1] |
| 3-8 | 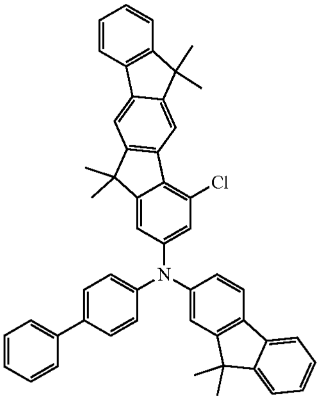 [SMILES: CC1(C)c2ccccc2-c2ccc(N(c3ccc(-c4ccccc4)cc3)c3cc(Cl)c4c(c3)C(C)(C)c3cc5c(cc3-4)C(C)(C)c3ccccc3-5)cc21] | 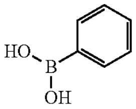 |
| 3-9 | 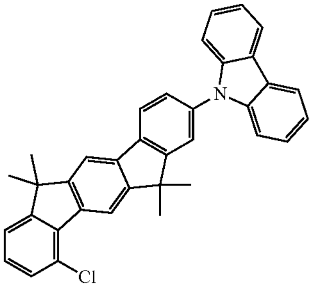 [SMILES: CC1(C)c2cc(-n3c4ccccc4c4ccccc43)ccc2-c2cc3c(cc21)-c1c(Cl)cccc1C3(C)C] | 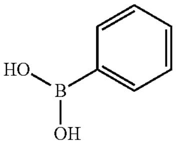 |

-continued
| | Reactant 1 | Reactant 2 |
| --- | --- | --- |
| 3-10 | 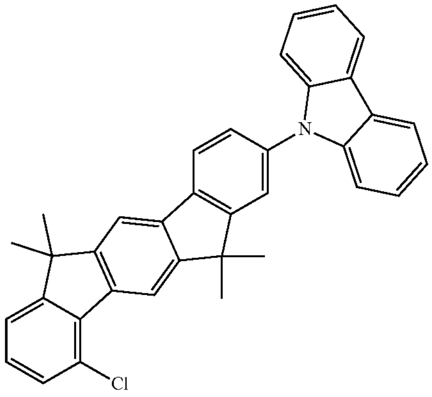 [SMILES: CC1(C)c2cc(-n3c4ccccc4c4ccccc43)ccc2-c2cc3c(cc21)-c1c(Cl)cccc1C3(C)C] | 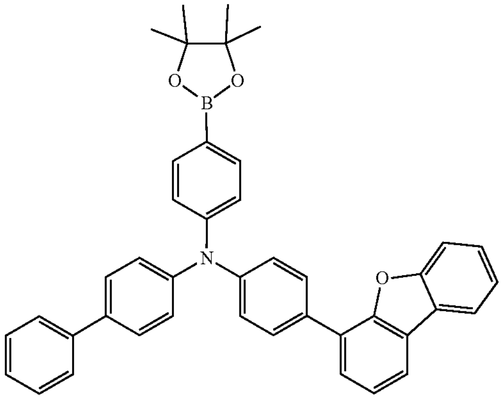 [SMILES: CC1(C)OB(c2ccc(N(c3ccc(-c4ccccc4)cc3)c3ccc(-c4cccc5c4oc4ccccc45)cc3)cc2)OC1(C)C] |
| 3-11 | 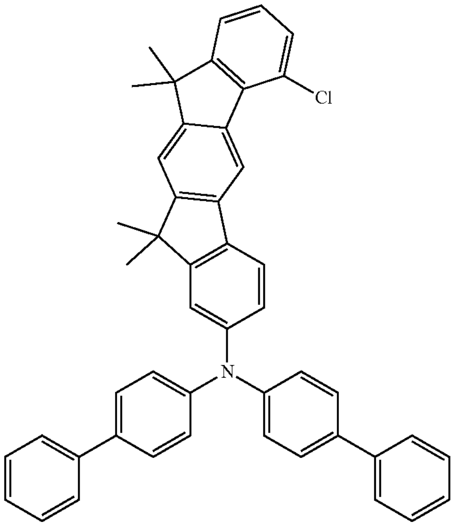 [SMILES: CC1(C)c2cc(N(c3ccc(-c4ccccc4)cc3)c3ccc(-c4ccccc4)cc3)ccc2-c2cc3c(cc21)C(C)(C)c1cccc(Cl)c1-3] | 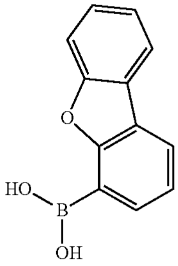 [SMILES: OB(O)c1cccc2c1oc1ccccc12] |
| 3-12 | 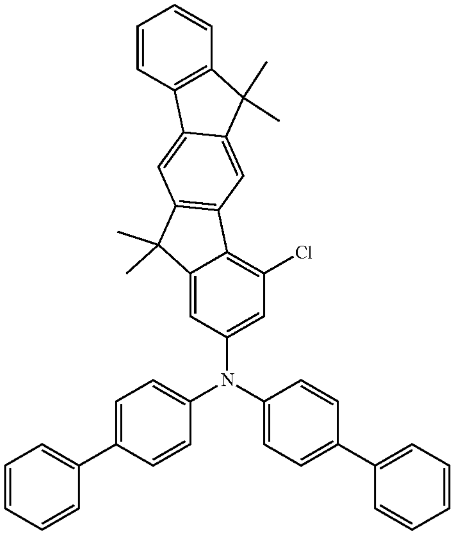 [SMILES: CC1(C)c2ccccc2-c2cc3c(cc21)-c1c(Cl)cc(N(c2ccc(-c4ccccc4)cc2)c2ccc(-c4ccccc4)cc2)cc1C3(C)C] | 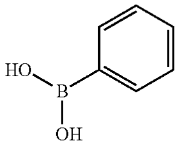 |

-continued
| Reactant 1 | Reactant 2 |
|---|---|
| 3-13 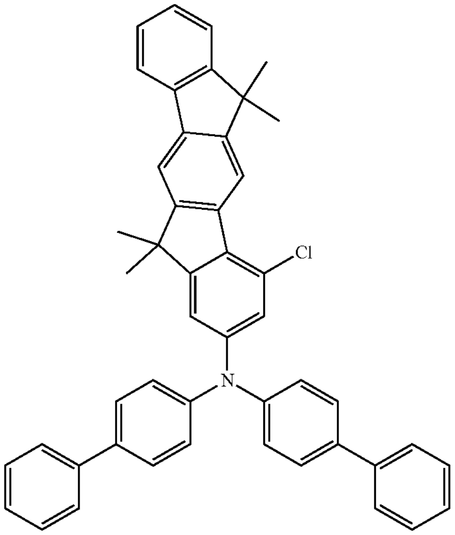 [SMILES: CC1(C)c2ccccc2-c2cc3c(cc21)-c1c(Cl)cc(N(c2ccc(-c4ccccc4)cc2)c2ccc(-c4ccccc4)cc2)cc1C3(C)C] | 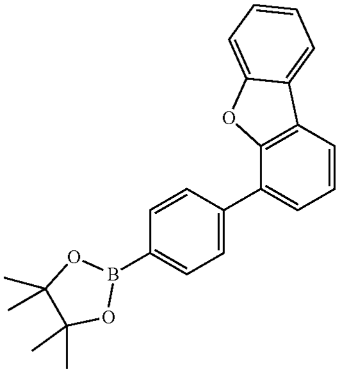 [SMILES: CC1(C)OB(c2ccc(-c3cccc4c3oc3ccccc34)cc2)OC1(C)C] |
| Product |
|---|
| 1-2 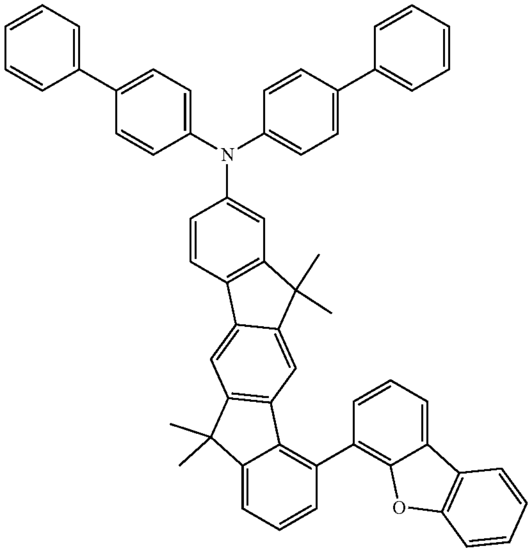 [SMILES: CC1(C)c2cc(N(c3ccc(-c4ccccc4)cc3)c3ccc(-c4ccccc4)cc3)ccc2-c2cc3c(cc21)-c1c(-c2cccc4c2oc2ccccc24)cccc1C3(C)C] |

-continued
| Reactant 1 | Reactant 2 |
| --- | --- |
3-3
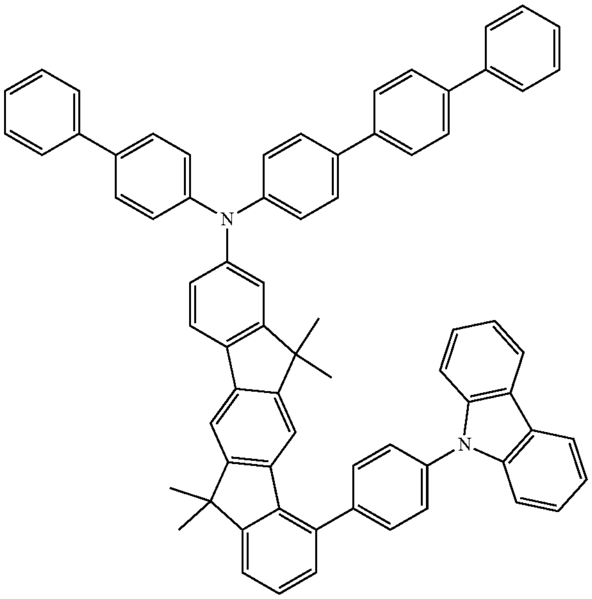 [SMILES: CC1(C)c2cc(N(c3ccc(-c4ccccc4)cc3)c3ccc(-c4ccc(-c5ccccc5)cc4)cc3)ccc2-c2cc3c(cc21)-c1c(-c2ccc(-n4c5ccccc5c5ccccc54)cc2)cccc1C3(C)C]
3-4
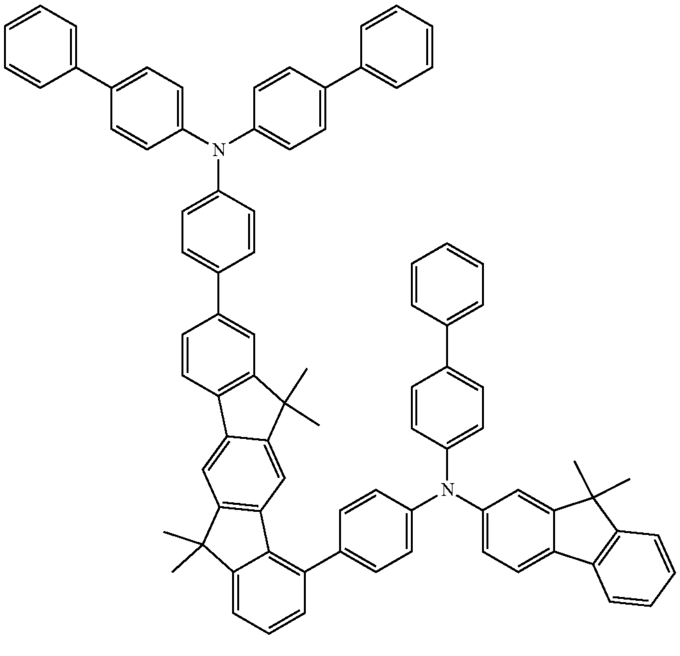 [SMILES: CC1(C)c2ccccc2-c2ccc(N(c3ccc(-c4ccccc4)cc3)c3ccc(-c4cccc5c4-c4cc6c(cc4C5(C)C)-c4ccc(-c5ccc(N(c7ccc(-c8ccccc8)cc7)c7ccc(-c8ccccc8)cc7)cc5)cc4C6(C)C)cc3)cc21]

-continued
| Reactant 1 | Reactant 2 |
| --- | --- |
| 3-5 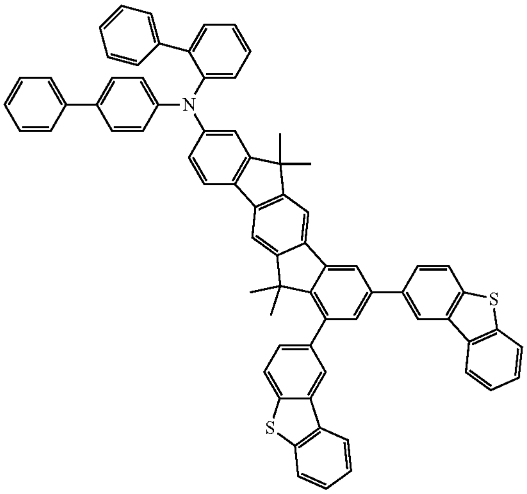 [SMILES: CC1(C)c2cc(N(c3ccc(-c4ccccc4)cc3)c3ccccc3-c3ccccc3)ccc2-c2cc3c(cc21)-c1cc(-c2ccc4sc5ccccc5c4c2)cc(-c2ccc4sc5ccccc5c4c2)c1C3(C)C] | |
| 3-6 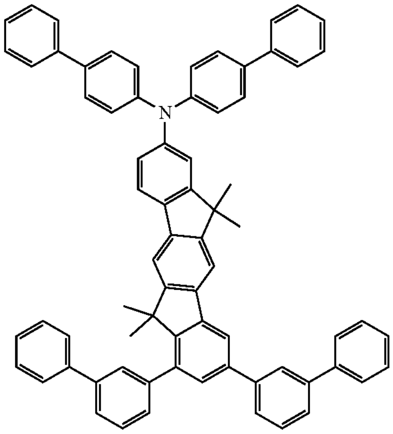 [SMILES: CC1(C)c2cc(N(c3ccc(-c4ccccc4)cc3)c3ccc(-c4ccccc4)cc3)ccc2-c2cc3c(cc21)-c1cc(-c2cccc(-c4ccccc4)c2)cc(-c2cccc(-c4ccccc4)c2)c1C3(C)C] | |
| 3-7 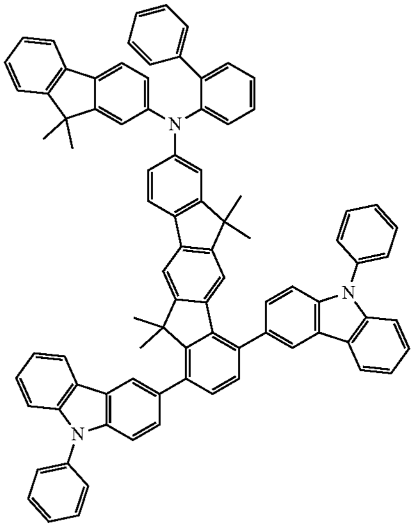 [SMILES: CC1(C)c2ccccc2-c2ccc(N(c3ccc4c(c3)C(C)(C)c3cc5c(cc3-4)C(C)(C)c3c(-c4ccc6c(c4)c4ccccc4n6-c4ccccc4)ccc(-c4ccc6c(c4)c4ccccc4n6-c4ccccc4)c3-5)c3ccccc3-c3ccccc3)cc21] | |

-continued
| | Reactant 1 | Reactant 2 |
|---|---|---|
| 3-8 | | 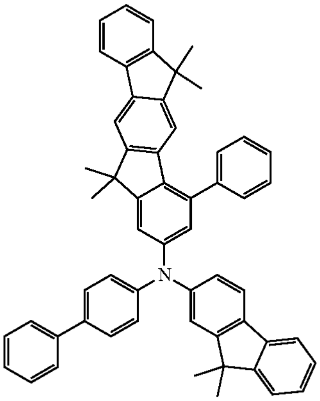 [SMILES: CC1(C)c2ccccc2-c2ccc(N(c3ccc(-c4ccccc4)cc3)c3cc(-c4ccccc4)c4c(c3)C(C)(C)c3cc5c(cc3-4)C(C)(C)c3ccccc3-5)cc21] |
| 3-9 | | 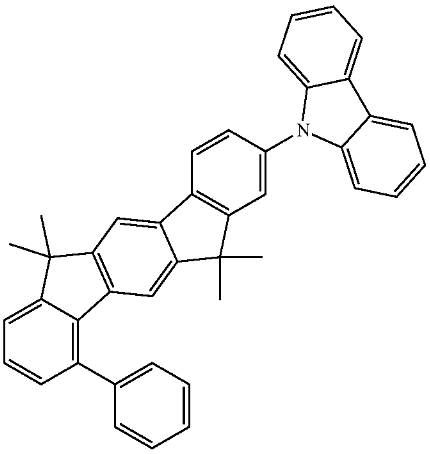 [SMILES: CC1(C)c2cc(-n3c4ccccc4c4ccccc43)ccc2-c2cc3c(cc21)-c1c(-c2ccccc2)cccc1C3(C)C] |
| 3-10 | | 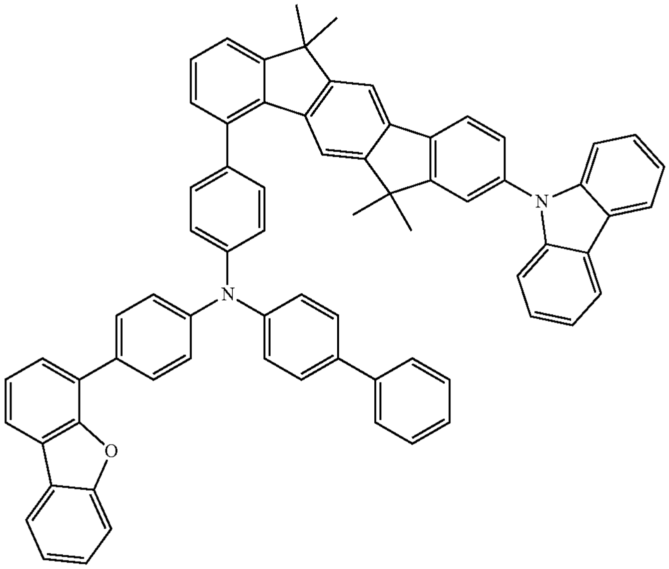 [SMILES: CC1(C)c2cc(-n3c4ccccc4c4ccccc43)ccc2-c2cc3c(cc21)-c1c(-c2ccc(N(c4ccc(-c5ccccc5)cc4)c4ccc(-c5cccc6c5oc5ccccc56)cc4)cc2)cccc1C3(C)C] |

-continued
| | Reactant 1 | Reactant 2 |
|---|---|---|
| 3-11 | | 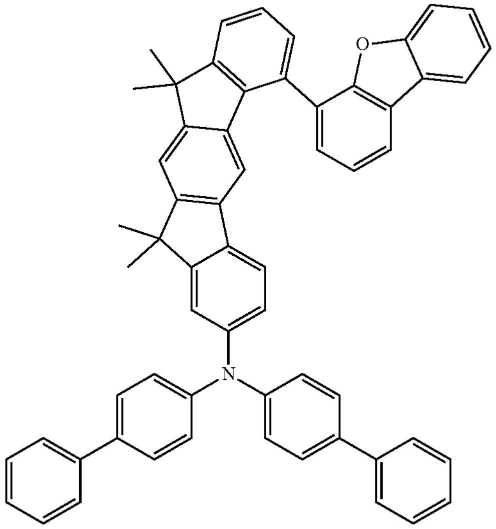 [SMILES: CC1(C)c2cc(N(c3ccc(-c4ccccc4)cc3)c3ccc(-c4ccccc4)cc3)ccc2-c2cc3c(cc21)C(C)(C)c1cccc(-c2cccc4c2oc2ccccc24)c1-3] |
| 3-12 | | 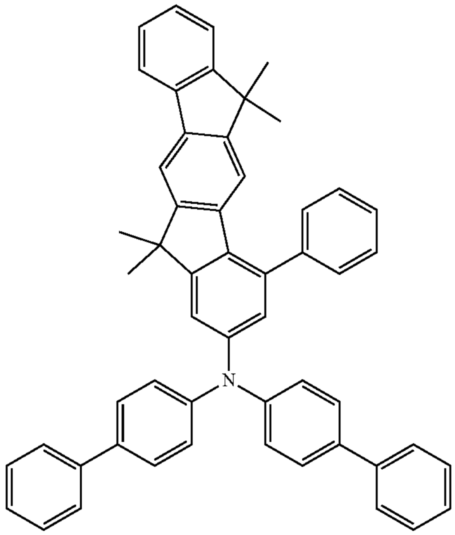 [SMILES: CC1(C)c2ccccc2-c2cc3c(cc21)-c1c(-c2ccccc2)cc(N(c2ccc(-c4ccccc4)cc2)c2ccc(-c4ccccc4)cc2)cc1C3(C)C] |
| 3-13 | | 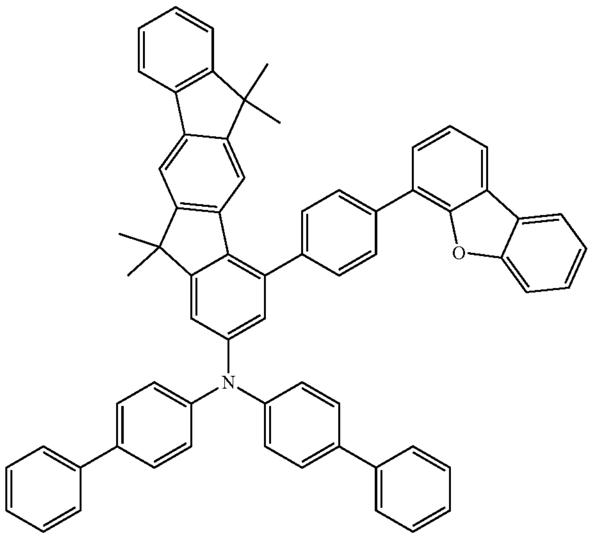 [SMILES: CC1(C)c2ccccc2-c2cc3c(cc21)-c1c(-c2ccc(-c4cccc5c4oc4ccccc45)cc2)cc(N(c2ccc(-c4ccccc4)cc2)c2ccc(-c4ccccc4)cc2)cc1C3(C)C] |

B) Device Examples

1) General Production Process for the OLEDs and Characterization of the OLEDs

Glass plaques which have been coated with structured ITO (indium tin oxide) in a thickness of 50 nm are the substrates to which the OLEDs are applied.

The OLEDs basically have the following layer structure: substrate/hole injection layer (HIL)/hole transport layer (HTL)/electron blocker layer (EBL)/emission layer (EML)/electron transport layer (ETL)/electron injection layer (EIL) and finally a cathode. The cathode is formed by an aluminium layer of thickness 100 nm. The exact structure of the OLEDs can be found in the tables which follow. The materials required for production of the OLEDs are shown in a table below.

All materials are applied by thermal vapour deposition in a vacuum chamber. In this case, the emission layer consists of at least one matrix material (host material) and an emitting dopant (emitter) which is added to the matrix material(s) in a particular proportion by volume by co-evaporation. Details given in such a form as IC1:EG1:TEG1 (55%:35%:10%) mean here that the material IC1 is present in the layer in a proportion by volume of 55%, EG1 in a proportion of 35% and TEG1 in a proportion of 10%.

In an analogous manner, the electron transport layer and the hole injection layer consist of a mixture of two materials. The structures of the materials that are used in the OLEDs are shown in Table 1.

The OLEDs are characterized in a standard manner. For this purpose, the electroluminescence spectra, the external quantum efficiency (EQE, measured in %) as a function of luminance, calculated from current-voltage-luminance characteristics assuming Lambertian radiation characteristics, and the lifetime are determined. The parameter EQE @ 10 $mA/cm^2$ refers to the external quantum efficiency which is attained at 10 $mA/cm^2$. The parameter U @ 10 $mA/cm^2$ refers to the operating voltage at 10 $mA/cm^2$. The lifetime LT80 @ 60 $mA/cm^2$ is defined as the time after which the luminance, in the case of operation with a current density of 60 $mA/cm^2$, has dropped to 80% of its starting value without use of an acceleration factor.

2) Use of the Compounds of the Invention in the HIL and HTL of Blue-Fluorescing Devices OLEDs are produced with the following structure:

| Ex. | HIL Thickness/nm | HTL Thickness/nm | EBL Thickness/nm | EML Thickness/nm | ETL Thickness/nm | EIL Thickness/nm |
|---|---|---|---|---|---|---|
| E1 | HTM-2:p-doped (5%) 20 nm | HTM-2 180 nm | EBM 10 nm | H:SEB(5%) 20 nm | ETM:LiQ (50%) 30 nm | LiQ 1 nm |

This gives very good results for the performance data of the OLED: the EQE @ 10 $mA/cm^2$ is about 7.5%, the operating voltage U @ 10 $mA/cm^2$ is about 4 V, and the lifetime LT80 @ 60 $mA/cm^2$ is more than 300 h.

3) Use of the Compounds of the Invention in the EBL of Green-Phosphorescing Devices OLEDs are produced with the following structure:

| Ex. | HIL Thickness/nm | HTL Thickness/nm | EBL Thickness/nm | EML Thickness/nm | ETL Thickness/nm | EIL Thickness/nm |
|---|---|---|---|---|---|---|
| E2 | HTM:p-doped (5%) 20 nm | HTM 220 nm | HTM-1 10 nm | TMM-1:TMM-2 (28%):TEG(12%) 30 nm | ETM:LiQ(50%) 30 nm | LiQ 1 nm |
| E3 | HTM:p-doped (5%) 20 nm | HTM 220 nm | HTM-2 10 nm | TMM-1:TMM-2 (28%):TEG(12%) 30 nm | ETM:LiQ(50%) 30 nm | LiQ 1 nm |
| E4 | HTM:p-doped (5%) 20 nm | HTM 220 nm | HTM-3 10 nm | TMM-1:TMM-2 (28%):TEG(12%) 30 nm | ETM:LiQ(50%) 30 nm | LiQ 1 nm |
| E5 | HTM:p-doped (5%) 20 nm | HTM 220 nm | HTM-4 10 nm | TMM-1:TMM-2 (28%):TEG(12%) 30 nm | ETM:LiQ(50%) 30 nm | LiQ 1 nm |
| E6 | HTM:p-doped (5%) 20 nm | HTM 220 nm | HTM-5 10 nm | TMM-1:TMM-2 (28%):TEG(12%) 30 nm | ETM:LiQ(50%) 30 nm | LiQ 1 nm |

This gives very good results in all cases for the performance data of the OLEDs: the EQE @ 10 $mA/cm^2$ is about 14% in all cases, the operating voltage U @ 10 $mA/cm^2$ is about 4 V in all cases, and the lifetime LT80 @ 60 $mA/cm^2$ is more than 300 h in all cases.

4) Comparison of the OLED Performance Data Between Inventive Compound HTM-1 and Comparative Compound RefHTM An inventive OLED I6 is produced, which has the same structure as the OLED I1 described in 2), with the sole difference that the compound HTM-1 is present in place of the compound HTM-2 in the HIL and the HTL of the OLED.

For comparison, an OLED C1 is produced, which has the same structure as the inventive OLED I6, with the sole difference that the compound RefHTM is present in place of the compound HTM-1 in the HIL and the HTL of the OLED.

In the case of the inventive OLED I6, a distinctly improved value for the EQE and a slightly reduced operating voltage is found, compared to the comparative OLED C1. The lifetime LT80 @ 60 $mA/cm^2$ is more than 300 h in both cases. The values obtained are shown in the following table:

TABLE 1

| Compounds used | | |
|---|---|---|
| | U @ 10 $mA/cm^2$ [V] | EQE @ 10 $mA/cm^2$ [%] |
| I1 | 3.8 | 7.7 |
| C1 | 4.0 | 7.4 |

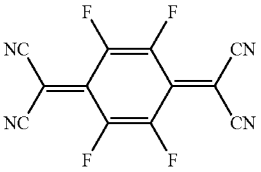 [SMILES: N#CC(C#N)=c1c(F)c(F)c(=C(C#N)C#N)c(F)c1F]

p-dopant F4TCNQ

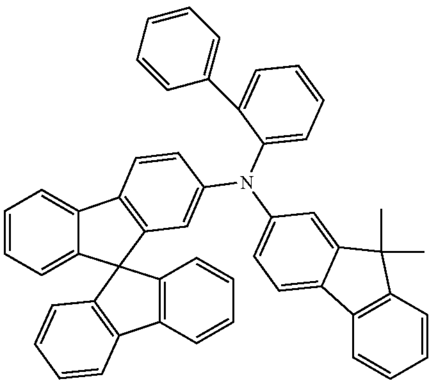 [SMILES: CC1(C)c2ccccc2-c2ccc(N(c3ccc4c(c3)C3(c5ccccc5-c5ccccc53)c3ccccc3-4)c3ccccc3-c3ccccc3)cc21]

HTM

TABLE 1-continued

| Compounds used | |
|---|---|
| U @ 10 $mA/cm^2$ [V] | EQE @ 10 $mA/cm^2$ [%] |

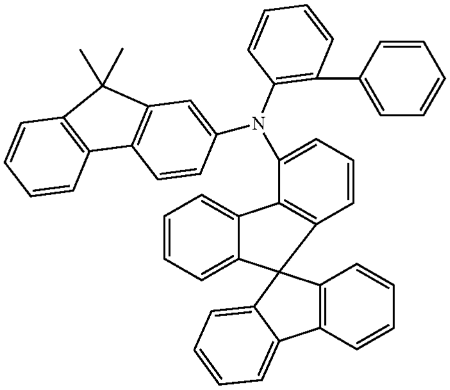 [SMILES: CC1(C)c2ccccc2-c2ccc(N(c3ccccc3-c3ccccc3)c3cccc4c3-c3ccccc3C43c4ccccc4-c4ccccc43)cc21]

EBM

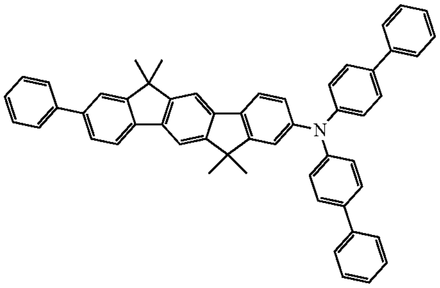 [SMILES: CC1(C)c2cc(-c3ccccc3)ccc2-c2cc3c(cc21)-c1ccc(N(c2ccc(-c4ccccc4)cc2)c2ccc(-c4ccccc4)cc2)cc1C3(C)C]

RefHTM

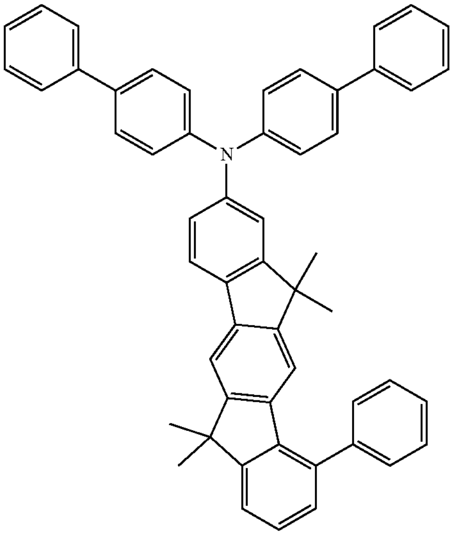 [SMILES: CC1(C)c2cc(N(c3ccc(-c4ccccc4)cc3)c3ccc(-c4ccccc4)cc3)ccc2-c2cc3c(cc21)-c1c(-c2ccccc2)cccc1C3(C)C]

HTM-1

TABLE 1-continued
| Compounds used | | |
|---|---|---|
| | U @ 10 $mA/cm^2$ [V] | EQE @ 10 $mA/cm^2$ [%] |
| 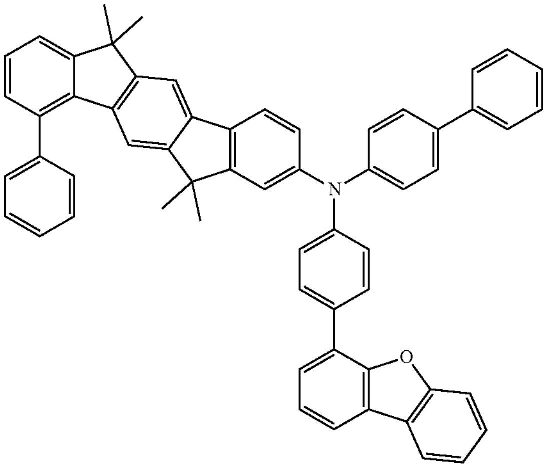 [SMILES: CC1(C)c2cc(N(c3ccc(-c4ccccc4)cc3)c3ccc(-c4cccc5c4oc4ccccc45)cc3)ccc2-c2cc3c(cc21)-c1c(-c2ccccc2)cccc1C3(C)C] HTM-2 | | |
| 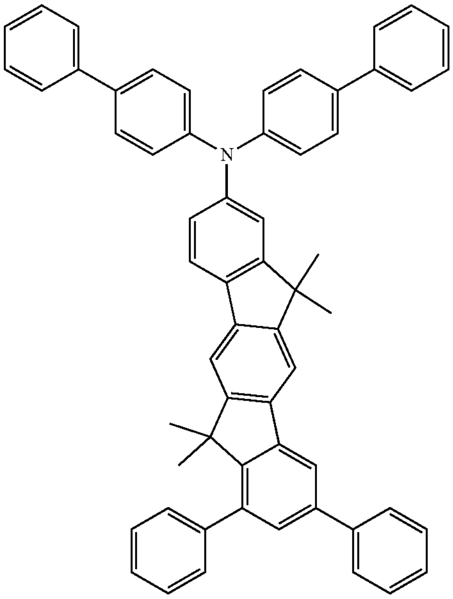 [SMILES: CC1(C)c2cc(N(c3ccc(-c4ccccc4)cc3)c3ccc(-c4ccccc4)cc3)ccc2-c2cc3c(cc21)-c1cc(-c2ccccc2)cc(-c2ccccc2)c1C3(C)C] HTM-3 | | |
| 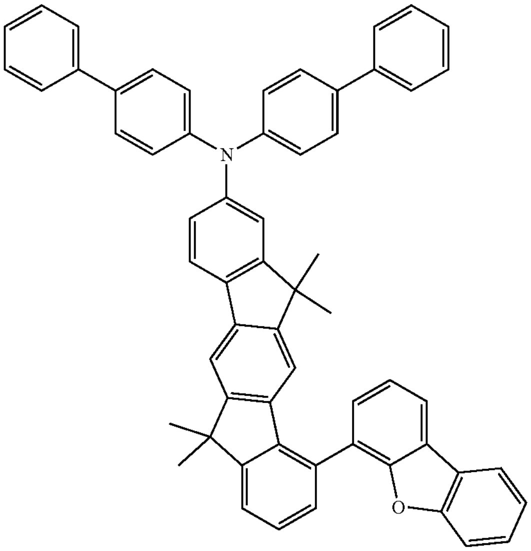 [SMILES: CC1(C)c2cc(N(c3ccc(-c4ccccc4)cc3)c3ccc(-c4ccccc4)cc3)ccc2-c2cc3c(cc21)-c1c(-c2cccc4c2oc2ccccc24)cccc1C3(C)C] HTM-4 | | |
| 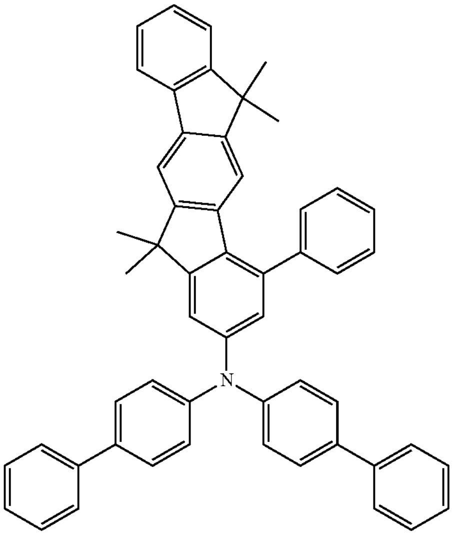 [SMILES: CC1(C)c2ccccc2-c2cc3c(cc21)-c1c(-c2ccccc2)cc(N(c2ccc(-c4ccccc4)cc2)c2ccc(-c4ccccc4)cc2)cc1C3(C)C] HTM-5 | | |
| 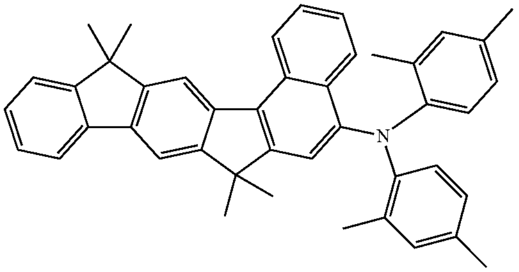 [SMILES: Cc1ccc(N(c2ccc(C)cc2C)c2cc3c(c4ccccc24)-c2cc4c(cc2C3(C)C)-c2ccccc2C4(C)C)c(C)c1] SEB | | |

TABLE 1-continued

| Compounds used | U @ 10 mA/cm² [V] | EQE @ 10 mA/cm² [%] |
| --- | --- | --- |
| 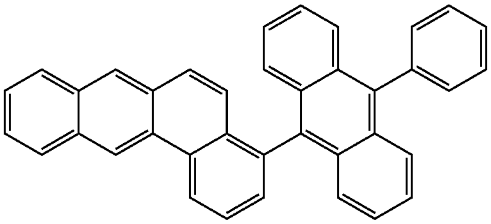 H | | |
| 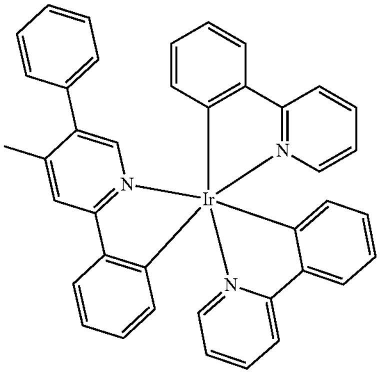 TEG | | |
| 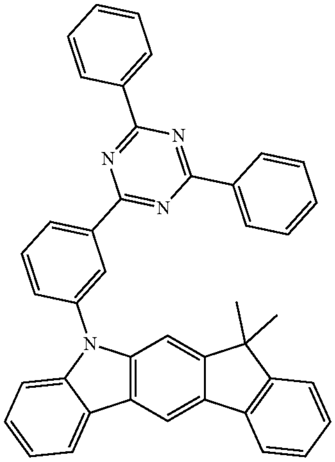 TMM-1 | | |
| 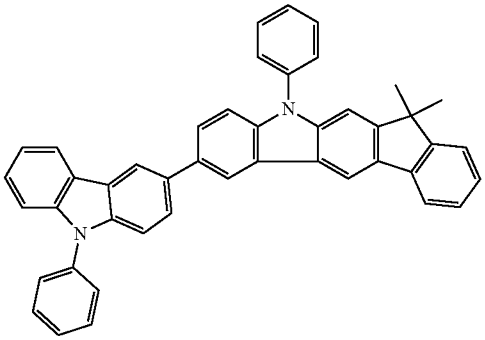 TMM-2 | | |

TABLE 1-continued

| Compounds used | U @ 10 mA/cm² [V] | EQE @ 10 mA/cm² [%] |
| --- | --- | --- |
| 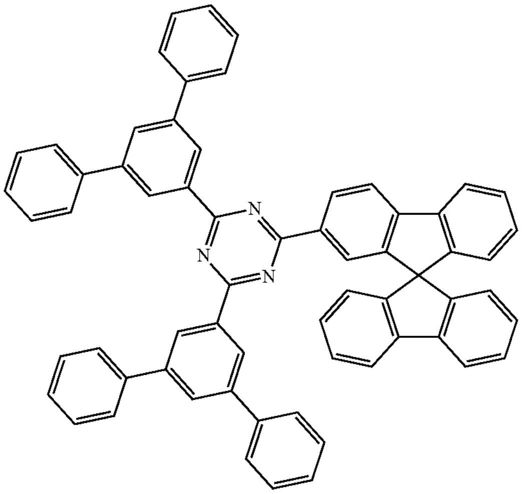 ETM | | |
| 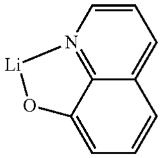 LiQ | | |

The invention claimed is:

1. A compound of the following formula (I) or (II):

Formula (I)

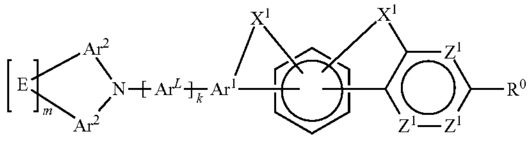

Formula (II)

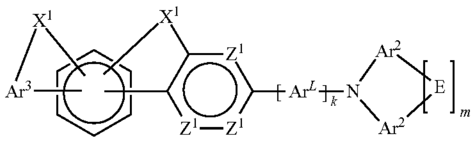

where the variables that occur are as follows:

$Z^1$ is the same or different at each instance and is selected from $CR^1$ and $CR^3$;

$Ar^1$ is an aryl group which has 6 to 20 aromatic ring atoms and may be substituted by one or more $R^3$ radicals, or a heteroaryl group which has 5 to 20 aromatic ring atoms and may be substituted by one or more $R^3$ radicals;

$Ar^2$ is the same or different at each instance and is selected from aromatic ring systems which have 6 to 40 aromatic ring atoms and may be substituted by one or more $R^5$ radicals, and heteroaromatic ring systems which have 5 to 40 aromatic ring atoms and may be substituted by one or more $R^5$ radicals;

$Ar^3$ is an aryl group which has 6 to 20 aromatic ring atoms and may be substituted by one or more $R^2$ radicals, or a heteroaryl group which has 5 to 20 aromatic ring atoms and may be substituted by one or more $R^2$ radicals;

$X^1$ is the same or different at each instance and is a divalent group selected from $—C(R^4)_2—$, $—C(R^4)_2—C(R^4)_2—$, $—CR^4═CR^4—$, $—Si(R^4)_2—$, O and S;

$Ar^L$ is selected from aromatic ring systems which have 6 to 40 aromatic ring atoms and may be substituted by one or more $R^5$ radicals, and heteroaromatic ring systems which have 5 to 40 aromatic ring atoms and may be substituted by one or more $R^5$ radicals;

E is a single bond or a divalent group selected from $C(R^5)_2$, $Si(R^5)_2$, $N(R^5)$, O, and S;

$R^0$ is selected from H, D, aromatic ring systems which have 6 to 40 aromatic ring atoms and may be substituted by one or more $R^6$ radicals, and heteroaromatic ring systems which have 5 to 40 aromatic ring atoms and may be substituted by one or more $R^6$ radicals;

$R^1$ is the same or different at each instance and is selected from aromatic ring systems which have 6 to 40 aromatic ring atoms and may be substituted by one or more $R^6$ radicals, and heteroaromatic ring systems which have 5 to 40 aromatic ring atoms and may be substituted by one or more $R^6$ radicals, with the proviso that two or more $R^1$ radicals are not joined to one another and form a ring;

$R^2$ is the same or different at each instance and is selected from H, D, F, $Si(R^6)_3$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^0$ radicals may be joined to one another and may form a ring; where the alkyl, alkoxy, alkenyl and alkynyl groups mentioned and the aromatic ring systems and heteroaromatic ring systems mentioned may each be substituted by one or more $R^6$ radicals; and where one or more $CH_2$ groups in the alkyl, alkoxy, alkenyl and alkynyl groups mentioned may be replaced by $—R^6C═CR^6—$, $—C≡C—$, $Si(R^6)_2$, C═O, $C═NR^6$, $—C(═O)O—$, $—C(═O)NR^6—$, $NR^6$, $P(═O)(R^6)$, —O—, —S—, SO or $SO_2$;

$R^3$, $R^4$, $R^5$ are the same or different at each instance and are selected from H, D, F, $C(═O)R^6$, $Si(R^6)_3$, $N(R^6)_2$, $P(═O)(R^6)_2$, $OR^6$, $S(═O)R^6$, $S(═O)_2R^6$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^4$ or $R^5$ radicals may be joined to one another and may form a ring; where the alkyl, alkoxy, alkenyl and alkynyl groups mentioned and the aromatic ring systems and heteroaromatic ring systems mentioned may each be substituted by one or more $R^6$ radicals; and where one or more $CH_2$ groups in the alkyl, alkoxy, alkenyl and alkynyl groups mentioned may be replaced by $—R^6C═CR^6—$, —C═C—, $Si(R^6)_2$, C═O, $C═NR^6$, $—C(═O)O—$, $—C(═O)NR^6—$, $NR^6$, $P(═O)(R^6)$, —O—, —S—, SO or $SO_2$, with the proviso that two or more $R^3$ radicals or two or more $R^1$ and $R^3$ radicals are not joined to one another and form a ring:

$R^6$ is the same or different at each instance and is selected from H, D, F, $C(═O)R^7$, $Si(R^7)_3$, $N(R^7)_2$, $P(═O)(R^7)_2$, $OR^7$, $S(═O)R^7$, $S(═O)_2R^7$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^6$ radicals may be joined to one another and may form a ring; where the alkyl, alkoxy, alkenyl and alkynyl groups mentioned and the aromatic ring systems and heteroaromatic ring systems mentioned may each be substituted by one or more $R^7$ radicals; and where one or more $CH_2$ groups in the alkyl, alkoxy, alkenyl and alkynyl groups mentioned may be replaced by $—R^7C═CR^7—$, $—C≡C—$, $Si(R^7)_2$, C═O, $C═NR^7$, $—C(═O)O—$, $—C(═O)NR^7—$, $NR^7$, $P(═O)(R^7)$, —O—, —S—, SO or $SO_2$;

$R^7$ is the same or different at each instance and is selected from H, D, F, alkyl or alkoxy groups having 1 to 20 carbon atoms, alkenyl or alkynyl groups having 2 to 20 carbon atoms, aromatic ring systems having 6 to 40 aromatic ring atoms and heteroaromatic ring systems having 5 to 40 aromatic ring atoms; where two or more $R^7$ radicals may be joined to one another and may form a ring; and where the alkyl, alkoxy, alkenyl and alkynyl groups, aromatic ring systems and heteroaromatic ring systems mentioned may be substituted by F or CN;

k is 0, 1, 2 or 3, where, in the case that k=0, the Art group is absent and the nitrogen atom of the group of the formula (N) constitutes the attachment position;

m is 0 or 1, where, in the case that m=0, the E group is absent and the $Ar^2$ groups are not bonded to one another;

where, in formula (I) and (II), all positions shown as unsubstituted may each be substituted by an $R^3$ radical;

wherein, in one of the formulae (I) and (II), one or two $Z^1$ groups in each case are $CR^1$, and the other $Z^1$ groups are $CR^3$, and where, in formula (I) and in formula (II), there is in each case at least one $Z^1$ group which is $CR^1$.

2. The compound according to claim 1, wherein $X^1$ is $C(R^4)_2$.

3. The compound according to claim 1, wherein k is 0.

4. The compound according to claim 1, wherein k is not 0 and $—(Ar^L)_k—$ conforms to one of the following formulae:

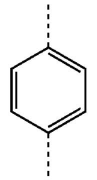

$Ar^L$-1

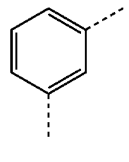

$Ar^L$-2

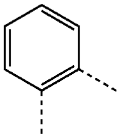
Ar$^L$-3
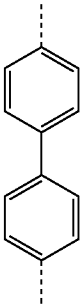
Ar$^L$-4
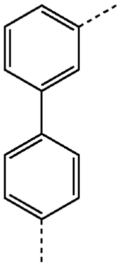
Ar$^L$-5
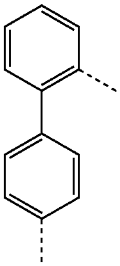
Ar$^L$-6
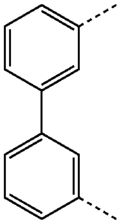
Ar$^L$-7
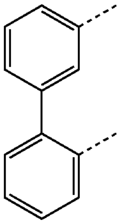
Ar$^L$-8
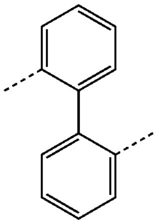
Ar$^L$-9
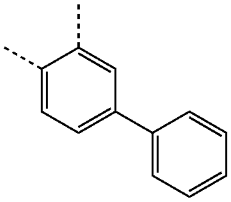
Ar$^L$-10
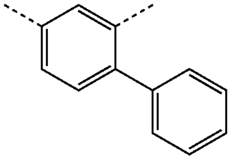
Ar$^L$-11
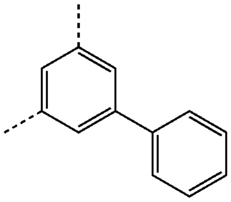
Ar$^L$-12
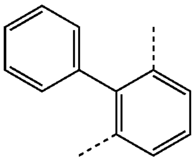
Ar$^L$-13
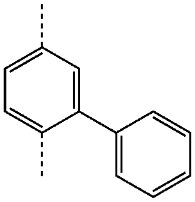
Ar$^L$-14
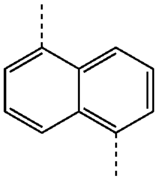
Ar$^L$-15
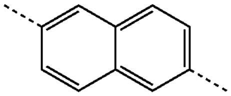
Ar$^L$-16

-continued
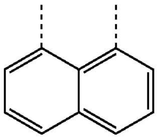
$Ar^L$-17
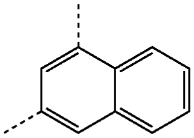
$Ar^L$-18
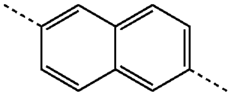
$Ar^L$-19
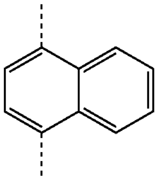
$Ar^L$-20
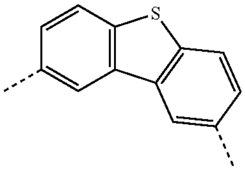
$Ar^L$-21
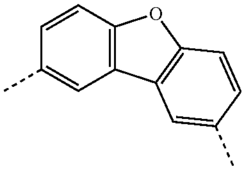
$Ar^L$-22
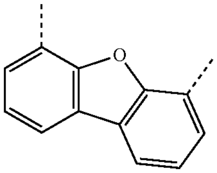
$Ar^L$-23
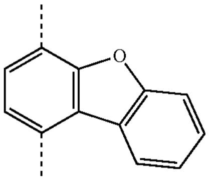
$Ar^L$-24
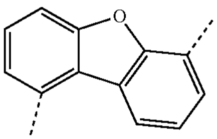
$Ar^L$-25
-continued
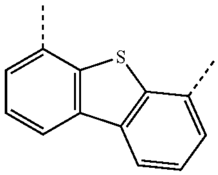
$Ar^L$-26
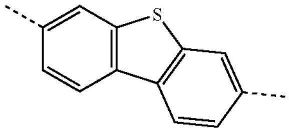
$Ar^L$-27
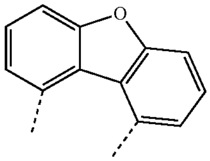
$Ar^L$-28
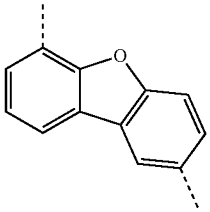
$Ar^L$-29
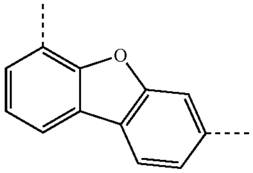
$Ar^L$-30
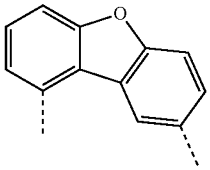
$Ar^L$-31
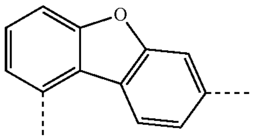
$Ar^L$-32
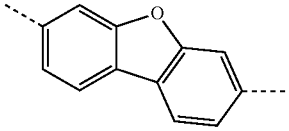
$Ar^L$-33
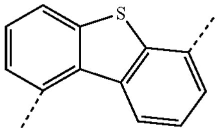
$Ar^L$-34

-continued
Ar$^L$-35
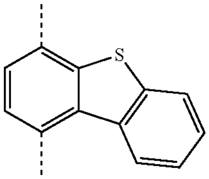
Ar$^L$-36
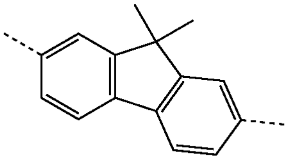
Ar$^L$-37
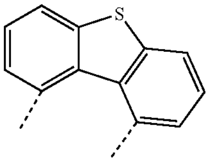
Ar$^L$-38
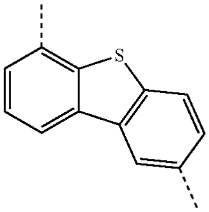
Ar$^L$-39
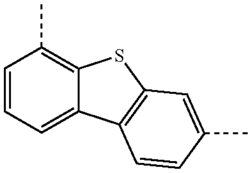
Ar$^L$-40
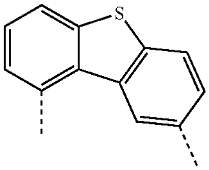
Ar$^L$-41
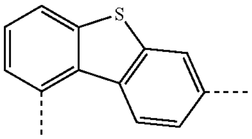
Ar$^L$-42
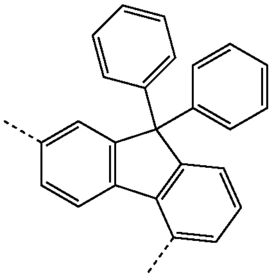
-continued
Ar$^L$-43
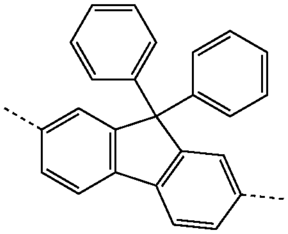
Ar$^L$-44
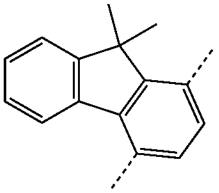
Ar$^L$-45
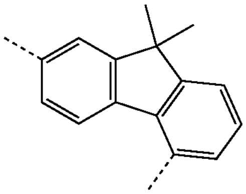
Ar$^L$-46
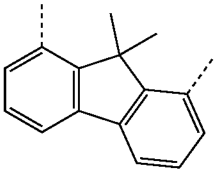
Ar$^L$-47
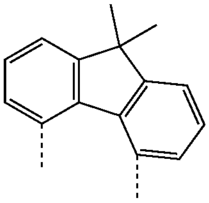
Ar$^L$-48
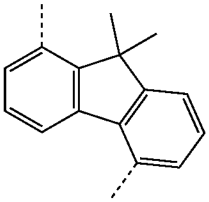
Ar$^L$-49
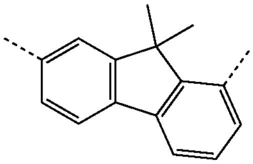

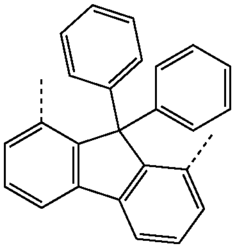
Ar^L-50
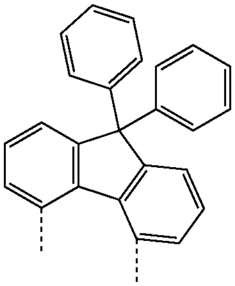
Ar^L-51
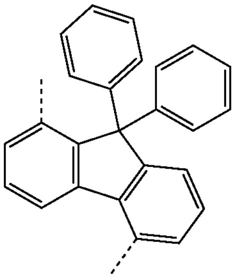
Ar^L-52
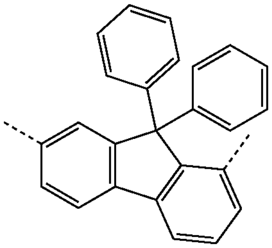
Ar^L-53
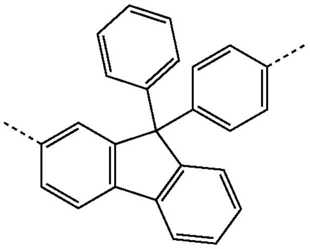
Ar^L-54
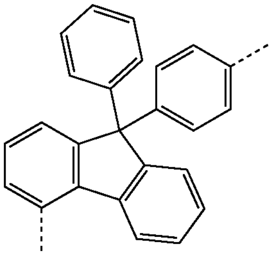
Ar^L-55
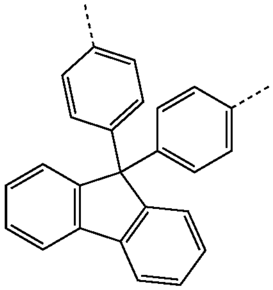
Ar^L-56
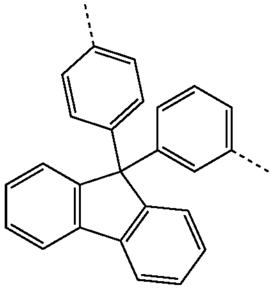
Ar^L-57
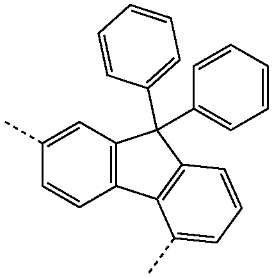
Ar^L-58
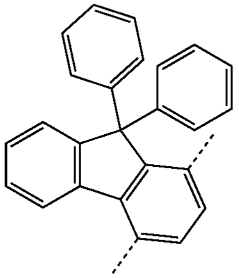
Ar^L-59
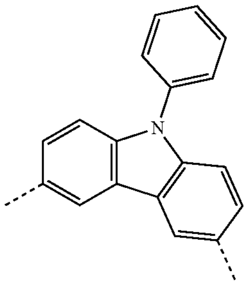
Ar^L-60

-continued
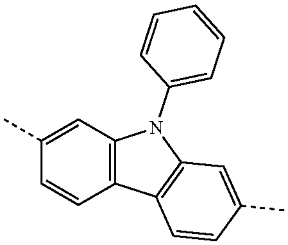
Ar^L-61
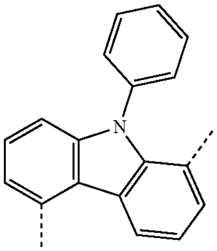
Ar^L-62
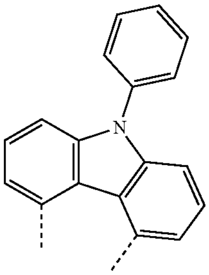
Ar^L-63
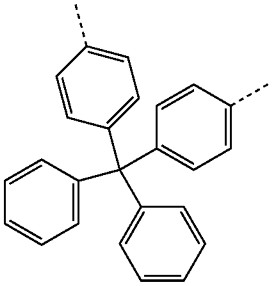
Ar^L-64
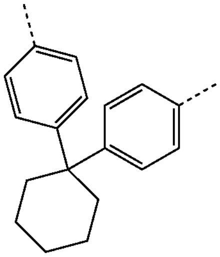
Ar^L-65
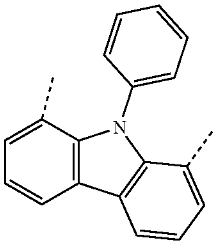
Ar^L-66
-continued
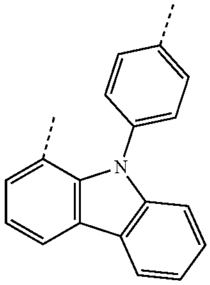
Ar^L-67
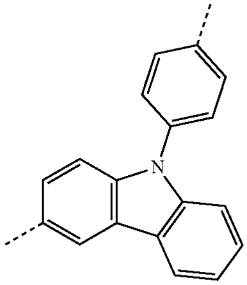
Ar^L-68
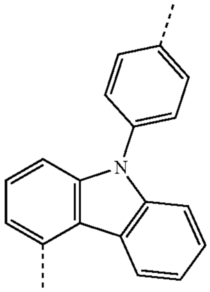
Ar^L-69
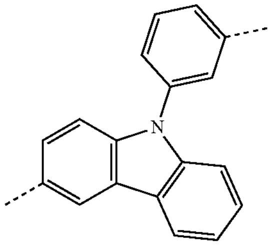
Ar^L-70
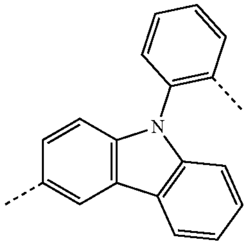
Ar^L-71
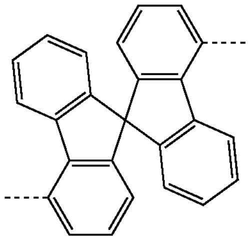
Ar^L-72

-continued

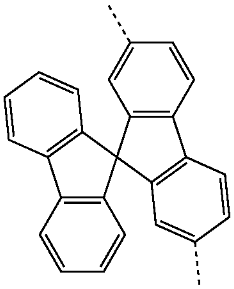

$Ar^L$-73

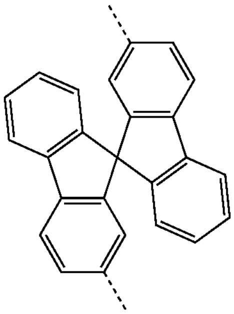

$Ar^L$-74

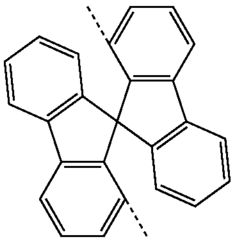

$Ar^L$-75 where the dotted lines in each case represent the bonds to the rest of the formula (I) or (II).

5. The compound according to claim 1, wherein $Ar^2$ is the same or different at each instance and is selected from phenyl, biphenyl, terphenyl, quaterphenyl, naphthyl, fluorenyl, especially 9,9'-dimethylfluorenyl and 9,9'-diphenylfluorenyl, benzofluorenyl, spirobifluorenyl, indenofluorenyl, indenocarbazolyl, dibenzofuranyl, dibenzothiophenyl, carbazolyl, benzofuranyl, benzothiophenyl, benzofused dibenzofuranyl, benzofused dibenzothiophenyl, naphthyl-substituted phenyl, fluorenyl-substituted phenyl, spirobifluorenyl-substituted phenyl, dibenzofuranyl-substituted phenyl, dibenzothiophenyl-substituted phenyl, carbazolyl-substituted phenyl, pyridyl-substituted phenyl, pyrimidyl-substituted phenyl, and triazinyl-substituted phenyl, where the groups mentioned may each be substituted by one or more $R^5$ radicals.

6. The compound according to claim 1, wherein the

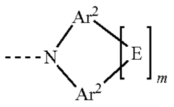

group in formula (I) and (II) is in each case selected from the following formulae:

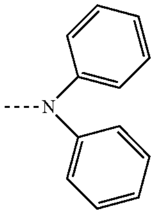

A-1

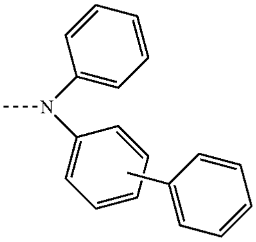

A-2

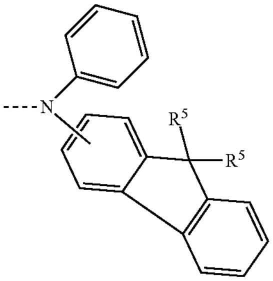

A-3

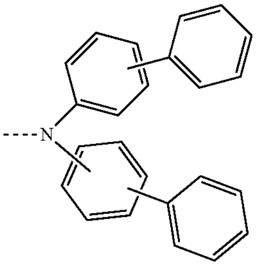

A-4

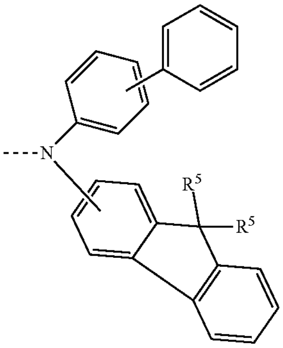

A-5

-continued
A-6
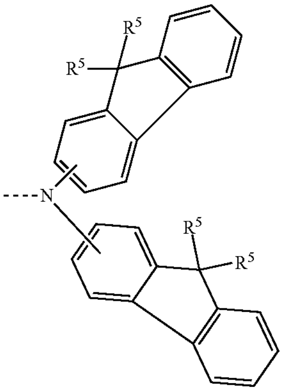
A-7
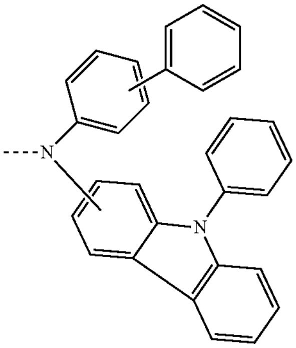
A-8
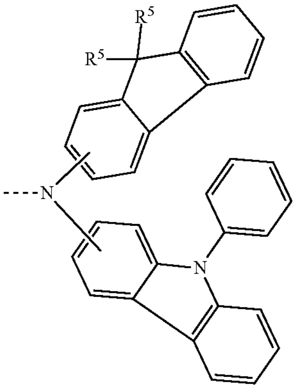
A-9
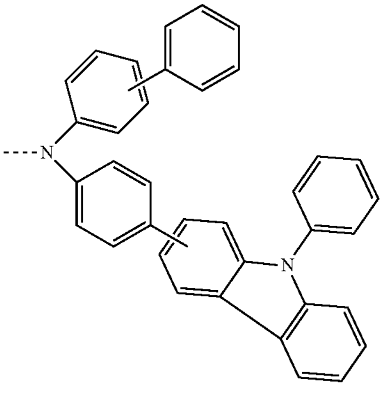
-continued
A-10
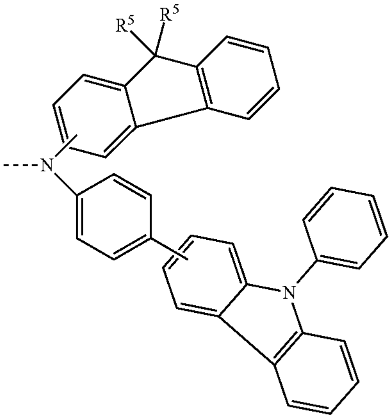
A-11
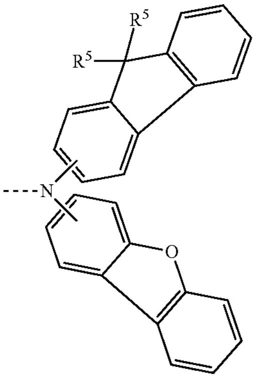
A-12
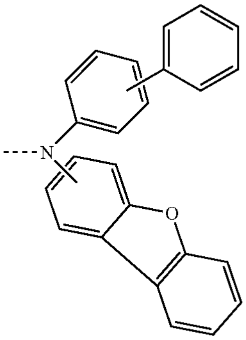
A-13
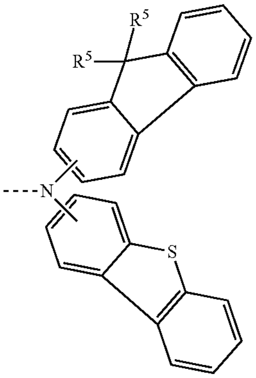

-continued
A-14
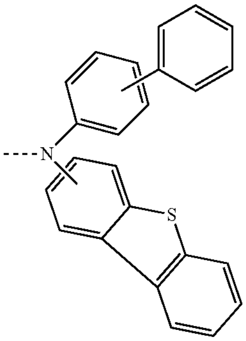
A-15
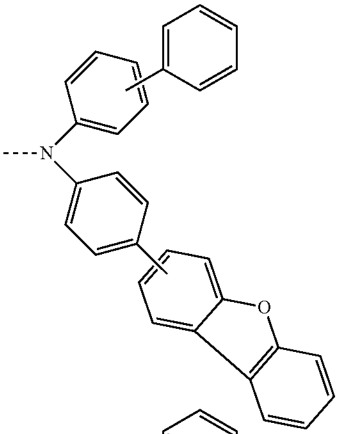
A-16
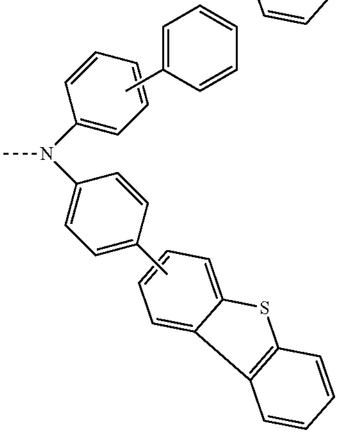
A-17
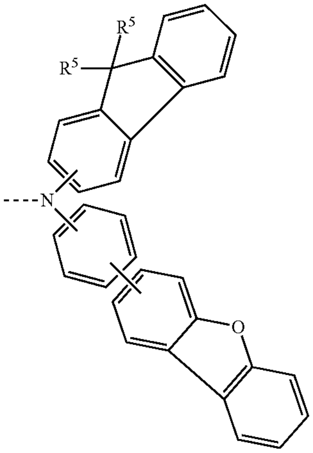
-continued
A-18
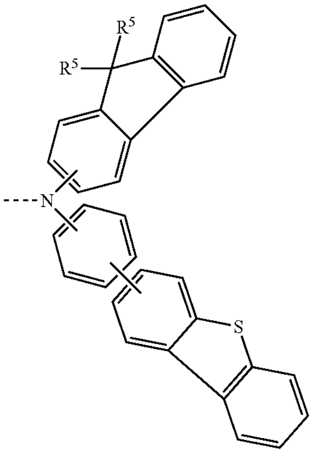
A-19
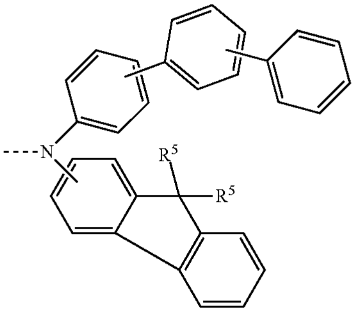
A-20
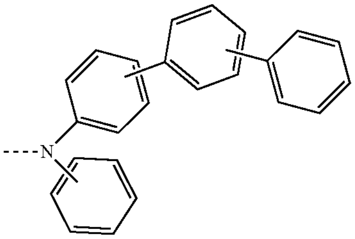
A-21
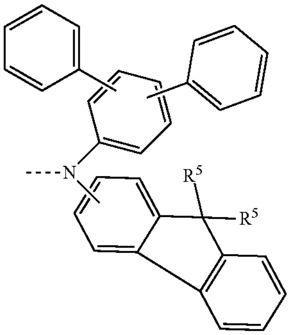
A-22
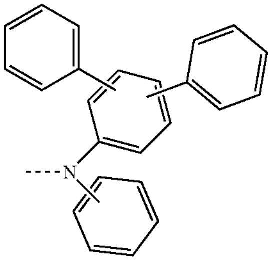

-continued
A-23
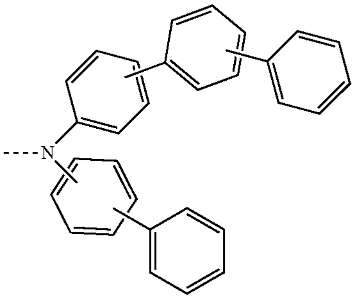
A-24
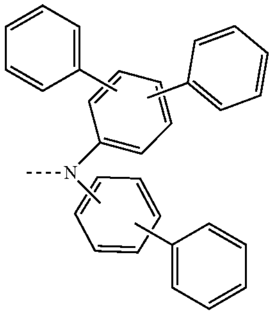
A-25
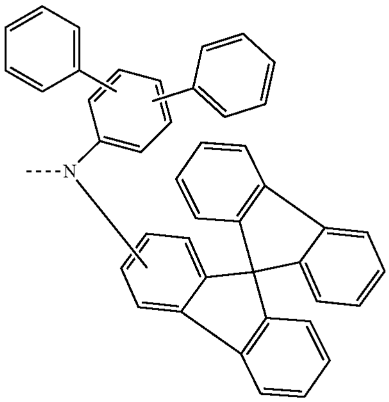
A-26
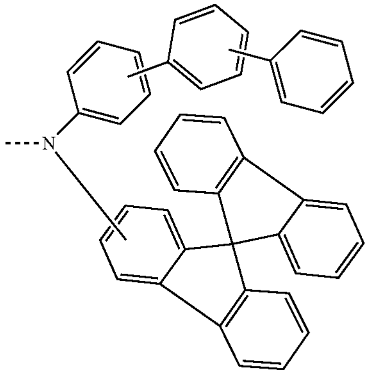
-continued
A-27
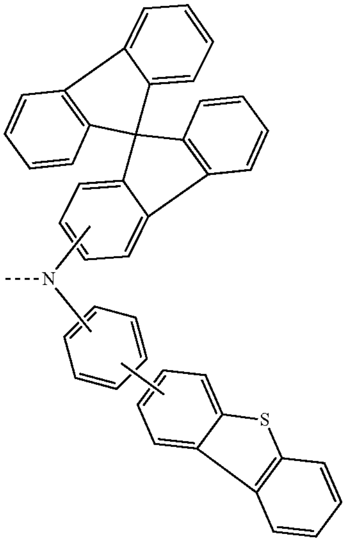
A-28
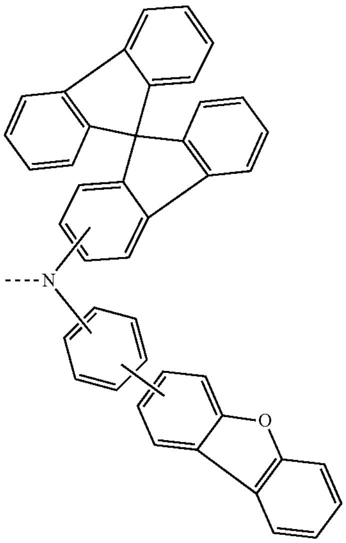
A-29
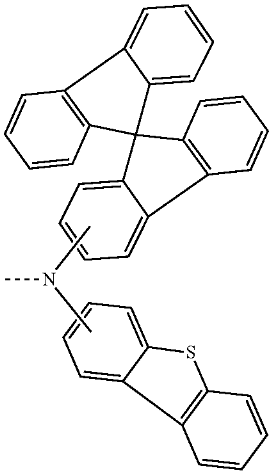

-continued
A-30
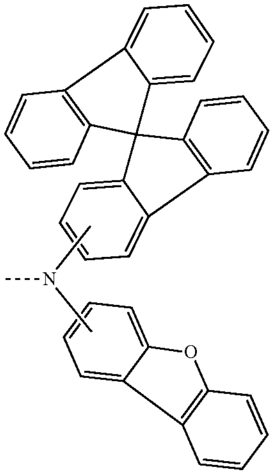
A-31
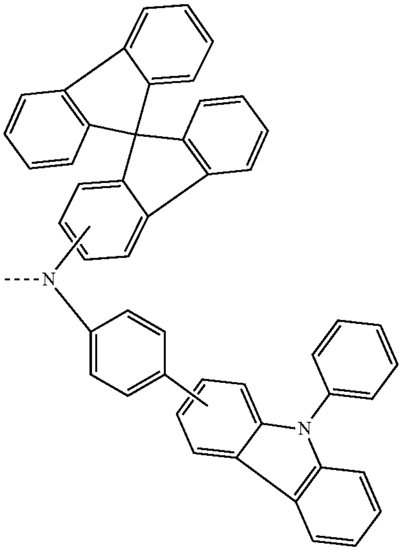
A-32
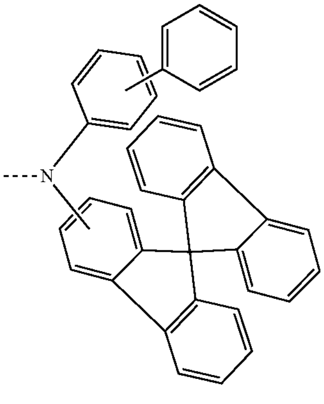
-continued
A-33
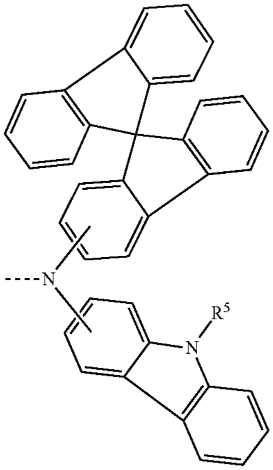
A-34
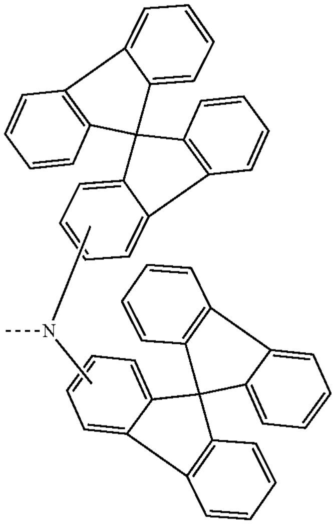
A-35
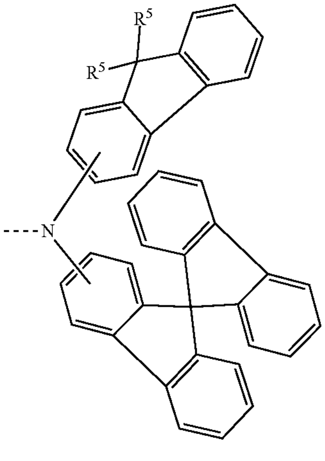

-continued

A-36

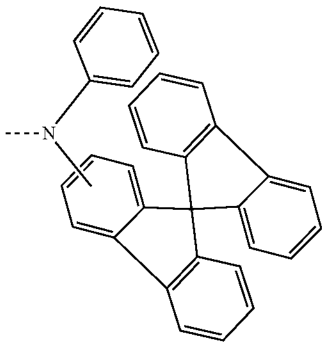

A-37

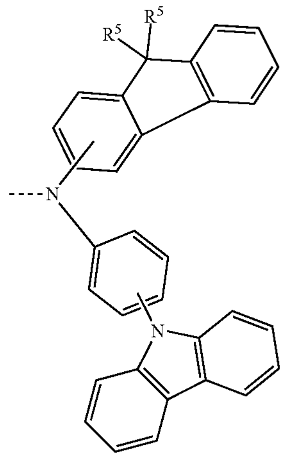

A-38

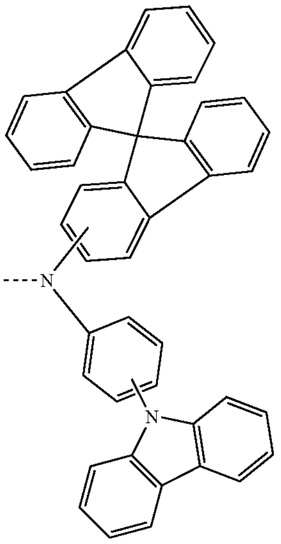

-continued

A-39

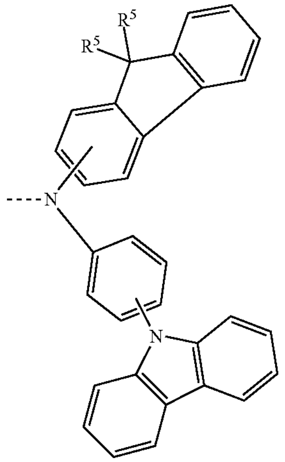

where the groups may each be substituted by an $R^5$ radical at their unoccupied positions, and are unsubstituted in the unoccupied positions, and where the dashed bonds represent the bonds to the rest of the formula (I) or (II).

7. The compound according to claim 1, wherein $R^0$ is H.

8. The compound according to claim 1, wherein $R^1$ is the same or different at each instance and is selected from monovalent groups derived from benzene, biphenyl, terphenyl, quaterphenyl, naphthalene, fluorene, especially 9,9'-dimethylfluorene and 9,9'-diphenylfluorene, benzofluorene, spirobifluorene, indenofluorene, indenocarbazole, dibenzofuran, dibenzothiophene, benzocarbazole, carbazole, benzofuran, benzothiophene, indole, quinoline, pyridine, pyrimidine, pyrazine, pyridazine and triazine, where the monovalent groups may each be substituted by one or more $R^6$ radicals.

9. The compound according to claim 1, wherein $R^2$ and $R^3$ are H.

10. The compound according to claim 1, wherein formula (I) conforms to one of the following formulae:

Formula (I-A-1-a)

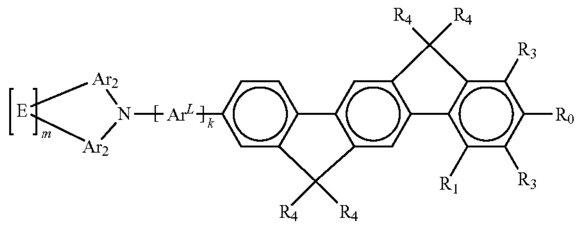

Formula (I-A-2-a)

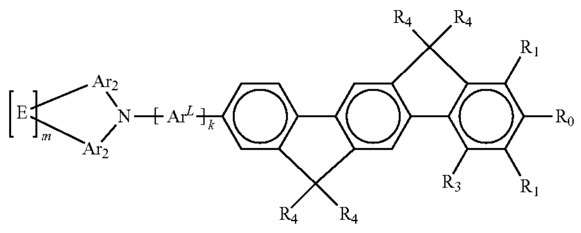

-continued

Formula (I-B-1-a)

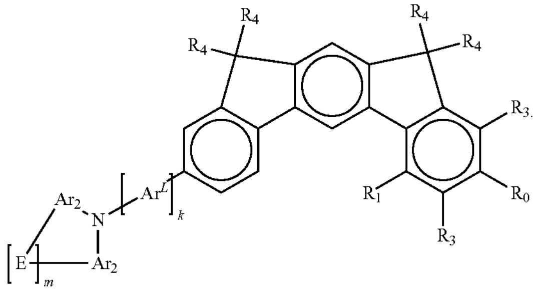

11. A process for preparing the compound of formula (I) or (II) according to claim 1, which comprises reacting a benzene compound bearing two carboxylic ester groups and at least one reactive group with a benzene compound containing a boronic acid group and at least one group selected from reactive groups X and aromatic or heteroaromatic Ar groups, where the boronic acid group and the at least one group selected from X and Ar groups are in ortho or meta positions to one another on the benzene ring.

12. An oligomer, polymer or dendrimer containing one or more compounds of formula (I) or (II) according to claim 1, wherein the bond(s) to the polymer, oligomer or dendrimer may be localized at any desired positions substituted by $R^1$, $R^2$, $R^3$, $R^4$ or $R^5$ in formula (I) or (II).

13. A formulation comprising at least one compound according to claim 1 and at least one solvent.

14. A formulation comprising at least one polymer, oligomer or dendrimer according to claim 12 and at least one solvent.

15. An electronic device comprising at least one compound according to claim 1.

16. An electronic device comprising at least one polymer, oligomer or dendrimer according to claim 12.

17. An electronic device according to claim 14, wherein the device is an organic electroluminescent device and comprises anode, cathode and at least one emitting layer, and in that the compound is present in a hole-transporting layer of the device.

18. The organic electroluminescent device according to claim 17, wherein the compound is present in an electron blocker layer of the device.

* * * * *